US012038446B2

(12) United States Patent
Sorek et al.

(10) Patent No.: US 12,038,446 B2
(45) Date of Patent: Jul. 16, 2024

(54) METHODS AND COMPOSITIONS FOR DIAGNOSING BRAIN INJURY OR NEURODEGENERATION

(71) Applicant: BRAINBOX SOLUTIONS, INC., Richmond, VA (US)

(72) Inventors: Rachel Sorek, Zafaria (IL); Keren Jakobi, Tel Aviv (IL); Donna Edmonds, Richmond, VA (US)

(73) Assignee: Brainbox Solutions, Inc., Richmond, VA (US)

(*) Notice: Subject to any disclaimer, the term of this patent is extended or adjusted under 35 U.S.C. 154(b) by 0 days.

(21) Appl. No.: 16/299,588

(22) Filed: Mar. 12, 2019

(65) Prior Publication Data
US 2019/0195893 A1 Jun. 27, 2019

Related U.S. Application Data

(63) Continuation of application No. 15/547,252, filed as application No. PCT/IL2016/050108 on Feb. 1, 2016, now abandoned.

(60) Provisional application No. 62/112,189, filed on Feb. 5, 2015.

(51) Int. Cl.
| | |
|---|---|
| *G01N 33/68* | (2006.01) |
| *C07K 14/47* | (2006.01) |
| *G01N 33/543* | (2006.01) |
| *G01N 33/96* | (2006.01) |

(52) U.S. Cl.
CPC ......... *G01N 33/6896* (2013.01); *C07K 14/47* (2013.01); *G01N 33/54366* (2013.01); *G01N 33/96* (2013.01); *G01N 2800/28* (2013.01); *G01N 2800/52* (2013.01); *G01N 2800/56* (2013.01)

(58) Field of Classification Search
CPC ......... G01N 33/6896; G01N 33/54366; G01N 33/96; G01N 2800/28; G01N 2800/52; G01N 2800/56; C07K 14/47
See application file for complete search history.

(56) References Cited

U.S. PATENT DOCUMENTS

| | | | |
|---|---|---|---|
| 6,235,489 B1 | 5/2001 | Jackowski | |
| 6,884,591 B2 | 4/2005 | Janigro et al. | |
| 7,144,708 B2 | 12/2006 | Janigro et al. | |
| 7,396,654 B2 | 7/2008 | Hayes et al. | |
| 7,456,027 B2 | 11/2008 | Wang et al. | |
| 8,460,888 B2 | 6/2013 | Lafaye et al. | |
| 8,492,107 B2 | 7/2013 | Wang et al. | |
| 8,557,526 B2 | 10/2013 | Ottens et al. | |
| 8,663,911 B2 | 3/2014 | Vojdani | |
| 8,778,343 B2 | 7/2014 | Kayed | |
| 9,194,867 B2 | 11/2015 | Vojdani | |
| 9,547,014 B2 | 1/2017 | Travis et al. | |
| 9,810,698 B2 | 11/2017 | Wang et al. | |
| 10,041,959 B2 | 8/2018 | Wang et al. | |
| 10,330,689 B2 | 6/2019 | Wang et al. | |
| 11,143,662 B2 * | 10/2021 | Edmonds | ........... G01N 33/6896 |
| 2003/0040660 A1 | 2/2003 | Jackowski et al. | |
| 2005/0260770 A1 | 11/2005 | Cohen et al. | |
| 2011/0177974 A1 | 7/2011 | Wang et al. | |
| 2013/0022982 A1 | 1/2013 | Wang et al. | |
| 2014/0045713 A1 | 2/2014 | Everett et al. | |
| 2014/0303041 A1 | 10/2014 | Hayes et al. | |
| 2014/0342381 A1 | 11/2014 | Hayes | |
| 2015/0004169 A1 | 1/2015 | Kayed | |
| 2015/0031048 A1 | 1/2015 | Van Eyk et al. | |
| 2015/0118218 A1 | 4/2015 | Travis et al. | |
| 2015/0119273 A1 | 4/2015 | Goldstein et al. | |
| 2015/0141528 A1 | 5/2015 | Lamer | |
| 2015/0247867 A1 | 9/2015 | Curdt et al. | |
| 2015/0268252 A1 | 9/2015 | Svetlov et al. | |
| 2017/0146555 A1 | 5/2017 | Wang et al. | |
| 2018/0024145 A1 | 1/2018 | Sorek et al. | |

FOREIGN PATENT DOCUMENTS

| | | |
|---|---|---|
| WO | 2002008755 A2 | 1/2002 |
| WO | 2003/042701 A1 | 3/2003 |
| WO | 2010148391 A2 | 12/2010 |
| WO | 2013104720 A2 | 7/2013 |
| WO | 2015009907 A1 | 1/2015 |
| WO | 2015157390 A1 | 10/2015 |
| WO | 2016055148 A2 | 4/2016 |
| WO | 2016087611 A1 | 6/2016 |
| WO | 2017008894 A1 | 1/2017 |

OTHER PUBLICATIONS

Martinez-Morillo et al., J. Proteome Res., 2014, 13(2):969-81.*
Uryu et al., Exp. Neurology, 2003, 184:214-224.*
Babcock, L. et al., "Ability of S100B to predict severity and cranial CT results in children with TBI," Brain Injury, vol. 26, No. 11, pp. 1372-1380 (2012).
Berger, R. et al., "Multiplex Assessment of Serum Biomarker Concentrations in Well-Appearing Children With Inflicted Traumatic Brain Injury," Pediatric Research, vol. 65, No. 1, pp. 97-102 (2009).
Biberthaler, P. et al., "Serum S-100B Concentration Provides Additional Information for the Indication of Computed Tomography in Patients After Minor Injury," SHOCK, vol. 25, No. 5, pp. 446-453 (2006).

(Continued)

*Primary Examiner* — Olga N Chernyshev
(74) *Attorney, Agent, or Firm* — Melissa Hunter-Ensor; Leslie Serunian; Greenberg Traurig, LLP

(57) ABSTRACT

Methods and compositions for diagnosing brain injury, neurodegeneration; or a predisposition thereto, in a subject are provided. Particularly, the present invention relates to specific antigen antibody reactivities useful in diagnosing brain injury, neurodegeneration or a predisposition thereto, in a subject.

9 Claims, 7 Drawing Sheets

Specification includes a Sequence Listing.

(56) References Cited

OTHER PUBLICATIONS

Ingebrigtsen, T. et al., "The clinical value of serum S-100 protein measurements in minor head injury: a Scandinavian multicentre study," Brain Injury, vol. 14, No. 12, pp. 1047-1055 (2000).
Jeter, C. et al., "Biomarkers for the Diagnosis and Prognosis of Mild Traumatic Brain Injury/Concussion," Journal of Neurotrauma, vol. 30, pp. 657-670 (2013).
Mondello, S. et al., "Glial Neuronal Ratio: A Novel Index for Differentiating Injury Type in Patients with Severe Traumatic Brain Injury," Journal of Neurotrauma, vol. 29, pp. 1096-1104 (2012).
Papa, L. et al., "[Elevated] Levels of Serum Glial Fibrillary Acidic Protein Breakdown Products in Mild and Moderate Traumatic Brain Injury are Associated With Intracranial Lesions and Neurosurgical Intervention," Ann. Emerg. Med., vol. 59, No. 6, pp. 1-24 (2012).
Papa, L et al., Serum levels of ubiquitin C-terminal hydrolase distinquish mild traumatic brain injury from trauma controls and are elevated in mild and moderate traumatic brain injury patients with intracranial lesions and neurosurgical intervention, J. Trauma, vol. 72, No. 5, pp. 1335-1344 (2012).
Rodrigues, E. et al., "Increased serum brain derived neurotrophic factor (BDNF) following isolated severe traumatic brain injury in humans," Abstract No. 0196, Brain Injury, 22 (Supplement 1), p. 165 (2008).
Rostami, E. et al., "Alteration in BDNF and its receptors, full-length and truncated TrkB and p75NTR following penetrating traumatic brain injury," Brain Research, vol. 1542, pp. 195-205 (2014).
Rostami, E. et al., Proteomic-based identification of injury-specific patterns of biomarkers following different types of TBI, Presentation Abstract, Presentation date: Nov. 15, 2010, XP009193994, 2 pages.
Griesbach, G. et al., "Alterations in BDNF and Synapsin I within the Occipital Cortex and Hippocampus after Mild Traumatic Brain Injury in the Developing Rat: Reflections of Injury-Induced Neuroplasticity," Journal of Neurotrauma, vol. 19, No. 7, pp. 803-814 (2002).
Horakova, D. et al., "Environmental Factors Associated with Disease Progression after the First Demyelinating Event: Results from the Multi-Center SET Study," PLOS ONE, vol. 8, No. 1, Jan. 8, 2013, p. e53996 (8 pages).
Liu, Y. et al., "Development of Recombinant Antigen Array for Simultaneous Detection of Viral Antibodies," PLOS ONE, vol. 8, No. 9, Sep. 13, 2013, p. e73842 (9 pages).
Supplementary Partial European Search Report in corresponding European Patent Application No. 16 74 6229, dated May 16, 2018 (5 pages).
Provisional Opinion in corresponding European Patent Application No. 16 74 6229, dated May 16, 2018 (6 pages).
International Search Report and Written Opinion for corresponding PCT/IL2016/050108 dated Jun. 15, 2016 (14 pages).
Marchi, N. et al., "Consequences of Repeated Blood-Brain Barrier Disruption in Football Players," PLoS ONE 8(3):e56805. doi: 10.1371/journal.pone.0056805, Mar. 6, 2013.
Ngankam, L. et al., "Immunological markers of severity and outcome of traumatic brain injury," Zhurnal nevrologii i psikhiatrii imeni SS Korsakova/Ministerstvo zdravookhraneniia i meditskinskoi promyshlennosti Rossiiskoi Federasstii, Vserossiiskoe obschestvo nevrologov [i] Vesrossiiskoe obshchestvo psikhiatrov, 111(7), pp. 61-65, Dec. 31, 2010 (Dec. 31, 2010). Abstract in English Provided (1 page).
Xu et al., BMC Neurology, 2012, 12(87):1-7.
Zhang, Y. and Popovich, P., "Roles of autoantibodies in central nervous system injury," Discovery Medicine, vol. 11(60), pp. 395-402. (http://www.discoverymedicine.com/Yi-Zhang/2011/05/10/roles-of-autoantibodies-in-central-nervous-system-injury).
Zhang, Z. et al., "Human Traumatic Brain Injury Induces Autoantibody Response against Glial Fibrillary Acidic Protein and Its Breakdown Products," PLoS ONE 9(3): e92698. doi:10.1371/journal pne. 0092698, Mar. 24, 2014.

Buki et al., "Minor and Repetitive Head Injury", Advances and Technical Standards in Neurosurgery 42, 2015, pp. 147-192, Springer International Publishing Switzerland.
Ichkova et al., "New Biomarker Stars for Traumatic Brain Injury", Journal of Cerebral Blood Flow & Metabolism, 2017, vol. 37(10), 3276-3277.
Ke et al., "Increased Expression of Small Heat Shock Protein αB-Crystallin After Intracerebral Hemorrhage in Adult Rats", J. Mol. Neurosci, 2013, 51:159-169, Springer Science+Business Media New York.
Lumpkins et al., "Glial Fibrillary Acidic Protein is Highly Correlated with Brain Injury", The Journal of Trauma, 2008, 65, pp. 778-784.
Martinez et al., "Type-Dependent Oxidative Damage in Frontotemporal Lobar Degeneration: Cortical Astrocytes are Targets of Oxidative Damage", j Neuropathol Exp Neurol, vol. 67, No. 12, Dec. 2008, pp. 1122-1136.
McMahon et al., "Measurement of the Glial Fibrillary Acidic protein and its Breakdown Products GFAP-BDP Biomarker for the Detection of Traumatic Brain Injury Compared to Computed Tomography and Magnetic Resonance Imaging", Journal of Neurotrauma, 35:527-533, Apr. 15, 2015.
Newcombe et al., "Distribution of Glial Fibrillary Acidic Protein in Gliosed Human White Matter", Journal of Neurochemistry, 47, 1986, pp. 1713-1719.
Okonkwo et al., "GFAP-BDP as an Acute Diagnostic Marker in Traumatic Brain Injury: Results from the Prospective Transforming Research and Clinical Knowledge in Traumatic Brain Injury Study", Journal of Neurotrauma, 30:1490-1497, Sep. 1, 2013.
Papa et al., "Elevated Levels of Serum Glial Fibrillary Acidic Protein Breakdown Products in Mild and Moderate Traumatic Brain Injury are Associated with Intracranial Lesions and Neurosurgical Intervention", Annals of Emergency Medicine, vol. 59, No. 6, Jun. 2012, pp. 471-483.
Pelinka et al., "Glial Fibrillary Acidic Protein in Serum After Traumatic Brain Injury and Multiple Trauma", The Journal of Trauma, 2004, 57:1006-1012.
Pelinka et al., "GFAP Versus S100B in Serum after Traumatic Brain Injury: Relationship to Brain Bamage and Outcome", Journal of Neurotrauma, vol. 21, No. 11, 2004, pp. 1553-1561.
Rohn et al., "Caspase-Cleaved Glial Fibrillary Acidic Protein within Cerebellar White Matter of the Alzheimer's Disease Brain", Int J Clin Pathol, 2013, 6(1), pp. 41-48.
Shen et al., "Addressing the Needs of Traumatic Brain Injury with Clinical Proteomics", Clinical Proteomics, 2014, 11:11, (13 pages).
Vasquez et al., "Creatine Kinase BB and Neuron-Specific Enolase in Cerebrospinal Fluid in the Diagnosis of Brain Insult", The American Journal of Forensic Medicine and Pathology, 16(3), pp. 210-214, 1995.
Yang et al., "Glial Fibrillary Acidic Protein: from Intermediate Filament Assembly and Gliosis to Neurobiomarker", Trends in Neuroscience, Jun. 2015, vol. 38, No. 6, pp. 364-374.
Zhang et al., "Human Traumatic Brain Injury Induces Autoantibody Response Against Glial Fibrillary Acidic Protein and Its Breakdown Products", PLOS One, Mar. 2014, vol. 9, Issue 3, (16 pages).
Zoltewicz et al., "Characterization of Antibodies that Detect Human GFAP after Traumatic Brain Injury", Biomarker Insights, 2012:7, pp. 71-79.
Cohen, Irun R., "Real and artificial immune systems: computing the state of the body," Nature Reviews Immunology, Jul. 2007, vol. 7, pp. 569-574.
Kanter et al., "Lipid microarrays identify key mediators of autoimmune brain inflammation," Nature Medicine, Jan. 2006, vol. 12, No. 1, pp. 138-143.
Merbl et al., "Newborn humans manifest autoantibodies to defined self molecules detected by antigen microarray informatics," The Journal of Clinical Investigation, Mar. 2007, vol. 117, No. 3, pp. 712-718.
Quintana et al., "Antigen-Chip Technology for Accessing Global Information about the State of the Body," Lupus, 2006, vol. 15, No. 7, pp. 428-430.

(56) References Cited

OTHER PUBLICATIONS

Quintana et al., "Autoantibody Patterns in Diabetes-prone NOD Mice and in Standard C57BL/6 Mice," Journal of Autoimmunity, Nov. 2001, vol. 17, No. 3, pp. 191-197.
Quintana et al., "Cluster analysis of human autoantibody reactivities in health and in type 1 diabetes mellitus: a bio-informatic approach to immune complexity," Journal of Autoimmunity, Aug. 2003, vol. 21, No. 1, pp. 65-75.
Quintana et al., "The natural autoantibody repertoire and autoimmune disease," Biomedicine & Pharmacotherapy, 2004, vol. 58, No. 5, pp. 276-281.
Robinson et al., "Autoantigen microarrays for multiplex characterization of autoantibody responses," Nature Medicine, Mar. 2002, vol. 8, No. 3, pp. 295-301.
Robinson et al., "Protein microarrays guide tolerizing DNA vaccine treatment of autoimmune encephalomyelitis," Nature Biotechnology, Sep. 2003, vol. 21, No. 9, pp. 1033-1039.
Zafonte et al., "Effect of Citicoline on Functional and Cognitive Status Among Patients With Traumatic Brain Injury: Citicoline Brain Injury Treatment Trial (COBRIT)," JAMA, Nov. 21, 2012, vol. 308, No. 19, pp. 1993-2000.

\* cited by examiner

METHODS AND COMPOSITIONS FOR DIAGNOSING BRAIN INJURY OR NEURODEGENERATION

CROSS REFERENCE TO RELATED APPLICATIONS

This application is a continuation of U.S. patent application Ser. No. 15/547,252, filed on Jul. 28, 2017, which is a national stage entry under 35 U.S.C. § 371 of International PCT Application No.: PCT/IL2016/050108, filed on Feb. 1, 2016, designating the United States and published in English, which claims priority to and benefit of U.S. Provisional Application No. 62/112,189, filed on Feb. 5, 2015, the contents of all of which are incorporated herein by reference in their entireties.

FIELD OF THE INVENTION

The present invention relates to methods and compositions for diagnosing brain injury, neurodegeneration; or a predisposition thereto, and more specifically to clinical methods for determining the presence and type of brain injury or neurodegeneration.

BACKGROUND OF THE INVENTION

Brain injuries are complex and can have multiple severe clinical outcomes. Injury of the brain and spinal cord can result from head trauma, stroke, traumatic birth, heart surgery, cardiac arrest and patients requiring cardiovascular support with ventricular assist devices or extracorporeal membrane oxygenation (ECMO).

About 1.7 Million Americans sustain a traumatic brain injury (TBI) each year, ranging from mild to severe, and this is in addition to about 360,000 soldiers involved in combat operations and public safety workers surviving terrorist attacks who develop mild TBI secondary to explosive (concussive) blasts. It contributes about 30% of all injury related deaths and costs about $60B per year. At least 230,000 people are hospitalized due to TBI and survive; more than a million are treated in an emergency department (ED) for TBI and 80,000 to 90,000 Americans experience long-term disability from TBIs.

Recent study was conducted to determine the dimensions of TBI evaluation in US emergency department. TBI was evaluated during 4.8 million visits per year; and head CT scan was performed in 82% of TBI evaluations (3.9 million visits per year). TBI was diagnosed in 52% of evaluations (2.5 million visits per year). Among those who received head CT scans, 9% had CT evidence of traumatic abnormalities. Among patients evaluated for TBI who had a Glasgow Coma Scale score recorded, 94.5% were classified as having mild TBI, 2.1% as moderate TBI, and 3.5% as severe TBI. Among patients with International Classification of Diseases, Ninth Revision, Clinical Modification, codes permitting the calculation of head Abbreviated Injury Scale scores 9.0%, 85.0%, 2.5%, 3.2%, 0.3%, and 0% had head Abbreviated Injury Scale scores of 1, 2, 3, 4, 5, and 6, respectively. Of patients evaluated for TBI, 31% had other head/face/neck injuries, 10% had spine and back injuries, 7% had torso injuries, and 14% had extremity injuries (Korley et al., Sep. 10, 2015, J Head Trauma Rehabil)

TBI is the result of a blunt blow, jolt or blast overpressure to the head that disrupts brain function. The subset of mild TBI (mTBI) has represented a harder segment of TBI to diagnose. The severity of head injuries range from a brief change in mental status or consciousness to extended unconsciousness and amnesia. In severe or multiple concussion cases, personality changes can occur with devastating results. Cognitive decline is recognized as part of the post injury syndrome.

Proper treatment of TBI injury requires an accurate diagnosis of the structures affected. The mechanisms of injury in TBI cause a variety of abnormalities in the peripheral vestibular mechanisms, central vestibular structures, ocularmotor tracts, cerebellum, as well as all portions of the brain communicating with these structures. The onset of vestibular deficits generally occurs within seven to ten days post injury. While reported symptoms of dizziness resolve after three months, 15% have persistent symptoms one year later.

At present, one of the rather subjective and not totally effective diagnostic procedures when traumatic brain injury is suspected involves a number of examining techniques. The patient receives a neurological examination which may consist of the following: 1) mental status, 2) motor function, 3) sensory examination, 4) deep tendon reflexes, 5) station, gait, and equilibrium, and 6) cranial nerve function. The mental status examination may include: a) level of consciousness, b) short and long term memory, c) knowledge of patient and place and d) questions about symptoms: headache, dizziness, blurry vision, etc. In addition, the patient may also have radiological studies which could include CT scan of the head, MRI, PET scan. It has been reported that in the early stages of (especially mild) traumatic brain injury, the imaging techniques may not be sufficiently sensitive to detect an abnormality. Furthermore, the patient's cognitive skills may not be impaired initially, and there may be few, if any, symptoms. Patients are often observed over 24-48 hours and are awakened at regular intervals (e.g., every 3-4 hours) to assure that they are able to be aroused. Narcotics for headache or other pain are not given, so that their effects do not cloud the issue of the patient's arousal state. A computerized test which determines level of cognition and reaction time is often employed with repetitive examinations.

One of the problems with this approach in diagnosing potential traumatic brain injuries is that it is not one which always provides precise, timely, objective information. It is also subject to individual variations from person-to-person. Further, if the person is asymptomatic at the time, the conclusion might be that there is no problem, and the individual might be encouraged to go back to normal activities. Such guidance could potentially be injurious to the person's health and could even lead to fatal consequences.

Once a patient has been diagnosed with a brain injury, it becomes important to treat the patient in a timely, effective manner in order to minimize the risk of permanent injury or death.

In spite of the foregoing known procedures, there remains a very real and substantial need for a method of early and effective determination as to whether an individual has suffered a brain injury, how severe it might be, and upon finding the presence of such an injury, effectively treating the patient.

SUMMARY OF THE INVENTION

The present invention provides methods and kits for diagnosing brain injury or neurodegeneration. The present invention further provides antigen probe arrays for practicing such a diagnosis, and antigen probe sets for generating such arrays.

The antigen probe sets of the present invention can be used to profile the antibody response to said antigens in patients suffering from brain injury or neurodegenerative disease, due to disruption of any or all components of the anatomic structure and the ability to detect elements which cross the blood brain barrier. This antibody response profile can be used for the diagnosis, monitoring and management of brain injury. According to some embodiments, the antibody profile reflects the patient status at time of injury. The profile of the antibody response can be measured on any platform including but not limited to a micro array or any array chip.

The present invention is based, in part, on the unexpected results obtained when testing the antibody reactivity of patients suffering from brain injury compared to healthy controls. Surprisingly, differential immunoglobulin G (IgG) and IgM reactivities to specific antigens were found in the tested brain injury patients, compared to healthy controls. The present invention is also based on the discovery that analysis of the pattern of an individual's antibody response to specific brain related molecules in combination with markers of immune response provides a novel and reliable method of ascertaining the nature and extent of brain injury and of other neurodegenerative conditions. Thus, the present invention provides unique antigens, indicative to brain injury. The present invention further provides antigen-autoantibody reactivity patterns relevant to brain injury. In particular embodiments, the present invention provides highly specific, reliable, accurate and discriminatory assays for diagnosing and monitoring brain injury, based on the indicative antigens, or on reactivity patterns thereof.

According to some embodiments, the 'pre-existing state' of the patient status at time of injury is monitored.

Thus, according to some embodiments of the invention, there are provided novel methods for diagnosing and monitoring the progression of brain injury. According to some embodiments of the invention, the methods comprise determining the reactivity of antibodies in a sample obtained or derived from a subject to at least one antigen as described herein. The methods of the invention further comprise a step of comparing the reactivity of antibodies in the sample to the at least one antigen to a control reactivity to said at least one antigen. According to certain embodiments, a significantly differential reactivity of the antibodies in the sample compared to the reactivity of the healthy control, or to the reactivity of baseline samples from the same patient, is an indication that the subject is afflicted with brain injury.

According to certain embodiments, the baseline samples from the same patient may be used [for measurements over time] to predict progression, resolution of event or remission of disease course.

According to certain embodiments, the methods of the present invention can discriminate which patients with brain injury require a head CT scan to rule out intracranial hemorrhage versus concussion alone. If implemented as an initial response (e.g., in the emergency department (ED) setting) or later (e.g., neurology department), the methods of present invention would decrease head CT scan utilization, decreasing health care costs and radiation exposure.

Thus, according to a first aspect, the present invention provides a method of diagnosing brain injury in a subject, the method comprising the steps of obtaining a sample from the subject, determining the reactivity of antibodies in the sample to at least one antigen selected from the groups consisting of SEQ ID NOs:1-115, isoforms thereof, post-translationally modified forms thereof, fragments thereof, or combinations of any of the foregoing; and comparing the reactivity of antibodies in the sample to a reactivity of a healthy control; wherein a significantly different reactivity of the antibody or antibodies in the sample compared to the reactivity of the healthy control is an indication that the subject is afflicted with brain injury.

In certain embodiments, the at least one antigen is selected from the groups consisting of SEQ ID NOs: 2, 14, 28, 42, 85, and 86, or any combination thereof.

In certain embodiments, said method further comprising measuring the levels of one or more biomarkers in the sample; and comparing the levels of the one or more biomarkers with predefined levels of the same biomarkers that correlate to a subject having brain injury and predefined levels of the same biomarkers that correlate to a healthy control, wherein a correlation to one of the predefined levels provides the diagnosis.

In certain embodiments, said brain injury is selected from the group consisting of: concussions, chronic traumatic encephalopathy, mild traumatic brain injuries, moderate traumatic brain injuries, severe traumatic brain injuries, head trauma, concussive blasts and brain neurodegenerative condition.

In certain embodiments, said brain injury causes disruption of the blood-brain barrier.

In certain embodiments, the brain neurodegenerative condition further comprises loss of memory or motor function and cognitive decline.

In certain embodiments, the neurodegenerative condition is selected from the group consisting of: Alzheimer's disease, Huntington's disease, Parkinson's disease, demyelinating disease, HTLV-1-associated myelopathy (HAM), multiple sclerosis (MS), amyotrophic lateral sclerosis (ALS), pathological neurological symptoms after injury or trauma, encephalopathy and viral encephalopathy.

In certain embodiments, a significantly higher reactivity of the antibodies in the sample compared to the reactivity of the healthy control is an indication that the subject is of increased likelihood to be afflicted with brain injury. In other certain embodiments, where the reactivity of the antibodies in the sample compared to the reactivity of the healthy control is not significantly higher, where the reactivity of the antibodies in the sample compared to the reactivity of the healthy control is the same, where the reactivity of the antibodies in the sample compared to the reactivity of the healthy control is lower or where the reactivity of the antibodies in the sample compared to the reactivity of the healthy control is significantly lower, it is an indication that the subject is of decreased likelihood to be afflicted with brain injury. Each possibility represents a separate embodiment of the present invention.

In certain embodiments of the methods of the present invention, the methods are preceded by a step comprising obtaining or deriving a sample from the subject. In certain embodiments, the sample is obtained or derived from the subject by non-invasive means or methods.

In certain embodiments, said obtaining is carried out within two hours of the head trauma. In certain embodiments, said obtaining is carried out within four hours of the head trauma. In certain embodiments, said obtaining is carried out within 24 hours of the head trauma. In certain embodiments, said obtaining is carried out within 72 hours of the head trauma. In certain embodiments, said obtaining is carried out during the post-acute care.

In certain embodiments, the subject is conscious at the time of said obtaining.

In certain embodiments, determining the reactivity of antibodies in the sample to a plurality of antigens produces a reactivity pattern, used for the diagnosis of brain injury in the subject. Thus, according to exemplary embodiments of the invention, the reactivity pattern of antibodies in the sample to the plurality of antigens is compared to the reactivity pattern of antibodies in a sample corresponding to healthy control subjects to said plurality of antigens, wherein a significant difference between the reactivity pattern of the sample and the reactivity pattern of healthy controls indicates that the subject is afflicted with, or in other embodiments has increased likelihood for having brain injury. Conveniently, the reactivity patterns are calculated and compared using e.g. learning and pattern recognition algorithms as described herein.

According to another embodiment, the reactivity of antibodies comprises IgG and IgM reactivities. According to another embodiment, the significantly higher reactivity of the antibodies in the sample comprises differential IgG and/or IgM reactivities. According to another embodiment, the increased IgM reactivity is of at least one antigen selected from the group consisting of SEQ ID NOs: 1-115, isoforms thereof, post-translationally modified forms thereof, fragments thereof, or combinations of any of the foregoing. According to another embodiment, the increased IgG reactivity is of at least one antigen selected from the group consisting of SEQ ID NOs: 1-115, isoforms thereof, post-translationally modified forms thereof, fragments thereof, or combinations of any of the foregoing. Each possibility represents a separate embodiment of the invention.

According to additional embodiments of the methods of the present invention, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. In certain embodiments, the sample is obtained or derived from the subject by non-invasive means or methods.

According to certain embodiments of the methods of the present invention, the control is selected from the group consisting of a sample from at least one healthy individual, a baseline sample from same subject, a panel of control samples from a set of healthy individuals, and a stored set of data from healthy individuals. Each possibility represents a separate embodiment of the invention. Typically, a healthy individual is a subject not afflicted with brain injury. In another embodiment, a healthy individual is a subject not afflicted with neurodegenerative disease.

According to another embodiment, the method comprises determining the reactivity of antibodies in the sample to a plurality of antigens.

According to another embodiment, the method comprises determining the reactivity of antibodies in the sample to at least one antigen selected from the group consisting of SEQ ID NOs: 1-115, isoforms thereof, post-translationally modified forms thereof, fragments thereof, or combinations of any of the foregoing. According to another embodiment, the method comprises determining the reactivity of antibodies in the sample to at least two antigens selected from the group consisting of SEQ ID NOs: 1-115, isoforms thereof, post-translationally modified forms thereof, fragments thereof, or combinations of any of the foregoing.

According to another embodiment, the plurality of antigens is used in the form of an antigen probe set, an antigen array, or an antigen chip.

According to another aspect, the present invention provides an antigen probe set comprising a plurality of antigen probes selected from the group consisting of SEQ ID NOs: 1-115, isoforms thereof, post-translationally modified forms thereof, fragments thereof, or combinations of any of the foregoing. In another embodiment, the antigen probe set comprises the antigen probes of SEQ ID NOs: 1-115, isoforms thereof, post-translationally modified forms thereof, fragments thereof, or combinations of any of the foregoing.

According to another aspect, the present invention provides an article of manufacture comprising the antigen probe set described above.

In certain embodiments, the article of manufacture, further comprising one or more biomarkers selected from the group consisting of glial fibrillary acidic protein (GFAP), Synuclein beta (Sncb), Metallothionein-3 (MT3), Neurogranin (NRGN), intercellular adhesion molecule-5 (ICAM5) and Brain derived neurotrophic factor (BDNF), or citrullinated forms thereof.

In certain embodiments, the article of manufacture is in the form of an antigen probe array or in the form of an antigen chip or in the form of a dipstick or in the form of a lateral flow test or in the form of an ELISA plate or in the form of a Quanterix system, an Agilent Plate reader, a Meso Scale Diagnostics platform, or any other platform known to those skilled in the art. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use of the kit for diagnosing brain injury.

According to another aspect, there is provided use of the at least one antigen selected from the group consisting of: SEQ ID NOs: 1-115, isoforms thereof, post-translationally modified forms thereof, fragments thereof, or combinations of any of the foregoing; for the preparation of a diagnostic kit for diagnosing brain injury in a subject. Each possibility represents a separate embodiment of the invention. The diagnostic kit is, in some embodiments, useful for determining the reactivity of antibodies in a sample, thereby determining the reactivity pattern of the sample to the at least one antigen. In some embodiments, a significant difference (e.g., increase) between the reactivity pattern of the sample compared to a reactivity pattern of a control sample is an indication for brain injury.

According to another aspect, there is provided a method for qualifying brain injury status in a subject the method comprising the steps of: obtaining a sample from the subject; determining the reactivity of antibodies in the sample to at least one antigen selected from the group consisting of SEQ ID NOs: 1-115, isoforms thereof, post-translationally modified forms thereof, fragments thereof, or combinations of any of the foregoing; and comparing the reactivity of antibodies in the sample to a predefined reactivity that correlate to one or more brain injury statuses selected from the group consisting of having brain injury, not having brain injury, predisposition to brain injury, sub-acute brain injury, acute brain injury, post-acute brain injury, progressing brain injury, regressing brain injury, subclinical brain injury, mild brain injury, moderate brain injury, severe brain injury and chronic brain injury, wherein a correlation to one of the predefined reactivities determines the brain injury status of the subject.

In certain embodiments, said method further comprising measuring the levels of one or more biomarkers in the sample; and comparing the levels of the one or more biomarkers with predefined levels of the same biomarkers that correlate to one or more brain injury statuses, wherein a correlation to one of the predefined levels determines the brain injury status of the subject.

According to another aspect, there is provided a method of detecting recovery from brain injury in a subject, the method comprising the steps of: obtaining a sample from the subject; determining the reactivity of antibodies in the sample to at least one antigen selected from the group consisting of SEQ ID NOS: 10, 44, 61, 66, 102, 104, isoforms thereof, post-translationally modified forms thereof, fragments thereof, or any combinations thereof; and comparing the reactivity of antibodies in the sample to a predefined reactivity threshold; wherein a significantly different reactivity of the antibodies in the sample compared to the predefined reactivity threshold is indicative of recovery from brain injury in said subject.

In certain embodiments, said method further comprising measuring the levels of one or more biomarkers in the sample; and comparing the levels of the one or more biomarkers with predefined levels of the same biomarkers that correlates with recovery from brain injury, wherein a correlation to one of the predefined levels is indicative of recovery from brain injury of the subject.

In certain embodiments, the one or more biomarkers is selected from the group consisting of glial fibrillary acidic protein (GFAP), Synuclein beta (Sncb), Metallothionein-3 (MT3), Neurogranin (NRGN), intercellular adhesion molecule-5 (ICAM5) and Brain derived neurotrophic factor (BDNF), or citrullinated forms thereof.

In certain embodiments, a combination of one or more antibodies and one or more biomarkers are used.

According to certain embodiments, the comparison is conducted by using at least one classifier algorithm.

According to certain embodiments, the at least one classifier algorithm is selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier and random forest classifier.

Other objects, features and advantages of the present invention will become clear from the following description and drawings.

Serum samples obtained from TBI patients at time 0 (t0, N=85) were compared with serum samples obtained from healthy control (HC, N=21). The analysis was based on 464 iChip features (232 antigen, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

Figure 7:
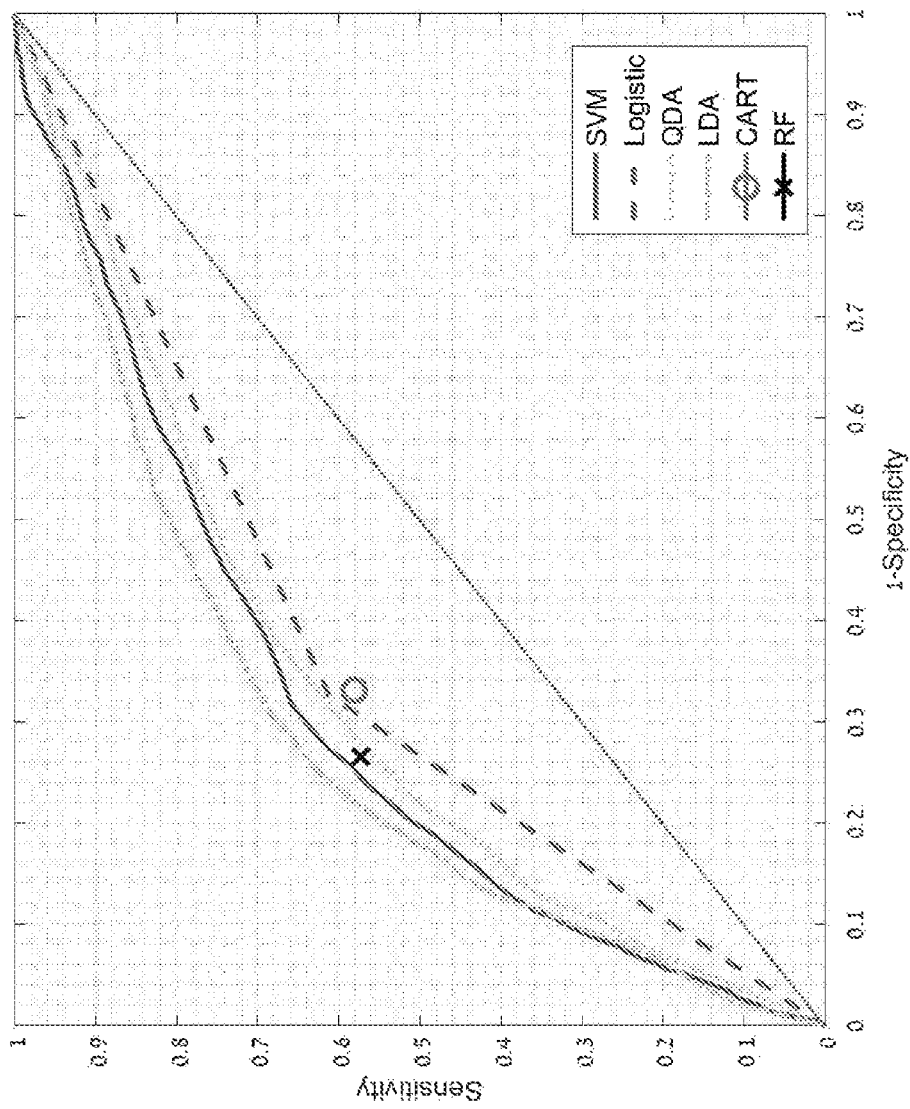

FIG. 7 shows ROC curves of six classification methods (SVM, LR, QDA, CART, RF and LDA), based on 100 iterations of 70:30 cross validation. Features were ranked according to their median scoring or frequency of model inclusion, depending on the method. Serum samples obtained from TBI patients at time 0 (t0) with abnormal CT were compared with samples obtained from TBI patients at time 0 (t0) with Normal CT. Analysis was based on 464 iChip features (232 antigen, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

DETAILED DESCRIPTION OF THE INVENTION

The present invention provides methods of diagnosing brain injury or a neurodegenerative disorder in a subject.

The present invention further provides antigen probe sets or arrays for practicing such a diagnosis, and identifies specific antigen probe sets for generating such sets or arrays.

Without wishing to be bound by any particular theory or mechanism of action, the invention is based, in part, on the finding of unique antigens highly distinctive between healthy subjects and patients suffering from brain injury. The invention is further based on the finding that the antibody reactivity profile in serum of patients suffering from brain injury was clearly distinct from healthy control individuals. Although protein biomarkers of brain injury patients have been extensively investigated, the unique antibody immune signatures as described herein have not been described before. Advantageously, the unique antibody signatures of the present disclosure provide highly sensitive and specific assays for diagnosing brain injury.

The present invention provides, in some embodiments, unique antigen-antibody reactivity patterns particularly relevant to brain injury. In the course of investigating specific antibodies, the inventors examined the reactivity of IgM and IgG antibodies in the sera of healthy persons and those diagnosed with brain injury to a variety of antigens, using antigen microarray and informatics analysis.

Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "about" as used herein means in quantitative terms plus or minus 5%, or in another embodiment plus or minus 10%, or in another embodiment plus or minus 15%, or in another embodiment plus or minus 20%.

As used herein, the term "autoantibodies" refers to antibodies that are capable of reacting against an antigenic constituent of an individual's own tissue or cells (e.g., the antibodies recognize and bind to "self-antigens").

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as an impact (percussive or concussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

According to some embodiments of the method of the present invention, a healthy subject's predisposition to future onset of brain injury is also diagnosed. According to some embodiments said predisposition is due to previous injury or due to family history.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia. Many of these origins can lead to Chronic Traumatic Encephalopathy (CTE).

As employed herein, the term "traumatic brain injury" shall mean a brain injury resulting from direct or indirect shock load or loads applied to the brain causing it to move rapidly and unnaturally within a patient's skull and shall expressly include, but not be limited to, brain injuries caused by: (a) objects penetrating the skull, such as, bullets, arrows, and other physical objects which pass through the skull and enter the brain, (b) impact loads applied to the head or other portions of the patient's body, (c) surgically induced trauma, (d) explosions, such as might exist in warfare, through impacting of grenades, bombs, and other explosives, which cause substantial tremors in the earth in relatively-close proximity to where an individual is standing, as well as similar tremors created by nonexplosive means, such as sports injuries, vehicular accidents, collapse of buildings and earthquakes, for example. The results of traumatic brain injury may be of various types, but in each instance, will involve temporary or permanent reduction in the ability of the brain to function normally and may cause death.

One of the consequences of a traumatic brain injury frequently is the generation of inflammation within the brain as the shock to the brain serves to increase the permeability of the endothelial cells, thereby permitting loss of fluids from the vascular structure into the brain. Such a leakage frequently occurs due to the increased porosity of the blood vessels resulting from the trauma, thereby causing blood serum to leak through the vessels into the brain area. As this builds up, this can generate inflammation and swelling of the brain, which may require surgical intervention.

Clinically, traumatic brain injury can be rated as mild, moderate or severe based on TBI variables that include duration of loss of consciousness (LOC), Glasgow Coma Score (GCS) and post-traumatic stress amnesia.

As used herein, "secondary brain trauma" refers to damage to the brain of a patient post-acute brain injury, i.e., during the secondary injury phase of a TBI.

"Chronic traumatic encephalopathy (CTE)" is a neurodegenerative disease that is most often identified in postmortem autopsies of individuals exposed to repetitive head impacts, such as boxers and football players. The neuropathology of CTE is characterized by the accumulation of hyperphosphorylated tau protein in a pattern that is unique from that of other neurodegenerative diseases, including Alzheimer's disease. The clinical features of CTE are often progressive, leading to dramatic changes in mood, behavior, and cognition, frequently resulting in debilitating dementia. In some cases, motor features, including Parkinsonism, can also be present.

A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

"Stroke" refers to the destruction of brain tissue as a result of intracerebral hemorrhage or infarction. Stroke is a leading cause of death in the developed world. It may be caused by reduced blood flow and death of tissues in one area of the brain (infarction). Causes of strokes include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke.

"Alzheimer's disease (AD)" is a very common yet irreversible, progressive brain disease that slowly destroys memory and thinking skills, and eventually the ability to carry out the simplest tasks. AD is the most common cause of dementia among older people causing the loss of cognitive functioning thinking, remembering, and reasoning to such an extent that it interferes with a person's daily life and activities. Estimates vary, but experts suggest that as many as 5.1 million Americans may have AD. Currently brain imaging of people with, and those with a family history, of AD or its earlier stage, amnesic mild cognitive impairment (MCI), are beginning to detect changes in the brain. The clinical dementia of AD is coupled with a distinct pathology of senile plaques. AD is characterized by abnormal amyloid beta accumulation and deposition in brain parenchyma and cerebral capillaries, which leads to blood-brain barrier (BBB) disruption.

As used herein, "chronic brain injury" refers to a subject who has suffered a brain injury from three days post injury until at least 12 months previously yet continues to present symptoms of brain injury.

As used herein, "sub-acute brain injury" refers to a subject who has suffered a brain injury from about 2-5 days post injury.

"Conscious", as used herein, has the conventional meaning, as set forth in Plum, et al., The Diagnosis of Stupor and Coma, CNS Series, Philadelphia:Davis (1982), which is hereby incorporated by reference. Conscious patients include those who have a capacity for reliable, reproducible, interactive behavior evidencing awareness of self or the environment. Conscious patients include patients who recover consciousness with less severe brain injury but who, because of their impaired cognitive function, do not reach independent living. Conscious patients do not include those who exhibit wakefulness but lack interaction (e.g., those deemed to be in a persistent vegetative state).

The subject who is conscious after exposure to a head trauma may be asymptomatic of any visible symptoms of traumatic brain injury. Conversely, the subject may exhibit various symptoms of brain injury and cognitive dysfunction.

This is in contrast to a subject who is unconscious at the time of the obtaining, as indicated by conditions such as a concussion or intracranial hemorrhage (e.g. intra-axial hematoma, epidural hematoma, and subdural hematoma).

The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in a method of the present invention, e.g., to diagnose brain injury in a patient. Brain injury biomarker proteins include, but are not limited to, SNCB, GFAP, S100B, MT3, ICAM5, BDNF, and/or NSE. The term also includes other brain injury biomarker proteins known in the art including neurogranin (NRGN), myelin basic protein (MBP), PAD-2, tubulin beta-4B chain, tubulin alpha-IB chain, CNPase, PPIA, Septin-7, Elongation factor 1-alpha2, TPPP, TPPP3, Ermin Isoform 2, NDRG2 Isoform 2, astrotactin 1 (ASTN1), brain angiogenesis inhibitor 3 (BAD); carnosine dipeptidase 1 (CNDP 1); ERMTN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD).

In addition, the term "brain injury biomarkers" also includes the isoforms and/or post-translationally modified forms of any of the foregoing. The present invention contemplates the detection, measurement, quantification, determination and the like of both unmodified and modified (e.g., citrullination or other post-translational modification) proteins/polypeptides/peptides as well as autoantibodies to any of the foregoing. In certain embodiments, it is understood that reference to the detection, measurement, determination, and the like, of a biomarker refers detection of the protein/polypeptide/peptide (modified and/or unmodified). In other embodiments, reference to the detection, measurement, determination, and the like, of a biomarker refers detection of autoantibodies of the protein/polypeptide/peptide.

As used herein, the term "comparing" refers to making an assessment of how the reactivity of antibodies in a sample from a patient relates to the reactivity of the corresponding antibodies in a standard or control sample. For example, "comparing" may refer to assessing whether the reactivity of antibodies from a sample of a patient to one or more antigens is the same as, more or less than, or different from the corresponding reactivity of antibodies from the standard or control sample. More specifically, the term may refer to assessing whether the reactivity of antibodies of a sample from a patient to one or more antigens is the same as, more or less than, different from or otherwise corresponds (or not) to a predefined reactivity of antibodies that correspond to, for example, a patient having subclinical brain injury (SCI), not having SCI, is responding to treatment for SCI, is not responding to treatment for SCI, is/is not likely to respond to a particular SCI treatment, or having/not having another disease or condition.

As used herein, the terms "indicates" or "correlates" (or "indicating" or "correlating," or "indication" or "correlation," depending on the context) in reference to a parameter, e.g., a modulated reactivity of antibodies of a sample from a patient, may mean that the patient has brain injury. In specific embodiments, the parameter may comprise the reactivity of antibodies to one or more antigens of the present invention. A particular reactivity of antibodies to one or more antigens may indicate that a patient has brain injury (i.e., correlates to a patient having brain injury). In other embodiments, a particular reactivity of antibodies to one or more antigens may be correlated to a patient being unaffected (i.e., indicates a patient does not have brain injury. In certain embodiments, "indicating," or "correlating," as used according to the present invention, may be by any linear or non-linear method of quantifying the relationship between levels of reactivity of antibodies to a standard, control or comparative value for the assessment of the diagnosis, prediction of brain injury or brain injury progression, assessment of efficacy of clinical treatment, identification of a patient that may respond to a particular treatment regime or pharmaceutical agent, monitoring of the progress of treatment, and in the context of a screening assay, for the identification of an anti-brain injury therapeutic.

According to some embodiments, monitoring the progression of brain injury is conducted at 7-20 day time point post injury, where the neural circulatory reconnections begin to occur. According to some embodiments, the risk of damage to the neural circulatory system is predicted.

The terms "patient," "individual," or "subject" are used interchangeably herein, and refer to a mammal, particularly, a human. The patient may have mild, intermediate or severe disease. The patient may be treatment naive, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The term "healthy control" as used herein refers to a healthy individual; a baseline from the same individual, a plurality of healthy individuals, a data set or value corresponding to or obtained from a healthy individual or a plurality of healthy individuals.

The term "Extended Glasgow Outcome Scale (GOSE)" as used herein categorizes functional disability after TBI on a scale of 1-8, where 1=Dead and 8=Upper Good Recovery. The functional disability is defined as a GOSE score of <8.

The terms "measuring", "detecting" and "determining" are used interchangeably throughout, and refer to methods which include obtaining a patient sample and detecting reactivity of antibodies in a sample. In some embodiments, the terms refer to obtaining a patient sample and detecting the reactivity of antibodies in the sample to one or more antigens. Measuring can be accomplished by methods known in the art and those further described herein.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid). In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The samples may be tested immediately after collection, after storage at 4 degrees, −20 degrees, or −80 degrees Celsius. After storage for 24 hours, 1 week, 1 month, 1 year, 10 years or up to 30 years.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the reactivity of antibodies in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., an brain injury treatment) on a patient. In yet another embodiment, a transcription rate, mRNA level, translation rate, protein level, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, etc. A "suitable control" can be a profile or pattern of reactivity of antibodies to at least one antigen that correlates to brain injury, to which a patient sample can be compared. The patient sample can also be compared to a negative control, i.e., a profile that correlates to not having brain injury.

Antigen probes to be used in the assays of the invention may be purified or synthesized using methods well known in the art. For example, an antigenic protein or peptide may be produced using known recombinant or synthetic methods, including, but not limited to, solid phase (e.g. Boc or f-Moc chemistry) and solution phase synthesis methods (Stewart and Young, 1963; Meienhofer, 1973; Schroder and Lupke, 1965; Sambrook et al., 2001). One of skill in the art will possess the required expertise to obtain or synthesize the antigen probes of the invention. Some of the antigen probes are also commercially available, e.g. from Sigma (St. Louis, Mo., USA), Prospec (Ness-Ziona, Israel), Abnova (Taipei City, Taiwan), Matreya LLC (Pleasant Gap, Pa., USA), Avanti Polar Lipids (Alabaster, Ala., USA), Calbiochem (San Diego, Calif., USA), Chemicon (Temecula, Calif., USA), GeneTex (San Antonio, Tex., USA), Novus Biologicals (Littleton, Colo., USA) Assay Designs (Ann Arbor, Mich., USA), ProSci Inc. (Poway, Calif., USA), EMD Biosciences (San Diego, Calif., USA), Cayman Chemical (Ann Arbor, Mich., USA), HyTest (Turku, Finland), Meridian Life Science (Memphis, Tenn. USA) and Biodesign International (Saco, Me., USA), as detailed herein below.

It should be noted, that the invention utilizes antigen probes as well as homologs, fragments, partial sequences, mutant forms, modified forms and derivatives thereof, as long as these homologs, fragments, partial sequences, mutant forms, modified forms and derivatives are immunologically cross-reactive with these antigen probes. The term "immunologically cross-reactive" as used herein refers to two or more antigens that are specifically bound by the same antibody. The term "homolog" as used herein refers to a peptide which having at least 70%, at least 75%, at least 80%, at least 85% or at least 90% identity to the antigen's amino acid sequence. Cross-reactivity can be determined by any of a number of immunoassay techniques, such as a competition assay (measuring the ability of a test antigen to competitively inhibit the binding of an antibody to its known antigen).

The term "peptide" typically refers to a polypeptide of up to about 50 amino acid residues in length. According to particular embodiments, the antigenic peptides of the invention may be 10-50 amino acids in length and are typically about 10-30 or about 15-25 amino acids in length.

The term encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications; backbone modifications; and residue modifications.

The peptide antigens of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. According to some embodiments, the peptide antigens of the invention are BSA-conjugated peptides.

Functional derivatives consist of chemical modifications to amino acid side chains and/or the carboxyl and/or amino moieties of said peptides. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides.

Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring or modified amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

The amino acid residues described herein are in the "L" isomeric form, unless otherwise indicated. However, residues in the "D" isomeric form can be substituted for any L-amino acid residue, as long as the peptide substantially retains the desired antibody specificity.

Suitable analogs may be readily synthesized by now-standard peptide synthesis methods and apparatus or recombinant methods. All such analogs will essentially be based on the antigens of the invention as regards their amino acid sequence but will have one or more amino acid residues deleted, substituted or added. When amino acid residues are substituted, such conservative replacements which are envisaged are those which do not significantly alter the structure or antigenicity of the polypeptide. For example basic amino acids will be replaced with other basic amino acids, acidic ones with acidic ones and neutral ones with neutral ones. In addition to analogs comprising conservative substitutions as detailed above, analogs comprising non-conservative amino acid substitutions are further contemplated, as long as these analogs are immunologically cross reactive with a peptide antigen of the invention.

In other aspects, there are provided nucleic acids encoding these peptides, vectors comprising these nucleic acids and host cells containing them. These nucleic acids, vectors and host cells are readily produced by recombinant methods known in the art (see, e.g., Sambrook et al., 2001). For example, an isolated nucleic acid sequence encoding an antigen of the invention can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

"Functionally equivalent variants" of the polypeptide or peptide antigens of the invention as used herein are polypeptides or peptides with partial sequence homology, polypeptides or peptides having one or more specific conservative and/or non-conservative amino acid changes and polypeptide or peptide conjugates which do not alter the biological or structural properties of the polypeptide or peptide.

In terms of "functional analogues", it is well understood by those skilled in the art, that inherent in the definition of a biologically functional polypeptide or peptide analogue is the concept that there is a limit to the number of changes that may be made within a defined portion of the molecule and still result in a molecule with an acceptable level of equivalent biological activity. A plurality of distinct polypeptides or peptides with different substitutions may easily be made and used in accordance with the invention. It is also understood that certain residues are particularly important to the biological or structural properties of a polypeptide, and such residues may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the polypeptide. Examples of such conservative changes are well-known to the skilled artisan and are within the scope of the present invention. Conservative substitution also includes the use of a chemically derivatized residue in place of a non-derivatized residue provided that the resulting polypeptide is a biologically functional equivalent to the polypeptide antigens.

Therefore, the "citrullinated polypeptides" encompass a polypeptide having an amino acid sequence that differs from the sequences provided herein by one or more conservative amino acid substitutions. The citrullinated polypeptides also encompass a polypeptide having an amino acid sequence that differs from the sequences provided herein by a single mutation, where the single mutation represents a single amino acid deletion, insertion or substitution.

The citrullinated peptides may be made by methods known to those of skill in the art most notably and preferably by chemical synthesis using techniques well known in the chemistry of proteins such as solid phase synthesis (Merrifield et al, 65 J. AM. CHEM. ASSOC. 2149 (1964); Merrifield et al, 85 J. AMER. CHEM. SOC. 2149 (1963); and Merrifield et al, 35 INT. J. PEPTIDE PROTEIN RES. 161-214 (1990)) or synthesis in homogenous solution (METHODS OF ORGANIC CHEMISTRY, E. Wansch (Ed.) Vol. 15, pts. I and II, Thieme, Stuttgart (1987)) to generate synthetic peptides. Citrulline is a post-translationally modified arginine that is created through the process of deimination which is catalyzed by the enzyme peptidylarginine deiminase 4 (PAD-4) that removes a positive charge from arginine and makes the resulting citrulline polar in nature.

In one embodiment, citrullinated peptides can be made from known commercially available sources. In this aspect, the lyophilized protein is reconstituted in an appropriate buffer to which the enzyme peptidylarginine deiminase 4 is added. Alternatively, $Ca^{2+}$ is added to PAD-4 in solution. The solution is allowed to stand at an appropriate temperature for a time sufficient to cause modification of arginine residues to citrulline and thus create a citrullinated protein. The citrullinated protein is then isolated by the removal of the enzyme using a high molecular weight membrane to separate the enzyme or other methods of chromatography. One of skill in the art will understand that the temperature of incubation, buffer condition and time of incubation may vary depending on the protein that is being deiminated (Masson-Bessiere et al, 166 J. IMMUNOL. 4177-4184 (2001)).

The citrullinated proteins may be further isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation).

Polyacrylamide gel electrophoresis can also be used to isolate the citrullinated proteins based on the molecular weight of the protein, charge properties and hydrophobicity. The purified citrullinated proteins can be used in further biochemical analyses to establish secondary and tertiary structure which may aid in the design of pharmaceuticals to interact with the protein, alter the protein charge configuration or charge interaction with other proteins or alter its function.

The term "oligonucleotide antigen" as used herein refer to a stretch of contiguous nucleotides of a certain length. Unless otherwise indicated, the term "oligonucleotide antigen" as used herein relates to a nucleotide sequence of between 15 and 40 nucleotides in length, alternatively between 17 and 28 nucleotides in length, or between 18-25 nucleotides in length. In certain embodiments, an oligonucleotide antigen consists of at least 4, at least 5, at least 6, at least 7, at least 8, at least 9, at least 10, at least 16, or more contiguous nucleotides. Each possibility represents a separate embodiment of the invention. In certain embodiments, an antigen consists of not more than 50, not more than 45, not more than 40, not more than 35, not more than 30, not more than 25, not more than 20, not more than 16, or less contiguous nucleotides. Each possibility represents a separate embodiment of the invention. In certain embodiments, an antigen consists of 10-30, 15-25 or 17-20 contiguous nucleotides. In certain embodiments, an antigen consists of 17, 18, 19 or 20 contiguous nucleotides.

As used herein, the "reactivity of antibodies in a sample" or "reactivity of an antibody in a sample" to "an antigen" or to "a plurality of antigens" refers to the immune reactivity of at least one antibody in the sample to at least one specific antigen selected from the plurality of antigens. The immune reactivity of the antibody to the antigen, i.e. its ability to specifically bind the antigen, may be used to determine the amount of the antibody in the sample. The calculated levels of each one of the tested antibodies in the sample are collectively referred to as the reactivity pattern of the sample to these antigens. The reactivity pattern of the sample reflects the levels of each one of the tested antibodies in the sample, thereby providing a quantitative assay. In a preferred embodiment, the antibodies are quantitatively determined.

A "significant difference" between reactivity patterns refers, in different embodiments, to a statistically significant difference, or in other embodiments to a significant difference as recognized by a skilled artisan. In another embodiment, a significant difference between the reactivity pattern of the sample obtained from the subject compared to the control reactivity pattern is an indication that the subject is afflicted with brain injury. In specific embodiments, up-regulation or higher reactivity of the reactivity of an antibody in a sample to an antigen refers to an increase (i.e., elevation) of about at least two, about at least three, about at least four, or about at least five times higher (i.e., greater) than the reactivity levels of the antibody to the antigen in the control. In another embodiment, down-regulation or lower reactivity of the reactivity of an antibody in a sample to an antigen refers to a decrease (i.e., reduction) of about at least two, about at least three, about at least four, or about at least five times lower than the reactivity levels of the antibody to the antigen in the control.

According to some embodiments, the at least one oligonucleotide antigen is an oligonucleotide sequence comprising at least 5, 6, 7, 8, 9, 10, 11, 12, 13, 14, 15, 16, 17, 18, 19 or 20 contiguous adenine nucleotides. According to another embodiment, the oligonucleotide sequence comprises at most 20 contiguous adenine nucleotides. According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous thymine nucleotides. According to another embodiment, the oligonucleotide sequence comprises at most 20 contiguous thymine nucleotides.

According to additional embodiments, the at least one oligonucleotide antigen is an oligonucleotide sequence comprising at least 5, 6, 7, 8, 9, 10, 11, 12, 13, 14, 15, 16, 17, 18, 19 or 20 contiguous cytosine nucleotides. According to another embodiment, the oligonucleotide sequence comprises at most 20 contiguous cytosine nucleotides. According to additional embodiments, the at least one oligonucleotide antigen is an oligonucleotide sequence comprising 5-17, 6-17, 7-17, 8-17, 9-17, 10-17, 11-17, 12-17, 13-17, 14-17, 15-17, 16-17, or at most 17 contiguous guanine nucleotides.

According to some embodiments, the at least one antigen is selected from the group consisting of SEQ ID NOs: 1-115, isoforms thereof, post-translationally modified forms thereof, fragments thereof; or combinations of any of the foregoing.

According to some embodiments, the antigens are selected from proteins, peptides, oligonucleotide antigens, or any combinations thereof.

It should be understood each antigen according to the present invention may be bound by IgM antibodies and/or IgG antibodies found or isolated from a sample obtained or derived from the tested subject. Since the relative amounts of IgM antibodies and IgG antibodies against a certain epitope or antigen naturally change over the course of time, each antigen according to the present invention may be bound by IgM antibodies, IgG antibodies or both. In certain embodiments, the reactivity of antibodies means the reactivity of IgG antibodies. In certain embodiments, the reactivity of antibodies means the reactivity of IgM antibodies. According to another embodiment, the significantly higher reactivity of the antibodies in the sample means increased IgG reactivity. According to another embodiment, the significantly higher reactivity of the antibodies in the sample comprises increased IgM reactivity.

According to another embodiment, the increased IgM reactivity is of at least one antigen selected from the group consisting of SEQ ID NOs: 1-115, isoforms thereof, post-translationally modified forms thereof, or combinations of any of the foregoing.

According to another embodiment, the increased IgG reactivity is of at least one antigen selected from the group consisting of SEQ ID NOs: 1-115, isoforms thereof, post-translationally modified forms thereof, or combinations of any of the foregoing.

In certain embodiments, the increased IgM and IgG reactivity is of at least one antigen selected from the group consisting of SEQ ID NOs: 1-115, isoforms thereof, post-translationally modified forms thereof, or combinations of any of the foregoing. In certain embodiments, the increased IgM reactivity is of at least one antigen selected from the group consisting of SEQ ID NOs: 1-115, isoforms thereof, post-translationally modified forms thereof, fragments thereof, or combinations of any of the foregoing. Each possibility represents a separate embodiment of the invention.

It should be understood that in order to perform the methods of the present invention, samples obtained or derived from subjects must comprise antibodies produced by the subject himself. Therefore, samples may be obtained or derived from any tissue, organ or liquid naturally comprising at least a subset of the subject's antibodies. In certain embodiments, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample. Methods for obtaining and isolating appropriate samples are well within the purview of the skilled artisan.

According to certain embodiments of the methods of the present invention, the control is selected from the group consisting of a sample from at least one healthy individual, base line of the same subject, a panel of control samples from a set of healthy individuals, and a stored set of data from healthy individuals. Each possibility represents a separate embodiment of the invention. Typically, a healthy individual is a subject not afflicted with brain injury.

In particular embodiments, the significant difference is determined using a cutoff of a positive predictive value (PPV) of at least 85%, preferably at least 90%. Determining a PPV for a selected marker (e.g., an antigen) is well known to the ordinarily skilled artisan and is exemplified in the methods described below. Typically, positivity for an antigen is determined if it detected above 10% of the subjects in a specific study subgroup using a selected cutoff value, such as PPV≥90%. For example, antigen i is determined to specifically characterize group A if it detected at least 10% of the subjects in group A with a PPV≥90% when compared to a different test group B. Subjects in group A that are above the cutoff of PPV≥90% for antigen i are considered to be positive for antigen i.

An antibody "directed to" an antigen, as used herein is an antibody which is capable of specific binding to the antigen. Determining the levels of antibodies directed to a plurality of antigens includes measuring the level of each antibody in the sample, wherein each antibody is directed to a specific antigen of the invention. This step is typically performed using an immunoassay, as detailed herein.

In other embodiments, determining the reactivity of antibodies in the sample to the at least one antigen (and the levels of each one of the tested antibodies in the sample) is performed by a process comprising contacting the sample, under conditions such that a specific antigen-antibody complex may be formed, with at least one antigen (or when a plurality of antigens is used, to an antigen probe set comprising the plurality of antigens), and quantifying the amount of antigen-antibody complex formed for each antigen probe. The amount of antigen-antibody complex is indicative of the level of the tested antibody in the sample (or the reactivity of the sample with the antigen).

In another embodiment the method comprises determining the reactivity of at least one IgG antibody and at least one IgM antibody in the sample to the plurality of antigens. In another embodiment, the method comprises determining the reactivity of a plurality of IgG antibodies and at least one IgM antibody in the sample to the plurality of antigens. In another embodiment, the method comprises determining the reactivity of at least one IgG antibody and a plurality of IgM antibodies in the sample to the plurality of antigens. According to another embodiment, the method comprises determining the reactivity of antibodies in the sample to a plurality of antigens.

Typically, determining the reactivity of antibodies in the sample to at least one antigen is performed using an immunoassay. Advantageously, when a plurality of antigens is used, the plurality of antigens may be used in the form of an antigen array.

Antigen Probes and Antigen Probe Sets

According to further embodiments, the invention provides antigen probes and antigen probe sets useful for diagnosing brain injury, as detailed herein.

The invention further provides a plurality of antigens also referred to herein as antigen probe sets. These antigen probe sets comprise a plurality of antigens which are reactive specifically with the sera of subjects having brain injury. According to the principles of the invention, the plurality of antigens may advantageously be used in the form of an antigen array. According to some embodiments the antigen array is conveniently arranged in the form of an antigen chip.

A "probe" as used herein means any compound capable of specific binding to a component. According to one aspect, the present invention provides an antigen probe set comprising a plurality of antigens selected from the group consisting of: SEQ ID NOs: 1-115, isoforms thereof, post-translationally modified forms thereof, fragments thereof, or combinations of any of the foregoing. According to certain embodiments, the antigen probe set comprises a subset of the antigens of the present invention. In a particular embodiment, the subset of antigens consists of: SEQ ID NOs: 1-24, 27-30, 42, 75, 76, isoforms thereof, post-translationally modified forms thereof, fragments thereof, or combinations of any of the foregoing.

In some embodiments, antigen probe set consists of up to 300 antigens. In some embodiments, the antigen probe set consists of 2-5 antigens.

According to another embodiment, the methods of the present invention comprise determining the reactivity of antibodies in the sample to at least one antigen selected from the group consisting of SEQ ID NO: 1-115, isoforms thereof, post-translationally modified forms thereof, fragments thereof, or combinations of any of the foregoing.

The reactivity of antibodies to the plurality of antigens of the invention may be determined according to techniques known in the art.

Preferably, the plurality of antigens of the methods and kits of the invention comprises a set of the antigens as disclosed herein. Yet in other embodiments, the plurality of antigens (or the antigen probe set) comprises or consists of a subset thereof, e.g. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 or 115 different antigens, each selected from the antigens of the present invention, wherein each possibility represents a separate embodiment of the invention. Such subsets may be selected so as to result in optimal sensitivity and/or specificity of the diagnostic assay.

Antigen probes to be used in the assays of the invention may be synthesized or purified using methods well known in the art.

It should be noted, that the invention utilizes antigen probes as well as homologs, fragments and derivatives thereof, as long as these homologs, fragments and derivatives are immunologically cross-reactive with these antigen probes. The term "f" as used herein refers to two or more antigens that are specifically bound by the same antibody. The term "homolog" as used herein refers to an antigen probes having at least 80%, at least 85% or at least 90% identity to the antigen's sequence or structure. Cross-reactivity can be determined by any of a number of immunoassay techniques, such as a competition assay (measuring the ability of a test antigen to competitively inhibit the binding of an antibody to its known antigen).

The term "fragment" as used herein refers to a portion of an antigen, or antigen analog which remains immunologically cross-reactive with the antigen probes, e.g., to immunospecifically recognize the target antigen. The fragment may have the length of about 80%, about 85%, about 90% or about 95% of the respective antigen.

According to another aspect, the present invention provides an antigen probe set comprising a plurality of antigen probes selected from the group consisting of SEQ ID NOs: 1-115, isoforms thereof, post-translationally modified forms thereof, fragments thereof, or combinations of any of the foregoing.

According to another related aspect, the present invention provides an antigen probe set comprising at least one antigen probe selected from the group consisting of SEQ ID NOs: 1-115, isoforms thereof, post-translationally modified forms thereof, fragments thereof, or combinations of any of the foregoing.

According to another aspect, the present invention provides an article of manufacture comprising the at least one of the antigen probe sets described above.

In certain embodiments, the article of manufacture is in the form of an antigen probe array or in the form of an antigen chip or in the form of a dipstick or in the form of a lateral flow test or any other platform known to those skilled in the art. An "antigen probe array" generally refers to a plurality of antigen probes, either mixed in a single container or arranges in to or more containers. An "antigen chip" generally refers to a substantially two dimensional surface, onto which a plurality of antigens are attached or adhered. A "dipstick" generally refers to an object, onto which one or a plurality of antigens are attached or adhered, which is dipped into a liquid to perform a chemical test or to provide a measure of quantity found in the liquid. A "lateral flow test" generally refers to devices intended to detect the presence (or absence) of a target analyte in sample (matrix) without the need for specialized and costly equipment. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use. For example, the aforementioned means may include reagents, detectable labels and/or containers which may be used for measuring specific binding of antibodies to the antigen probes of the invention. "Means" as used herein may also refer to devices, reagents and chemicals, such as vials, buffers and written protocols or instructions, used to perform biological or chemical assays.

According to another aspect, there is provided use of the at least one antigen selected from the group consisting of: SEQ ID NOs: 1-115, isoforms thereof, post-translationally modified forms thereof, fragments thereof, or combinations of any of the foregoing; for the preparation of a diagnostic kit for diagnosing brain injury in a subject. The diagnostic kit is, in some embodiments, useful for determining the reactivity of antibodies in a sample, thereby determining the reactivity pattern of the sample to the at least one antigen. In some embodiments, a significant difference (e.g., increase) between the reactivity pattern of the sample compared to a reactivity pattern of a control sample is an indication for brain injury.

In other embodiments, the plurality of antigens comprised in the antigen probe set comprises or consists up to 50, 55, 60, 70, 80, 90 or 100 different antigens. In other embodiments, the plurality of antigens comprised in the antigen probe set comprises or consists at least 50, 100, 150, 200 or 500 different antigens.

In other aspects, there are provided nucleic-acid vectors comprising the oligonucleotides of the invention and host cells containing them. These nucleic acids, vectors and host cells are readily produced by recombinant methods known in the art. A poly-nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to perform the methods of the present invention.

According to the invention, the kits comprise a plurality of antigens also referred to herein as antigen probe sets. These antigen probe sets comprising a plurality of antigens are reactive specifically with the sera of subjects having brain injury. In some embodiments, the antigen probe sets can differentiate between sera of subjects having brain injury and normal subject. According to the principles of the invention, the plurality of antigens may advantageously be used in the form of an antigen array. According to some embodiments the antigen array is conveniently arranged in the form of an antigen chip.

In other embodiments, the kit may further comprise means for determining the reactivity of antibodies in a sample to the plurality of antigens. For example, the kit may contain reagents, detectable labels and/or containers which may be used for measuring specific binding of antibodies to the antigen probes of the invention. In a particular embodiment, the kit is in the form of an antigen array.

In some embodiments, the kit comprises means for comparing reactivity patterns of antibodies in different samples to the plurality of antigens. In other embodiments, the kit may further comprise negative and/or positive control samples. For example, a negative control sample may contain a sample from at least one healthy individual (e.g., an individual not-afflicted with brain injury). A positive control may contain a sample from at least one individual afflicted with brain injury, or a subtype of brain injury which is being diagnosed. Other non-limiting examples are a panel of control samples from a set of healthy individuals or diseased individuals, or a stored set of data from control individuals.

Antibodies, Samples and Immunoassays

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows: (i) Fv, defined as a genetically engineered fragment consisting of the variable region of the light chain and the variable region of the heavy chain expressed as two chains; (ii) single-chain Fv ("scFv"), a genetically engineered single-chain molecule including the variable region of the light chain and the variable region of the heavy chain, linked by a suitable polypeptide linker; (iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof: (iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab') 2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" is a peptide which is capable of specifically binding an antibody.

In another embodiment, detection of the capacity of an antibody to specifically bind an antigen probe may be performed by quantifying specific antigen-antibody complex formation. The term "specifically bind" as used herein means that the binding of an antibody to a specific antigen probe is not affected by the presence of non-related molecules.

In certain embodiments, the method of the present invention is performed by determining the capacity of an antigen of the invention to specifically bind antibodies of the IgG isotype, or, in other embodiments, antibodies of the IgM, isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. CSF, urine and saliva samples.

Numerous well known fluid collection methods can be utilized to collect the biological sample from the subject in order to perform the methods of the invention.

In accordance with the present invention, any suitable immunoassay can be used with the subject antigens. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum of the subject so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe.

In various embodiments, the method of the present invention further comprises diluting the sample before performing the determining step. In one embodiment, the sample is diluted 1:2, for instance, using PBS. In another embodiment, the sample is diluted 1:4, 1:6, 1:8, 1:15, 1:20, 1:50, or preferably 1:10. Each possibility represents a separate embodiment of the present invention. In another embodiment, the sample is diluted in the range of times 2-times 10. In another embodiment, the sample is diluted in the range of times 4-times 10. In another embodiment, the sample is diluted in the range of times 6-times 10. In another embodiment, the sample is diluted in the range of times 8-times 10.

The Antigen Chip

Antigen microarrays are used for the high-throughput characterization of the immune response (Robinson et al., 2002, *Nat Med* 8, 295-301), and have been used to analyze immune responses in vaccination and in autoimmune disorders (Robinson et al., 2002; Robinson et al., 2003, *Nat Biotechnol.* 21, 1033-9; Quintana et al., 2004; Kanter et al., 2006, *Nat Med* 12, 138-43). It has been hypothesized, that patterns of multiple reactivities may be more revealing than single antigen-antibody relationships (Quintana et al., 2006, *Lupus* 15, 428-30) as shown in previous analyses of autoimmune repertoires of mice (Quintana et al., 2004; Quintana et al., 2001, *J Autoimmun* 17, 191-7) and humans (Merbl et al., 2007, *J Clin Invest* 117, 712-8; Quintana et al., 2003, *J Autoimmun* 21, 65-75) in health and disease. Thus, autoantibody repertoires have the potential to provide both new insights into the pathogenesis of the disease and to serve as immune biomarkers (Cohen, 2007, *Nat Rev Immunol.* 7, 569-74) of the disease process.

According to some aspects the methods of the present invention may be practiced using antigen arrays as disclosed in WO 02/08755 and U.S. 2005/0260770, the contents of which are incorporated herein by reference. WO 02/08755 is directed to a system and an article of manufacture for clustering and thereby identifying predefined antigens reactive with undetermined immunoglobulins of sera derived from patient subjects in need of diagnosis of disease or monitoring of treatment. Further disclosed are diagnostic methods, and systems useful in these methods, employing the step of clustering a subset of antigens of a plurality of antigens, the subset of antigens being reactive with a plurality of antibodies being derived from a plurality of patients, and associating or disassociating the antibodies of a subject with the resulting cluster.

U.S. Pat. App. Pub. No. 2005/0260770 discloses an antigen array system and diagnostic uses thereof. The application provides a method of diagnosing an immune disease, particularly diabetes type 1, or a predisposition thereto in a subject, comprising determining a capacity of immunoglobulins of the subject to specifically bind each antigen probe of an antigen probe set. The teachings of the disclosures are incorporated in their entirety as if fully set forth herein.

In other embodiments, various other immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, electronic, magnetic detecting and any other system that allows quantitative measurement of antigen-antibody binding.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. First, the glass surface is activated by a chemical treatment that leaves a layer of reactive groups such as epoxy groups on the surface, which bind covalently any molecule containing free amine or thiol groups. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

According to additional embodiments, the antigen probe set comprises at least 5, at least 25, at least 100, at least 150, at least 200, at least 250, at least 300 or more antigens, including one or a plurality of the antigens provided by the present invention.

In addition to antigen probes of the invention, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements. Normalization control probes can be bound to various addressable locations on the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgM isotype, the antibody ligand is preferably an antibody capable of specifically binding to the Fc region of IgM antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, Dy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g. 1:10 dilution), the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Combination Measurement of the Levels of One or More Antibodies and One or More Biomarkers in the Sample Obtained from the Subject The present invention is based, at least in part, on the discovery that a combination measurement of the levels of one or more antibodies and one or more biomarkers in the sample obtained from the subject can measure both the real-time background physiology of the subject and the status of the acute event.

In a patient with Brain Injury, the response to injury and the recovery process from the injury is dependent upon a combination of the nature of the injury and the state of the individual prior to injury. Patients that are injured on top of a 'healthy' background will likely have a better (faster, more complete) recovery profile than patients that are injured on a 'sick' or 'previously injured' background.

Determination of the autoantibody profile of a patient can be used as a surrogate measurement of the state of the patient prior to brain injury and determination of the levels of circulating antigen shortly after injury can be used as a surrogate measurement of the nature/degree of injury. Algorithms that combine the information about the state of the patient prior to injury and the nature/degree of the injury can be used in order to predict outcomes.

Determination of the autoantibody profile can be performed using any platform where antigens are bound to a surface, circulating antibodies bind to the antigen and are detected with a tagged secondary antibody. Determination of the circulating antigen profile can be done in any ELISA type sandwich assay format which includes a capture antibody and a detection antibody.

The platforms used for antibody and antigen detection may be independent (eg. iCHIP for autoantibody, MSD ELISA for antigens or any relevant ELISA based platform) or may be combined into a single platform to simultaneously measure both circulating autoantibody and antigen. This can be done by printing an iCHIP with both relevant antigens and capture antibodies, contacting serum with the printed surface such that circulating antibodies will bind to the surface bound antigen, and circulating antigens will bind to the surface bound capture antibodies. Detection can be with a cocktail of secondary and detection antibodies.

In the case where there is a need to measure autoantibodies to the same antigen that is informative about the disease state, these measurements can we done in two separate chambers. The data from multiple tests can be combined for the purpose of an algorithmic analysis to finally predict the status of the patient.

Kits for the Detection of Biomarkers

In another aspect, the present invention provides kits for qualifying brain injury status, which kits are used to detect the biomarkers described herein. In a specific embodiment, the kit is provided as an ELISA kit comprising antibodies to the biomarkers of the present invention including, but not limited to, glial fibrillary acidic protein (GFAP) and Synuclein beta (Sncb).

In an alternative embodiment, the panel of biomarkers comprises BDNF, GFAP, MT3 and SNCB. In another embodiment, the panel of biomarkers comprises BDNF, GFAP, NRGN and SNCB. In a further embodiment, the panel of biomarkers comprises BDNF, ICAM5, MT3 and SNCB.

The ELISA kit may comprise a solid support, such as a chip, microtiter plate (e.g., a 96-well plate), bead, or resin having biomarker capture reagents attached thereon.

The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

Data Analysis

Advantageously, the methods of the invention may employ the use of learning and pattern recognition analyzers, clustering algorithms and the like, in order to discriminate between reactivity patterns of healthy control subjects to those of patients having brain injury. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from control subjects which are not afflicted with brain injury or patients afflicted with brain injury, respectively) using such algorithms and/or analyzers. The difference may also be measured by comparing the reactivity pattern of the test sample to a predetermined classification rule obtained in such manner.

In some embodiments, the methods of the invention may employ the use of learning and pattern recognition analyzers, clustering algorithms and the like, in order to discriminate between reactivity patterns of subjects having a subtype of brain injury to control subjects. For example, the methods may include determining the reactivity of antibodies in a test sample to a plurality of antigens, and comparing the resulting pattern to the reactivity patterns of negative and positive control samples using such algorithms and/or analyzers.

Thus, in another embodiment, a significant difference between the reactivity patterns of a test sample compared to a reactivity pattern of a control sample, wherein the difference is computed using a learning and pattern recognition algorithm, indicates that the subject is afflicted with brain injury. For example, the algorithm may include, without limitation, supervised or non-supervised classifiers including statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor, artificial neural networks, coupled two-way clustering algorithms, multi-layer perceptrons (MLP), generalized regression neural network (GRNN), fuzzy inference systems (FIS), self-organizing map (SOM), genetic algorithms (GAS), neuro-fuzzy systems (NFS), adaptive resonance theory (ART).

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Diagnostic Methods

As used herein the term "diagnosing" or "diagnosis" refers to the process of identifying a medical condition or disease (e.g., brain injury) by its signs, symptoms, and in particular from the results of various diagnostic procedures, including e.g. detecting the reactivity, or reactivity pattern, of antibodies in a biological sample (e.g. serum) obtained from an individual, to one or more antigens. Furthermore, as used herein the term "diagnosing" or "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy (dose/schedule) for a disease, monitoring the treatment of a disease, and/or predicting the suitability of a therapy for specific patients or subpopulations or determining the appropriate dosing of a therapeutic product in patients or subpopulations.

In one embodiment, diagnosing brain injury further permits assessing a risk of said brain injury evolving to brain damage and leading to long-term dysfunction. In another embodiment, assessment of a risk of said brain injury evolving to long-term dysfunction permits therapeutic intervention at an early stage.

The immediate issue facing an individual that has suffered a TBI is determining when it is safe to return to high risk activities after a concussive injury without risking permanent brain damage that occurs at a cellular level. According to some embodiments, the present invention provides a broad immune system test to monitor, assess chronic outcomes and verify safety to return to work or play.

Assessment of pathology and neurological impairment immediately after TBI is crucial for determination of appropriate clinical management and for predicting long-term outcome. The outcome measures most often used in head injuries are the Glasgow Coma Scale (GCS), the Glasgow Outcome Scale (GOS), computed tomography, and magnetic resonance imaging (MRI) to detect intracranial pathology. However, despite dramatically improved emergency triage systems based on these outcome measures, most TBI suffer long term impairment and a large number of TBI survivors are severely affected despite predictions of "good recovery" on the GOS. In addition, CT and MRI are expensive and cannot be rapidly employed in an emergency room environment. Moreover, in austere medical environments associated with combat, accurate diagnosis of TBI would be an essential prerequisite for appropriate triage of casualties.

In one embodiment, the type of brain damage associated with brain injury is a white matter structural abnormality. In another embodiment, the white matter structural abnormality or damage is in the corpus callosum region. In another embodiment, the abnormality or damage is in the uncinate fasciculus. In another embodiment, the abnormality or damage is in the right brain frontal lobe. In another embodiment, the abnormality or damage is in the left frontal lobe. In another embodiment, the abnormality or damage is diffuse axonal injury (DAI). In another embodiment, the abnormality or damage is diffuse vascular injury.

In some embodiments, the brain injury is a mild TBI, in one embodiment a concussion is a mild TBI. In another embodiment, mild TBI is caused by a head injury, where the head injury is, in another embodiment, blunt trauma, acceleration, or deceleration forces. It will be appreciated that such head injuries can be characterized by having one or more of the following conditions: (1) observed or self-reported contusion, disorientation, or impaired consciousness, dysfunction of memory at the time of the injury, loss of consciousness lasting less than 30 minutes; and, (2) symptoms such as headache, dizziness, fatigue, irritability, and poor concentration soon after the injury. Head injuries are also categorized as mild based on clinical examinations using the Glasgow Coma Scale. In one embodiment, the head injury has a Glasgow Coma Scale score (GCS) of 13-15 upon examination at an emergency center, with no abnormal findings on head CT, duration of loss of consciousness for no more than 30 minutes, post-traumatic amnesia for less than 24 hours, and an Abbreviated Injury Score (AIS) S3 and an ISS of <12 modified to exclude the head region.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis. The "accuracy" of a diagnostic assay is the proximity of measurement results to the true value. The "p value" of a diagnostic assay is the probability of obtaining the observed sample results (or a more extreme result) when the null hypothesis is actually true.

In certain embodiments, the use of an antigen probe set provided by the present invention, or an antigen probe array provided by the present invention, results in an antibody reactivity profile which is brain injury-indicative (p value≤1.00E-08), sensitive (≥0.600), specific (≥0.700) and accurate (≥0.600). In certain embodiments, the use results in an antibody reactivity profile which is more brain injury-indicative (p value≤1.00E-10), sensitive (≥0.700), specific (≥0.800) and accurate (≥0.700). In certain embodiments, the use results in an antibody reactivity profile which is even more brain injury-indicative (p value≤1.00E-12), sensitive (≥0.800), specific (≥0.900) and accurate (≥0.800). In certain embodiments, the use results in an antibody reactivity profile which is yet even more brain injury-indicative (p value≤1.00E-14), sensitive (≥0.900), specific (≥0.950) and accurate (≥0.900). In certain embodiments, the use results in an antibody reactivity profile which highly brain injury-indicative (p value≤1.00E-16), sensitive (≥0.950), specific (≥0.990) and accurate (≥0.950). Each possibility represents a separate embodiment of the invention.

In certain embodiments, the antigens provided by the present invention, or the antigen patterns provided by the present invention, are brain injury-indicative (p value≤1.87E-08), sensitive (≥0.609), specific (≥0.769) and accurate (≥0.687). In certain embodiments, the antigens provided by the present invention, or the antigen patterns provided by the present invention, are advantageously brain injury-indicative (p value≤2.81E-12), sensitive (≥0.657), specific (≥0.798) and accurate (≥0.725). In certain embodiments, the antigens provided by the present invention, or the antigen patterns provided by the present invention, are further advantageously brain injury-indicative (p value≤8.00E-14), sensitive (≥0.663), specific (≥0.814) and accurate (≥0.738).

In another embodiment, the methods may result in determining a level of brain injury progression. In a further embodiment, the methods may result in providing the comparison to an entity for monitoring brain injury progression. In these embodiments, the methods can be used, for example, to differentiate between subjects with progressing brain injury, and subjects with regressing brain injury.

In one embodiment, the subject being diagnosed according to the methods of the invention is symptomatic. In other embodiments, the subject is asymptomatic. In certain embodiments the subject shows immediate symptoms. In certain embodiments the subject shows delayed symptoms. In certain embodiments, the subject is not or was not receiving a treatment.

As used herein, the term "treating" may encompass curing, preventing, reducing the incidence of, ameliorating symptoms of, to inducing remission of, or slowing the progression of a disease. The terms "reducing", "suppressing" and "inhibiting" refer to lessening or decreasing.

The diagnostic procedure can be performed in vivo or in vitro, preferably in vitro. In certain embodiments of the methods of the present invention, the diagnostic procedure is performed by non-invasive means or methods.

The diagnostic procedure and platform of the present invention may be suitable for use as point of care device or point of service in clinic, in physician's office, in hospital laboratories, or in commercial diagnostic laboratories.

The following examples are presented in order to more fully illustrate some embodiments of the invention. They should, in no way be construed, however, as limiting the broad scope of the invention.

EXAMPLES

Materials and Methods

Human Subjects

The study was approved by the Institutional Review Boards of the participating clinical unit; informed consent was obtained from all participants. In an initial study, sera derived from blood samples obtained from healthy subjects, and subjects suffering from brain injury at varying times post injury, and with varying GOSE scores, were tested using an antigen microarray that included 228 antigens (see Table 1).

Blood samples and clinical data were collected from patients in the HeadSMART trial, arriving at the emergency departments (ED) of Johns Hopkins Hospital (JHH, Baltimore; n=61) or at one of the participating centers of the COBRIT clinical trial (n=31; as described in JAMA. 2012; 308(19):1993-2000).

Defined human serum samples were used for this study. Samples from adult TBI patients were analyzed retrospectively. The healthy control cohort of patients, evaluated for non-TBI complaints was obtained from Baylor College of Medicine (Houston, Tex.; n=21).

To be considered a TBI patient for the HeadSMART trial, the following criteria had to be met: 18 years old or greater, blunt TBI presenting within 24 hours of injury, met the American College of Emergency Physicians (ACEP) criteria for obtaining head CT scans in TBI. Patients having brain tumor, brain surgery, pregnant, non-English speakers, were excluded. Serial serum samples were collected from enrollment to up to 6 months from 61 TBI patients. Three samples per patient at eight different time points after brain injury were collected, a selection of which were used in the analysis For COBRIT trial samples, the following criteria were used: Inclusion Criteria were that the patient had a non-penetrating traumatic brain injury, age 18 (19 in Alabama)—70 years, GCS criteria on/off paralytics as specified in protocol, reasonable expectation of completion of outcome measures at a network center at six months post-injury, reasonable expectation of enrollment within 24-hour time window, and English-speaking. Exclusion criteria included: Intubated patients with GCS motor score=6 and not meeting CT criteria, bilaterally fixed and dilated pupils, positive pregnancy test, known pregnancy, or currently breast feeding, evidence of diseases that interfere with outcome assessment, current acetylcholinesterase inhibitor use, imminent death or current life-threatening disease, currently enrolment in another study, or prisoners. For healthy controls, 21 non-TBI individuals at least 18 years of age were recruited under informed consent at Baylor College of Medicine. One blood sample was collected per control individual and processed to obtain replicate vials of serum and plasma, which were stored at −80° Celsius until use. All patient identifiers were kept confidential.

Antigens and Serum Testing 228 different antigens were spotted on in-house produced epoxyhexyltriethoxysilane (EHTES) activated epoxy slides using a Scienion S-11 non-contact microarray printer (Scienion AG, Germany). The microarrays were then blocked for 1 hour at room temperature with 1% casein. Test serum samples in 1% casein blocking buffer (1:20 dilution) were incubated under a coverslip for 1 hour at 37°. The arrays were then washed and incubated for 1 hour at 37° with a 1:500 dilution of two detection antibodies, mixed together: a goat anti-human IgG Cy3-conjugated antibody, and a goat anti-human IgM AF647-conjugated antibody (both purchased from Jackson ImmunoResearch Laboratories Inc., West Grove, PA). Image acquisition was performed by laser at two wavelengths 530 nm and 630 nm (Agilent Technologies, Santa Clara, CA) and the results were analyzed using Genepix pro 7 software (Molecular devices, Sunnyvale, CA). The quantitative range of signal intensity of binding to each antigen spot was 0-65,000; this range of detection made it possible to obtain reliable data at a 1:20 dilution of test serum samples.

Image Analysis and Data Processing

Each spot's intensity is represented by its pixels' mean after subtraction of its local background median, followed by Log 2 transform. Negative spots (following background subtraction) are imputed with background-like intensity. Background intensity was subtracted for each spot, to obtain net signals. For every antigen in every slide, outlier spots were removed. Outliers spots are defined as having Z score >2 or <−2. The intensity of multiple spots was combined through median, following removal of outlier spots. The foreground and background intensities of multiple spots of each antigen were averaged, and the difference between the foreground and the background was calculated. The resulting value was taken as the antigen reactivity of the antibodies binding to that spotted antigen. All antigens showed meaningful reactivity in a significant number of slides; thus no antigen was excluded.

Statistical Analysis of Antibody Results

Antigens whose reactivity was higher or lower in a specific study subgroup compared to other subgroups were identified. Univariare analysis was used for separating antigens in a T test. Antigens that allowed for setting a classification threshold such as positive predictive value (PPV)≥90% and sensitivity ≥20% were achieved and determined to significantly characterize a specific subgroup. For added restriction, only antigens whose p value for a two sided t-test (after Benjamini-Hochberg correction for multiple hypothesis) was smaller than 0.05 were selected.

ELISA Plate Assay Methods

Biomarkers are tested by either the colorimetric, fluorescence, chemiluminescent, or electrochemiluminescent detection methodologies. For the colorimetric detection methods, Maxisorb 96 well plates are used. For fluorescence assays, black opaque-walled plates are used. For luminescence based-assays, microtiter plates suitable for luminescence are used. Plates are prepared as follows. Plates are rinsed once with coating buffer specific to each plate type. Capture antibodies are added to each well at an optimized concentration for an optimal time period. Generally coating is performed over 12 hours at 4° C. in optimal coating buffer. Following the coating period, the excess antibody is removed and the plates are blocked in an optimized blocking buffer consisting of buffered saline with one of the following: Casein, bovine serum Albumin, species-specific whole serum, or filtered non-fat dry milk powder, or other blocking agent, and/or non-ionic detergent. A series of sequential incubations of optimal length are used to allow: 1) masking of non-specific binding sites (i.e., blocking), 2), capture antibody-antigen binding, 3) binding of antigen followed by washing for removal of excess and non-bound antigens, 4) incubation of anti-antigen detection antibody solution and detection tag, 5) washing for removal of excess non-bound detection antibody and tag, and 6) addition of detection substrate (ELISA) or optimal detection solution (fluorescence or luminescence). Colorimetric detection is performed on a microtiter plate reader, or similar technology, by measuring absorbance of a colored substrate at an appropriate wavelength of light. Fluorescence assays are performed using a fluorescence based plate reader. Luminescence is detected on a luminescence based reader. Data are collected and biomarker concentrations are determined using a standard curve of recombinant protein of known concentration.

Example 1: Association Between FABP (SEQ ID No: 61) and MBPR149 (SEQ ID No: 10) with TBI Outcomes Each patient was profiled with its own measured time-points in order to explore its autoantibodies profile change with time post injury. Samples from TBI patients with Extended Glasgow Outcome Scale (GOSE) equals 8 were compared to samples from TBI patients with GOSE lower than 8 at a specific time-point (3 months/1 month).

Antibodies' Binding

Sera samples from healthy subjects and brain injury patients at varying times post injury, and with varying GOSE scores were tested for binding of serum IgG and/or IgM antibodies to the various antigens disclosed in Table 1.

TABLE 1

List of brain injury related antigens.

| Antigen | Amino acid sequence or manufacture (Catalog number) | SEQ ID NO: |
|---|---|---|
| MBP (myelin basic protein) | MASQKRPSQRHGSKYLATASTMDHARHGFLPRHRDTGILDSIGRFFGGDRGAPKRGSG KVPWLKPGRSPLPSHARSQPGLCNMYKDSHHPARTAHYGSLPQKSHGRTQDENPVVHF FKNIVTPRTPPPSQGKGRGLSLSRFSWGAEGQRPGFGYGGRASDYKSAHKGFKGVDAQ GTLSKIFKLGGRDSRSGSPMARR Enzo LS (ALX-200-606-M001) | 1 |
| MBP- in vitro citrullinated | Post translational citullination of arginine(s) in Enzo LS (ALX-200-606-M001) | 2 |
| MBP R26 | Ac-TMDHA(Cit)HGFLPC-amide | 3 |
| MBP R32, R34 | Ac-GFLP(Cit)H(Cit)DTGIC-amide | 4 |
| MBP R44 | Ac-CILDSIG(Cit)FFGG-amide | 5 |
| MBP R50 | Ac-FGGD(Cit)GAPKRGC-amide | 6 |
| MBP R92 | Ac-CDSHHPA(Cit)TAHYG-amide | 7 |
| MBP R106 | Ac-CQKSHG(Cit)TQDEN-amide | 8 |
| MBP R124 | Ac-CFKNIVTP(Cit)TP-amide | 9 |
| MBP R149 | Ac-GAEGQ(Cit)PGFGYC-amide | 10 |
| MBP R157 | Ac-CGYGG(Cit)ASDYKS-amide | 11 |
| MBP R186, R189 | Ac-CKLGG(Cit)DS(Cit)SG-amide | 12 |
| MBP R196, R197 | Ac-C(Ahx)SGSPMA(Cit)(Cit)-OH | 13 |
| GFAP (glial fibrillary acid protein) | MERRRITSAARRSYVSSGEMMVGGLAPGRRLGPGTRLSLARMPPPLPTRVDFSLAGAL NAGFKETRASERAEMMELNDRFASYIEKVRFLEQQNKALAAELNQLRAKEPTKLADVY QAELRELRLRLDQLTANSARLEVERDNLAQDLATVRQKLQDETNLRLEAENNLAAYRQ EADEATLARLDLERKIESLEEEIRFLRKIHEEEVRELQEQLARQQVHVELDVAKPDLT AALKEIRTQYEAMASSNMHEAEEWYRSKFADLTDAAARNAELLRQAKHEANDYRRQLQ SLTCDLESLRGTNESLERQMREQEERHVREAASYQEALARLEEEGQSLKDEMARHLQE YQDLLNVKLALDIEIATYRKLLEGEENRITIPVQTFSNLQIRETSLDTKSVSEGHLKR NIVVKTVEMRDGEVIKESKQEHKDVM Calbiochem (345996) | 14 |
| GFAP- in in vitro citrullinated | Post translational citullination of arginine(s) Calbiochem (345996) | 15 |
| GFAP R30 | Ac-LAPGR(Cit)LGPGTC-amide | 16 |
| GFAP R36 | Ac-CLGPGT(Cit)LSLAR-amide | 17 |
| GFAP R270 | Ac-AA(Cit)NAELLRQC-amide | 18 |

TABLE 1-continued

List of brain injury related antigens.

| Antigen | Amino acid sequence or manufacture (Catalog number) | SEQ ID NO: |
|---|---|---|
| GFAP R406 | Ac-CEGHLK(Cit)NIVVK-amide | 19 |
| GFAP R416 | Ac-CVKTVEM(Cit)DGEVI-amide | 20 |
| NRGN (neurogranin) | MDCCTENACSKPDDDILDIPLDDPGANAAAAKIQASFRGHMARKKIKSGERGRKGPGP GGPGGAGVARGGAGGGPSGD | 21 |
| NRGN- in vitro citrullinated | Post translational citullination of arginine(s) in NRGN | 22 |
| NRGN R51, R53 | Ac-CKSGE(Cit)G(Cit)KGPG-amide | 23 |
| NRGN R68 | Ac-CGGAGVA(Cit)GGAG-amide | 24 |
| ERMIN | MKTLSPDRIQPHIMTDVPATFTQAECNGDKPPENGQQTITKISEELTDVDSPLPHYRV EPSLEGALTKGSQEERRKLQGNMLLNSSMEDKMLKENPEEKLFIVHKAITDLSLQETS ADEMTFREGHQWEKIPLSGSNQEIRRQKERITEQPLKEEEDEDRKNKGHQAAEIEWLG FRKPSQADMLHSKHDEEQKVWDEEIDDDDDDNCNNDEDEVRVIEFKKKHEEVSQFKEE GDASEDSPLSSASSQAVTPDEQPTLGKKSDISRNAYSRYNTISYRKIRKGNTKQRIDE FESMMHL | 25 |
| ERMIN- in vitro citrullinated | Post translational citullination of arginine(s) in ERMIN | 26 |
| Ermin R57 | Ac-DSPLPHY(Cit)VEPSLEC-amide | 27 |
| ICAM5 | MPGPSPGLRRALLGLWAALGLGLFGLSAVSQEPFWADLQPRVAFVERGGSLWLNCSTN CPRPERGGLETSLRRNGTQRGLRWLARQLVDIREPETQPVCFFRCARRTLQARGLIRT FQRPDRVELMPLPPWQPVGENFTLSCRVPGAGPRASLTLTLLRGAQELIRRSFAGEPP RARGAVLTATVLARREDHGANFSCRAELDLRPHGLGLFENSSAPRELRTFSLSPDAPR LAAPRLLEVGSERPVSCTLDGLFPASEARVYLALGDQNLSPDVTLEGADFVATATATA SAEQEGARQLVCNVTLGGENRETRENVTIYSFPAPLLTLSEPSVSEGQMVTVTCAAGA QALVTLEGVPAAVPGQPAQLQLNATENDDRRSFFCDATLDVDGETLIKNRSAELRVLY APRLDDSDCPRSWTWPEGPEQTLRCEARGNPEPSVHCARSDGGAVLALGLLGPVTRAL SGTYRCKAANDQGEAVKDVTLTVEYAPALDSVGCPERITWLEGTEASLSCVAHGVPYD DVICVRSGELGAVIEGLLRVAREHAGTYRCEATNPRGSAAKNVAVTVEYGPRFEEPSC PSNWTWVEGSGRLFSCEVDGKPQPSVKCVGSGGATEGVLLPLAPPDPSPRAPRIPRVL APGIYVCNATNRHGSVAKTVVVSAESPPEMDESTCPSHQTWLEGAEASALACAARGRP SPGVRCSREGIPWPEQQRVSREDAGTYHCVATNAHGTDSRTVTVGVEYRPVVAELAAS PPGGVRPGGNFTLTCRAEAWPPAQISWRAPPGALNIGLSSNNSTLSVAGAMGSHGGEY ECAATNAHGRHARRITVRVAGPWLWVAVGGAAGGAALLAAGAGLAFYVQSTACKKGEY NVQEAESSGEAVCLNGAGGGAGGAAGAEGGPEAAGGAAESPAEGEVFAIQLTSA R&D (1950-M5) | 28 |
| SNCB (Beta-synuclein) | MDVFMKGLSMAKEGVVAAAEKTKQGVTEAAEKTKEGVLYVGSKTREGVVQGVASVAEK TKEQASHLGGAVFSGAGNIAAATGLVKREEFPTDLKPEEVAQEAAEEPLIEPLMEPEG ESYEDPPQEEYQEYEPEA OriGene (TP315165) | 29 |
| MT3 (Metallothionein III) | MDPETCPCPSGGSCTCADSKCKCEGCKCTSCKKSCCSCCPAECEKCAKDCVCKGGEAAE AEAEKCSCCQ | 30 |
| OMG (Oligodenrocyte Myelin Glycoprotein) | MEYQILKMSLCLFILLFLTPGILCICPLQCICTERHRHVDCSGRNLSTLPSGLQENII HLNLSYNHFTDLHNQLTQYTNLRTLDISNNRLESLPAHLPRSLWNMSAANNNIKLLDK SDTAYQWNLKYLDVSKNMLEKVVLIKNTLRSLEVLNLSSNKLWTVPTNMPSKLHIVDL SNNSLTQILPGTLINLTNLTHLYLHNNKFTFIPDQSFDQLFQLQEITLYNNRWSCDHK QNITYLLKWMMETKAHVIGTPCSTQISSLKEHNMYPTPSGFTSSLFTVSGMQTVDTIN SLSVVTQPKVTKIPKQYRTKETTFGATLSKDTTFTSTDKAFVPYPEDTSTETINSHEA AAATLTIHLQDGMVTNTSLTSSTKSSPTPMTLSITSGMPNNFSEMPQQSTTLNLWREE TTTNVKTPLPSVANAWKVNASFLLLLNVVVMLAV | 31 |
| CNDP1 (Carnosine dipeptidase 1) |  | 32 |
| Reticulon 1 | MAAPGDPQDELLPLAGPGSQWLRHRGEGENEAVTPKGATPAPQAGEPSPGLGARAREA ASREAGSGPARQSPVAMETASTGVAGVSSAMDHTFSTTSKDGEGSCYTSLISDICYPP QEDSTYFTGILQKENGHVTISESPEELGTPGPSLPDVPGIESRGLFSSDSGIEMTPAE STEVNKILADPLDQMKAEAYKYIDITRPEEVKHQEQHHPELEDKDLDFKNKDTDISIK PEGVREPDKPAPVEGKIIKDHLLEESTFAPYIDDLSEEQRRAPQITTPVKITLTEIEP SVETTTQEKTPEKQDICLKPSPDTVPTVTVSEPEDDSPGSITPPSSGTEPSAAESQGK GSISEDELITAIKEAKGLSYETAENPRPVGQLADRPEVKARSGPPTIPSPLDHEASSA | 33 |

TABLE 1-continued

List of brain injury related antigens.

| Antigen | Amino acid sequence or manufacture (Catalog number) | SEQ ID NO: |
|---|---|---|
| | ESGDSEIELVSEDPMAAEDALPSGYVSFGHVGGPPPSPASPSIQYSILREEREAELDS ELIIESCDASSASEESPKREQDSPPMKPSALDAIREETGVRAEERAPSRRGLAEPGSF LDYPSTEPQPGPELPPGDGALEPETPMLRPKPEEDSSSNQSPAATKGPGPLGPGAPPP LLFLNKQKAIDLLYWRDIKQTGIVFGSFLLLLFSLTQFSVVSVVAYLALAALSATISF RIYKSVLQAVQKTDEGHPFKAYLELEITLSQEQIQKYTDCLQFYVNSTLKELRRLFLV QDLVDSLKFAVLMWLLTYVGALFNGLTLLLMAVVSMFTLPVVYVKHQAQIDQYLGLVR THINAVVAKIQAKIPGAKRHAE | |
| Astrotactin 1 | MALAGLCALLACCWGPAAVLATAAGDVDPSKELECKLKSITVSALPFLRENDLSIMHS PSASEPKLLFSVRNDFPGEMVVVDDLENTELPYFVLEISGNTEDIPLVRWRQQWLENG TLLFHIHHQDGAPSLPGQDPTEEPQHESAEEELRILHISVMGGMIALLLSILCLVMIL YTRRRWCKRRRVPQPQKSASAEAANEIHYIPSVLIGGHGRESLRNARVQGHNSSGTLS IRETPILDGYEYDITDLRHHLQRECMNGGEDFASQVTRTLDSLQGCNEKSGMDLTPGS DNAKLSLMNKYKDNIIATSPVDSNHQQATLLSHTSSSQRKRINNKARAGSAFLNPEGD SGTEAENDPQLTFYTDPSRSRRRSRVGSPRSPVNKTTLTLISITSCVIGLVCSSHVNC PLVVKITLHVPEHLIADGSRFILLEGSQLDASDWLNPAQVVLFSQQNSSGPWAMDLCA RRLLDPCEHQCDPETGECLCYEGYMKDPVHKHLCIRNEWGTNQGPWPYTIFQRGFDLV LGEQPSDKIFRFTYTLGEGMWLPLSKSFVIPPAELAINPSAKCKTDMTVMEDAVEVRE ELMTSSSFDSLEVLLDSFGPVRDCSKDNGGCSKNFRCISDRKLDSTGCVCPSGLSPMK DSSGCYDRHIGVDCSDGFNGGCEQLCLQQMAPFPDDPTLYNILMFCGCIEDYKLGVDG RSCQLITETCPEGSDCGESRELPMNQTLFGEMFFGYNNHSKEVAAGQVLKGTFRQNNF ARGLDQQLPDGLVVATVPLENQCLEEISEPTPDPDFLTGMVNFSEVSGYPVLQHWKVR SVMYHIKLNQVAISQALSNALHSLDGATSRADFVALLDQFGNHYIQEAIYGFEESCSI WYPNKQVQRRLWLEYEDISKGNSPSDESEERERDPKVLTFPEYITSLSDSGTKHMAAG VRMECHSKGRCPSSCPLCHVTSSPDTPAEPVLLEVTKAAPIYELVTNNQTQRLLQEAT MSSLWCSGTGDVIEDWCRCDSTAFGADGLPTCAPLPQPVLRLSTVHEPSSTLVVLEWE HSEPPIGVQIVDYLLRQEKVTDRMDHSKVETETVLSFVDDIISGAKSPCAMPSQVPDK QLTTISLIIRCLEPDTIYMFTLWGVDNTGRRSRPSDVIVKTPCPVVDDVKAQEIADKI YNLFNGYTSGKEQQTAYNTLLDLGSPTLHRVLHYNQHYESFGEFTWRCEDELGPRKA GLILSQLGDLSSWCNGLLQEPKISLRRSSLKYLGCRYSEIKPYGLDWAELSRDLRKTC EEQTLSIPYNDYGDSKEI | 34 |
| Brain Angiogenesis Inhibitor 3 | uniprot# O60242 | 35 |
| Glutamate Receptor, Metabotrophic 3 | uniprot# Q14832 | 36 |
| Kelch like 32 | uniprot# Q96NJ5 | 37 |
| Matrix metalloproteinase-9 | uniprot# P14780 | 38 |
| Melanoma Antigen Family E, 2 | uniprot# Q8TD90 | 39 |
| Neuregulin 3 | uniprot# P56975 | 40 |
| SLIT and NTRK-Like Family, Member 3 | uniprot# O94933 | 41 |
| BDNF (Brain derived neurotrophic factor) | MTILFLTMVISYFGCMKAAPMKEANIRGQGGLAYPGVRTHGTLESVNGPKAGSRGLTS LADTFEHVIEELLDEDQKVRPNEENNKDADLYTSRVMLSSQVPLEPPLLFLLEEYKNY LDAANMSMRVRRHSDPARRGELSVCDSISEWVTAADKKTAVDMSGGTVTVLEKVPVSK GQLKQYFYETKCNPMGYTKEGCRGIDKRHWNSQCRTTQSYVRALTMDSKKRIGWRHRI DTSCVCTLTIKRGR R&D (248BD005) | 42 |
| UBIQUITIN CTERMINAL HYDROLASE L1 | uniprot# P09936 | 43 |
| Oligo24 | T16G1: TTT TTT TTT TTT TTT TG | 44 |
| Tubulin beta-4B chain in vitro citrullinated | uniprot# P68371 | 45 |

TABLE 1-continued

List of brain injury related antigens.

| Antigen | Amino acid sequence or manufacture (Catalog number) | SEQ ID NO: |
|---|---|---|
| Tubulin beta-4B chain | (K)IREEYPDrIMNTF(S) | 46 |
| Tubulin alpha-1B chain | uniprot# P68363 | 47 |
| Tubulin alpha-1B chain in vitro citrullinated | | 48 |
| Tubulin alpha-1B chain | (K)YMAccLLYrGDVVPK(D) | 49 |
| Tubulin alpha-1B chain | (E)VrTGTYrQLFHPE(Q) | 50 |
| synaptotagmin | uniprot# P21579 | 51 |
| AB1-42 | | 52 |
| CNPase | (K)STLArVIVDK(Y) | 53 |
| CNPase | (K)ITPGArGAFSEEYK(R) | 54 |
| Laminin | uniprot# Q13753 | 55 |
| PPIA in vitro citrullinated | uniprot# P62937 | 56 |
| PPIA | (K)TAENFrALSTGEK(G) | 57 |
| S100A10 | Uniprot# P60903 | 58 |
| Septin-7 in vitro citrullinated | | 59 |
| Septin-7 | (R)ILEQQNSSrTLEK(N) | 60 |
| Fatty acid binding Protein (FABP-3) | Prospec (PRO-340) | 61 |
| Elongation factor 1-alpha 2 in vitro citrullinated | Uniprot# Q05639 | 62 |
| Elongation factor 1-alpha 2 | (K)PLrLPLQDVYK(I) | 63 |
| Elongation factor 1-alpha 2 | (D)VYKIGGIGTVPVGrVE(T) | 64 |
| ICNPase (2',3-cyclic nucleotide 3'-phosphodiesterase) | uniprot# P09543 | 65 |
| Collagen-IV | uniprot# P02462 | 66 |
| TPPP | (K)AISSPTVSrLTDTTK(F) | 67 |
| Phospho-c-Jun | uniprot# P05412 | 68 |

TABLE 1-continued

List of brain injury related antigens.

| Antigen | Amino acid sequence or manufacture (Catalog number) | SEQ ID NO: |
|---|---|---|
| TPPP3 in vitro citrullinated | (K)TGGAVD(Cit)LTDTSrYTGSHK(E) | 69 |
| TPPP3 | (K)TGGAVDRLTDTSrYTGSHK(E) | 70 |
| TPPP3 | (K)GIAGrQDILDDSGYVSAYK(N) | 71 |
| vesicular membrane protein neurensin-1 (p24 | uniprot# Q8IZ57 | 72 |
| NDRG2, Isoform 2 in vitro citrullinated | uniprot# Q9UN36 | 73 |
| NDRG2, Isoform 2 | (R)TASLTSAASVDGNrSR(S) | 74 |
| S100 calcium binding protein B (S100B) | MSELEKAMVALIDVFHQYSGREGDKHKLKKSELKELINNELSHFLEEIKEQEVVDKVM ETLDNDGDGECDFQEFMAFVAMVTTACHEFFEHE<br>Sigma (S6677) | 75 |
| NSE (neuron specific enolase aka ENO2) | MSIEKIWAREILDSRGNPTVEVDLYTAKGLFRAAVPSGASTGIYEALELRDGDKQRYL GKGVLKAVDHINSTIAPALISSGLSVVEQEKLDNLMLELDGTENKSKFGANAILGVSL AVCKAGAAERELPLYRHIAQLAGNSDLILPVPAFNVINGGSHAGNKLAMQEFMILPVG AESFRDAMRLGAEVYHTLKGVIKDKYGKDATNVGDEGGFAPNILENSEALELVKEAID KAGYTEKIVIGMDVAASEFYRDGKYDLDFKSPTDPSRYITGDQLGALYQDFVRDYPVV SIEDPFDQDDWAAWSKFTANVGIQIVGDDLTVTNPKRIERAVEEKACNCLLLKVNQIG SVTEAIQACKLAQENGWGVMVSHRSGETEDTFIADLVVGLCTGQIKTGAPCRSERLAK YNQLMRIEEELGDEARFAGHNFRNPSVL<br>Abnova (H00002026-P01) | 76 |
| MCP1 (monocyte chemotactic protein-1) | Pro spec (CHM-271) | 77 |
| Tau, total | Sigma (T9392) | 78 |
| Neurofilament light polypeptide | | 79 |
| Neurofilament heavy polypeptide | | 80 |
| y-Enolase | | 81 |
| Prothrombin-FactorII | | 82 |
| EXOSC10 | uniprot# Q01780 | 83 |
| Spectrin, breakdown products | Sigma (S3644) | 84 |
| Myeloperoxidase (MPO) | Sigma (M6908) | 85 |
| CMV | Prospec (CMV Pp150) | 86 |
| ICAM | uniprot# Q8N6I2 | 87 |
| SLC39A11 | uniprot# Q8N1S5 | 88 |
| MAP2 (Microtubule-associated protein 2 | | 89 |

TABLE 1-continued

List of brain injury related antigens.

| Antigen | Amino acid sequence or manufacture (Catalog number) | SEQ ID NO: |
|---|---|---|
| MAPT (microtubule-associated protein tau gene) | | 90 |
| HTR1A (Serotonin receptor 1A gene) | | 91 |
| PLXNA4 (PlexinsA4) | | 92 |
| Interleukin-6 | PVPPGEDSKD VAAPHRQPLT SSERIDKQIR YILDGISALR KETCNKSNMC ESSKEALAEN NLNLPKMAEK DGCFQSGFNE ETCLVKIITG LLEFEVYLEY LQNRFESSEE QARAVQMSTK VLIQFLQKKA KNLDAITTPD PTTNASLLTK LQAQNQWLQD MTTHLILRSF KEFLQSSLRA LRQM<br>Peprotech (200-06) | 93 |
| Interleukin-12 | p40 Subunit: IWELKK DVYVVELDWY PDAPGEMVVL TCDTPEEDGI TWTLDQSSEV LGSGKTLTIQ VKEFGDAGQY TCHKGGEVLS HSLLLLHKKE DGIWSTDILK DQKEPKNKTF LRCEAKNYSG RFTCWWLTTI STDLTFSVKS SRGSSDPQGV TCGAATLSAE RVRGDNKEYE YSVECQEDSA CPAAEESLPI EVMVDAVHKL KYENYTSSFF IRDIIKPDPP KNLQLKPLKN SRQVEVSWEY PDTWSTPHSY FSLTFCVQVQ GKSKREKKDR VFTDKTSATV ICRKNASISV RAQDRYYSSS WSEWASVPCS<br>Peprotech (200-12) | 94 |
| Interleukin-15 | MNWVNVISDL KKIEDLIQSM HIDATLYTES DVHPSCKVTA MKCFLLELQV ISLESGDASI HDTVENLIIL ANNSLSSNGN VTESGCKECE ELEEKNIKEF LQSFVHIVQM FINTS<br>Peprotech (200-15) | 95 |
| Interleukin-17 | MIVKAGITIP RNPGCPNSED KNFPRTVMVN LNIHNRNTNT NPKRSSDYYN RSTSPWNLHR NEDPERYPSV IWEAKCRHLG CINADGNVDY HMNSVPIQQE ILVLRREPPH CPNSFRLEKI LVSVGCTCVT PIVHHVA<br>Peprotech (200-17) | 96 |
| Interleukin-1ra | MRPSGRKSSK MQAFRIWDVN QKTFYLRNNQ LVAGYLQGPN VNLEEKIDVV PIEPHALFLG IHGGKMCLSC VKSGDETRLQ LEAVNITDLS ENRKQDKRFA FIRSDSGPTT SFESAACPGW FLCTAMEADQ PVSLTNMPDE GVMVTKFYFQ EDE<br>Peprotech (200-01RA) | 97 |
| TNFRI | MDSVCPQGKY IHPQNNSICC TKCHKGTYLY NDCPGPGQDT DCRECESGSF TASENHLRHC LSCSKCRKEM GQVEISSCTV DRDTVCGCRK NQYRHYWSEN LFQCFNCSLC LNGTVHLSCQ EKQNTVCTCH AGFFLRENEC VSCSNCKKSL ECTKLCLPQI EN<br>Peprotech (310-07) | 98 |
| VEGF | APMAEGGGQN HHEVVKFMDV YQRSYCHPIE TLVDIFQEYP DEIEYIFKPS CVPLMRCGGC CNDEGLECVP TEESNITMQI MRIKPHQGQH IGEMSFLQHN KCECRPKKDR ARQENPCGPC SERRKHLFVQ DPQTCKCSCK NTDSRCKARQ LELNERTCRC DKPRR<br>Peprotech (100-20) | 99 |
| VCAM1 | FKIETTPESR YLAQIGDSVS LTCSTTGCES PFFSWRTQID SPLNGKVTNE GTTSTLTMNP VSFGNEHSYL CTATCESRKL EKGIQVEIYS FPKDPEIHLS GPLEAGKPIT VKCSVADVYP FDRLEIDLLK GDHLMKSQEF LEDADRKSLE TKSLEVTFTP VIEDIGKVLV CRAKLHIDEM DSVPTVRQAV KELQVYISPK NTVISVNPST KLQEGGSVTM TCSSEGLPAP EIFWSKKLDN GNLQHLSGNA TLTLIAMRME DSGIYVCEGV NLIGKNRKEV ELIVQEKPFT VEISPGPRIA AQIGDSVMLT CSVMGCESPS FSWRTQIDSP LSGKVRSEGT NSTLTLSPVS FENEHSYLCT VTCGHKKLEK GIQVELYSFP RDPEIEMSGG LVNGSSVTVS CKVPSVYPLD RLEIELLKGE TILENIEFLE DTDMKSLENK SLEMTFIPTI EDTGKALVCQ AKLHIDDMEF EPKQRQSTQT LYVNVAPRDT TVLVSPSSIL EEGSSVNMTC LSQGFPAPKI LWSRQLPNGE LQPLSENATL TLISTKMEDS GVYLCEGINQ AGRSRKEVEL IIQVTPKDIK LTAFPSESVK EGDTVIISCT CGNVPETWII LKKKAETGDT VLKSIDGAYT IRKAQLKDAG VYECESKNKV GSQLRSLTLD VQGRENNKDY FSP<br>Peprotech (150-04) | 100 |
| Factor VIIa | AKRONbiotech (AK9916) | 101 |
| Collagen II | | 102 |

TABLE 1-continued

List of brain injury related antigens.

| Antigen | Amino acid sequence or manufacture (Catalog number) | SEQ ID NO: |
|---|---|---|
| Microglobulin-b2 | Sigma (M4890) | 103 |
| TNFRSF12A | EQAPGTAPCS RGSSWSADLD KCMDCASCRA RPHSDFCLGC AAAPPAPFRL LWP<br>Peprotech (310-21) | 104 |
| TNFRII | MAPEPGSTCR LREYYDQTAQ MCCSKCSPGQ HAKVFCTKTS DTVCDSCEDS TYTQLWNWVP ECLSCGSRCS SDQVETQACT REQNRICTCR PGWYCALSKQ EGCRLCAPLR KCRPGFGVAR PGTETSDVVC KPCAPGTFSN TTSSTDICRP HQICNVVAIP GNASMDAVCT STSP<br>Peprotech (310-12) | 105 |
| CRP | Sigma (C4063) | 106 |
| BAFF-R | MRRGPRSLRG RDAPAPTPCV PAECFDLLVR HCVACGLLRT PRPKPAGASS PAPRTALQPQ ESVGAGAGEA ALPLPG<br>Peprotech (310-13R) | 107 |
| BAFF | AVQGPEETVT QDCLQLIADS ETPTIQKGSY TFVPWLLSFK RGSALEEKEN KILVKETGYF FIYGQVLYTD KTYAMGHLIQ RKKVHVFGDE LSLVTLFRCI QNMPETLPNN SCYSAGIAKL EEGDELQLAI PRENAQISLD GDVTFFGALK LL<br>Peprotech (310-13) | 108 |
| GLP1 | HAEGTFTSDV SSYLEGQAAK EFIAWLVKGR G<br>Peprotech (130-08) | 109 |
| HSP90 | Sigma (H6774) | 110 |
| EGFP | Prospec (cyt-332) | 111 |
| C4 | Sigma (C8195) | 112 |
| C3 | Sigma (C2910) | 113 |
| C1q | Prospec (pro-554) | 114 |
| Fibrinogen | AKRONbiotech (AK9026) | 115 |

Figure 1:
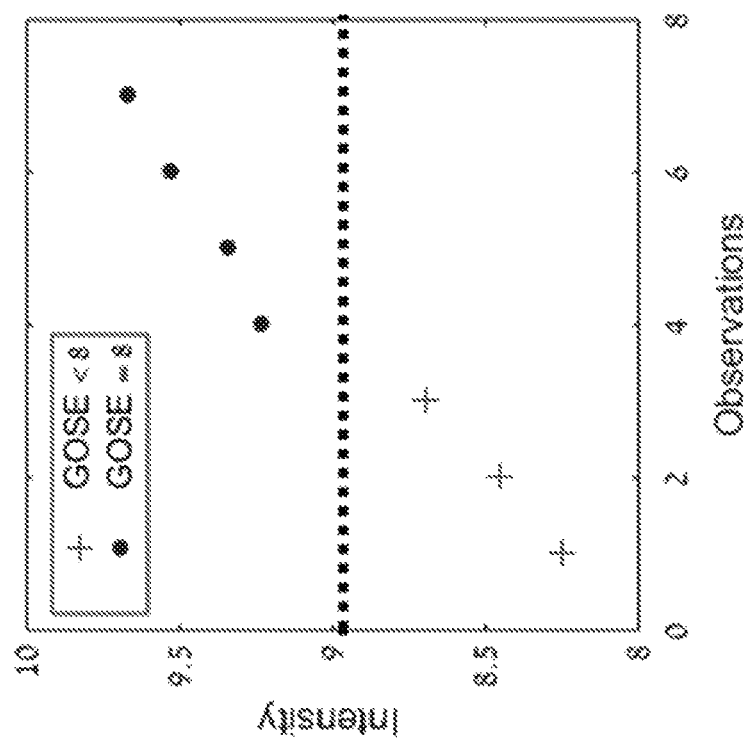
FIG. 1 illustrates anti-Fatty acid-binding protein (FABP-3, SEQ ID No: 61) IgM autoantibody levels at day 30 post brain injury. TBI patients with Glasgow Outcome Scale Extended (GOSE) score <8 (cross labeled) represent lower IgM levels than patients with GOSE score=8 (circle labeled).

As shown in FIG. 1, the levels of anti-Fatty acid-binding protein (FABP, SEQ ID No: 61) IgM autoantibodies in serum samples obtained from TBI patients at day 30 post injury, with Glasgow Outcome Scale Extended (GOSE) score <8 (cross labeled) are lower in comparison to patients with GOSE score=8 (circle labeled).

Figure 2:
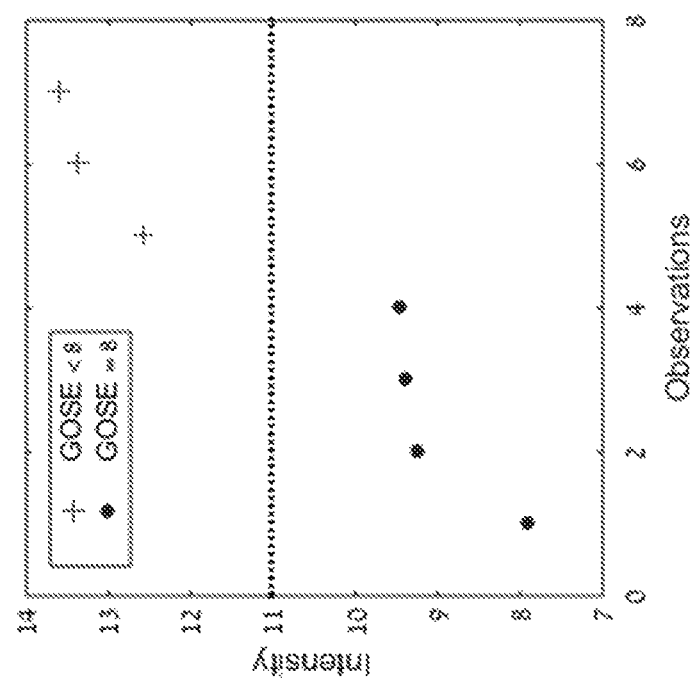
FIG. 2 illustrates anti-Myelin basic protein (MBPR149, SEQ ID No: 10) derived BSA conjugated peptide IgM autoantibody levels at day 30 post brain injury. TBI patients with Glasgow Outcome Scale Extended (GOSE) score <8 (cross labeled) represent higher IgM levels than patients with GOSE score=8 (circle labeled).

As shown in FIG. 2, the levels of anti-Myelin basic protein (MBPR149, SEQ ID No: 10, MBP derived BSA conjugated peptide) IgM autoantibodies in serum samples obtained from TBI patients at day 30 post injury, with Glasgow Outcome Scale Extended (GOSE) score <8 (cross labeled) are higher in comparison to patients with GOSE score=8 (circle labeled). These results demonstrate for the first time that increased levels of anti-FABP IgM autoantibodies in serum samples obtained from a TBI patient are indicative of recovery from brain injury of said TBI patient. Furthermore, decreased levels of anti-MBPR149 IgM autoantibodies in serum samples obtained from a TBI patient are indicative of recovery from brain injury of said TBI patient. Thus the present invention disclosed specific antigen antibody reactivities that can be used for monitoring, and/or prognosis of brain injury.

Figure 3:
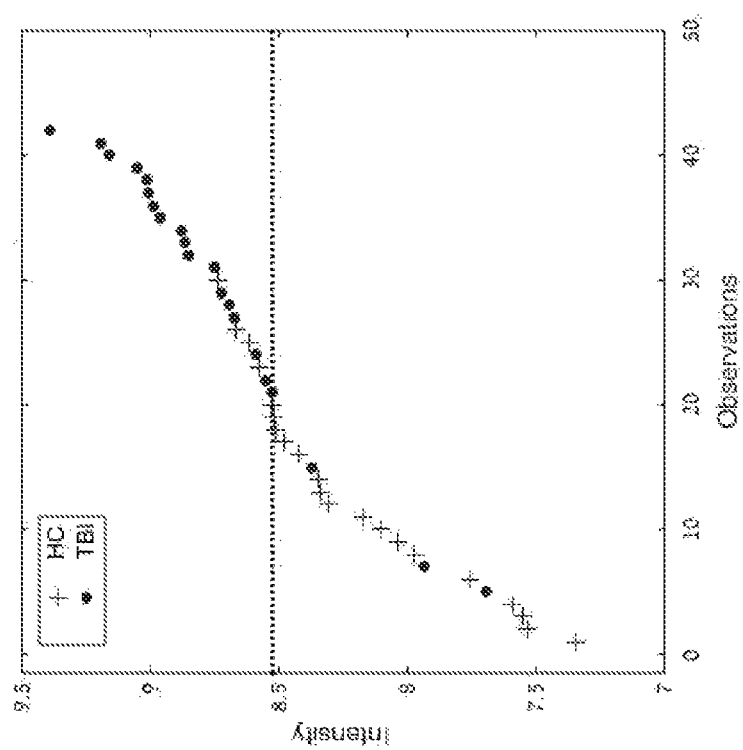
FIG. 3 illustrates anti-Myeloperoxidase (MPO, SEQ ID No: 85) IgM autoantibody levels in serum samples obtained from TBI patients (circle labeled) in comparison with healthy controls (cross labeled).

Example 2: Elevated Levels of Anti-Myeloperoxidase (MPO, SEQ ID No: 85) IgM Autoantibodies in Serum Samples Obtained from TBI Patients as Compared to Healthy Controls As shown in FIG. 3, the levels of anti-MPO IgM autoantibodies in serum samples obtained from TBI patients (circle labeled) are higher in comparison with healthy controls (cross labeled). These results demonstrate for the first time that increased levels of anti-MPO autoantibodies are indicative of brain injury.

Figure 4B:
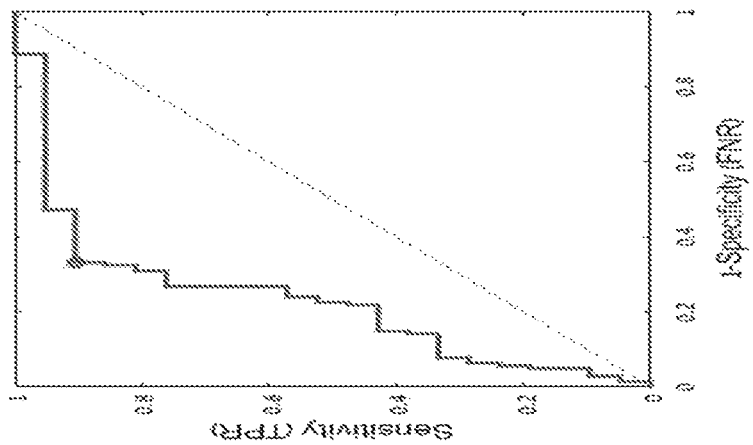
FIG. 4B shows the above separation performance by receivers operating characteristic (ROC) curves of anti-Cytomegalovirus (CMV) IgG autoantibody levels. T test P value for separation: 3.746E-07, after FDR correction: 5.02E-05. Kruskal-Wallis test P value for separation: 4.567E-05, after FDR correction: 0.0081593.
Figure 4A:
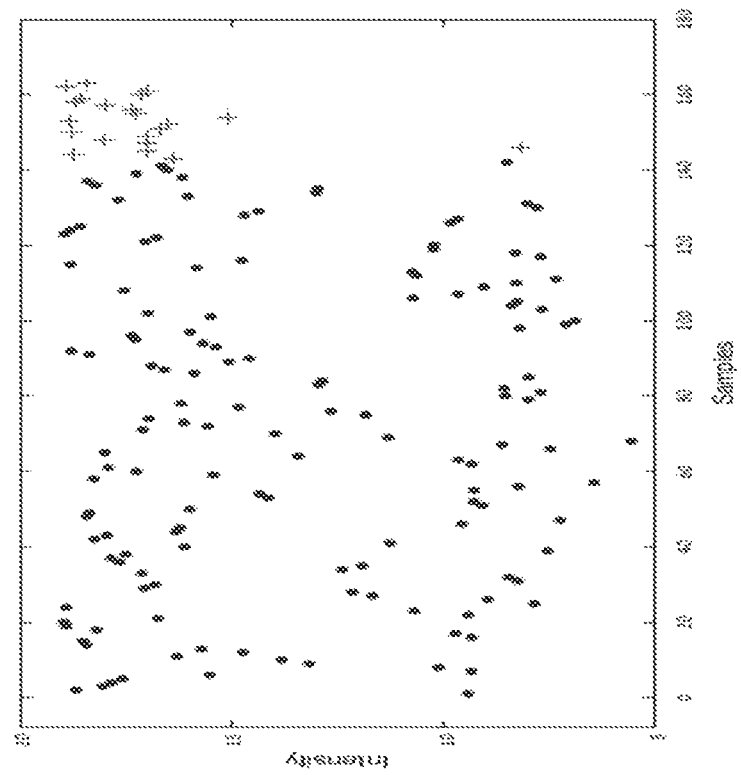
FIG. 4A illustrates anti-CMV (SEQ ID No: 86) IgG autoantibody levels in serum samples obtained from TBI patients (circle labeled) at day 30 and day 90 post injury (N=142) in comparison with healthy controls (cross labeled) (N=21).

Example 3: Decreased Levels of Anti-CMV (SEQ ID No: 86) IgG Autoantibody in Serum Samples Obtained from TBI Patients as Compared to Healthy Controls As shown in FIG. 4A, the levels of anti-CMV (SEQ ID No: 86) IgG autoantibody levels in serum samples obtained from TBI patients (circle labeled) at day 30 and day 90 post injury (N=142) are lower in comparison with healthy controls (cross labeled) (N=21). FIG. 4B shows the separation performance by receivers operating characteristic (ROC) curves of anti-CMV IgG autoantibody levels.

Figure 5B:
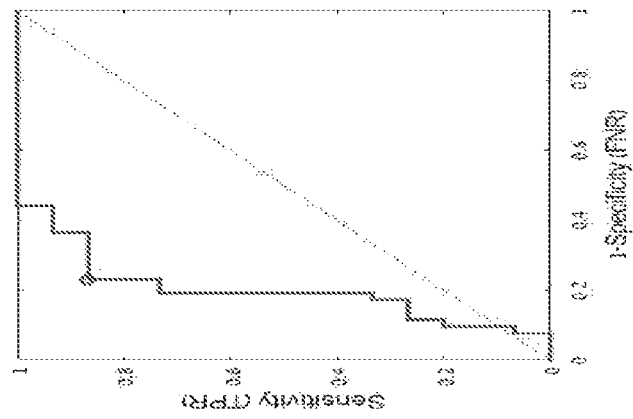
FIG. 5B shows the above separation performance by receivers operating characteristic (ROC) curves of anti-TNFRSF12A IgM autoantibody levels. T test P value for separation: 6.808E-06, after FDR correction: 0.0036493. Kruskal-Wallis test P value for separation: 0.0004082, after FDR correction: 0.1541973
Figure 5A:
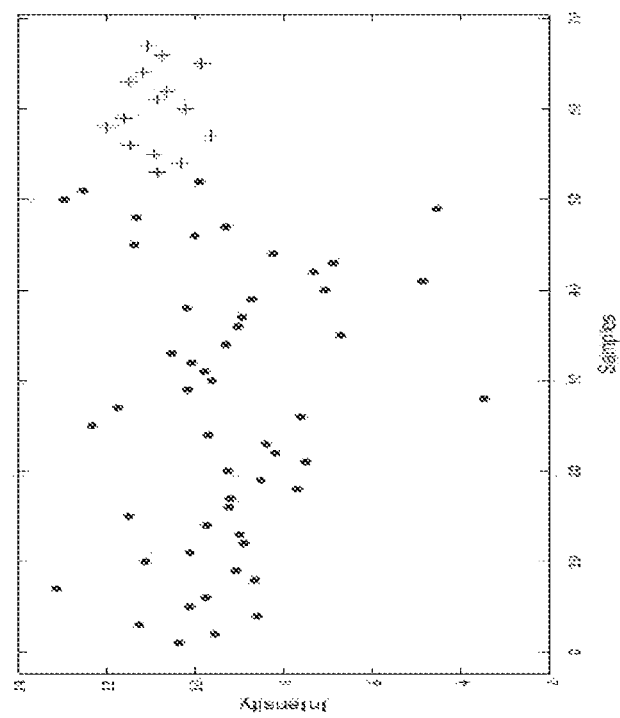
FIG. 5A demonstrates the prediction of the clinical status of TBI patients at day 90 post injury, based on the anti-TNFRSF12A (SEQ ID No: 104) IgM autoantibody levels in serum samples obtained from TBI patients at day 30 post injury. TBI patients, with GOSE <8 at day 90 post injury (circle labeled) (N=52) were compared with TBI patients, with GOSE=8 at day 90 post injury (cross labeled) (N=15).

Example 4: The Prediction of the Clinical Status of TBI Patients at Day 90 Post Injury, Based on the Anti-TNFRSF12A (SEQ ID No: 104) IgM Autoantibody Levels in Serum Samples Obtained from TBI Patients at Day 30 Post Injury As shown in FIG. 5A, the levels of anti-TNFRSF12A (SEQ ID No:104) IgM autoantibody in serum samples obtained from TBI patients at day 30 post injury can be used for the prediction of the clinical status (GOSE <8 or GOSE =8) of TBI patients at day 90 post injury. FIG. 5B shows the separation performance by receivers operating characteristic (ROC) curves of anti-TNFRSF12A IgM autoantibody levels.

Example 5: Combination Measurement of the Levels of Autoantibodies and Biomarkers in Serum Samples Obtained from TBI Patients as Compared to Healthy Controls To determine whether combination measurement of the levels of antibodies and biomarkers in serum samples can differentiate between TBI patients and healthy controls, a combined analysis was conducted. Serum samples obtained from TBI patients at time 0 (t0, N=85) were compared with serum samples obtained from healthy control (HC, N=21). The analysis was based on 464 iChip features (232 antigens, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

Figure 6:
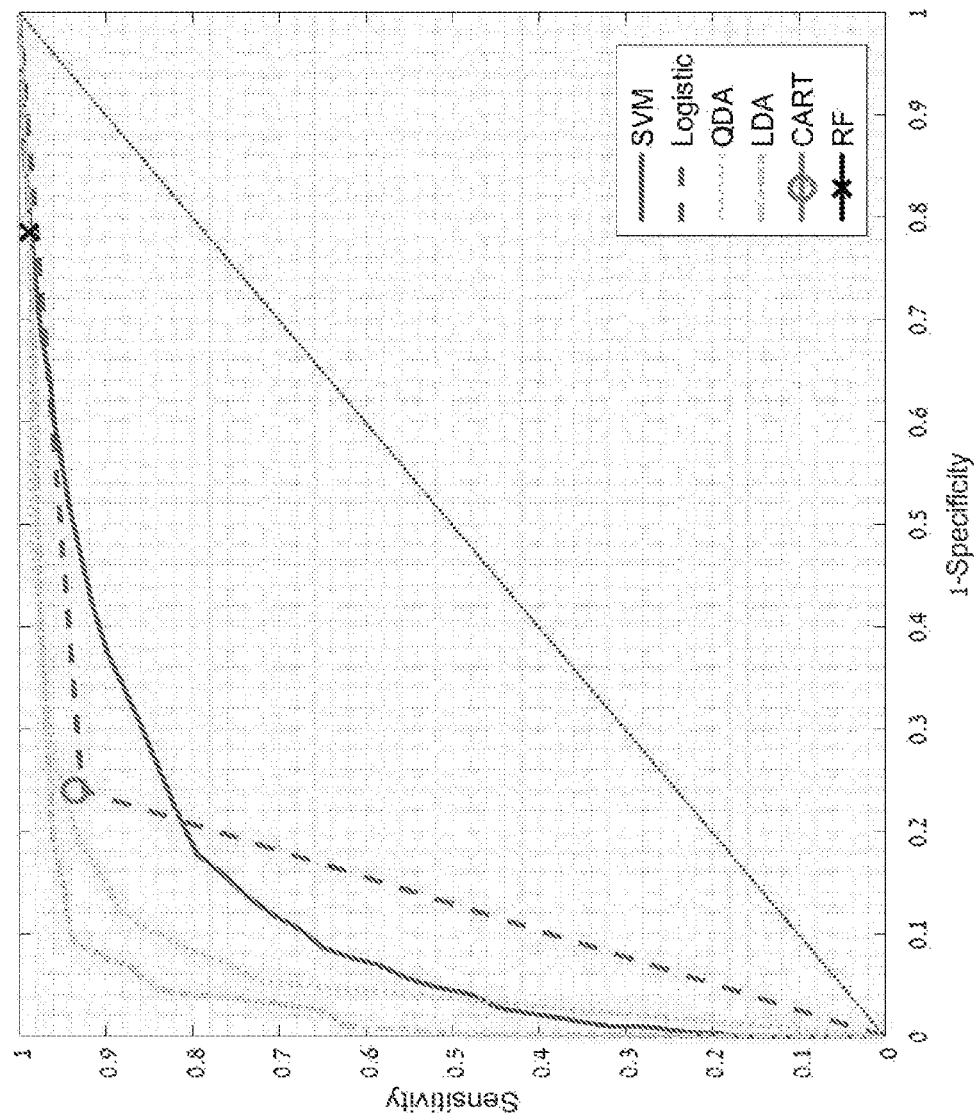
FIG. 6 shows the area under the Receiver Operating Characteristics (ROC) curves of six classification methods (SVM, LR, QDA, CART, RF and LDA) based on 100 iterations of 70:30 cross validation. Features were ranked according to their median scoring or frequency of model inclusion, depending on the method.

FIG. 6 shows the area under the Receiver Operating Characteristics (ROC) curves of six classification methods (SVM, LR, QDA, CART, RF and LDA) based on 100 iterations of 70:30 cross validation. Features were ranked according to their median scoring or frequency of model inclusion, depending on the method.

Using the LDA classification method revealed that the top six features above the random background level are the biomarkers: GFAP and SNCB in combination with the autoantibodies: anti-MBP in vitro citrullinated (SEQ ID No: 2) IgM, anti-GFAP (SEQ ID No: 14) IgM, anti-ICAM5 (SEQ ID No: 28) IgM, and anti-BDNF (SEQ ID No: 42) IgM.

Using the QDA classification method revealed that the top three features above the random background level are the biomarkers: GFAP and SNCB in combination with the autoantibodies: anti-MBP in vitro citrullinated (SEQ ID No: 2).

Example 6: Combination Measurement of the Levels of Antibodies and Biomarkers in Serum Samples Obtained from TBI Patients with Intracranial Hemorrhage on Head CT as Compared to TBI Patients with Normal CT To determine whether combination measurement of the levels of antibodies and biomarkers in serum samples can differentiate between TBI patients with intracranial hemorrhage on head CT and those with normal CT, a combined analysis was conducted. Serum samples obtained from TBI patients at time 0 (t0) with abnormal CT were compared with samples obtained from TBI patients at time 0 (t0) with normal CT. Analysis was based on 464 iChip features (232 antigen, IgM and IgG) and four ELISA features. iChip data is based on average of two block replicates, following correction procedure. ELISA features were selected based on data availability; only features with data available for >80% of the iChip samples were used. Samples with missing ELISA data were removed from the analysis.

FIG. 7 shows ROC curves of six classification methods (SVM, LR, QDA, CART, RF and LDA), based on 100 iterations of 70:30 cross validation. Features were ranked according to their median scoring or frequency of model inclusion, depending on the method.

Using the LDA classification method revealed that the top five features above the random background level are the biomarker: SNCB in combination with the autoantibodies: anti-Collagen IV (SEQ ID No: 66) IgG, anti-Oligo24 (SEQ ID No: 44) IgM, anti-EBV IgM and anti-Collagen II (SEQ ID No: 102) IgG.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of detecting biomarker protein in a subject having or suspected of having brain injury, the method comprising:
(i) detecting biomarker protein synuclein beta (SNCB) in a biological sample obtained from the subject using a detecting assay selected from an immunoassay, an antigen probe set assay, a microarray assay, a dipstick assay, or a chip assay;
(ii) measuring the level of the SNCB biomarker protein detected in the sample relative to the level of the SNCB biomarker protein in a healthy control;
(iii) diagnosing the subject as having or suspected of having brain injury when the level of the SNCB biomarker protein measured in step (ii) is higher than the level of the SNCB biomarker protein in the healthy control; and
(iv) treating brain injury in the subject diagnosed as having or suspected of having brain injury in step (iii); and, prior to step (iv),
further comprising detecting and measuring in the biological sample a level of glial fibrillary acidic protein (GFAP) biomarker protein that is higher the level of GFAP in the healthy control.

2. The method of claim 1, wherein the antigen probe set assay is in the form of an array, wherein the biomarkers are localized and detected at specific addressable locations of the array.

3. The method of claim 1, wherein the detecting assay is in the form of a kit, which optionally comprises reagents, buffers, detectable labels, and instructions for use.

4. The method of claim 1, wherein the detecting assay comprises an immunoassay selected from the group consisting of an enzymatic assay, a fluorescence assay, a luminescence assay, a colorimetric detection assay, or a combination thereof.

5. The method of claim 1, wherein the biological sample is plasma, serum, blood, or cerebrospinal fluid.

6. The method of claim 1, wherein a citrullinated form or a post-translationally modified form of the SNCB biomarker protein and/or the GFAP biomarker protein is detected in the biological sample.

7. The method of claim 1, further comprising detecting in the biological sample Metallothionein-3 protein (MT3).

8. The method of claim 1, wherein the healthy control comprises a biological sample obtained from a healthy individual without brain injury; a panel of samples obtained from a set of healthy individuals without brain injury; or a stored set of data obtained from healthy individuals without brain injury.

9. The method of claim 1, further comprising detecting in the subject's biological sample levels of autoantibodies directed against a protein selected from the group consisting of myelin basic protein (MBP), glial fibrillary acidic protein (GFAP), intercellular adhesion molecule-5 (ICAMS), brain derived neurotrophic factor (BDNF), Collagen II, Collagen IV, Oligo24 of SEQ ID NO: 44, Epstein Barr Virus (EBV) antigen and a combination thereof that are higher than the levels of autoantibodies directed against the same proteins in a healthy control.

* * * * *

SEQUENCE LISTING

```
<160> NUMBER OF SEQ ID NOS: 115

<210> SEQ ID NO 1
<211> LENGTH: 197
<212> TYPE: PRT
<213> ORGANISM: human

<400> SEQUENCE: 1

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30
```

```
His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
 50                  55                  60

Pro Gly Arg Ser Pro Leu Pro Ser His Ala Arg Ser Gln Pro Gly Leu
 65                  70                  75                  80

Cys Asn Met Tyr Lys Asp Ser His His Pro Ala Arg Thr Ala His Tyr
                 85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
            115                 120                 125

Ser Gln Gly Lys Gly Arg Gly Leu Ser Leu Ser Arg Phe Ser Trp Gly
        130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
            195

<210> SEQ ID NO 2
<211> LENGTH: 197
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Citrulline
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (10)..(10)
<223> OTHER INFORMATION: Citrulline
<220> FEATURE:
<221> NAME/KEY: MISC_FEATURE
<222> LOCATION: (26)..(26)
<223> OTHER INFORMATION: Citrulline
<220> FEATURE:
<221> NAME/KEY: MISC_FEATURE
<222> LOCATION: (32)..(32)
<223> OTHER INFORMATION: Citrulline
<220> FEATURE:
<221> NAME/KEY: MISC_FEATURE
<222> LOCATION: (34)..(34)
<223> OTHER INFORMATION: Citrulline
<220> FEATURE:
<221> NAME/KEY: MISC_FEATURE
<222> LOCATION: (44)..(44)
<223> OTHER INFORMATION: Citrulline
<220> FEATURE:
<221> NAME/KEY: MISC_FEATURE
<222> LOCATION: (50)..(50)
<223> OTHER INFORMATION: Citrulline
<220> FEATURE:
<221> NAME/KEY: MISC_FEATURE
<222> LOCATION: (55)..(55)
<223> OTHER INFORMATION: Citrulline
<220> FEATURE:
<221> NAME/KEY: MISC_FEATURE
```

-continued

```
<222> LOCATION: (67)..(67)
<223> OTHER INFORMATION: Citrulline
<220> FEATURE:
<221> NAME/KEY: MISC_FEATURE
<222> LOCATION: (75)..(75)
<223> OTHER INFORMATION: Citrulline
<220> FEATURE:
<221> NAME/KEY: MISC_FEATURE
<222> LOCATION: (92)..(92)
<223> OTHER INFORMATION: Citrulline
<220> FEATURE:
<221> NAME/KEY: MISC_FEATURE
<222> LOCATION: (106)..(106)
<223> OTHER INFORMATION: Citrulline
<220> FEATURE:
<221> NAME/KEY: MISC_FEATURE
<222> LOCATION: (124)..(124)
<223> OTHER INFORMATION: Citrulline
<220> FEATURE:
<221> NAME/KEY: MISC_FEATURE
<222> LOCATION: (134)..(134)
<223> OTHER INFORMATION: Citrulline
<220> FEATURE:
<221> NAME/KEY: MISC_FEATURE
<222> LOCATION: (140)..(140)
<223> OTHER INFORMATION: Citrulline
<220> FEATURE:
<221> NAME/KEY: MISC_FEATURE
<222> LOCATION: (149)..(149)
<223> OTHER INFORMATION: Citrulline
<220> FEATURE:
<221> NAME/KEY: MISC_FEATURE
<222> LOCATION: (157)..(157)
<223> OTHER INFORMATION: Citrulline
<220> FEATURE:
<221> NAME/KEY: MISC_FEATURE
<222> LOCATION: (186)..(186)
<223> OTHER INFORMATION: Citrulline
<220> FEATURE:
<221> NAME/KEY: MISC_FEATURE
<222> LOCATION: (189)..(189)
<223> OTHER INFORMATION: Citrulline
<220> FEATURE:
<221> NAME/KEY: MISC_FEATURE
<222> LOCATION: (196)..(196)
<223> OTHER INFORMATION: Citrulline
<220> FEATURE:
<221> NAME/KEY: MISC_FEATURE
<222> LOCATION: (197)..(197)
<223> OTHER INFORMATION: Citrulline

<400> SEQUENCE: 2

Met Ala Ser Gln Lys Xaa Pro Ser Gln Xaa His Gly Ser Lys Tyr Leu
1               5                   10                  15

Ala Thr Ala Ser Thr Met Asp His Ala Xaa His Gly Phe Leu Pro Xaa
            20                  25                  30

His Xaa Asp Thr Gly Ile Leu Asp Ser Ile Gly Xaa Phe Phe Gly Gly
        35                  40                  45

Asp Xaa Gly Ala Pro Lys Xaa Gly Ser Gly Lys Val Pro Trp Leu Lys
    50                  55                  60

Pro Gly Xaa Ser Pro Leu Pro Ser His Ala Xaa Ser Gln Pro Gly Leu
65                  70                  75                  80

Cys Asn Met Tyr Lys Asp Ser His His Pro Ala Xaa Thr Ala His Tyr
                85                  90                  95

Gly Ser Leu Pro Gln Lys Ser His Gly Xaa Thr Gln Asp Glu Asn Pro
            100                 105                 110

Val Val His Phe Phe Lys Asn Ile Val Thr Pro Xaa Thr Pro Pro Pro
        115                 120                 125

Ser Gln Gly Lys Gly Xaa Gly Leu Ser Leu Ser Xaa Phe Ser Trp Gly
    130                 135                 140
```

Ala Glu Gly Gln Xaa Pro Gly Phe Gly Tyr Gly Xaa Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Xaa Asp Ser Xaa Ser Gly Ser
            180                 185                 190

Pro Met Ala Xaa Xaa
        195

<210> SEQ ID NO 3
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 3

Thr Met Asp His Ala Xaa His Gly Phe Leu Pro Cys
1               5                   10

<210> SEQ ID NO 4
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (5)..(5)
<223> OTHER INFORMATION: Citrulline
<220> FEATURE:
<221> NAME/KEY: MISC_FEATURE
<222> LOCATION: (7)..(7)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 4

Gly Phe Leu Pro Xaa His Xaa Asp Thr Gly Ile Cys
1               5                   10

<210> SEQ ID NO 5
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:

```
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 5

Cys Ile Leu Asp Ser Ile Gly Xaa Phe Phe Gly Gly
1               5                  10

<210> SEQ ID NO 6
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (5)..(5)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 6

Phe Gly Gly Asp Xaa Gly Ala Pro Lys Arg Gly Cys
1               5                  10

<210> SEQ ID NO 7
<211> LENGTH: 13
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (13)..(13)
<223> OTHER INFORMATION: Amidation

<400> SEQUENCE: 7

Cys Asp Ser His His Pro Ala Xaa Thr Ala His Tyr Gly
1               5                  10

<210> SEQ ID NO 8
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (7)..(7)
<223> OTHER INFORMATION: Citrulline
<220> FEATURE:
```

```
<221> NAME/KEY: MISC_FEATURE
<222> LOCATION: (12)..(12)
<223> OTHER INFORMATION: Amidation

<400> SEQUENCE: 8

Cys Gln Lys Ser His Gly Xaa Thr Gln Asp Glu Asn
1               5                   10

<210> SEQ ID NO 9
<211> LENGTH: 11
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (11)..(11)
<223> OTHER INFORMATION: Amidation

<400> SEQUENCE: 9

Cys Phe Lys Asn Ile Val Thr Pro Xaa Thr Pro
1               5                   10

<210> SEQ ID NO 10
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 10

Gly Ala Glu Gly Gln Xaa Pro Gly Phe Gly Tyr Cys
1               5                   10

<210> SEQ ID NO 11
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (12)..(12)
<223> OTHER INFORMATION: Amidation
```

```
<400> SEQUENCE: 11

Cys Gly Tyr Gly Gly Xaa Ala Ser Asp Tyr Lys Ser
1               5                   10

<210> SEQ ID NO 12
<211> LENGTH: 11
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (11)..(11)
<223> OTHER INFORMATION: Amidation

<400> SEQUENCE: 12

Cys Lys Leu Gly Gly Xaa Asp Ser Xaa Ser Gly
1               5                   10

<210> SEQ ID NO 13
<211> LENGTH: 10
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (2)..(2)
<223> OTHER INFORMATION: Aminocaproic acid
<220> FEATURE:
<221> NAME/KEY: MISC_FEATURE
<222> LOCATION: (9)..(9)
<223> OTHER INFORMATION: Citrulline
<220> FEATURE:
<221> NAME/KEY: MISC_FEATURE
<222> LOCATION: (10)..(10)
<223> OTHER INFORMATION: Citrulline
<220> FEATURE:
<221> NAME/KEY: MISC_FEATURE
<222> LOCATION: (10)..(10)
<223> OTHER INFORMATION: hydroxylation

<400> SEQUENCE: 13

Cys Xaa Ser Gly Ser Pro Met Ala Xaa Xaa
1               5                   10

<210> SEQ ID NO 14
<211> LENGTH: 432
<212> TYPE: PRT
<213> ORGANISM: human

<400> SEQUENCE: 14

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
```

```
                    20                  25                  30
Pro Gly Thr Arg Leu Ser Leu Ala Arg Met Pro Pro Leu Pro Thr
                35                  40                  45

Arg Val Asp Phe Ser Leu Ala Gly Ala Leu Asn Ala Gly Phe Lys Glu
50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
            115                 120                 125

Gln Leu Thr Ala Asn Ser Ala Arg Leu Glu Val Glu Arg Asp Asn Leu
        130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
        195                 200                 205

Arg Glu Leu Gln Glu Gln Leu Ala Arg Gln Gln Val His Val Glu Leu
    210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
    290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
        355                 360                 365

Leu Leu Glu Gly Glu Glu Asn Arg Ile Thr Ile Pro Val Gln Thr Phe
    370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430

<210> SEQ ID NO 15
```

```
<211> LENGTH: 432
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Citrulline
<220> FEATURE:
<221> NAME/KEY: MISC_FEATURE
<222> LOCATION: (4)..(4)
<223> OTHER INFORMATION: Citrulline
<220> FEATURE:
<221> NAME/KEY: MISC_FEATURE
<222> LOCATION: (5)..(5)
<223> OTHER INFORMATION: Citrulline
<220> FEATURE:
<221> NAME/KEY: MISC_FEATURE
<222> LOCATION: (11)..(11)
<223> OTHER INFORMATION: Citrulline
<220> FEATURE:
<221> NAME/KEY: MISC_FEATURE
<222> LOCATION: (12)..(12)
<223> OTHER INFORMATION: Citrulline
<220> FEATURE:
<221> NAME/KEY: MISC_FEATURE
<222> LOCATION: (29)..(29)
<223> OTHER INFORMATION: Citrulline
<220> FEATURE:
<221> NAME/KEY: MISC_FEATURE
<222> LOCATION: (30)..(30)
<223> OTHER INFORMATION: Citrulline
<220> FEATURE:
<221> NAME/KEY: MISC_FEATURE
<222> LOCATION: (36)..(36)
<223> OTHER INFORMATION: Citrulline
<220> FEATURE:
<221> NAME/KEY: MISC_FEATURE
<222> LOCATION: (41)..(41)
<223> OTHER INFORMATION: Citrulline
<220> FEATURE:
<221> NAME/KEY: MISC_FEATURE
<222> LOCATION: (49)..(49)
<223> OTHER INFORMATION: Citrulline
<220> FEATURE:
<221> NAME/KEY: MISC_FEATURE
<222> LOCATION: (66)..(66)
<223> OTHER INFORMATION: Citrulline
<220> FEATURE:
<221> NAME/KEY: MISC_FEATURE
<222> LOCATION: (70)..(70)
<223> OTHER INFORMATION: Citrulline
<220> FEATURE:
<221> NAME/KEY: MISC_FEATURE
<222> LOCATION: (79)..(79)
<223> OTHER INFORMATION: Citrulline
<220> FEATURE:
<221> NAME/KEY: MISC_FEATURE
<222> LOCATION: (88)..(88)
<223> OTHER INFORMATION: Citrulline
<220> FEATURE:
<221> NAME/KEY: MISC_FEATURE
<222> LOCATION: (105)..(105)
<223> OTHER INFORMATION: Citrulline
<220> FEATURE:
<221> NAME/KEY: MISC_FEATURE
<222> LOCATION: (121)..(121)
<223> OTHER INFORMATION: Citrulline
<220> FEATURE:
<221> NAME/KEY: MISC_FEATURE
<222> LOCATION: (124)..(124)
<223> OTHER INFORMATION: Citrulline
<220> FEATURE:
<221> NAME/KEY: MISC_FEATURE
<222> LOCATION: (126)..(126)
<223> OTHER INFORMATION: Citrulline
<220> FEATURE:
<221> NAME/KEY: MISC_FEATURE
```

```
<222> LOCATION: (136)..(136)
<223> OTHER INFORMATION: Citrulline
<220> FEATURE:
<221> NAME/KEY: MISC_FEATURE
<222> LOCATION: (141)..(141)
<223> OTHER INFORMATION: Citrulline
<220> FEATURE:
<221> NAME/KEY: MISC_FEATURE
<222> LOCATION: (152)..(152)
<223> OTHER INFORMATION: Citrulline
<220> FEATURE:
<221> NAME/KEY: MISC_FEATURE
<222> LOCATION: (162)..(162)
<223> OTHER INFORMATION: Citrulline
<220> FEATURE:
<221> NAME/KEY: MISC_FEATURE
<222> LOCATION: (173)..(173)
<223> OTHER INFORMATION: Citrulline
<220> FEATURE:
<221> NAME/KEY: MISC_FEATURE
<222> LOCATION: (183)..(183)
<223> OTHER INFORMATION: Citrulline
<220> FEATURE:
<221> NAME/KEY: MISC_FEATURE
<222> LOCATION: (188)..(188)
<223> OTHER INFORMATION: Citrulline
<220> FEATURE:
<221> NAME/KEY: MISC_FEATURE
<222> LOCATION: (198)..(198)
<223> OTHER INFORMATION: Citrulline
<220> FEATURE:
<221> NAME/KEY: MISC_FEATURE
<222> LOCATION: (201)..(201)
<223> OTHER INFORMATION: Citrulline
<220> FEATURE:
<221> NAME/KEY: MISC_FEATURE
<222> LOCATION: (209)..(209)
<223> OTHER INFORMATION: Citrulline
<220> FEATURE:
<221> NAME/KEY: MISC_FEATURE
<222> LOCATION: (217)..(217)
<223> OTHER INFORMATION: Citrulline
<220> FEATURE:
<221> NAME/KEY: MISC_FEATURE
<222> LOCATION: (239)..(239)
<223> OTHER INFORMATION: Citrulline
<220> FEATURE:
<221> NAME/KEY: MISC_FEATURE
<222> LOCATION: (258)..(258)
<223> OTHER INFORMATION: Citrulline
<220> FEATURE:
<221> NAME/KEY: MISC_FEATURE
<222> LOCATION: (270)..(270)
<223> OTHER INFORMATION: Citrulline
<220> FEATURE:
<221> NAME/KEY: MISC_FEATURE
<222> LOCATION: (276)..(276)
<223> OTHER INFORMATION: Citrulline
<220> FEATURE:
<221> NAME/KEY: MISC_FEATURE
<222> LOCATION: (286)..(286)
<223> OTHER INFORMATION: Citrulline
<220> FEATURE:
<221> NAME/KEY: MISC_FEATURE
<222> LOCATION: (287)..(287)
<223> OTHER INFORMATION: Citrulline
<220> FEATURE:
<221> NAME/KEY: MISC_FEATURE
<222> LOCATION: (300)..(300)
<223> OTHER INFORMATION: Citrulline
<220> FEATURE:
<221> NAME/KEY: MISC_FEATURE
<222> LOCATION: (308)..(308)
<223> OTHER INFORMATION: Citrulline
<220> FEATURE:
<221> NAME/KEY: MISC_FEATURE
<222> LOCATION: (311)..(311)
<223> OTHER INFORMATION: Citrulline
<220> FEATURE:
```

```
<221> NAME/KEY: MISC_FEATURE
<222> LOCATION: (316)..(316)
<223> OTHER INFORMATION: Citrulline
<220> FEATURE:
<221> NAME/KEY: MISC_FEATURE
<222> LOCATION: (319)..(319)
<223> OTHER INFORMATION: Citrulline
<220> FEATURE:
<221> NAME/KEY: MISC_FEATURE
<222> LOCATION: (330)..(330)
<223> OTHER INFORMATION: Citrulline
<220> FEATURE:
<221> NAME/KEY: MISC_FEATURE
<222> LOCATION: (344)..(344)
<223> OTHER INFORMATION: Citrulline
<220> FEATURE:
<221> NAME/KEY: MISC_FEATURE
<222> LOCATION: (367)..(367)
<223> OTHER INFORMATION: Citrulline
<220> FEATURE:
<221> NAME/KEY: MISC_FEATURE
<222> LOCATION: (376)..(376)
<223> OTHER INFORMATION: Citrulline
<220> FEATURE:
<221> NAME/KEY: MISC_FEATURE
<222> LOCATION: (390)..(390)
<223> OTHER INFORMATION: Citrulline
<220> FEATURE:
<221> NAME/KEY: MISC_FEATURE
<222> LOCATION: (406)..(416)
<223> OTHER INFORMATION: Citrulline

<400> SEQUENCE: 15

Met Glu Xaa Xaa Xaa Ile Thr Ser Ala Ala Xaa Xaa Ser Tyr Val Ser
1               5                   10                  15

Ser Gly Glu Met Met Val Gly Gly Leu Ala Pro Gly Xaa Xaa Leu Gly
            20                  25                  30

Pro Gly Thr Xaa Leu Ser Leu Ala Xaa Met Pro Pro Leu Pro Thr
        35                  40                  45

Xaa Val Asp Phe Ser Leu Ala Gly Ala Leu Asn Ala Gly Phe Lys Glu
    50                  55                  60

Thr Xaa Ala Ser Glu Xaa Ala Glu Met Met Glu Leu Asn Asp Xaa Phe
65                  70                  75                  80

Ala Ser Tyr Ile Glu Lys Val Xaa Phe Leu Glu Gln Gln Asn Lys Ala
                85                  90                  95

Leu Ala Ala Glu Leu Asn Gln Leu Xaa Ala Lys Glu Pro Thr Lys Leu
            100                 105                 110

Ala Asp Val Tyr Gln Ala Glu Leu Xaa Glu Leu Xaa Leu Xaa Leu Asp
        115                 120                 125

Gln Leu Thr Ala Asn Ser Ala Xaa Leu Glu Val Glu Xaa Asp Asn Leu
    130                 135                 140

Ala Gln Asp Leu Ala Thr Val Xaa Gln Lys Leu Gln Asp Glu Thr Asn
145                 150                 155                 160

Leu Xaa Leu Glu Ala Glu Asn Asn Leu Ala Ala Tyr Xaa Gln Glu Ala
                165                 170                 175

Asp Glu Ala Thr Leu Ala Xaa Leu Asp Leu Glu Xaa Lys Ile Glu Ser
            180                 185                 190

Leu Glu Glu Glu Ile Xaa Phe Leu Xaa Lys Ile His Glu Glu Glu Val
        195                 200                 205

Xaa Glu Leu Gln Glu Gln Leu Ala Xaa Gln Gln Val His Val Glu Leu
    210                 215                 220

Asp Val Ala Lys Pro Asp Leu Thr Ala Ala Leu Lys Glu Ile Xaa Thr
225                 230                 235                 240
```

```
Gln Tyr Glu Ala Met Ala Ser Ser Asn Met His Glu Ala Glu Glu Trp
            245                 250                 255

Tyr Xaa Ser Lys Phe Ala Asp Leu Thr Asp Ala Ala Ala Xaa Asn Ala
        260                 265                 270

Glu Leu Leu Xaa Gln Ala Lys His Glu Ala Asn Asp Tyr Xaa Xaa Gln
            275                 280                 285

Leu Gln Ser Leu Thr Cys Asp Leu Glu Ser Leu Xaa Gly Thr Asn Glu
            290                 295                 300

Ser Leu Glu Xaa Gln Met Xaa Glu Gln Glu Xaa His Val Xaa Glu
305                 310                 315                 320

Ala Ala Ser Tyr Gln Glu Ala Leu Ala Xaa Leu Glu Glu Gly Gln
            325                 330                 335

Ser Leu Lys Asp Glu Met Ala Xaa His Leu Gln Glu Tyr Gln Asp Leu
            340                 345                 350

Leu Asn Val Lys Leu Ala Leu Asp Ile Glu Ile Ala Thr Tyr Xaa Lys
            355                 360                 365

Leu Leu Glu Gly Glu Glu Asn Xaa Ile Thr Ile Pro Val Gln Thr Phe
            370                 375                 380

Ser Asn Leu Gln Ile Xaa Glu Thr Ser Leu Asp Thr Lys Ser Val Ser
385                 390                 395                 400

Glu Gly His Leu Lys Xaa Asn Ile Val Val Lys Thr Val Glu Met Xaa
            405                 410                 415

Asp Gly Glu Val Ile Lys Glu Ser Lys Gln Glu His Lys Asp Val Met
            420                 425                 430

<210> SEQ ID NO 16
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 16

Leu Ala Pro Gly Arg Xaa Leu Gly Pro Gly Thr Cys
1               5                   10

<210> SEQ ID NO 17
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (7)..(7)
<223> OTHER INFORMATION: Citrulline
<220> FEATURE:
<221> NAME/KEY: MISC_FEATURE
<222> LOCATION: (12)..(12)
```

<223> OTHER INFORMATION: Amidation

<400> SEQUENCE: 17

Cys Leu Gly Pro Gly Thr Xaa Leu Ser Leu Ala Arg
1               5                   10

<210> SEQ ID NO 18
<211> LENGTH: 11
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (3)..(3)
<223> OTHER INFORMATION: Citrulline
<220> FEATURE:
<221> NAME/KEY: MISC_FEATURE
<222> LOCATION: (11)..(11)
<223> OTHER INFORMATION: Amidation

<400> SEQUENCE: 18

Ala Ala Xaa Asn Ala Glu Leu Leu Arg Gln Cys
1               5                   10

<210> SEQ ID NO 19
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (7)..(7)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 19

Cys Glu Gly His Leu Lys Xaa Asn Ile Val Val Lys
1               5                   10

<210> SEQ ID NO 20
<211> LENGTH: 13
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (13)..(13)
<223> OTHER INFORMATION: Amidation

<400> SEQUENCE: 20

Cys Val Lys Thr Val Glu Met Xaa Asp Gly Glu Val Ile
1               5                   10

<210> SEQ ID NO 21
<211> LENGTH: 78
<212> TYPE: PRT
<213> ORGANISM: human

<400> SEQUENCE: 21

Met Asp Cys Cys Thr Glu Asn Ala Cys Ser Lys Pro Asp Asp Ile
1               5                   10                  15

Leu Asp Ile Pro Leu Asp Asp Pro Gly Ala Asn Ala Ala Ala Lys
                20                  25                  30

Ile Gln Ala Ser Phe Arg Gly His Met Ala Arg Lys Lys Ile Lys Ser
            35                  40                  45

Gly Glu Arg Gly Arg Lys Gly Pro Gly Pro Gly Pro Gly Gly Ala
    50                  55                  60

Gly Val Ala Arg Gly Gly Ala Gly Gly Pro Ser Gly Asp
65                  70                  75

<210> SEQ ID NO 22
<211> LENGTH: 78
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (38)..(38)
<223> OTHER INFORMATION: Citrulline
<220> FEATURE:
<221> NAME/KEY: MISC_FEATURE
<222> LOCATION: (43)..(43)
<223> OTHER INFORMATION: Citrulline
<220> FEATURE:
<221> NAME/KEY: MISC_FEATURE
<222> LOCATION: (51)..(51)
<223> OTHER INFORMATION: Citrulline
<220> FEATURE:
<221> NAME/KEY: MISC_FEATURE
<222> LOCATION: (53)..(53)
<223> OTHER INFORMATION: Citrulline
<220> FEATURE:
<221> NAME/KEY: MISC_FEATURE
<222> LOCATION: (68)..(68)
<223> OTHER INFORMATION: Citrulline

<400> SEQUENCE: 22

Met Asp Cys Cys Thr Glu Asn Ala Cys Ser Lys Pro Asp Asp Ile
1               5                   10                  15

Leu Asp Ile Pro Leu Asp Asp Pro Gly Ala Asn Ala Ala Ala Lys
                20                  25                  30

Ile Gln Ala Ser Phe Xaa Gly His Met Ala Xaa Lys Lys Ile Lys Ser
            35                  40                  45

Gly Glu Xaa Gly Xaa Lys Gly Pro Gly Pro Gly Gly Pro Gly Gly Ala
    50                  55                  60

Gly Val Ala Xaa Gly Gly Ala Gly Gly Pro Ser Gly Asp
65                  70                  75

<210> SEQ ID NO 23
<211> LENGTH: 12
<212> TYPE: PRT
<213> ORGANISM: artificial sequence
<220> FEATURE:
<223> OTHER INFORMATION: synthetic
<220> FEATURE:

```
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (6)..(6)
<223> OTHER INFORMATION: Citrulline
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 23

Cys Lys Ser Gly Glu Xaa Gly Xaa Lys Gly Pro Gly
1               5                   10

<210> SEQ ID NO 24
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (12)..(12)
<223> OTHER INFORMATION: Amidation

<400> SEQUENCE: 24

Cys Gly Gly Ala Gly Val Ala Xaa Gly Gly Ala Gly
1               5                   10

<210> SEQ ID NO 25
<211> LENGTH: 297
<212> TYPE: PRT
<213> ORGANISM: human

<400> SEQUENCE: 25

Met Lys Thr Leu Ser Pro Asp Arg Ile Gln Pro His Ile Met Thr Asp
1               5                   10                  15

Val Pro Ala Thr Phe Thr Gln Ala Glu Cys Asn Gly Asp Lys Pro Pro
            20                  25                  30

Glu Asn Gly Gln Gln Thr Ile Thr Lys Ile Ser Glu Glu Leu Thr Asp
        35                  40                  45

Val Asp Ser Pro Leu Pro His Tyr Arg Val Glu Pro Ser Leu Glu Gly
    50                  55                  60

Ala Leu Thr Lys Gly Ser Gln Glu Glu Arg Arg Lys Leu Gln Gly Asn
65                  70                  75                  80

Met Leu Leu Asn Ser Ser Met Glu Asp Lys Met Leu Lys Glu Asn Pro
                85                  90                  95

Glu Glu Lys Leu Phe Ile Val His Lys Ala Ile Thr Asp Leu Ser Leu
            100                 105                 110

Gln Glu Thr Ser Ala Asp Glu Met Thr Phe Arg Glu Gly His Gln Trp
        115                 120                 125

Glu Lys Ile Pro Leu Ser Gly Ser Asn Gln Glu Ile Arg Arg Gln Lys
```

```
                    130                 135                 140
Glu Arg Ile Thr Glu Gln Pro Leu Lys Glu Glu Asp Glu Asp Arg
145                 150                 155                 160

Lys Asn Lys Gly His Gln Ala Ala Glu Ile Glu Trp Leu Gly Phe Arg
                165                 170                 175

Lys Pro Ser Gln Ala Asp Met Leu His Ser Lys His Asp Glu Glu Gln
            180                 185                 190

Lys Val Trp Asp Glu Glu Ile Asp Asp Asp Asp Asp Asn Cys Asn
        195                 200                 205

Asn Asp Glu Asp Glu Val Arg Val Ile Glu Phe Lys Lys Lys His Glu
    210                 215                 220

Glu Val Ser Gln Phe Lys Glu Glu Gly Asp Ala Ser Glu Asp Ser Pro
225                 230                 235                 240

Leu Ser Ser Ala Ser Ser Gln Ala Val Thr Pro Asp Glu Gln Pro Thr
                245                 250                 255

Leu Gly Lys Lys Ser Asp Ile Ser Arg Asn Ala Tyr Ser Arg Tyr Asn
            260                 265                 270

Thr Ile Ser Tyr Arg Lys Ile Arg Lys Gly Asn Thr Lys Gln Arg Ile
        275                 280                 285

Asp Glu Phe Glu Ser Met Met His Leu
    290                 295

<210> SEQ ID NO 26
<211> LENGTH: 297
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (57)..(57)
<223> OTHER INFORMATION: Citrulline
<220> FEATURE:
<221> NAME/KEY: MISC_FEATURE
<222> LOCATION: (74)..(74)
<223> OTHER INFORMATION: Citrulline
<220> FEATURE:
<221> NAME/KEY: MISC_FEATURE
<222> LOCATION: (75)..(75)
<223> OTHER INFORMATION: Citrulline
<220> FEATURE:
<221> NAME/KEY: MISC_FEATURE
<222> LOCATION: (123)..(123)
<223> OTHER INFORMATION: Citrulline
<220> FEATURE:
<221> NAME/KEY: MISC_FEATURE
<222> LOCATION: (141)..(141)
<223> OTHER INFORMATION: Citrulline
<220> FEATURE:
<221> NAME/KEY: MISC_FEATURE
<222> LOCATION: (142)..(142)
<223> OTHER INFORMATION: Citrulline
<220> FEATURE:
<221> NAME/KEY: MISC_FEATURE
<222> LOCATION: (146)..(146)
<223> OTHER INFORMATION: Citrulline
<220> FEATURE:
<221> NAME/KEY: MISC_FEATURE
<222> LOCATION: (160)..(160)
<223> OTHER INFORMATION: Citrulline
<220> FEATURE:
<221> NAME/KEY: MISC_FEATURE
<222> LOCATION: (176)..(176)
<223> OTHER INFORMATION: Citrulline
```

```
<220> FEATURE:
<221> NAME/KEY: MISC_FEATURE
<222> LOCATION: (215)..(215)
<223> OTHER INFORMATION: Citrulline
<220> FEATURE:
<221> NAME/KEY: MISC_FEATURE
<222> LOCATION: (265)..(265)
<223> OTHER INFORMATION: Citrulline
<220> FEATURE:
<221> NAME/KEY: MISC_FEATURE
<222> LOCATION: (270)..(270)
<223> OTHER INFORMATION: Citrulline
<220> FEATURE:
<221> NAME/KEY: MISC_FEATURE
<222> LOCATION: (277)..(277)
<223> OTHER INFORMATION: Citrulline
<220> FEATURE:
<221> NAME/KEY: MISC_FEATURE
<222> LOCATION: (280)..(280)
<223> OTHER INFORMATION: Citrulline
<220> FEATURE:
<221> NAME/KEY: MISC_FEATURE
<222> LOCATION: (287)..(287)
<223> OTHER INFORMATION: Citrulline

<400> SEQUENCE: 26

Met Lys Thr Leu Ser Pro Asp Xaa Ile Gln Pro His Ile Met Thr Asp
1               5                   10                  15

Val Pro Ala Thr Phe Thr Gln Ala Glu Cys Asn Gly Asp Lys Pro Pro
            20                  25                  30

Glu Asn Gly Gln Gln Thr Ile Thr Lys Ile Ser Glu Leu Thr Asp
        35                  40                  45

Val Asp Ser Pro Leu Pro His Tyr Xaa Val Glu Pro Ser Leu Glu Gly
50                  55                  60

Ala Leu Thr Lys Gly Ser Gln Glu Glu Xaa Xaa Lys Leu Gln Gly Asn
65                  70                  75                  80

Met Leu Leu Asn Ser Ser Met Glu Asp Lys Met Leu Lys Glu Asn Pro
                85                  90                  95

Glu Glu Lys Leu Phe Ile Val His Lys Ala Ile Thr Asp Leu Ser Leu
            100                 105                 110

Gln Glu Thr Ser Ala Asp Glu Met Thr Phe Xaa Glu Gly His Gln Trp
        115                 120                 125

Glu Lys Ile Pro Leu Ser Gly Ser Asn Gln Glu Ile Xaa Xaa Gln Lys
130                 135                 140

Glu Xaa Ile Thr Glu Gln Pro Leu Lys Glu Glu Asp Glu Asp Xaa
145                 150                 155                 160

Lys Asn Lys Gly His Gln Ala Ala Glu Ile Glu Trp Leu Gly Phe Xaa
                165                 170                 175

Lys Pro Ser Gln Ala Asp Met Leu His Ser Lys His Asp Glu Glu Gln
            180                 185                 190

Lys Val Trp Asp Glu Glu Ile Asp Asp Asp Asp Asp Asn Cys Asn
        195                 200                 205

Asn Asp Glu Asp Glu Val Xaa Val Ile Glu Phe Lys Lys Lys His Glu
210                 215                 220

Glu Val Ser Gln Phe Lys Glu Glu Gly Asp Ala Ser Glu Asp Ser Pro
225                 230                 235                 240

Leu Ser Ser Ala Ser Ser Gln Ala Val Thr Pro Asp Glu Gln Pro Thr
                245                 250                 255

Leu Gly Lys Lys Ser Asp Ile Ser Xaa Asn Ala Tyr Ser Xaa Tyr Asn
            260                 265                 270

Thr Ile Ser Tyr Xaa Lys Ile Xaa Lys Gly Asn Thr Lys Gln Xaa Ile
```

-continued

```
                 275                 280                 285

Asp Glu Phe Glu Ser Met Met His Leu
    290                 295

<210> SEQ ID NO 27
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (15)..(15)
<223> OTHER INFORMATION: Amidation

<400> SEQUENCE: 27

Asp Ser Pro Leu Pro His Tyr Xaa Val Glu Pro Ser Leu Glu Cys
1               5                   10                  15

<210> SEQ ID NO 28
<211> LENGTH: 924
<212> TYPE: PRT
<213> ORGANISM: human

<400> SEQUENCE: 28

Met Pro Gly Pro Ser Pro Gly Leu Arg Arg Ala Leu Leu Gly Leu Trp
1               5                   10                  15

Ala Ala Leu Gly Leu Gly Leu Phe Gly Leu Ser Ala Val Ser Gln Glu
            20                  25                  30

Pro Phe Trp Ala Asp Leu Gln Pro Arg Val Ala Phe Val Glu Arg Gly
        35                  40                  45

Gly Ser Leu Trp Leu Asn Cys Ser Thr Asn Cys Pro Arg Pro Glu Arg
    50                  55                  60

Gly Gly Leu Glu Thr Ser Leu Arg Arg Asn Gly Thr Gln Arg Gly Leu
65                  70                  75                  80

Arg Trp Leu Ala Arg Gln Leu Val Asp Ile Arg Glu Pro Glu Thr Gln
                85                  90                  95

Pro Val Cys Phe Phe Arg Cys Ala Arg Arg Thr Leu Gln Ala Arg Gly
            100                 105                 110

Leu Ile Arg Thr Phe Gln Arg Pro Asp Arg Val Glu Leu Met Pro Leu
        115                 120                 125

Pro Pro Trp Gln Pro Val Gly Glu Asn Phe Thr Leu Ser Cys Arg Val
    130                 135                 140

Pro Gly Ala Gly Pro Arg Ala Ser Leu Thr Leu Thr Leu Leu Arg Gly
145                 150                 155                 160

Ala Gln Glu Leu Ile Arg Arg Ser Phe Ala Gly Glu Pro Pro Arg Ala
                165                 170                 175

Arg Gly Ala Val Leu Thr Ala Thr Val Leu Ala Arg Arg Glu Asp His
            180                 185                 190

Gly Ala Asn Phe Ser Cys Arg Ala Glu Leu Asp Leu Arg Pro His Gly
        195                 200                 205

Leu Gly Leu Phe Glu Asn Ser Ser Ala Pro Arg Glu Leu Arg Thr Phe
    210                 215                 220
```

```
Ser Leu Ser Pro Asp Ala Pro Arg Leu Ala Ala Pro Arg Leu Leu Glu
225                 230                 235                 240

Val Gly Ser Glu Arg Pro Val Ser Cys Thr Leu Asp Gly Leu Phe Pro
            245                 250                 255

Ala Ser Glu Ala Arg Val Tyr Leu Ala Leu Gly Asp Gln Asn Leu Ser
            260                 265                 270

Pro Asp Val Thr Leu Glu Gly Asp Ala Phe Val Ala Thr Ala Thr Ala
        275                 280                 285

Thr Ala Ser Ala Glu Gln Gly Ala Arg Gln Leu Val Cys Asn Val
290                 295                 300

Thr Leu Gly Gly Glu Asn Arg Glu Thr Arg Glu Asn Val Thr Ile Tyr
305                 310                 315                 320

Ser Phe Pro Ala Pro Leu Leu Thr Leu Ser Glu Pro Ser Val Ser Glu
                325                 330                 335

Gly Gln Met Val Thr Val Thr Cys Ala Ala Gly Ala Gln Ala Leu Val
                340                 345                 350

Thr Leu Glu Gly Val Pro Ala Ala Val Pro Gly Gln Pro Ala Gln Leu
            355                 360                 365

Gln Leu Asn Ala Thr Glu Asn Asp Asp Arg Arg Ser Phe Phe Cys Asp
370                 375                 380

Ala Thr Leu Asp Val Asp Gly Glu Thr Leu Ile Lys Asn Arg Ser Ala
385                 390                 395                 400

Glu Leu Arg Val Leu Tyr Ala Pro Arg Leu Asp Asp Ser Asp Cys Pro
                405                 410                 415

Arg Ser Trp Thr Trp Pro Glu Gly Pro Glu Gln Thr Leu Arg Cys Glu
                420                 425                 430

Ala Arg Gly Asn Pro Glu Pro Ser Val His Cys Ala Arg Ser Asp Gly
            435                 440                 445

Gly Ala Val Leu Ala Leu Gly Leu Leu Gly Pro Val Thr Arg Ala Leu
450                 455                 460

Ser Gly Thr Tyr Arg Cys Lys Ala Ala Asn Asp Gln Gly Glu Ala Val
465                 470                 475                 480

Lys Asp Val Thr Leu Thr Val Glu Tyr Ala Pro Ala Leu Asp Ser Val
                485                 490                 495

Gly Cys Pro Glu Arg Ile Thr Trp Leu Glu Gly Thr Glu Ala Ser Leu
                500                 505                 510

Ser Cys Val Ala His Gly Val Pro Pro Asp Val Ile Cys Val Arg
            515                 520                 525

Ser Gly Glu Leu Gly Ala Val Ile Glu Gly Leu Leu Arg Val Ala Arg
530                 535                 540

Glu His Ala Gly Thr Tyr Arg Cys Glu Ala Thr Asn Pro Arg Gly Ser
545                 550                 555                 560

Ala Ala Lys Asn Val Ala Val Thr Val Glu Tyr Gly Pro Arg Phe Glu
            565                 570                 575

Glu Pro Ser Cys Pro Ser Asn Trp Thr Trp Val Glu Gly Ser Gly Arg
            580                 585                 590

Leu Phe Ser Cys Glu Val Asp Gly Lys Pro Gln Pro Ser Val Lys Cys
            595                 600                 605

Val Gly Ser Gly Gly Ala Thr Glu Gly Val Leu Leu Pro Leu Ala Pro
            610                 615                 620

Pro Asp Pro Ser Pro Arg Ala Pro Arg Ile Pro Arg Val Leu Ala Pro
625                 630                 635                 640
```

```
Gly Ile Tyr Val Cys Asn Ala Thr Asn Arg His Gly Ser Val Ala Lys
                645                 650                 655

Thr Val Val Ser Ala Glu Ser Pro Glu Met Asp Glu Ser Thr
            660                 665                 670

Cys Pro Ser His Gln Thr Trp Leu Glu Gly Ala Glu Ala Ser Ala Leu
            675                 680                 685

Ala Cys Ala Ala Arg Gly Arg Pro Ser Pro Gly Val Arg Cys Ser Arg
            690                 695                 700

Glu Gly Ile Pro Trp Pro Glu Gln Gln Arg Val Ser Arg Glu Asp Ala
705                 710                 715                 720

Gly Thr Tyr His Cys Val Ala Thr Asn Ala His Gly Thr Asp Ser Arg
                725                 730                 735

Thr Val Thr Val Gly Val Glu Tyr Arg Pro Val Val Ala Glu Leu Ala
            740                 745                 750

Ala Ser Pro Pro Gly Gly Val Arg Pro Gly Gly Asn Phe Thr Leu Thr
            755                 760                 765

Cys Arg Ala Glu Ala Trp Pro Pro Ala Gln Ile Ser Trp Arg Ala Pro
770                 775                 780

Pro Gly Ala Leu Asn Ile Gly Leu Ser Ser Asn Asn Ser Thr Leu Ser
785                 790                 795                 800

Val Ala Gly Ala Met Gly Ser His Gly Gly Glu Tyr Glu Cys Ala Ala
                805                 810                 815

Thr Asn Ala His Gly Arg His Ala Arg Arg Ile Thr Val Arg Val Ala
            820                 825                 830

Gly Pro Trp Leu Trp Val Ala Val Gly Ala Ala Gly Gly Ala Ala
            835                 840                 845

Leu Leu Ala Ala Gly Ala Gly Leu Ala Phe Tyr Val Gln Ser Thr Ala
850                 855                 860

Cys Lys Lys Gly Glu Tyr Asn Val Gln Glu Ala Glu Ser Ser Gly Glu
865                 870                 875                 880

Ala Val Cys Leu Asn Gly Ala Gly Gly Ala Gly Gly Ala Ala Gly
                885                 890                 895

Ala Glu Gly Gly Pro Glu Ala Ala Gly Gly Ala Ala Glu Ser Pro Ala
            900                 905                 910

Glu Gly Glu Val Phe Ala Ile Gln Leu Thr Ser Ala
            915                 920

<210> SEQ ID NO 29
<211> LENGTH: 134
<212> TYPE: PRT
<213> ORGANISM: human

<400> SEQUENCE: 29

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45

Val Gln Gly Val Ala Ser Val Ala Glu Lys Thr Lys Glu Gln Ala Ser
    50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95
```

Glu Val Ala Gln Glu Ala Ala Glu Glu Pro Leu Ile Glu Pro Leu Met
                100                 105                 110

Glu Pro Glu Gly Glu Ser Tyr Glu Asp Pro Pro Gln Glu Glu Tyr Gln
                115                 120                 125

Glu Tyr Glu Pro Glu Ala
                130

<210> SEQ ID NO 30
<211> LENGTH: 68
<212> TYPE: PRT
<213> ORGANISM: human

<400> SEQUENCE: 30

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
                35                  40                  45

Cys Val Cys Lys Gly Gly Glu Ala Ala Glu Ala Glu Ala Glu Lys Cys
        50                  55                  60

Ser Cys Cys Gln
65

<210> SEQ ID NO 31
<211> LENGTH: 440
<212> TYPE: PRT
<213> ORGANISM: human

<400> SEQUENCE: 31

Met Glu Tyr Gln Ile Leu Lys Met Ser Leu Cys Leu Phe Ile Leu Leu
1               5                   10                  15

Phe Leu Thr Pro Gly Ile Leu Cys Ile Cys Pro Leu Gln Cys Ile Cys
                20                  25                  30

Thr Glu Arg His Arg His Val Asp Cys Ser Gly Arg Asn Leu Ser Thr
                35                  40                  45

Leu Pro Ser Gly Leu Gln Glu Asn Ile Ile His Leu Asn Leu Ser Tyr
        50                  55                  60

Asn His Phe Thr Asp Leu His Asn Gln Leu Thr Gln Tyr Thr Asn Leu
65                  70                  75                  80

Arg Thr Leu Asp Ile Ser Asn Asn Arg Leu Glu Ser Leu Pro Ala His
                85                  90                  95

Leu Pro Arg Ser Leu Trp Asn Met Ser Ala Ala Asn Asn Ile Lys
                100                 105                 110

Leu Leu Asp Lys Ser Asp Thr Ala Tyr Gln Trp Asn Leu Lys Tyr Leu
                115                 120                 125

Asp Val Ser Lys Asn Met Leu Glu Lys Val Val Leu Ile Lys Asn Thr
        130                 135                 140

Leu Arg Ser Leu Glu Val Leu Asn Leu Ser Ser Asn Lys Leu Trp Thr
145                 150                 155                 160

Val Pro Thr Asn Met Pro Ser Lys Leu His Ile Val Asp Leu Ser Asn
                165                 170                 175

Asn Ser Leu Thr Gln Ile Leu Pro Gly Thr Leu Ile Asn Leu Thr Asn
                180                 185                 190

Leu Thr His Leu Tyr Leu His Asn Asn Lys Phe Thr Phe Ile Pro Asp
                195                 200                 205

-continued

Gln Ser Phe Asp Gln Leu Phe Gln Leu Gln Glu Ile Thr Leu Tyr Asn
    210                 215                 220

Asn Arg Trp Ser Cys Asp His Lys Gln Asn Ile Thr Tyr Leu Leu Lys
225                 230                 235                 240

Trp Met Met Glu Thr Lys Ala His Val Ile Gly Thr Pro Cys Ser Thr
                245                 250                 255

Gln Ile Ser Ser Leu Lys Glu His Asn Met Tyr Pro Thr Pro Ser Gly
            260                 265                 270

Phe Thr Ser Ser Leu Phe Thr Val Ser Gly Met Gln Thr Val Asp Thr
        275                 280                 285

Ile Asn Ser Leu Ser Val Val Thr Gln Pro Lys Val Thr Lys Ile Pro
    290                 295                 300

Lys Gln Tyr Arg Thr Lys Glu Thr Thr Phe Gly Ala Thr Leu Ser Lys
305                 310                 315                 320

Asp Thr Thr Phe Thr Ser Thr Asp Lys Ala Phe Val Pro Tyr Pro Glu
                325                 330                 335

Asp Thr Ser Thr Glu Thr Ile Asn Ser His Glu Ala Ala Ala Ala Thr
            340                 345                 350

Leu Thr Ile His Leu Gln Asp Gly Met Val Thr Asn Thr Ser Leu Thr
        355                 360                 365

Ser Ser Thr Lys Ser Ser Pro Thr Pro Met Thr Leu Ser Ile Thr Ser
    370                 375                 380

Gly Met Pro Asn Asn Phe Ser Glu Met Pro Gln Gln Ser Thr Thr Leu
385                 390                 395                 400

Asn Leu Trp Arg Glu Glu Thr Thr Thr Asn Val Lys Thr Pro Leu Pro
                405                 410                 415

Ser Val Ala Asn Ala Trp Lys Val Asn Ala Ser Phe Leu Leu Leu Leu
            420                 425                 430

Asn Val Val Val Met Leu Ala Val
    435                 440

<210> SEQ ID NO 32
<211> LENGTH: 507
<212> TYPE: PRT
<213> ORGANISM: human

<400> SEQUENCE: 32

Met Asp Pro Lys Leu Gly Arg Met Ala Ala Ser Leu Leu Ala Val Leu
1               5                   10                  15

Leu Leu Leu Leu Glu Arg Gly Met Phe Ser Ser Pro Ser Pro Pro Pro
                20                  25                  30

Ala Leu Leu Glu Lys Val Phe Gln Tyr Ile Asp Leu His Gln Asp Glu
            35                  40                  45

Phe Val Gln Thr Leu Lys Glu Trp Val Ala Ile Glu Ser Asp Ser Val
    50                  55                  60

Gln Pro Val Pro Arg Phe Arg Gln Glu Leu Phe Arg Met Met Ala Val
65                  70                  75                  80

Ala Ala Asp Thr Leu Gln Arg Leu Gly Ala Arg Val Ala Ser Val Asp
                85                  90                  95

Met Gly Pro Gln Gln Leu Pro Asp Gly Gln Ser Leu Pro Ile Pro Pro
            100                 105                 110

Ile Ile Leu Ala Glu Leu Gly Ser Asp Pro Thr Lys Gly Thr Val Cys
    115                 120                 125

Phe Tyr Gly His Leu Asp Val Gln Pro Ala Asp Arg Gly Asp Gly Trp

```
                130             135             140
Leu Thr Asp Pro Tyr Val Leu Thr Glu Val Asp Gly Lys Leu Tyr Gly
145                 150                 155                 160

Arg Gly Ala Thr Asp Asn Lys Gly Pro Val Leu Ala Trp Ile Asn Ala
                165                 170                 175

Val Ser Ala Phe Arg Ala Leu Glu Gln Asp Leu Pro Val Asn Ile Lys
            180                 185                 190

Phe Ile Ile Glu Gly Met Glu Glu Ala Gly Ser Val Ala Leu Glu Glu
        195                 200                 205

Leu Val Glu Lys Glu Lys Asp Arg Phe Phe Ser Gly Val Asp Tyr Ile
210                 215                 220

Val Ile Ser Asp Asn Leu Trp Ile Ser Gln Arg Lys Pro Ala Ile Thr
225                 230                 235                 240

Tyr Gly Thr Arg Gly Asn Ser Tyr Phe Met Val Glu Val Lys Cys Arg
                245                 250                 255

Asp Gln Asp Phe His Ser Gly Thr Phe Gly Gly Ile Leu His Glu Pro
            260                 265                 270

Met Ala Asp Leu Val Ala Leu Leu Gly Ser Leu Val Asp Ser Ser Gly
        275                 280                 285

His Ile Leu Val Pro Gly Ile Tyr Asp Glu Val Val Pro Leu Thr Glu
290                 295                 300

Glu Glu Ile Asn Thr Tyr Lys Ala Ile His Leu Asp Leu Glu Glu Tyr
305                 310                 315                 320

Arg Asn Ser Ser Arg Val Glu Lys Phe Leu Phe Asp Thr Lys Glu Glu
                325                 330                 335

Ile Leu Met His Leu Trp Arg Tyr Pro Ser Leu Ser Ile His Gly Ile
            340                 345                 350

Glu Gly Ala Phe Asp Glu Pro Gly Thr Lys Thr Val Ile Pro Gly Arg
        355                 360                 365

Val Ile Gly Lys Phe Ser Ile Arg Leu Val Pro His Met Asn Val Ser
370                 375                 380

Ala Val Glu Lys Gln Val Thr Arg His Leu Glu Asp Val Phe Ser Lys
385                 390                 395                 400

Arg Asn Ser Ser Asn Lys Met Val Val Ser Met Thr Leu Gly Leu His
                405                 410                 415

Pro Trp Ile Ala Asn Ile Asp Asp Thr Gln Tyr Leu Ala Ala Lys Arg
            420                 425                 430

Ala Ile Arg Thr Val Phe Gly Thr Glu Pro Asp Met Ile Arg Asp Gly
        435                 440                 445

Ser Thr Ile Pro Ile Ala Lys Met Phe Gln Glu Ile Val His Lys Ser
450                 455                 460

Val Val Leu Ile Pro Leu Gly Ala Val Asp Asp Gly Glu His Ser Gln
465                 470                 475                 480

Asn Glu Lys Ile Asn Arg Trp Asn Tyr Ile Glu Gly Thr Lys Leu Phe
                485                 490                 495

Ala Ala Phe Phe Leu Glu Met Ala Gln Leu His
            500                 505

<210> SEQ ID NO 33
<211> LENGTH: 776
<212> TYPE: PRT
<213> ORGANISM: human

<400> SEQUENCE: 33
```

```
Met Ala Ala Pro Gly Asp Pro Gln Asp Glu Leu Leu Pro Leu Ala Gly
1               5                   10                  15

Pro Gly Ser Gln Trp Leu Arg His Arg Gly Glu Gly Glu Asn Glu Ala
            20                  25                  30

Val Thr Pro Lys Gly Ala Thr Pro Ala Pro Gln Ala Gly Glu Pro Ser
        35                  40                  45

Pro Gly Leu Gly Ala Arg Ala Arg Glu Ala Ala Ser Arg Glu Ala Gly
    50                  55                  60

Ser Gly Pro Ala Arg Gln Ser Pro Val Ala Met Glu Thr Ala Ser Thr
65                  70                  75                  80

Gly Val Ala Gly Val Ser Ser Ala Met Asp His Thr Phe Ser Thr Thr
                85                  90                  95

Ser Lys Asp Gly Glu Gly Ser Cys Tyr Thr Ser Leu Ile Ser Asp Ile
            100                 105                 110

Cys Tyr Pro Pro Gln Glu Asp Ser Thr Tyr Phe Thr Gly Ile Leu Gln
            115                 120                 125

Lys Glu Asn Gly His Val Thr Ile Ser Glu Ser Pro Glu Glu Leu Gly
            130                 135                 140

Thr Pro Gly Pro Ser Leu Pro Asp Val Pro Gly Ile Glu Ser Arg Gly
145                 150                 155                 160

Leu Phe Ser Ser Asp Ser Gly Ile Glu Met Thr Pro Ala Glu Ser Thr
                165                 170                 175

Glu Val Asn Lys Ile Leu Ala Asp Pro Leu Asp Gln Met Lys Ala Glu
            180                 185                 190

Ala Tyr Lys Tyr Ile Asp Ile Thr Arg Pro Glu Glu Val Lys His Gln
            195                 200                 205

Glu Gln His His Pro Glu Leu Glu Asp Lys Asp Leu Asp Phe Lys Asn
            210                 215                 220

Lys Asp Thr Asp Ile Ser Ile Lys Pro Glu Gly Val Arg Glu Pro Asp
225                 230                 235                 240

Lys Pro Ala Pro Val Glu Gly Lys Ile Ile Lys Asp His Leu Leu Glu
            245                 250                 255

Glu Ser Thr Phe Ala Pro Tyr Ile Asp Asp Leu Ser Glu Glu Gln Arg
            260                 265                 270

Arg Ala Pro Gln Ile Thr Thr Pro Val Lys Ile Thr Leu Thr Glu Ile
            275                 280                 285

Glu Pro Ser Val Glu Thr Thr Thr Gln Glu Lys Thr Pro Glu Lys Gln
            290                 295                 300

Asp Ile Cys Leu Lys Pro Ser Pro Asp Thr Val Pro Thr Val Thr Val
305                 310                 315                 320

Ser Glu Pro Glu Asp Asp Ser Pro Gly Ser Ile Thr Pro Pro Ser Ser
            325                 330                 335

Gly Thr Glu Pro Ser Ala Ala Glu Ser Gln Gly Lys Gly Ser Ile Ser
            340                 345                 350

Glu Asp Glu Leu Ile Thr Ala Ile Lys Glu Ala Lys Gly Leu Ser Tyr
            355                 360                 365

Glu Thr Ala Glu Asn Pro Arg Pro Val Gly Gln Leu Ala Asp Arg Pro
            370                 375                 380

Glu Val Lys Ala Arg Ser Gly Pro Pro Thr Ile Pro Ser Pro Leu Asp
385                 390                 395                 400

His Glu Ala Ser Ser Ala Glu Ser Gly Asp Ser Glu Ile Glu Leu Val
            405                 410                 415

Ser Glu Asp Pro Met Ala Ala Glu Asp Ala Leu Pro Ser Gly Tyr Val
```

```
                420                 425                 430
Ser Phe Gly His Val Gly Gly Pro Pro Ser Pro Ala Ser Pro Ser
        435                 440                 445
Ile Gln Tyr Ser Ile Leu Arg Glu Arg Glu Ala Glu Leu Asp Ser
    450                 455                 460
Glu Leu Ile Ile Glu Ser Cys Asp Ala Ser Ser Ala Ser Glu Glu Ser
465                 470                 475                 480
Pro Lys Arg Glu Gln Asp Ser Pro Pro Met Lys Pro Ser Ala Leu Asp
            485                 490                 495
Ala Ile Arg Glu Glu Thr Gly Val Arg Ala Glu Glu Arg Ala Pro Ser
                500                 505                 510
Arg Arg Gly Leu Ala Glu Pro Gly Ser Phe Leu Asp Tyr Pro Ser Thr
            515                 520                 525
Glu Pro Gln Pro Gly Pro Glu Leu Pro Pro Gly Asp Gly Ala Leu Glu
            530                 535                 540
Pro Glu Thr Pro Met Leu Pro Arg Lys Pro Glu Glu Asp Ser Ser Ser
545                 550                 555                 560
Asn Gln Ser Pro Ala Ala Thr Lys Gly Pro Gly Pro Leu Gly Pro Gly
                565                 570                 575
Ala Pro Pro Pro Leu Leu Phe Leu Asn Lys Gln Lys Ala Ile Asp Leu
                580                 585                 590
Leu Tyr Trp Arg Asp Ile Lys Gln Thr Gly Ile Val Phe Gly Ser Phe
            595                 600                 605
Leu Leu Leu Leu Phe Ser Leu Thr Gln Phe Ser Val Val Ser Val Val
                610                 615                 620
Ala Tyr Leu Ala Leu Ala Ala Leu Ser Ala Thr Ile Ser Phe Arg Ile
625                 630                 635                 640
Tyr Lys Ser Val Leu Gln Ala Val Gln Lys Thr Asp Glu Gly His Pro
                645                 650                 655
Phe Lys Ala Tyr Leu Glu Leu Glu Ile Thr Leu Ser Gln Glu Gln Ile
                660                 665                 670
Gln Lys Tyr Thr Asp Cys Leu Gln Phe Tyr Val Asn Ser Thr Leu Lys
            675                 680                 685
Glu Leu Arg Arg Leu Phe Leu Val Gln Asp Leu Val Asp Ser Leu Lys
            690                 695                 700
Phe Ala Val Leu Met Trp Leu Leu Thr Tyr Val Gly Ala Leu Phe Asn
705                 710                 715                 720
Gly Leu Thr Leu Leu Leu Met Ala Val Val Ser Met Phe Thr Leu Pro
                725                 730                 735
Val Val Tyr Val Lys His Gln Ala Gln Ile Asp Gln Tyr Leu Gly Leu
                740                 745                 750
Val Arg Thr His Ile Asn Ala Val Val Ala Lys Ile Gln Ala Lys Ile
            755                 760                 765
Pro Gly Ala Lys Arg His Ala Glu
770                 775

<210> SEQ ID NO 34
<211> LENGTH: 1294
<212> TYPE: PRT
<213> ORGANISM: human

<400> SEQUENCE: 34

Met Ala Leu Ala Gly Leu Cys Ala Leu Leu Ala Cys Cys Trp Gly Pro
1               5                   10                  15
```

Ala Ala Val Leu Ala Thr Ala Ala Gly Asp Val Asp Pro Ser Lys Glu
            20                  25                  30

Leu Glu Cys Lys Leu Lys Ser Ile Thr Val Ser Ala Leu Pro Phe Leu
        35                  40                  45

Arg Glu Asn Asp Leu Ser Ile Met His Ser Pro Ser Ala Ser Glu Pro
    50                  55                  60

Lys Leu Leu Phe Ser Val Arg Asn Asp Phe Pro Gly Glu Met Val Val
65                  70                  75                  80

Val Asp Asp Leu Glu Asn Thr Glu Leu Pro Tyr Phe Val Leu Glu Ile
                85                  90                  95

Ser Gly Asn Thr Glu Asp Ile Pro Leu Val Arg Trp Arg Gln Gln Trp
            100                 105                 110

Leu Glu Asn Gly Thr Leu Leu Phe His Ile His His Gln Asp Gly Ala
        115                 120                 125

Pro Ser Leu Pro Gly Gln Asp Pro Thr Glu Glu Pro Gln His Glu Ser
    130                 135                 140

Ala Glu Glu Glu Leu Arg Ile Leu His Ile Ser Val Met Gly Gly Met
145                 150                 155                 160

Ile Ala Leu Leu Leu Ser Ile Leu Cys Leu Val Met Ile Leu Tyr Thr
                165                 170                 175

Arg Arg Arg Trp Cys Lys Arg Arg Val Pro Gln Pro Gln Lys Ser
            180                 185                 190

Ala Ser Ala Glu Ala Ala Asn Glu Ile His Tyr Ile Pro Ser Val Leu
        195                 200                 205

Ile Gly Gly His Gly Arg Glu Ser Leu Arg Asn Ala Arg Val Gln Gly
    210                 215                 220

His Asn Ser Ser Gly Thr Leu Ser Ile Arg Glu Thr Pro Ile Leu Asp
225                 230                 235                 240

Gly Tyr Glu Tyr Asp Ile Thr Asp Leu Arg His His Leu Gln Arg Glu
                245                 250                 255

Cys Met Asn Gly Gly Glu Asp Phe Ala Ser Gln Val Thr Arg Thr Leu
            260                 265                 270

Asp Ser Leu Gln Gly Cys Asn Glu Lys Ser Gly Met Asp Leu Thr Pro
        275                 280                 285

Gly Ser Asp Asn Ala Lys Leu Ser Leu Met Asn Lys Tyr Lys Asp Asn
    290                 295                 300

Ile Ile Ala Thr Ser Pro Val Asp Ser Asn His Gln Gln Ala Thr Leu
305                 310                 315                 320

Leu Ser His Thr Ser Ser Gln Arg Lys Arg Ile Asn Asn Lys Ala
                325                 330                 335

Arg Ala Gly Ser Ala Phe Leu Asn Pro Glu Gly Asp Ser Gly Thr Glu
            340                 345                 350

Ala Glu Asn Asp Pro Gln Leu Thr Phe Tyr Thr Asp Pro Ser Arg Ser
        355                 360                 365

Arg Arg Arg Ser Arg Val Gly Ser Pro Arg Ser Pro Val Asn Lys Thr
    370                 375                 380

Thr Leu Thr Leu Ile Ser Ile Thr Ser Cys Val Ile Gly Leu Val Cys
385                 390                 395                 400

Ser Ser His Val Asn Cys Pro Leu Val Val Lys Ile Thr Leu His Val
                405                 410                 415

Pro Glu His Leu Ile Ala Asp Gly Ser Arg Phe Ile Leu Leu Glu Gly
            420                 425                 430

Ser Gln Leu Asp Ala Ser Asp Trp Leu Asn Pro Ala Gln Val Val Leu

```
                    435                 440                 445
        Phe Ser Gln Gln Asn Ser Ser Gly Pro Trp Ala Met Asp Leu Cys Ala
        450                 455                 460

Arg Arg Leu Leu Asp Pro Cys Glu His Gln Cys Asp Pro Glu Thr Gly
        465                 470                 475                 480

Glu Cys Leu Cys Tyr Glu Gly Tyr Met Lys Asp Pro Val His Lys His
                        485                 490                 495

Leu Cys Ile Arg Asn Glu Trp Gly Thr Asn Gln Gly Pro Trp Pro Tyr
                        500                 505                 510

Thr Ile Phe Gln Arg Gly Phe Asp Leu Val Leu Gly Glu Gln Pro Ser
                        515                 520                 525

Asp Lys Ile Phe Arg Phe Thr Tyr Thr Leu Gly Glu Gly Met Trp Leu
        530                 535                 540

Pro Leu Ser Lys Ser Phe Val Ile Pro Pro Ala Glu Leu Ala Ile Asn
        545                 550                 555                 560

Pro Ser Ala Lys Cys Lys Thr Asp Met Thr Val Met Glu Asp Ala Val
                        565                 570                 575

Glu Val Arg Glu Glu Leu Met Thr Ser Ser Phe Asp Ser Leu Glu
                        580                 585                 590

Val Leu Leu Asp Ser Phe Gly Pro Val Arg Asp Cys Ser Lys Asp Asn
                        595                 600                 605

Gly Gly Cys Ser Lys Asn Phe Arg Cys Ile Ser Asp Arg Lys Leu Asp
        610                 615                 620

Ser Thr Gly Cys Val Cys Pro Ser Gly Leu Ser Pro Met Lys Asp Ser
        625                 630                 635                 640

Ser Gly Cys Tyr Asp Arg His Ile Gly Val Asp Cys Ser Asp Gly Phe
                        645                 650                 655

Asn Gly Gly Cys Glu Gln Leu Cys Leu Gln Gln Met Ala Pro Phe Pro
                        660                 665                 670

Asp Asp Pro Thr Leu Tyr Asn Ile Leu Met Phe Cys Gly Cys Ile Glu
                        675                 680                 685

Asp Tyr Lys Leu Gly Val Asp Gly Arg Ser Cys Gln Leu Ile Thr Glu
                        690                 695                 700

Thr Cys Pro Glu Gly Ser Asp Cys Gly Glu Ser Arg Glu Leu Pro Met
        705                 710                 715                 720

Asn Gln Thr Leu Phe Gly Glu Met Phe Gly Tyr Asn Asn His Ser
                        725                 730                 735

Lys Glu Val Ala Ala Gly Gln Val Leu Lys Gly Thr Phe Arg Gln Asn
                        740                 745                 750

Asn Phe Ala Arg Gly Leu Asp Gln Gln Leu Pro Asp Gly Leu Val Val
                        755                 760                 765

Ala Thr Val Pro Leu Glu Asn Gln Cys Leu Glu Gly Ile Ser Glu Pro
                        770                 775                 780

Thr Pro Asp Pro Asp Phe Leu Thr Gly Met Val Asn Phe Ser Glu Val
        785                 790                 795                 800

Ser Gly Tyr Pro Val Leu Gln His Trp Lys Val Arg Ser Val Met Tyr
                        805                 810                 815

His Ile Lys Leu Asn Gln Val Ala Ile Ser Gln Ala Leu Ser Asn Ala
                        820                 825                 830

Leu His Ser Leu Asp Gly Ala Thr Ser Arg Ala Asp Phe Val Ala Leu
                        835                 840                 845

Leu Asp Gln Phe Gly Asn His Tyr Ile Gln Glu Ala Ile Tyr Gly Phe
        850                 855                 860
```

```
Glu Glu Ser Cys Ser Ile Trp Tyr Pro Asn Lys Gln Val Gln Arg Arg
865                 870                 875                 880

Leu Trp Leu Glu Tyr Glu Asp Ile Ser Lys Gly Asn Ser Pro Ser Asp
                885                 890                 895

Glu Ser Glu Glu Arg Glu Arg Asp Pro Lys Val Leu Thr Phe Pro Glu
            900                 905                 910

Tyr Ile Thr Ser Leu Ser Asp Ser Gly Thr Lys His Met Ala Ala Gly
        915                 920                 925

Val Arg Met Glu Cys His Ser Lys Gly Arg Cys Pro Ser Ser Cys Pro
    930                 935                 940

Leu Cys His Val Thr Ser Ser Pro Asp Thr Pro Ala Glu Pro Val Leu
945                 950                 955                 960

Leu Glu Val Thr Lys Ala Ala Pro Ile Tyr Glu Leu Val Thr Asn Asn
                965                 970                 975

Gln Thr Gln Arg Leu Leu Gln Glu Ala Thr Met Ser Ser Leu Trp Cys
            980                 985                 990

Ser Gly Thr Gly Asp Val Ile Glu Asp Trp Cys Arg Cys Asp Ser Thr
            995                 1000                1005

Ala Phe Gly Ala Asp Gly Leu Pro Thr Cys Ala Pro Leu Pro Gln
1010                1015                1020

Pro Val Leu Arg Leu Ser Thr Val His Glu Pro Ser Ser Thr Leu
1025                1030                1035

Val Val Leu Glu Trp Glu His Ser Glu Pro Pro Ile Gly Val Gln
1040                1045                1050

Ile Val Asp Tyr Leu Leu Arg Gln Glu Lys Val Thr Asp Arg Met
1055                1060                1065

Asp His Ser Lys Val Glu Thr Glu Thr Val Leu Ser Phe Val Asp
1070                1075                1080

Asp Ile Ile Ser Gly Ala Lys Ser Pro Cys Ala Met Pro Ser Gln
1085                1090                1095

Val Pro Asp Lys Gln Leu Thr Thr Ile Ser Leu Ile Ile Arg Cys
1100                1105                1110

Leu Glu Pro Asp Thr Ile Tyr Met Phe Thr Leu Trp Gly Val Asp
1115                1120                1125

Asn Thr Gly Arg Arg Ser Arg Pro Ser Asp Val Ile Val Lys Thr
1130                1135                1140

Pro Cys Pro Val Val Asp Asp Val Lys Ala Gln Glu Ile Ala Asp
1145                1150                1155

Lys Ile Tyr Asn Leu Phe Asn Gly Tyr Thr Ser Gly Lys Glu Gln
1160                1165                1170

Gln Thr Ala Tyr Asn Thr Leu Leu Asp Leu Gly Ser Pro Thr Leu
1175                1180                1185

His Arg Val Leu Tyr His Tyr Asn Gln His Tyr Glu Ser Phe Gly
1190                1195                1200

Glu Phe Thr Trp Arg Cys Glu Asp Glu Leu Gly Pro Arg Lys Ala
1205                1210                1215

Gly Leu Ile Leu Ser Gln Leu Gly Asp Leu Ser Ser Trp Cys Asn
1220                1225                1230

Gly Leu Leu Gln Glu Pro Lys Ile Ser Leu Arg Arg Ser Ser Leu
1235                1240                1245

Lys Tyr Leu Gly Cys Arg Tyr Ser Glu Ile Lys Pro Tyr Gly Leu
1250                1255                1260
```

```
Asp Trp Ala Glu Leu Ser Arg Asp Leu Arg Lys Thr Cys Glu Glu
    1265                1270                1275

Gln Thr Leu Ser Ile Pro Tyr Asn Asp Tyr Gly Asp Ser Lys Glu
    1280                1285                1290

Ile

<210> SEQ ID NO 35
<211> LENGTH: 1522
<212> TYPE: PRT
<213> ORGANISM: human

<400> SEQUENCE: 35

Met Lys Ala Val Arg Asn Leu Leu Ile Tyr Ile Phe Ser Thr Tyr Leu
1               5                   10                  15

Leu Val Met Phe Gly Phe Asn Ala Ala Gln Asp Phe Trp Cys Ser Thr
                20                  25                  30

Leu Val Lys Gly Val Ile Tyr Gly Ser Tyr Ser Val Ser Glu Met Phe
            35                  40                  45

Pro Lys Asn Phe Thr Asn Cys Thr Trp Thr Leu Glu Asn Pro Asp Pro
    50                  55                  60

Thr Lys Tyr Ser Ile Tyr Leu Lys Phe Ser Lys Asp Leu Ser Cys
65                  70                  75                  80

Ser Asn Phe Ser Leu Leu Ala Tyr Gln Phe Asp His Phe Ser His Glu
                85                  90                  95

Lys Ile Lys Asp Leu Leu Arg Lys Asn His Ser Ile Met Gln Leu Cys
            100                 105                 110

Asn Ser Lys Asn Ala Phe Val Phe Leu Gln Tyr Asp Lys Asn Phe Ile
        115                 120                 125

Gln Ile Arg Arg Val Phe Pro Thr Asn Phe Pro Gly Leu Gln Lys Lys
    130                 135                 140

Gly Glu Glu Asp Gln Lys Ser Phe Phe Glu Phe Leu Val Leu Asn Lys
145                 150                 155                 160

Val Ser Pro Ser Gln Phe Gly Cys His Val Leu Cys Thr Trp Leu Glu
                165                 170                 175

Ser Cys Leu Lys Ser Glu Asn Gly Arg Thr Glu Ser Cys Gly Ile Met
            180                 185                 190

Tyr Thr Lys Cys Thr Cys Pro Gln His Leu Gly Glu Trp Gly Ile Asp
        195                 200                 205

Asp Gln Ser Leu Ile Leu Asn Asn Val Val Leu Pro Leu Asn Glu
    210                 215                 220

Gln Thr Glu Gly Cys Leu Thr Gln Glu Leu Gln Thr Gln Val Cys
225                 230                 235                 240

Asn Leu Thr Arg Glu Ala Lys Arg Pro Pro Lys Glu Glu Phe Gly Met
                245                 250                 255

Met Gly Asp His Thr Ile Lys Ser Gln Arg Pro Arg Ser Val His Glu
            260                 265                 270

Lys Arg Val Pro Gln Glu Gln Ala Asp Ala Lys Phe Met Ala Gln
    275                 280                 285

Thr Gly Glu Ser Gly Val Glu Glu Trp Ser Gln Trp Ser Thr Cys Ser
    290                 295                 300

Val Thr Cys Gly Gln Gly Ser Gln Val Arg Thr Arg Thr Cys Val Ser
305                 310                 315                 320

Pro Tyr Gly Thr His Cys Ser Gly Pro Leu Arg Glu Ser Arg Val Cys
                325                 330                 335
```

-continued

Asn Asn Thr Ala Leu Cys Pro Val His Gly Val Trp Glu Trp Ser
            340                 345                 350

Pro Trp Ser Leu Cys Ser Phe Thr Cys Gly Arg Gly Gln Arg Thr Arg
        355                 360                 365

Thr Arg Ser Cys Thr Pro Pro Gln Tyr Gly Gly Arg Pro Cys Glu Gly
    370                 375                 380

Pro Glu Thr His His Lys Pro Cys Asn Ile Ala Leu Cys Pro Val Asp
385                 390                 395                 400

Gly Gln Trp Gln Glu Trp Ser Ser Trp Ser Gln Cys Ser Val Thr Cys
                405                 410                 415

Ser Asn Gly Thr Gln Gln Arg Ser Arg Gln Cys Thr Ala Ala His
            420                 425                 430

Gly Gly Ser Glu Cys Arg Gly Pro Trp Ala Glu Ser Arg Glu Cys Tyr
        435                 440                 445

Asn Pro Glu Cys Thr Ala Asn Gly Gln Trp Asn Gln Trp Gly His Trp
    450                 455                 460

Ser Gly Cys Ser Lys Ser Cys Asp Gly Trp Glu Arg Arg Ile Arg
465                 470                 475                 480

Thr Cys Gln Gly Ala Val Ile Thr Gly Gln Gln Cys Glu Gly Thr Gly
                485                 490                 495

Glu Glu Val Arg Arg Cys Asn Glu Gln Arg Cys Pro Ala Pro Tyr Glu
            500                 505                 510

Ile Cys Pro Glu Asp Tyr Leu Met Ser Met Val Trp Lys Arg Thr Pro
        515                 520                 525

Ala Gly Asp Leu Ala Phe Asn Gln Cys Pro Leu Asn Ala Thr Gly Thr
    530                 535                 540

Thr Ser Arg Arg Cys Ser Leu Ser Leu His Gly Val Ala Phe Trp Glu
545                 550                 555                 560

Gln Pro Ser Phe Ala Arg Cys Ile Ser Asn Glu Tyr Arg His Leu Gln
                565                 570                 575

His Ser Ile Lys Glu His Leu Ala Lys Gly Gln Arg Met Leu Ala Gly
            580                 585                 590

Asp Gly Met Ser Gln Val Thr Lys Thr Leu Leu Asp Leu Thr Gln Arg
        595                 600                 605

Lys Asn Phe Tyr Ala Gly Asp Leu Leu Met Ser Val Glu Ile Leu Arg
    610                 615                 620

Asn Val Thr Asp Thr Phe Lys Arg Ala Ser Tyr Ile Pro Ala Ser Asp
625                 630                 635                 640

Gly Val Gln Asn Phe Phe Gln Ile Val Ser Asn Leu Leu Asp Glu Glu
                645                 650                 655

Asn Lys Glu Lys Trp Glu Asp Ala Gln Gln Ile Tyr Pro Gly Ser Ile
            660                 665                 670

Glu Leu Met Gln Val Ile Glu Asp Phe Ile His Ile Val Gly Met Gly
        675                 680                 685

Met Met Asp Phe Gln Asn Ser Tyr Leu Met Thr Gly Asn Val Val Ala
    690                 695                 700

Ser Ile Gln Lys Leu Pro Ala Ala Ser Val Leu Thr Asp Ile Asn Phe
705                 710                 715                 720

Pro Met Lys Gly Arg Lys Gly Met Val Asp Trp Ala Arg Asn Ser Glu
                725                 730                 735

Asp Arg Val Val Ile Pro Lys Ser Ile Phe Thr Pro Val Ser Ser Lys
            740                 745                 750

Glu Leu Asp Glu Ser Ser Val Phe Val Leu Gly Ala Val Leu Tyr Lys

-continued

```
                755                 760                 765
Asn Leu Asp Leu Ile Leu Pro Thr Leu Arg Asn Tyr Thr Val Ile Asn
770                 775                 780

Ser Lys Ile Ile Val Val Thr Ile Arg Pro Glu Pro Lys Thr Thr Asp
785                 790                 795                 800

Ser Phe Leu Glu Ile Glu Leu Ala His Leu Ala Asn Gly Thr Leu Asn
                805                 810                 815

Pro Tyr Cys Val Leu Trp Asp Asp Ser Lys Thr Asn Glu Ser Leu Gly
                820                 825                 830

Thr Trp Ser Thr Gln Gly Cys Lys Thr Val Leu Thr Asp Ala Ser His
                835                 840                 845

Thr Lys Cys Leu Cys Asp Arg Leu Ser Thr Phe Ala Ile Leu Ala Gln
850                 855                 860

Gln Pro Arg Glu Ile Ile Met Glu Ser Ser Gly Thr Pro Ser Val Thr
865                 870                 875                 880

Leu Ile Val Gly Ser Gly Leu Ser Cys Leu Ala Leu Ile Thr Leu Ala
                885                 890                 895

Val Val Tyr Ala Ala Leu Trp Arg Tyr Ile Arg Ser Glu Arg Ser Ile
                900                 905                 910

Ile Leu Ile Asn Phe Cys Leu Ser Ile Ile Ser Ser Asn Ile Leu Ile
                915                 920                 925

Leu Val Gly Gln Thr Gln Thr His Asn Lys Ser Ile Cys Thr Thr Thr
930                 935                 940

Thr Ala Phe Leu His Phe Phe Leu Ala Ser Phe Cys Trp Val Leu
945                 950                 955                 960

Thr Glu Ala Trp Gln Ser Tyr Met Ala Val Thr Gly Lys Ile Arg Thr
                965                 970                 975

Arg Leu Ile Arg Lys Arg Phe Leu Cys Leu Gly Trp Gly Leu Pro Ala
                980                 985                 990

Leu Val Val Ala Thr Ser Val Gly Phe Thr Arg Thr Lys Gly Tyr Gly
                995                 1000                1005

Thr Asp His Tyr Cys Trp Leu Ser Leu Glu Gly Gly Leu Leu Tyr
1010                1015                1020

Ala Phe Val Gly Pro Ala Ala Val Val Leu Val Asn Met Val
1025                1030                1035

Ile Gly Ile Leu Val Phe Asn Lys Leu Val Ser Arg Asp Gly Ile
1040                1045                1050

Leu Asp Lys Lys Leu Lys His Arg Ala Gly Gln Met Ser Glu Pro
1055                1060                1065

His Ser Gly Leu Thr Leu Lys Cys Ala Lys Cys Gly Val Val Ser
1070                1075                1080

Thr Thr Ala Leu Ser Ala Thr Thr Ala Ser Asn Ala Met Ala Ser
1085                1090                1095

Leu Trp Ser Ser Cys Val Val Leu Pro Leu Leu Ala Leu Thr Trp
1100                1105                1110

Met Ser Ala Val Leu Ala Met Thr Asp Lys Arg Ser Ile Leu Phe
1115                1120                1125

Gln Ile Leu Phe Ala Val Phe Asp Ser Leu Gln Gly Phe Val Ile
1130                1135                1140

Val Met Val His Cys Ile Leu Arg Arg Glu Val Gln Asp Ala Phe
1145                1150                1155

Arg Cys Arg Leu Arg Asn Cys Gln Asp Pro Ile Asn Ala Asp Ser
1160                1165                1170
```

```
Ser Ser Ser Phe Pro Asn Gly His Ala Gln Ile Met Thr Asp Phe
1175                1180                1185

Glu Lys Asp Val Asp Ile Ala Cys Arg Ser Val Leu His Lys Asp
    1190                1195                1200

Ile Gly Pro Cys Arg Ala Ala Thr Ile Thr Gly Thr Leu Ser Arg
1205                1210                1215

Ile Ser Leu Asn Asp Asp Glu Glu Lys Gly Thr Asn Pro Glu
1220                1225                1230

Gly Leu Ser Tyr Ser Thr Leu Pro Gly Asn Val Ile Ser Lys Val
1235                1240                1245

Ile Ile Gln Gln Pro Thr Gly Leu His Met Pro Met Ser Met Asn
1250                1255                1260

Glu Leu Ser Asn Pro Cys Leu Lys Lys Glu Asn Ser Glu Leu Arg
    1265                1270                1275

Arg Thr Val Tyr Leu Cys Thr Asp Asp Asn Leu Arg Gly Ala Asp
    1280                1285                1290

Met Asp Ile Val His Pro Gln Glu Arg Met Met Glu Ser Asp Tyr
    1295                1300                1305

Ile Val Met Pro Arg Ser Ser Val Asn Asn Gln Pro Ser Met Lys
1310                1315                1320

Glu Glu Ser Lys Met Asn Ile Gly Met Glu Thr Leu Pro His Glu
1325                1330                1335

Arg Leu Leu His Tyr Lys Val Asn Pro Glu Phe Asn Met Asn Pro
    1340                1345                1350

Pro Val Met Asp Gln Phe Asn Met Asn Leu Glu Gln His Leu Ala
    1355                1360                1365

Pro Gln Glu His Met Gln Asn Leu Pro Phe Glu Pro Arg Thr Ala
    1370                1375                1380

Val Lys Asn Phe Met Ala Ser Glu Leu Asp Asp Asn Ala Gly Leu
    1385                1390                1395

Ser Arg Ser Glu Thr Gly Ser Thr Ile Ser Met Ser Ser Leu Glu
    1400                1405                1410

Arg Arg Lys Ser Arg Tyr Ser Asp Leu Asp Phe Glu Lys Val Met
    1415                1420                1425

His Thr Arg Lys Arg His Met Glu Leu Phe Gln Glu Leu Asn Gln
    1430                1435                1440

Lys Phe Gln Thr Leu Asp Arg Phe Arg Asp Ile Pro Asn Thr Ser
    1445                1450                1455

Ser Met Glu Asn Pro Ala Pro Asn Lys Asn Pro Trp Asp Thr Phe
    1460                1465                1470

Lys Asn Pro Ser Glu Tyr Pro His Tyr Thr Thr Ile Asn Val Leu
    1475                1480                1485

Asp Thr Glu Ala Lys Asp Ala Leu Glu Leu Arg Pro Ala Glu Trp
    1490                1495                1500

Glu Lys Cys Leu Asn Leu Pro Leu Asp Val Gln Glu Gly Asp Phe
    1505                1510                1515

Gln Thr Glu Val
    1520

<210> SEQ ID NO 36
<211> LENGTH: 879
<212> TYPE: PRT
<213> ORGANISM: human
```

```
<400> SEQUENCE: 36

Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Gly Arg Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Ala Asn Ala Ser Phe Thr Trp Val Ala Ser Asp Gly Trp Gly
    290                 295                 300

Ala Gln Glu Ser Ile Ile Lys Gly Ser Glu His Val Ala Tyr Gly Ala
305                 310                 315                 320

Ile Thr Leu Glu Leu Ala Ser Gln Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Arg Val Cys Asp Lys His Leu Ala Ile Asp Ser Ser Asn Tyr
    370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415
```

```
Lys Leu Cys Asp Ala Met Lys Ile Leu Asp Gly Lys Lys Leu Tyr Lys
                420                 425                 430

Asp Tyr Leu Leu Lys Ile Asn Phe Thr Ala Pro Phe Asn Pro Asn Lys
            435                 440                 445

Asp Ala Asp Ser Ile Val Lys Phe Asp Thr Phe Gly Asp Gly Met Gly
450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
                485                 490                 495

Ile His Trp Ser Arg Asn Ser Val Pro Thr Ser Gln Cys Ser Asp Pro
                500                 505                 510

Cys Ala Pro Asn Glu Met Lys Asn Met Gln Pro Gly Asp Val Cys Cys
            515                 520                 525

Trp Ile Cys Ile Pro Cys Glu Pro Tyr Glu Tyr Leu Ala Asp Glu Phe
            530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
                565                 570                 575

Ala Ile Gly Pro Val Thr Ile Ala Cys Leu Gly Phe Met Cys Thr Cys
                580                 585                 590

Met Val Val Thr Val Phe Ile Lys His Asn Asn Thr Pro Leu Val Lys
                595                 600                 605

Ala Ser Gly Arg Glu Leu Cys Tyr Ile Leu Leu Phe Gly Val Gly Leu
            610                 615                 620

Ser Tyr Cys Met Thr Phe Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
                645                 650                 655

Ser Ala Leu Leu Thr Lys Thr Asn Cys Ile Ala Arg Ile Phe Asp Gly
                660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
                725                 730                 735

Met Leu Ile Ser Leu Thr Tyr Asp Val Ile Leu Val Ile Leu Cys Thr
                740                 745                 750

Val Tyr Ala Phe Lys Thr Arg Lys Cys Pro Glu Asn Phe Asn Glu Ala
            755                 760                 765

Lys Phe Ile Gly Phe Thr Met Tyr Thr Thr Cys Ile Ile Trp Leu Ala
            770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
                805                 810                 815

Cys Leu Phe Ala Pro Lys Val His Ile Ile Leu Phe Gln Pro Gln Lys
            820                 825                 830
```

```
Asn Val Val Thr His Arg Leu His Leu Asn Arg Phe Ser Val Ser Gly
            835                 840                 845

Thr Gly Thr Thr Tyr Ser Gln Ser Ser Ala Ser Thr Tyr Val Pro Thr
850                     855                 860

Val Cys Asn Gly Arg Glu Val Leu Asp Ser Thr Thr Ser Ser Leu
865                 870                 875

<210> SEQ ID NO 37
<211> LENGTH: 620
<212> TYPE: PRT
<213> ORGANISM: human

<400> SEQUENCE: 37

Met Pro Ser Glu Arg Cys Leu Ser Ile Gln Glu Met Leu Thr Gly Gln
1               5                   10                  15

Arg Leu Cys His Ser Glu Ser His Asn Asp Ser Val Leu Ala Ala Leu
            20                  25                  30

Asn Gln Gln Arg Ser Asp Gly Ile Leu Cys Asp Ile Thr Leu Ile Ala
        35                  40                  45

Glu Glu Gln Lys Phe His Ala His Lys Ala Val Leu Ala Ala Cys Ser
    50                  55                  60

Asp Tyr Phe Arg Ala Met Phe Ser Leu Cys Met Val Glu Ser Gly Ala
65                  70                  75                  80

Asp Glu Val Asn Leu His Gly Val Thr Ser Leu Gly Leu Lys Gln Ala
                85                  90                  95

Leu Glu Phe Ala Tyr Thr Gly Gln Ile Leu Leu Glu Pro Gly Val Ile
            100                 105                 110

Gln Asp Val Leu Ala Ala Gly Ser His Leu Gln Leu Leu Glu Leu Leu
        115                 120                 125

Asn Leu Cys Ser His Tyr Leu Ile Gln Glu Leu Asn Ser Phe Asn Tyr
    130                 135                 140

Leu Asp Leu Tyr Arg Leu Ala Asp Leu Phe Asn Leu Thr Leu Leu Glu
145                 150                 155                 160

Lys Ala Val Ile Asp Phe Leu Val Lys His Leu Ser Glu Leu Leu Lys
                165                 170                 175

Ser Arg Pro Glu Glu Val Leu Thr Leu Pro Tyr Cys Leu Leu Gln Glu
            180                 185                 190

Val Leu Lys Ser Asp Arg Leu Thr Ser Leu Ser Glu Glu Gln Ile Trp
        195                 200                 205

Gln Leu Ala Val Arg Trp Leu Glu His Asn Cys His Tyr Gln Tyr Met
    210                 215                 220

Asp Glu Leu Leu Gln Tyr Ile Arg Phe Gly Leu Met Asp Val Asp Thr
225                 230                 235                 240

Leu His Thr Val Ala Leu Ser His Pro Leu Val Gln Ala Ser Glu Thr
                245                 250                 255

Ala Thr Ala Leu Val Asn Glu Ala Leu Glu Tyr His Gln Ser Ile Tyr
            260                 265                 270

Ala Gln Pro Val Trp Gln Thr Arg Arg Thr Lys Pro Arg Phe Gln Ser
        275                 280                 285

Asp Thr Leu Tyr Ile Ile Gly Gly Lys Lys Arg Glu Val Cys Lys Val
    290                 295                 300

Lys Glu Leu Arg Tyr Phe Asn Pro Val Asp Gln Glu Asn Ala Leu Ile
305                 310                 315                 320

Ala Ala Ile Ala Asn Trp Ser Glu Leu Ala Pro Met Pro Val Gly Arg
                325                 330                 335
```

Ser His His Cys Val Ala Val Met Gly Asp Phe Leu Phe Val Ala Gly
            340                 345                 350

Gly Glu Val Glu His Ala Ser Gly Arg Thr Cys Ala Val Arg Thr Ala
            355                 360                 365

Cys Arg Tyr Asp Pro Arg Ser Asn Ser Trp Ala Glu Ile Ala Pro Met
370                 375                 380

Lys Asn Cys Arg Glu His Phe Val Leu Gly Ala Met Glu Glu Tyr Leu
385                 390                 395                 400

Tyr Ala Val Gly Gly Arg Asn Glu Leu Arg Gln Val Leu Pro Thr Val
            405                 410                 415

Glu Arg Tyr Cys Pro Lys Lys Asn Lys Trp Thr Phe Val Gln Ser Phe
            420                 425                 430

Asp Arg Ser Leu Ser Cys His Ala Gly Tyr Val Ala Asp Gly Leu Leu
            435                 440                 445

Trp Ile Ser Gly Gly Val Thr Asn Thr Ala Gln Tyr Gln Asn Arg Leu
            450                 455                 460

Met Val Tyr Glu Pro Asn Gln Asn Lys Trp Ile Ser Arg Ser Pro Met
465                 470                 475                 480

Leu Gln Arg Arg Val Tyr His Ser Met Ala Ala Val Gln Arg Lys Leu
            485                 490                 495

Tyr Val Leu Gly Gly Asn Asp Leu Asp Tyr Asn Asn Asp Arg Ile Leu
            500                 505                 510

Val Arg His Ile Asp Ser Tyr Asn Ile Asp Thr Asp Gln Trp Thr Arg
            515                 520                 525

Cys Asn Phe Asn Leu Leu Thr Gly Gln Asn Glu Ser Gly Val Ala Val
530                 535                 540

His Asn Gly Arg Ile Tyr Leu Val Gly Gly Tyr Ser Ile Trp Thr Asn
545                 550                 555                 560

Glu Pro Leu Ala Cys Ile Gln Val Leu Asp Val Ser Arg Glu Gly Lys
            565                 570                 575

Glu Glu Val Phe Tyr Gly Pro Thr Leu Pro Phe Ala Ser Asn Gly Ile
            580                 585                 590

Ala Ala Cys Phe Leu Pro Ala Pro Tyr Phe Thr Cys Pro Asn Leu Gln
            595                 600                 605

Thr Leu Gln Val Pro His His Arg Ile Gly Thr Ile
610                 615                 620

<210> SEQ ID NO 38
<211> LENGTH: 707
<212> TYPE: PRT
<213> ORGANISM: human

<400> SEQUENCE: 38

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
            50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr

```
                85                  90                  95
Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
            130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Val Pro Thr Arg Phe Gly Asn
            210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
            275                 280                 285

Gln Phe Pro Phe Ile Phe Gln Gly Gln Ser Tyr Ser Ala Cys Thr Thr
            290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
            370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Thr Pro Gln Pro Thr Ala Pro
            450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510
```

```
Asp Asp Ala Cys Asn Val Asn Ile Phe Asp Ala Ile Ala Glu Ile Gly
        515                 520                 525

Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
        610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
        690                 695                 700

Pro Glu Asp
705

<210> SEQ ID NO 39
<211> LENGTH: 523
<212> TYPE: PRT
<213> ORGANISM: human

<400> SEQUENCE: 39

Met Ser Leu Val Ser Gln Asn Ala Arg His Cys Ser Ala Glu Ile Thr
1               5                   10                  15

Ala Asp Tyr Gly Asp Gly Arg Gly Glu Ile Gln Ala Thr Asn Ala Ser
                20                  25                  30

Gly Ser Pro Thr Ser Met Leu Val Val Asp Ala Pro Gln Cys Pro Gln
            35                  40                  45

Ala Pro Ile Asn Ser Gln Cys Val Asn Thr Ser Gln Ala Val Gln Asp
        50                  55                  60

Pro Asn Asp Leu Glu Val Leu Ile Asp Glu Gln Ser Arg Arg Leu Gly
65                  70                  75                  80

Ala Leu Arg Val His Asp Pro Leu Glu Asp Arg Ser Ile Ala Leu Val
                85                  90                  95

Asn Phe Met Arg Met Lys Ser Gln Thr Glu Gly Ser Ile Gln Gln Ser
            100                 105                 110

Glu Met Leu Glu Phe Leu Arg Glu Tyr Ser Asp Gln Phe Pro Glu Ile
        115                 120                 125

Leu Arg Arg Ala Ser Ala His Leu Asp Gln Val Phe Gly Leu Asn Leu
    130                 135                 140

Arg Val Ile Asp Pro Gln Ala Asp Thr Tyr Asn Leu Val Ser Lys Arg
145                 150                 155                 160

Gly Phe Gln Ile Thr Asp Arg Ile Ala Glu Ser Leu Asp Met Pro Lys
```

165                 170                 175
Ala Ser Leu Leu Ala Leu Val Leu Gly His Ile Leu Leu Asn Gly Asn
            180                 185                 190

Arg Ala Arg Glu Ala Ser Ile Trp Asp Leu Leu Lys Val Asp Met
        195                 200                 205

Trp Asp Lys Pro Gln Arg Ile Asn Asn Leu Phe Gly Asn Thr Arg Asn
210                 215                 220

Leu Leu Thr Thr Asp Phe Val Cys Met Arg Phe Leu Glu Tyr Trp Pro
225                 230                 235                 240

Val Tyr Gly Thr Asn Pro Leu Glu Phe Glu Phe Leu Trp Gly Ser Arg
                245                 250                 255

Ala His Arg Glu Ile Thr Lys Met Glu Ala Leu Lys Phe Val Ser Asp
            260                 265                 270

Ala His Asp Glu Glu Pro Trp Ser Trp Pro Glu Glu Tyr Asn Lys Ala
        275                 280                 285

Leu Glu Gly Asp Lys Thr Lys Glu Arg Ser Leu Thr Ala Gly Leu Glu
    290                 295                 300

Phe Trp Ser Glu Asp Thr Met Asn Asp Lys Ala Asn Asp Leu Val Gln
305                 310                 315                 320

Leu Ala Ile Ser Val Thr Glu Glu Met Leu Pro Ile His Gln Asp Glu
                325                 330                 335

Leu Leu Ala His Thr Gly Lys Glu Phe Glu Asp Val Phe Pro Asn Ile
            340                 345                 350

Leu Asn Arg Ala Thr Leu Ile Leu Asp Met Phe Tyr Gly Leu Ser Leu
        355                 360                 365

Ile Glu Val Asp Thr Ser Glu His Ile Tyr Leu Leu Val Gln Gln Pro
    370                 375                 380

Glu Ser Glu Glu Glu Gln Val Met Leu Glu Ser Leu Gly Arg Pro Thr
385                 390                 395                 400

Gln Glu Tyr Val Met Pro Ile Leu Gly Leu Ile Phe Leu Met Gly Asn
                405                 410                 415

Arg Val Lys Glu Ala Asn Val Trp Asn Leu Leu Arg Arg Phe Ser Val
            420                 425                 430

Asp Val Gly Arg Lys His Ser Ile Thr Arg Lys Leu Met Arg Gln Arg
        435                 440                 445

Tyr Leu Glu Cys Arg Pro Leu Ser Tyr Ser Asn Pro Val Glu Tyr Glu
    450                 455                 460

Leu Leu Trp Gly Pro Arg Ala His His Glu Thr Ile Lys Met Lys Val
465                 470                 475                 480

Leu Glu Tyr Met Ala Arg Leu Tyr Arg Lys Arg Pro Gln Asn Trp Pro
                485                 490                 495

Glu Gln Tyr Arg Glu Ala Val Glu Asp Glu Glu Ala Arg Ala Lys Ser
            500                 505                 510

Glu Ala Thr Ile Met Phe Phe Leu Asp Pro Thr
        515                 520

<210> SEQ ID NO 40
<211> LENGTH: 720
<212> TYPE: PRT
<213> ORGANISM: human

<400> SEQUENCE: 40

Met Ser Glu Gly Ala Ala Ala Ser Pro Gly Ala Ala Ser Ala
1               5                   10                  15

-continued

```
Ala Ala Ala Ser Ala Glu Glu Gly Thr Ala Ala Ala Ala Ala
             20              25              30

Ala Ala Gly Gly Gly Pro Asp Gly Gly Gly Ala Ala Glu Pro
         35              40              45

Pro Arg Glu Leu Arg Cys Ser Asp Cys Ile Val Trp Asn Arg Gln Gln
 50              55              60

Thr Trp Leu Cys Val Val Pro Leu Phe Ile Gly Phe Ile Gly Leu Gly
65              70              75              80

Leu Ser Leu Met Leu Leu Lys Trp Ile Val Val Gly Ser Val Lys Glu
             85              90              95

Tyr Val Pro Thr Asp Leu Val Asp Ser Lys Gly Met Gly Gln Asp Pro
            100             105             110

Phe Phe Leu Ser Lys Pro Ser Ser Phe Pro Lys Ala Met Glu Thr Thr
            115             120             125

Thr Thr Thr Thr Ser Thr Thr Ser Pro Ala Thr Pro Ser Ala Gly Gly
            130             135             140

Ala Ala Ser Ser Arg Thr Pro Asn Arg Ile Ser Thr Arg Leu Thr Thr
145             150             155             160

Ile Thr Arg Ala Pro Thr Arg Phe Pro Gly His Arg Val Pro Ile Arg
                165             170             175

Ala Ser Pro Arg Ser Thr Thr Ala Arg Asn Thr Ala Ala Pro Ala Thr
            180             185             190

Val Pro Ser Thr Thr Ala Pro Phe Phe Ser Ser Ser Thr Leu Gly Ser
            195             200             205

Arg Pro Pro Val Pro Gly Thr Pro Ser Thr Gln Ala Met Pro Ser Trp
210             215             220

Pro Thr Ala Ala Tyr Ala Thr Ser Ser Tyr Leu His Asp Ser Thr Pro
225             230             235             240

Ser Trp Thr Leu Ser Pro Phe Gln Asp Ala Ala Ser Ser Ser Ser Ser
            245             250             255

Ser Ser Ser Ser Ala Thr Thr Thr Thr Pro Glu Thr Ser Thr Ser Pro
            260             265             270

Lys Phe His Thr Thr Thr Tyr Ser Thr Glu Arg Ser Glu His Phe Lys
            275             280             285

Pro Cys Arg Asp Lys Asp Leu Ala Tyr Cys Leu Asn Asp Gly Glu Cys
290             295             300

Phe Val Ile Glu Thr Leu Thr Gly Ser His Lys His Cys Arg Cys Lys
305             310             315             320

Glu Gly Tyr Gln Gly Val Arg Cys Asp Gln Phe Leu Pro Lys Thr Asp
            325             330             335

Ser Ile Leu Ser Asp Pro Thr Asp His Leu Gly Ile Glu Phe Met Glu
            340             345             350

Ser Glu Glu Val Tyr Gln Arg Gln Val Leu Ser Ile Ser Cys Ile Ile
            355             360             365

Phe Gly Ile Val Ile Val Gly Met Phe Cys Ala Ala Phe Tyr Phe Lys
            370             375             380

Ser Lys Lys Gln Ala Lys Gln Ile Gln Glu Gln Leu Lys Val Pro Gln
385             390             395             400

Asn Gly Lys Ser Tyr Ser Leu Lys Ala Ser Ser Thr Met Ala Lys Ser
            405             410             415

Glu Asn Leu Val Lys Ser His Val Gln Leu Gln Asn Tyr Ser Lys Val
            420             425             430

Glu Arg His Pro Val Thr Ala Leu Glu Lys Met Met Glu Ser Ser Phe
```

```
                        435                 440                 445
Val Gly Pro Gln Ser Phe Pro Glu Val Pro Pro Asp Arg Gly Ser
    450                 455                 460

Gln Ser Val Lys His His Arg Ser Leu Ser Cys Cys Ser Pro Gly
465                 470                 475                 480

Gln Arg Ser Gly Met Leu His Arg Asn Ala Phe Arg Thr Pro Pro
                485                 490                 495

Ser Pro Arg Ser Arg Leu Gly Gly Ile Val Gly Pro Ala Tyr Gln Gln
            500                 505                 510

Leu Glu Glu Ser Arg Ile Pro Asp Gln Asp Thr Ile Pro Cys Gln Gly
            515                 520                 525

Ile Glu Val Arg Lys Thr Ile Ser His Leu Pro Ile Gln Leu Trp Cys
        530                 535                 540

Val Glu Arg Pro Leu Asp Leu Lys Tyr Ser Ser Ser Gly Leu Lys Thr
545                 550                 555                 560

Gln Arg Asn Thr Ser Ile Asn Met Gln Leu Pro Ser Arg Glu Thr Asn
                565                 570                 575

Pro Tyr Phe Asn Ser Leu Glu Gln Lys Asp Leu Val Gly Tyr Ser Ser
            580                 585                 590

Thr Arg Ala Ser Ser Val Pro Ile Ile Pro Ser Val Gly Leu Glu Glu
        595                 600                 605

Thr Cys Leu Gln Met Pro Gly Ile Ser Glu Val Lys Ser Ile Lys Trp
610                 615                 620

Cys Lys Asn Ser Tyr Ser Ala Asp Val Val Asn Val Ser Ile Pro Val
625                 630                 635                 640

Ser Asp Cys Leu Ile Ala Glu Gln Gln Glu Val Lys Ile Leu Leu Glu
                645                 650                 655

Thr Val Gln Glu Gln Ile Arg Ile Leu Thr Asp Ala Arg Arg Ser Glu
            660                 665                 670

Asp Tyr Glu Leu Ala Ser Val Glu Thr Glu Asp Ser Ala Ser Glu Asn
        675                 680                 685

Thr Ala Phe Leu Pro Leu Ser Pro Thr Ala Lys Ser Glu Arg Glu Ala
        690                 695                 700

Gln Phe Val Leu Arg Asn Glu Ile Gln Arg Asp Ser Ala Leu Thr Lys
705                 710                 715                 720

<210> SEQ ID NO 41
<211> LENGTH: 977
<212> TYPE: PRT
<213> ORGANISM: human

<400> SEQUENCE: 41

Met Lys Pro Ser Ile Ala Glu Met Leu His Arg Gly Arg Met Leu Trp
1               5                   10                  15

Ile Ile Leu Leu Ser Thr Ile Ala Leu Gly Trp Thr Thr Pro Ile Pro
            20                  25                  30

Leu Ile Glu Asp Ser Glu Glu Ile Asp Glu Pro Cys Phe Asp Pro Cys
        35                  40                  45

Tyr Cys Glu Val Lys Glu Ser Leu Phe His Ile His Cys Asp Ser Lys
    50                  55                  60

Gly Phe Thr Asn Ile Ser Gln Ile Thr Glu Phe Trp Ser Arg Pro Phe
65              70                  75                  80

Lys Leu Tyr Leu Gln Arg Asn Ser Met Arg Lys Leu Tyr Thr Asn Ser
                85                  90                  95
```

```
Phe Leu His Leu Asn Asn Ala Val Ser Ile Asn Leu Gly Asn Asn Ala
            100                 105                 110

Leu Gln Asp Ile Gln Thr Gly Ala Phe Asn Gly Leu Lys Ile Leu Lys
        115                 120                 125

Arg Leu Tyr Leu His Glu Asn Lys Leu Asp Val Phe Arg Asn Asp Thr
    130                 135                 140

Phe Leu Gly Leu Glu Ser Leu Glu Tyr Leu Gln Ala Asp Tyr Asn Val
145                 150                 155                 160

Ile Lys Arg Ile Glu Ser Gly Ala Phe Arg Asn Leu Ser Lys Leu Arg
                165                 170                 175

Val Leu Ile Leu Asn Asp Asn Leu Ile Pro Met Leu Pro Thr Asn Leu
            180                 185                 190

Phe Lys Ala Val Ser Leu Thr His Leu Asp Leu Arg Gly Asn Arg Leu
        195                 200                 205

Lys Val Leu Phe Tyr Arg Gly Met Leu Asp His Ile Gly Arg Ser Leu
    210                 215                 220

Met Glu Leu Gln Leu Glu Glu Asn Pro Trp Asn Cys Thr Cys Glu Ile
225                 230                 235                 240

Val Gln Leu Lys Ser Trp Leu Glu Arg Ile Pro Tyr Thr Ala Leu Val
                245                 250                 255

Gly Asp Ile Thr Cys Glu Thr Pro Phe His Phe His Gly Lys Asp Leu
            260                 265                 270

Arg Glu Ile Arg Lys Thr Glu Leu Cys Pro Leu Leu Ser Asp Ser Glu
        275                 280                 285

Val Glu Ala Ser Leu Gly Ile Pro His Ser Ser Ser Lys Glu Asn
290                 295                 300

Ala Trp Pro Thr Lys Pro Ser Ser Met Leu Ser Ser Val His Phe Thr
305                 310                 315                 320

Ala Ser Ser Val Glu Tyr Lys Ser Ser Asn Lys Gln Pro Lys Pro Thr
                325                 330                 335

Lys Gln Pro Arg Thr Pro Arg Pro Ser Thr Ser Gln Ala Leu Tyr
        340                 345                 350

Pro Gly Pro Asn Gln Pro Ile Ala Pro Tyr Gln Thr Arg Pro Pro
355                 360                 365

Ile Pro Ile Ile Cys Pro Thr Gly Cys Thr Cys Asn Leu His Ile Asn
    370                 375                 380

Asp Leu Gly Leu Thr Val Asn Cys Lys Glu Arg Gly Phe Asn Asn Ile
385                 390                 395                 400

Ser Glu Leu Leu Pro Arg Pro Leu Asn Ala Lys Lys Leu Tyr Leu Ser
                405                 410                 415

Ser Asn Leu Ile Gln Lys Ile Tyr Arg Ser Asp Phe Trp Asn Phe Ser
            420                 425                 430

Ser Leu Asp Leu Leu His Leu Gly Asn Asn Arg Ile Ser Tyr Val Gln
        435                 440                 445

Asp Gly Ala Phe Ile Asn Leu Pro Asn Leu Lys Ser Leu Phe Leu Asn
    450                 455                 460

Gly Asn Asp Ile Glu Lys Leu Thr Pro Gly Met Phe Arg Gly Leu Gln
465                 470                 475                 480

Ser Leu His Tyr Leu Tyr Phe Glu Phe Asn Val Ile Arg Glu Ile Gln
                485                 490                 495

Pro Ala Ala Phe Ser Leu Met Pro Asn Leu Lys Leu Leu Phe Leu Asn
            500                 505                 510

Asn Asn Leu Leu Arg Thr Leu Pro Thr Asp Ala Phe Ala Gly Thr Ser
```

```
            515                 520                 525
Leu Ala Arg Leu Asn Leu Arg Lys Asn Tyr Phe Leu Tyr Leu Pro Val
            530                 535                 540
Ala Gly Val Leu Glu His Leu Asn Ala Ile Val Gln Ile Asp Leu Asn
545                 550                 555                 560
Glu Asn Pro Trp Asp Cys Thr Cys Asp Leu Val Pro Phe Lys Gln Trp
                565                 570                 575
Ile Glu Thr Ile Ser Ser Val Ser Val Val Gly Asp Val Leu Cys Arg
                580                 585                 590
Ser Pro Glu Asn Leu Thr His Arg Asp Val Arg Thr Ile Glu Leu Glu
                595                 600                 605
Val Leu Cys Pro Glu Met Leu His Val Ala Pro Ala Gly Glu Ser Pro
            610                 615                 620
Ala Gln Pro Gly Asp Ser His Leu Ile Gly Ala Pro Thr Ser Ala Ser
625                 630                 635                 640
Pro Tyr Glu Phe Ser Pro Pro Gly Gly Pro Val Pro Leu Ser Val Leu
                645                 650                 655
Ile Leu Ser Leu Leu Val Leu Phe Phe Ser Ala Val Phe Val Ala Ala
                660                 665                 670
Gly Leu Phe Ala Tyr Val Leu Arg Arg Arg Lys Lys Leu Pro Phe
            675                 680                 685
Arg Ser Lys Arg Gln Glu Gly Val Asp Leu Thr Gly Ile Gln Met Gln
690                 695                 700
Cys His Arg Leu Phe Glu Asp Gly Gly Gly Gly Gly Ser Gly
705                 710                 715                 720
Gly Gly Gly Arg Pro Thr Leu Ser Ser Pro Glu Lys Ala Pro Pro Val
                725                 730                 735
Gly His Val Tyr Glu Tyr Ile Pro His Pro Val Thr Gln Met Cys Asn
                740                 745                 750
Asn Pro Ile Tyr Lys Pro Arg Glu Glu Glu Val Ala Val Ser Ser
            755                 760                 765
Ala Gln Glu Ala Gly Ser Ala Glu Arg Gly Gly Pro Gly Thr Gln Pro
770                 775                 780
Pro Gly Met Gly Glu Ala Leu Leu Gly Ser Glu Gln Phe Ala Glu Thr
785                 790                 795                 800
Pro Lys Glu Asn His Ser Asn Tyr Arg Thr Leu Leu Glu Lys Glu Lys
                805                 810                 815
Glu Trp Ala Leu Ala Val Ser Ser Ser Gln Leu Asn Thr Ile Val Thr
                820                 825                 830
Val Asn His His His Pro His His Pro Ala Val Gly Val Ser Gly
            835                 840                 845
Val Val Gly Gly Thr Gly Gly Asp Leu Ala Gly Phe Arg His His Glu
            850                 855                 860
Lys Asn Gly Gly Val Val Leu Phe Pro Gly Gly Gly Cys Gly Ser
865                 870                 875                 880
Gly Ser Met Leu Leu Asp Arg Glu Arg Pro Gln Pro Ala Pro Cys Thr
                885                 890                 895
Val Gly Phe Val Asp Cys Leu Tyr Gly Thr Val Pro Lys Leu Lys Glu
                900                 905                 910
Leu His Val His Pro Pro Gly Met Gln Tyr Pro Asp Leu Gln Gln Asp
            915                 920                 925
Ala Arg Leu Lys Glu Thr Leu Leu Phe Ser Ala Gly Lys Gly Phe Thr
            930                 935                 940
```

```
Asp His Gln Thr Gln Lys Ser Asp Tyr Leu Glu Leu Arg Ala Lys Leu
945                 950                 955                 960

Gln Thr Lys Pro Asp Tyr Leu Glu Val Leu Glu Lys Thr Thr Tyr Arg
            965                 970                 975

Phe

<210> SEQ ID NO 42
<211> LENGTH: 247
<212> TYPE: PRT
<213> ORGANISM: human

<400> SEQUENCE: 42

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 43
<211> LENGTH: 223
<212> TYPE: PRT
<213> ORGANISM: human

<400> SEQUENCE: 43

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30
```

```
Gly Leu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
 50                  55                  60

Lys Gln Ile Glu Glu Leu Lys Gly Gln Glu Val Ser Pro Lys Val Tyr
 65                  70                  75                  80

Phe Met Lys Gln Thr Ile Gly Asn Ser Cys Gly Thr Ile Gly Leu Ile
                 85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220

<210> SEQ ID NO 44
<211> LENGTH: 17
<212> TYPE: DNA
<213> ORGANISM: Artificial Sequence
<220> FEATURE:
<223> OTHER INFORMATION: synthetic

<400> SEQUENCE: 44
tttttttttt tttttg                                                  17

<210> SEQ ID NO 45
<211> LENGTH: 445
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Citrulline
<220> FEATURE:
<221> NAME/KEY: MISC_FEATURE
<222> LOCATION: (46)..(46)
<223> OTHER INFORMATION: Citrulline
<220> FEATURE:
<221> NAME/KEY: MISC_FEATURE
<222> LOCATION: (62)..(62)
<223> OTHER INFORMATION: Citrulline
<220> FEATURE:
<221> NAME/KEY: MISC_FEATURE
<222> LOCATION: (77)..(77)
<223> OTHER INFORMATION: Citrulline
<220> FEATURE:
<221> NAME/KEY: MISC_FEATURE
<222> LOCATION: (86)..(86)
<223> OTHER INFORMATION: Citrulline
<220> FEATURE:
<221> NAME/KEY: MISC_FEATURE
<222> LOCATION: (121)..(121)
<223> OTHER INFORMATION: Citrulline
```

```
<220> FEATURE:
<221> NAME/KEY: MISC_FEATURE
<222> LOCATION: (156)..(156)
<223> OTHER INFORMATION: Citrulline
<220> FEATURE:
<221> NAME/KEY: MISC_FEATURE
<222> LOCATION: (162)..(162)
<223> OTHER INFORMATION: Citrulline
<220> FEATURE:
<221> NAME/KEY: MISC_FEATURE
<222> LOCATION: (213)..(213)
<223> OTHER INFORMATION: Citrulline
<220> FEATURE:
<221> NAME/KEY: MISC_FEATURE
<222> LOCATION: (241)..(241)
<223> OTHER INFORMATION: Citrulline
<220> FEATURE:
<221> NAME/KEY: MISC_FEATURE
<222> LOCATION: (251)..(251)
<223> OTHER INFORMATION: Citrulline
<220> FEATURE:
<221> NAME/KEY: MISC_FEATURE
<222> LOCATION: (262)..(262)
<223> OTHER INFORMATION: Citrulline
<220> FEATURE:
<221> NAME/KEY: MISC_FEATURE
<222> LOCATION: (276)..(276)
<223> OTHER INFORMATION: Citrulline
<220> FEATURE:
<221> NAME/KEY: MISC_FEATURE
<222> LOCATION: (282)..(282)
<223> OTHER INFORMATION: Citrulline
<220> FEATURE:
<221> NAME/KEY: MISC_FEATURE
<222> LOCATION: (306)..(306)
<223> OTHER INFORMATION: Citrulline
<220> FEATURE:
<221> NAME/KEY: MISC_FEATURE
<222> LOCATION: (309)..(309)
<223> OTHER INFORMATION: Citrulline
<220> FEATURE:
<221> NAME/KEY: MISC_FEATURE
<222> LOCATION: (318)..(318)
<223> OTHER INFORMATION: Citrulline
<220> FEATURE:
<221> NAME/KEY: MISC_FEATURE
<222> LOCATION: (320)..(320)
<223> OTHER INFORMATION: Citrulline
<220> FEATURE:
<221> NAME/KEY: MISC_FEATURE
<222> LOCATION: (359)..(359)
<223> OTHER INFORMATION: Citrulline
<220> FEATURE:
<221> NAME/KEY: MISC_FEATURE
<222> LOCATION: (380)..(380)
<223> OTHER INFORMATION: Citrulline
<220> FEATURE:
<221> NAME/KEY: MISC_FEATURE
<222> LOCATION: (390)..(390)
<223> OTHER INFORMATION: Citrulline
<220> FEATURE:
<221> NAME/KEY: MISC_FEATURE
<222> LOCATION: (391)..(391)
<223> OTHER INFORMATION: Citrulline

<400> SEQUENCE: 45

Met Xaa Glu Ile Val His Leu Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Glu Xaa Ile Asn
        35                  40                  45

Val Tyr Tyr Asn Glu Ala Thr Gly Gly Lys Tyr Val Pro Xaa Ala Val
    50                  55                  60
```

-continued

Leu Val Asp Leu Glu Pro Gly Thr Met Asp Ser Val Xaa Ser Gly Pro
65                  70                  75                  80

Phe Gly Gln Ile Phe Xaa Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Xaa Lys Glu Ala Glu Ser Cys Asp
            115                 120                 125

Cys Leu Gln Gly Phe Gln Leu Thr His Ser Leu Gly Gly Thr Gly
    130                 135                 140

Ser Gly Met Gly Thr Leu Leu Ile Ser Lys Ile Xaa Glu Glu Tyr Pro
145                 150                 155                 160

Asp Xaa Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
            195                 200                 205

Asp Ile Cys Phe Xaa Thr Leu Lys Leu Thr Thr Pro Thr Tyr Gly Asp
210                 215                 220

Leu Asn His Leu Val Ser Ala Thr Met Ser Gly Val Thr Thr Cys Leu
225                 230                 235                 240

Xaa Phe Pro Gly Gln Leu Asn Ala Asp Leu Xaa Lys Leu Ala Val Asn
                245                 250                 255

Met Val Pro Phe Pro Xaa Leu His Phe Phe Met Pro Gly Phe Ala Pro
            260                 265                 270

Leu Thr Ser Xaa Gly Ser Gln Gln Tyr Xaa Ala Leu Thr Val Pro Glu
            275                 280                 285

Leu Thr Gln Gln Met Phe Asp Ala Lys Asn Met Met Ala Ala Cys Asp
            290                 295                 300

Pro Xaa His Gly Xaa Tyr Leu Thr Val Ala Ala Val Phe Xaa Gly Xaa
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Xaa Gly Leu Lys Met Ser Ala Thr Phe Ile
            355                 360                 365

Gly Asn Ser Thr Ala Ile Gln Glu Leu Phe Lys Xaa Ile Ser Glu Gln
370                 375                 380

Phe Thr Ala Met Phe Xaa Xaa Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Ala Glu Glu Val Ala
            435                 440                 445

<210> SEQ ID NO 46
<211> LENGTH: 15
<212> TYPE: PRT
<213> ORGANISM: artificial sequence
<220> FEATURE:
<223> OTHER INFORMATION: synthetic

```
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (15)..(15)
<223> OTHER INFORMATION: serine or no amino acid

<400> SEQUENCE: 46

Xaa Ile Arg Glu Glu Tyr Pro Asp Arg Ile Met Asn Thr Phe Xaa
1               5                   10                  15

<210> SEQ ID NO 47
<211> LENGTH: 451
<212> TYPE: PRT
<213> ORGANISM: human

<400> SEQUENCE: 47

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
                20                  25                  30

Asp Gly Gln Met Pro Ser Asp Lys Thr Ile Gly Gly Asp Asp Ser
            35                  40                  45

Phe Asn Thr Phe Phe Ser Glu Thr Gly Ala Gly Lys His Val Pro Arg
50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300
```

```
Cys Asp Pro Arg His Gly Lys Tyr Met Ala Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450

<210> SEQ ID NO 48
<211> LENGTH: 451
<212> TYPE: PRT
<213> ORGANISM: human

<400> SEQUENCE: 48

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220
```

```
Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
            245                 250                 255

Thr Asn Leu Val Pro Tyr Pro Arg Ile His Phe Pro Leu Ala Thr Tyr
        260                 265                 270

Ala Pro Val Ile Ser Ala Glu Lys Ala Tyr His Glu Gln Leu Ser Val
    275                 280                 285

Ala Glu Ile Thr Asn Ala Cys Phe Glu Pro Ala Asn Gln Met Val Lys
290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450

<210> SEQ ID NO 49
<211> LENGTH: 17
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (17)..(17)
<223> OTHER INFORMATION: aspartic acid or no amino acid

<400> SEQUENCE: 49

Xaa Tyr Met Ala Cys Cys Leu Leu Tyr Arg Gly Asp Val Val Pro Lys
1               5                   10                  15

Xaa

<210> SEQ ID NO 50
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: glutamic acid or no amino acid
<220> FEATURE:
<221> NAME/KEY: MISC_FEATURE
<222> LOCATION: (15)..(15)
<223> OTHER INFORMATION: glutamine or no amino acid at

<400> SEQUENCE: 50

Xaa Val Arg Thr Gly Thr Tyr Arg Gln Leu Phe His Pro Glu Xaa
1               5                   10                  15

<210> SEQ ID NO 51
<211> LENGTH: 422
<212> TYPE: PRT
<213> ORGANISM: human

<400> SEQUENCE: 51

Met Val Ser Glu Ser His His Glu Ala Leu Ala Ala Pro Pro Val Thr
1               5                   10                  15

Thr Val Ala Thr Val Leu Pro Ser Asn Ala Thr Glu Pro Ala Ser Pro
                20                  25                  30

Gly Glu Gly Lys Glu Asp Ala Phe Ser Lys Leu Lys Glu Lys Phe Met
            35                  40                  45

Asn Glu Leu His Lys Ile Pro Leu Pro Pro Trp Ala Leu Ile Ala Ile
50                  55                  60

Ala Ile Val Ala Val Leu Leu Val Leu Thr Cys Cys Phe Cys Ile Cys
65                  70                  75                  80

Lys Lys Cys Leu Phe Lys Lys Lys Asn Lys Lys Lys Gly Lys Glu Lys
                85                  90                  95

Gly Gly Lys Asn Ala Ile Asn Met Lys Asp Val Lys Asp Leu Gly Lys
            100                 105                 110

Thr Met Lys Asp Gln Ala Leu Lys Asp Asp Asp Ala Glu Thr Gly Leu
        115                 120                 125

Thr Asp Gly Glu Glu Lys Glu Glu Pro Lys Glu Glu Glu Lys Leu Gly
    130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Phe Glu Thr Lys Val His Arg Lys Thr Leu Asn Pro Val Phe Asn
        195                 200                 205

Glu Gln Phe Thr Phe Lys Val Pro Tyr Ser Glu Leu Gly Gly Lys Thr
    210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Glu Gln Glu
            260                 265                 270

Lys Leu Gly Asp Ile Cys Phe Ser Leu Arg Tyr Val Pro Thr Ala Gly
        275                 280                 285

Lys Leu Thr Val Val Ile Leu Glu Ala Lys Asn Leu Lys Lys Met Asp
    290                 295                 300

Val Gly Gly Leu Ser Asp Pro Tyr Val Lys Ile His Leu Met Gln Asn
305                 310                 315                 320
```

-continued

```
Gly Lys Arg Leu Lys Lys Lys Thr Thr Ile Lys Lys Asn Thr Leu
            325                 330                 335

Asn Pro Tyr Tyr Asn Glu Ser Phe Ser Phe Glu Val Pro Phe Glu Gln
        340                 345                 350

Ile Gln Lys Val Gln Val Val Thr Val Leu Asp Tyr Asp Lys Ile
        355                 360                 365

Gly Lys Asn Asp Ala Ile Gly Lys Val Phe Val Gly Tyr Asn Ser Thr
    370                 375                 380

Gly Ala Glu Leu Arg His Trp Ser Asp Met Leu Ala Asn Pro Arg Arg
385                 390                 395                 400

Pro Ile Ala Gln Trp His Thr Leu Gln Val Glu Glu Val Asp Ala
            405                 410                 415

Met Leu Ala Val Lys Lys
            420
```

<210> SEQ ID NO 52
<211> LENGTH: 42
<212> TYPE: PRT
<213> ORGANISM: human

<400> SEQUENCE: 52

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 53
<211> LENGTH: 12
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (12)..(12)
<223> OTHER INFORMATION: tyrosine or no amino acid

<400> SEQUENCE: 53

```
Xaa Ser Thr Leu Ala Arg Val Ile Val Asp Lys Xaa
1               5                   10
```

<210> SEQ ID NO 54
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (16)..(16)
<223> OTHER INFORMATION: arginine or no amino acid

<400> SEQUENCE: 54

```
Xaa Ile Thr Pro Gly Ala Arg Gly Ala Phe Ser Glu Glu Tyr Lys Xaa
1               5                   10                  15
```

<210> SEQ ID NO 55
<211> LENGTH: 1193
<212> TYPE: PRT
<213> ORGANISM: human

<400> SEQUENCE: 55

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys

```
            370                 375                 380
Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Ala Cys Asp Pro Asp Thr Gly Asp Cys Tyr
            420                 425                 430

Ser Gly Asp Glu Asn Pro Asp Ile Glu Cys Ala Asp Cys Pro Ile Gly
            435                 440                 445

Phe Tyr Asn Asp Pro His Asp Pro Arg Ser Cys Lys Pro Cys Pro Cys
    450                 455                 460

His Asn Gly Phe Ser Cys Ser Val Met Pro Glu Thr Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
            500                 505                 510

Pro Cys Gln Pro Cys Gln Cys Asn Asn Asn Val Asp Pro Ser Ala Ser
            515                 520                 525

Gly Asn Cys Asp Arg Leu Thr Gly Arg Cys Leu Lys Cys Ile His Asn
530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
            580                 585                 590

Cys Lys Pro Gly Phe Gly Gly Pro Asn Cys Glu His Gly Ala Phe Ser
            595                 600                 605

Cys Pro Ala Cys Tyr Asn Gln Val Lys Ile Gln Met Asp Gln Phe Met
        610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
            660                 665                 670

Ala Ser Arg Ser Leu Gly Leu Gln Leu Ala Lys Val Arg Ser Gln Glu
            675                 680                 685

Asn Ser Tyr Gln Ser Arg Leu Asp Asp Leu Lys Met Thr Val Glu Arg
690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
            770                 775                 780

Tyr Ser Lys Gln Ala Leu Ser Leu Val Arg Lys Ala Leu His Glu Gly
785                 790                 795                 800
```

```
Val Gly Ser Gly Ser Gly Ser Pro Asp Gly Ala Val Val Gln Gly Leu
            805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
            850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
            885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
            930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
            965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
            995                 1000                1005

Asn Gly Ala Gly Glu Ala Leu Glu Ile Ser Ser Glu Ile Glu Gln
    1010                1015                1020

Glu Ile Gly Ser Leu Asn Leu Glu Ala Asn Val Thr Ala Asp Gly
    1025                1030                1035

Ala Leu Ala Met Glu Lys Gly Leu Ala Ser Leu Lys Ser Glu Met
    1040                1045                1050

Arg Glu Val Glu Gly Glu Leu Glu Arg Lys Glu Leu Glu Phe Asp
    1055                1060                1065

Thr Asn Met Asp Ala Val Gln Met Val Ile Thr Glu Ala Gln Lys
    1070                1075                1080

Val Asp Thr Arg Ala Lys Asn Ala Gly Val Thr Ile Gln Asp Thr
    1085                1090                1095

Leu Asn Thr Leu Asp Gly Leu Leu His Leu Met Asp Gln Pro Leu
    1100                1105                1110

Ser Val Asp Glu Glu Gly Leu Val Leu Leu Glu Gln Lys Leu Ser
    1115                1120                1125

Arg Ala Lys Thr Gln Ile Asn Ser Gln Leu Arg Pro Met Met Ser
    1130                1135                1140

Glu Leu Glu Glu Arg Ala Arg Gln Gln Arg Gly His Leu His Leu
    1145                1150                1155

Leu Glu Thr Ser Ile Asp Gly Ile Leu Ala Asp Val Lys Asn Leu
    1160                1165                1170

Glu Asn Ile Arg Asp Asn Leu Pro Pro Gly Cys Tyr Asn Thr Gln
    1175                1180                1185

Ala Leu Glu Gln Gln
    1190
```

```
<210> SEQ ID NO 56
<211> LENGTH: 165
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (19)..(19)
<223> OTHER INFORMATION: Citrulline
<220> FEATURE:
<221> NAME/KEY: MISC_FEATURE
<222> LOCATION: (37)..(37)
<223> OTHER INFORMATION: Citrulline
<220> FEATURE:
<221> NAME/KEY: MISC_FEATURE
<222> LOCATION: (55)..(55)
<223> OTHER INFORMATION: Citrulline
<220> FEATURE:
<221> NAME/KEY: MISC_FEATURE
<222> LOCATION: (69)..(69)
<223> OTHER INFORMATION: Citrulline
<220> FEATURE:
<221> NAME/KEY: MISC_FEATURE
<222> LOCATION: (144)..(144)
<223> OTHER INFORMATION: Citrulline
<220> FEATURE:
<221> NAME/KEY: MISC_FEATURE
<222> LOCATION: (148)..(148)
<223> OTHER INFORMATION: Citrulline

<400> SEQUENCE: 56

Met Val Asn Pro Thr Val Phe Phe Asp Ile Ala Val Asp Gly Glu Pro
1               5                   10                  15

Leu Gly Xaa Val Ser Phe Glu Leu Phe Ala Asp Lys Val Pro Lys Thr
            20                  25                  30

Ala Glu Asn Phe Xaa Ala Leu Ser Thr Gly Glu Lys Gly Phe Gly Tyr
        35                  40                  45

Lys Gly Ser Cys Phe His Xaa Ile Ile Pro Gly Phe Met Cys Gln Gly
50                  55                  60

Gly Asp Phe Thr Xaa His Asn Gly Thr Gly Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Xaa
    130                 135                 140

Phe Gly Ser Xaa Asn Gly Lys Thr Ser Lys Lys Ile Thr Ile Ala Asp
145                 150                 155                 160

Cys Gly Gln Leu Glu
                165

<210> SEQ ID NO 57
<211> LENGTH: 14
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
```

```
<221> NAME/KEY: MISC_FEATURE
<222> LOCATION: (14)..(14)
<223> OTHER INFORMATION: glycine or no amino acid

<400> SEQUENCE: 57

Xaa Ala Glu Asn Phe Arg Ala Leu Ser Thr Gly Glu Lys Xaa
1               5                   10

<210> SEQ ID NO 58
<211> LENGTH: 60
<212> TYPE: PRT
<213> ORGANISM: human

<400> SEQUENCE: 58

Met Pro Ser Gln Met Glu His Ala Met Glu Thr Met Met Phe Thr Phe
1               5                   10                  15

His Lys Phe Ala Gly Asp Lys Gly Tyr Leu Thr Lys Glu Asp Leu Arg
            20                  25                  30

Val Leu Met Glu Lys Glu Phe Pro Gly Phe Leu Glu Asn Gln Lys Asp
        35                  40                  45

Pro Leu Ala Val Asp Lys Ile Met Lys Asp Leu Asp
    50                  55                  60

<210> SEQ ID NO 59
<211> LENGTH: 37
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Citrulline

<400> SEQUENCE: 59

Gln Cys Xaa Asp Gly Lys Val Gly Phe Gln Ser Phe Phe Ser Leu Ile
1               5                   10                  15

Ala Gly Leu Thr Ile Ala Cys Asn Asp Tyr Phe Val Val His Met Lys
            20                  25                  30

Gln Lys Gly Lys Lys
        35

<210> SEQ ID NO 60
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: arginine or no amino acid at first
<220> FEATURE:
<221> NAME/KEY: MISC_FEATURE
<222> LOCATION: (15)..(15)
<223> OTHER INFORMATION: asparagine or no amino acid

<400> SEQUENCE: 60

Xaa Ile Leu Glu Gln Gln Asn Ser Ser Arg Thr Leu Glu Lys Xaa
1               5                   10                  15

<210> SEQ ID NO 61
<211> LENGTH: 133
<212> TYPE: PRT
<213> ORGANISM: human
```

-continued

<400> SEQUENCE: 61

Met Ala Asp Ala Phe Leu Gly Thr Trp Lys Leu Val Asp Ser Lys Asn
1               5                   10                  15

Phe Asp Asp Tyr Met Lys Ser Leu Gly Val Gly Phe Ala Thr Arg Gln
            20                  25                  30

Val Ala Ser Met Thr Lys Pro Thr Thr Ile Ile Glu Lys Asn Gly Asp
        35                  40                  45

Ile Leu Thr Leu Lys Thr His Ser Thr Phe Lys Asn Thr Glu Ile Ser
    50                  55                  60

Phe Lys Leu Gly Val Glu Phe Asp Glu Thr Thr Ala Asp Asp Arg Lys
65                  70                  75                  80

Val Lys Ser Ile Val Thr Leu Asp Gly Gly Lys Leu Val His Leu Gln
                85                  90                  95

Lys Trp Asp Gly Gln Glu Thr Thr Leu Val Arg Glu Leu Ile Asp Gly
            100                 105                 110

Lys Leu Ile Leu Thr Leu Thr His Gly Thr Ala Val Cys Thr Arg Thr
        115                 120                 125

Tyr Glu Lys Glu Ala
    130

<210> SEQ ID NO 62
<211> LENGTH: 463
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (37)..(37)
<223> OTHER INFORMATION: Citrulline
<220> FEATURE:
<221> NAME/KEY: MISC_FEATURE
<222> LOCATION: (67)..(67)
<223> OTHER INFORMATION: Citrulline
<220> FEATURE:
<221> NAME/KEY: MISC_FEATURE
<222> LOCATION: (69)..(69)
<223> OTHER INFORMATION: Citrulline
<220> FEATURE:
<221> NAME/KEY: MISC_FEATURE
<222> LOCATION: (96)..(96)
<223> OTHER INFORMATION: Citrulline
<220> FEATURE:
<221> NAME/KEY: MISC_FEATURE
<222> LOCATION: (134)..(134)
<223> OTHER INFORMATION: Citrulline
<220> FEATURE:
<221> NAME/KEY: MISC_FEATURE
<222> LOCATION: (166)..(166)
<223> OTHER INFORMATION: Citrulline
<220> FEATURE:
<221> NAME/KEY: MISC_FEATURE
<222> LOCATION: (218)..(218)
<223> OTHER INFORMATION: Citrulline
<220> FEATURE:
<221> NAME/KEY: MISC_FEATURE
<222> LOCATION: (240)..(240)
<223> OTHER INFORMATION: Citrulline
<220> FEATURE:
<221> NAME/KEY: MISC_FEATURE
<222> LOCATION: (247)..(247)
<223> OTHER INFORMATION: Citrulline
<220> FEATURE:
<221> NAME/KEY: MISC_FEATURE
<222> LOCATION: (266)..(266)
<223> OTHER INFORMATION: Citrulline
<220> FEATURE:
<221> NAME/KEY: MISC_FEATURE
<222> LOCATION: (273)..(273)

```
<223> OTHER INFORMATION: Citrulline
<220> FEATURE:
<221> NAME/KEY: MISC_FEATURE
<222> LOCATION: (321)..(321)
<223> OTHER INFORMATION: Citrulline
<220> FEATURE:
<221> NAME/KEY: MISC_FEATURE
<222> LOCATION: (322)..(322)
<223> OTHER INFORMATION: Citrulline
<220> FEATURE:
<221> NAME/KEY: MISC_FEATURE
<222> LOCATION: (381)..(381)
<223> OTHER INFORMATION: Citrulline
<220> FEATURE:
<221> NAME/KEY: MISC_FEATURE
<222> LOCATION: (382)..(382)
<223> OTHER INFORMATION: Citrulline
<220> FEATURE:
<221> NAME/KEY: MISC_FEATURE
<222> LOCATION: (423)..(423)
<223> OTHER INFORMATION: Citrulline
<220> FEATURE:
<221> NAME/KEY: MISC_FEATURE
<222> LOCATION: (427)..(427)
<223> OTHER INFORMATION: Citrulline
<220> FEATURE:
<221> NAME/KEY: MISC_FEATURE
<222> LOCATION: (430)..(430)
<223> OTHER INFORMATION: Citrulline

<400> SEQUENCE: 62

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Xaa Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
50                  55                  60

Ala Glu Xaa Glu Xaa Gly Ile Thr Ile Asp Ile Ser Leu Trp Lys Phe
65                  70                  75                  80

Glu Thr Thr Lys Tyr Tyr Ile Thr Ile Ile Asp Ala Pro Gly His Xaa
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Xaa Glu His Ala Leu Leu Ala Tyr Thr Leu Gly
130                 135                 140

Val Lys Gln Leu Ile Val Gly Val Asn Lys Met Asp Ser Thr Glu Pro
145                 150                 155                 160

Ala Tyr Ser Glu Lys Xaa Tyr Asp Glu Ile Val Lys Glu Val Ser Ala
                165                 170                 175

Tyr Ile Lys Lys Ile Gly Tyr Asn Pro Ala Thr Val Pro Phe Val Pro
            180                 185                 190

Ile Ser Gly Trp His Gly Asp Asn Met Leu Glu Pro Ser Pro Asn Met
        195                 200                 205

Pro Trp Phe Lys Gly Trp Lys Val Glu Xaa Lys Glu Gly Asn Ala Ser
210                 215                 220

Gly Val Ser Leu Leu Glu Ala Leu Asp Thr Ile Leu Pro Pro Thr Xaa
225                 230                 235                 240

Pro Thr Asp Lys Pro Leu Xaa Leu Pro Leu Gln Asp Val Tyr Lys Ile
                245                 250                 255
```

```
Gly Gly Ile Gly Thr Val Pro Val Gly Xaa Val Glu Thr Gly Ile Leu
            260                 265                 270

Xaa Pro Gly Met Val Val Thr Phe Ala Pro Val Asn Ile Thr Thr Glu
            275                 280                 285

Val Lys Ser Val Glu Met His His Glu Ala Leu Ser Glu Ala Leu Pro
            290                 295                 300

Gly Asp Asn Val Gly Phe Asn Val Lys Asn Val Ser Val Lys Asp Ile
305                 310                 315                 320

Xaa Xaa Gly Asn Val Cys Gly Asp Ser Lys Ser Asp Pro Pro Gln Glu
            325                 330                 335

Ala Ala Gln Phe Thr Ser Gln Val Ile Ile Leu Asn His Pro Gly Gln
            340                 345                 350

Ile Ser Ala Gly Tyr Ser Pro Val Ile Asp Cys His Thr Ala His Ile
            355                 360                 365

Ala Cys Lys Phe Ala Glu Leu Lys Glu Lys Ile Asp Xaa Xaa Ser Gly
            370                 375                 380

Lys Lys Leu Glu Asp Asn Pro Lys Ser Leu Lys Ser Gly Asp Ala Ala
385                 390                 395                 400

Ile Val Glu Met Val Pro Gly Lys Pro Met Cys Val Glu Ser Phe Ser
            405                 410                 415

Gln Tyr Pro Pro Leu Gly Xaa Phe Ala Val Xaa Asp Met Xaa Gln Thr
            420                 425                 430

Val Ala Val Gly Val Ile Lys Asn Val Glu Lys Lys Ser Gly Gly Ala
            435                 440                 445

Gly Lys Val Thr Lys Ser Ala Gln Lys Ala Gln Lys Ala Gly Lys
            450                 455                 460

<210> SEQ ID NO 63
<211> LENGTH: 13
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (13)..(13)
<223> OTHER INFORMATION: isoleucine or no amino acid

<400> SEQUENCE: 63

Xaa Pro Leu Arg Leu Pro Leu Gln Asp Val Tyr Lys Xaa
1               5                   10

<210> SEQ ID NO 64
<211> LENGTH: 18
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: aspartic acid or no amino acid
<220> FEATURE:
<221> NAME/KEY: MISC_FEATURE
<222> LOCATION: (18)..(18)
<223> OTHER INFORMATION: threonine or no amino acid

<400> SEQUENCE: 64
```

Xaa Val Tyr Lys Ile Gly Gly Ile Gly Thr Val Pro Val Gly Arg Val
1               5                   10                  15

Glu Xaa

<210> SEQ ID NO 65
<211> LENGTH: 421
<212> TYPE: PRT
<213> ORGANISM: human

<400> SEQUENCE: 65

Met Asn Arg Gly Phe Ser Arg Lys Ser His Thr Phe Leu Pro Lys Ile
1               5                   10                  15

Phe Phe Arg Lys Met Ser Ser Gly Ala Lys Asp Lys Pro Glu Leu
                20                  25                  30

Gln Phe Pro Phe Leu Gln Asp Glu Asp Thr Val Ala Thr Leu Leu Glu
            35                  40                  45

Cys Lys Thr Leu Phe Ile Leu Arg Gly Leu Pro Gly Ser Gly Lys Ser
        50                  55                  60

Thr Leu Ala Arg Val Ile Val Asp Lys Tyr Arg Asp Gly Thr Lys Met
65                  70                  75                  80

Val Ser Ala Asp Ala Tyr Lys Ile Thr Pro Gly Ala Arg Gly Ala Phe
                85                  90                  95

Ser Glu Glu Tyr Lys Arg Leu Asp Glu Asp Leu Ala Ala Tyr Cys Arg
            100                 105                 110

Arg Arg Asp Ile Arg Ile Leu Val Leu Asp Asp Thr Asn His Glu Arg
        115                 120                 125

Glu Arg Leu Glu Gln Leu Phe Glu Met Ala Asp Gln Tyr Gln Tyr Gln
130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
            180                 185                 190

Phe Leu Thr Lys Lys Ser Ser Glu Thr Leu Arg Lys Ala Gly Gln Val
        195                 200                 205

Phe Leu Glu Glu Leu Gly Asn His Lys Ala Phe Lys Lys Glu Leu Arg
210                 215                 220

Gln Phe Val Pro Gly Asp Glu Pro Arg Glu Lys Met Asp Leu Val Thr
225                 230                 235                 240

Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350

-continued

```
Arg Gln Glu Lys Gly Gly Ser Arg Gly Glu Val Gly Glu Leu Ser
            355                 360                 365
Arg Gly Lys Leu Tyr Ser Leu Gly Asn Gly Arg Trp Met Leu Thr Leu
370                 375                 380
Ala Lys Asn Met Glu Val Arg Ala Ile Phe Thr Gly Tyr Tyr Gly Lys
385                 390                 395                 400
Gly Lys Pro Val Pro Thr Gln Gly Ser Arg Lys Gly Ala Leu Gln
                405                 410                 415
Ser Cys Thr Ile Ile
            420

<210> SEQ ID NO 66
<211> LENGTH: 1669
<212> TYPE: PRT
<213> ORGANISM: human

<400> SEQUENCE: 66

Met Gly Pro Arg Leu Ser Val Trp Leu Leu Leu Leu Pro Ala Ala Leu
1               5                   10                  15
Leu Leu His Glu Glu His Ser Arg Ala Ala Lys Gly Gly Cys Ala
            20                  25                  30
Gly Ser Gly Cys Gly Lys Cys Asp Cys His Gly Val Lys Gly Gln Lys
        35                  40                  45
Gly Glu Arg Gly Leu Pro Gly Leu Gln Gly Val Ile Gly Phe Pro Gly
    50                  55                  60
Met Gln Gly Pro Glu Gly Pro Gln Gly Pro Pro Gly Gln Lys Gly Asp
65                  70                  75                  80
Thr Gly Glu Pro Gly Leu Pro Gly Thr Lys Gly Thr Arg Gly Pro Pro
                85                  90                  95
Gly Ala Ser Gly Tyr Pro Gly Asn Pro Gly Leu Pro Gly Ile Pro Gly
            100                 105                 110
Gln Asp Gly Pro Pro Gly Pro Pro Gly Ile Pro Gly Cys Asn Gly Thr
        115                 120                 125
Lys Gly Glu Arg Gly Pro Leu Gly Pro Pro Gly Leu Pro Gly Phe Ala
    130                 135                 140
Gly Asn Pro Gly Pro Pro Gly Leu Pro Gly Met Lys Gly Asp Pro Gly
145                 150                 155                 160
Glu Ile Leu Gly His Val Pro Gly Met Leu Leu Lys Gly Glu Arg Gly
                165                 170                 175
Phe Pro Gly Ile Pro Gly Thr Pro Gly Pro Pro Gly Leu Pro Gly Leu
            180                 185                 190
Gln Gly Pro Val Gly Pro Pro Gly Phe Thr Gly Pro Pro Gly Pro Pro
        195                 200                 205
Gly Pro Gly Pro Pro Gly Glu Lys Gly Gln Met Gly Leu Ser Phe
    210                 215                 220
Gln Gly Pro Lys Gly Asp Lys Gly Asp Gln Gly Val Ser Gly Pro Pro
225                 230                 235                 240
Gly Val Pro Gly Gln Ala Gln Val Gln Glu Lys Gly Asp Phe Ala Thr
                245                 250                 255
Lys Gly Glu Lys Gly Gln Lys Gly Glu Pro Gly Phe Gln Gly Met Pro
            260                 265                 270
Gly Val Gly Glu Lys Gly Glu Pro Gly Lys Pro Gly Pro Arg Gly Lys
        275                 280                 285
Pro Gly Lys Asp Gly Asp Lys Gly Glu Lys Gly Ser Pro Gly Phe Pro
    290                 295                 300
```

Gly Glu Pro Gly Tyr Pro Gly Leu Ile Gly Arg Gln Gly Pro Gln Gly
305                 310                 315                 320

Glu Lys Gly Glu Ala Gly Pro Pro Gly Pro Pro Gly Ile Val Ile Gly
            325                 330                 335

Thr Gly Pro Leu Gly Glu Lys Gly Glu Arg Gly Tyr Pro Gly Thr Pro
            340                 345                 350

Gly Pro Arg Gly Glu Pro Gly Pro Lys Gly Phe Pro Gly Leu Pro Gly
            355                 360                 365

Gln Pro Gly Pro Pro Gly Leu Pro Val Pro Gly Gln Ala Gly Ala Pro
370                 375                 380

Gly Phe Pro Gly Glu Arg Gly Glu Lys Gly Asp Arg Gly Phe Pro Gly
385                 390                 395                 400

Thr Ser Leu Pro Gly Pro Ser Gly Arg Asp Gly Leu Pro Gly Pro Pro
            405                 410                 415

Gly Ser Pro Gly Pro Pro Gly Gln Pro Gly Tyr Thr Asn Gly Ile Val
            420                 425                 430

Glu Cys Gln Pro Gly Pro Pro Gly Asp Gln Gly Pro Pro Gly Ile Pro
            435                 440                 445

Gly Gln Pro Gly Phe Ile Gly Glu Ile Gly Glu Lys Gly Gln Lys Gly
450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
            485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
            515                 520                 525

Glu Pro Gly Glu Phe Tyr Phe Asp Leu Arg Leu Lys Gly Asp Lys Gly
            530                 535                 540

Asp Pro Gly Phe Pro Gly Gln Pro Gly Met Thr Gly Arg Ala Gly Ser
545                 550                 555                 560

Pro Gly Arg Asp Gly His Pro Gly Leu Pro Gly Pro Lys Gly Ser Pro
            565                 570                 575

Gly Ser Val Gly Leu Lys Gly Glu Arg Gly Pro Pro Gly Gly Val Gly
            580                 585                 590

Phe Pro Gly Ser Arg Gly Asp Thr Gly Pro Pro Gly Pro Pro Gly Tyr
            595                 600                 605

Gly Pro Ala Gly Pro Ile Gly Asp Lys Gly Gln Ala Gly Phe Pro Gly
            610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
            645                 650                 655

Pro Gly Phe Pro Gly Pro Gln Gly Asp Arg Gly Phe Pro Gly Thr Pro
            660                 665                 670

Gly Arg Pro Gly Leu Pro Gly Glu Lys Gly Ala Val Gly Gln Pro Gly
            675                 680                 685

Ile Gly Phe Pro Gly Pro Pro Gly Pro Lys Gly Val Asp Gly Leu Pro
            690                 695                 700

Gly Asp Met Gly Pro Pro Gly Thr Pro Gly Arg Pro Gly Phe Asn Gly
705                 710                 715                 720

-continued

Leu Pro Gly Asn Pro Gly Val Gln Gly Gln Lys Gly Glu Pro Gly Val
                725                 730                 735

Gly Leu Pro Gly Leu Lys Gly Leu Pro Gly Leu Pro Gly Ile Pro Gly
            740                 745                 750

Thr Pro Gly Glu Lys Gly Ser Ile Gly Val Pro Gly Val Pro Gly Glu
        755                 760                 765

His Gly Ala Ile Gly Pro Pro Gly Leu Gln Gly Ile Arg Gly Glu Pro
    770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gln Gly Pro Pro
            805                 810                 815

Gly Leu Ser Gly Pro Pro Gly Ile Lys Gly Glu Lys Gly Phe Pro Gly
            820                 825                 830

Phe Pro Gly Leu Asp Met Pro Gly Pro Lys Gly Asp Lys Gly Ala Gln
        835                 840                 845

Gly Leu Pro Gly Ile Thr Gly Gln Ser Gly Leu Pro Gly Leu Pro Gly
        850                 855                 860

Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
            885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
        915                 920                 925

Val Gly Leu Pro Gly Lys Pro Gly Ser Met Asp Lys Val Asp Met Gly
        930                 935                 940

Ser Met Lys Gly Gln Lys Gly Asp Gln Gly Glu Lys Gly Gln Ile Gly
945                 950                 955                 960

Pro Ile Gly Glu Lys Gly Ser Arg Gly Asp Pro Gly Thr Pro Gly Val
            965                 970                 975

Pro Gly Lys Asp Gly Gln Ala Gly Gln Pro Gly Gln Pro Gly Pro Lys
        980                 985                 990

Gly Asp Pro Gly Ile Ser Gly Thr Pro Gly Ala Pro Gly Leu Pro Gly
        995                 1000                1005

Pro Lys Gly Ser Val Gly Gly Met Gly Leu Pro Gly Thr Pro Gly
        1010                1015                1020

Glu Lys Gly Val Pro Gly Ile Pro Gly Pro Gln Gly Ser Pro Gly
        1025                1030                1035

Leu Pro Gly Asp Lys Gly Ala Lys Gly Glu Lys Gly Gln Ala Gly
        1040                1045                1050

Pro Pro Gly Ile Gly Ile Pro Gly Leu Arg Gly Glu Lys Gly Asp
        1055                1060                1065

Gln Gly Ile Ala Gly Phe Pro Gly Ser Pro Gly Glu Lys Gly Glu
        1070                1075                1080

Lys Gly Ser Ile Gly Ile Pro Gly Met Pro Gly Ser Pro Gly Leu
        1085                1090                1095

Lys Gly Ser Pro Gly Ser Val Gly Tyr Pro Gly Ser Pro Gly Leu
        1100                1105                1110

Pro Gly Glu Lys Gly Asp Lys Gly Leu Pro Gly Leu Asp Gly Ile
        1115                1120                1125

Pro Gly Val Lys Gly Glu Ala Gly Leu Pro Gly Thr Pro Gly Pro

-continued

```
              1130                1135                1140
Thr Gly Pro Ala Gly Gln Lys Gly Glu Pro Gly Ser Asp Gly Ile
         1145                1150                1155

Pro Gly Ser Ala Gly Glu Lys Gly Glu Pro Gly Leu Pro Gly Arg
         1160                1165                1170

Gly Phe Pro Gly Phe Pro Gly Ala Lys Gly Asp Lys Gly Ser Lys
         1175                1180                1185

Gly Glu Val Gly Phe Pro Gly Leu Ala Gly Ser Pro Gly Ile Pro
         1190                1195                1200

Gly Ser Lys Gly Glu Gln Gly Phe Met Gly Pro Pro Gly Pro Gln
         1205                1210                1215

Gly Gln Pro Gly Leu Pro Gly Ser Pro Gly His Ala Thr Glu Gly
         1220                1225                1230

Pro Lys Gly Asp Arg Gly Pro Gln Gly Gln Pro Gly Leu Pro Gly
         1235                1240                1245

Leu Pro Gly Pro Met Gly Pro Pro Gly Leu Pro Gly Ile Asp Gly
         1250                1255                1260

Val Lys Gly Asp Lys Gly Asn Pro Gly Trp Pro Gly Ala Pro Gly
         1265                1270                1275

Val Pro Gly Pro Lys Gly Asp Pro Gly Phe Gln Gly Met Pro Gly
         1280                1285                1290

Ile Gly Gly Ser Pro Gly Ile Thr Gly Ser Lys Gly Asp Met Gly
         1295                1300                1305

Pro Pro Gly Val Pro Gly Phe Gln Gly Pro Lys Gly Leu Pro Gly
         1310                1315                1320

Leu Gln Gly Ile Lys Gly Asp Gln Gly Asp Gln Gly Val Pro Gly
         1325                1330                1335

Ala Lys Gly Leu Pro Gly Pro Pro Gly Pro Pro Gly Pro Tyr Asp
         1340                1345                1350

Ile Ile Lys Gly Glu Pro Gly Leu Pro Gly Pro Glu Gly Pro Pro
         1355                1360                1365

Gly Leu Lys Gly Leu Gln Gly Leu Pro Gly Pro Lys Gly Gln Gln
         1370                1375                1380

Gly Val Thr Gly Leu Val Gly Ile Pro Gly Pro Pro Gly Ile Pro
         1385                1390                1395

Gly Phe Asp Gly Ala Pro Gly Gln Lys Gly Glu Met Gly Pro Ala
         1400                1405                1410

Gly Pro Thr Gly Pro Arg Gly Phe Pro Gly Pro Pro Gly Pro Asp
         1415                1420                1425

Gly Leu Pro Gly Ser Met Gly Pro Pro Gly Thr Pro Ser Val Asp
         1430                1435                1440

His Gly Phe Leu Val Thr Arg His Ser Gln Thr Ile Asp Asp Pro
         1445                1450                1455

Gln Cys Pro Ser Gly Thr Lys Ile Leu Tyr His Gly Tyr Ser Leu
         1460                1465                1470

Leu Tyr Val Gln Gly Asn Glu Arg Ala His Gly Gln Asp Leu Gly
         1475                1480                1485

Thr Ala Gly Ser Cys Leu Arg Lys Phe Ser Thr Met Pro Phe Leu
         1490                1495                1500

Phe Cys Asn Ile Asn Asn Val Cys Asn Phe Ala Ser Arg Asn Asp
         1505                1510                1515

Tyr Ser Tyr Trp Leu Ser Thr Pro Glu Pro Met Pro Met Ser Met
         1520                1525                1530
```

```
Ala Pro Ile Thr Gly Glu Asn Ile Arg Pro Phe Ile Ser Arg Cys
    1535                1540                1545

Ala Val Cys Glu Ala Pro Ala Met Val Met Ala Val His Ser Gln
    1550                1555                1560

Thr Ile Gln Ile Pro Pro Cys Pro Ser Gly Trp Ser Ser Leu Trp
    1565                1570                1575

Ile Gly Tyr Ser Phe Val Met His Thr Ser Ala Gly Ala Glu Gly
    1580                1585                1590

Ser Gly Gln Ala Leu Ala Ser Pro Gly Ser Cys Leu Glu Glu Phe
    1595                1600                1605

Arg Ser Ala Pro Phe Ile Glu Cys His Gly Arg Gly Thr Cys Asn
    1610                1615                1620

Tyr Tyr Ala Asn Ala Tyr Ser Phe Trp Leu Ala Thr Ile Glu Arg
    1625                1630                1635

Ser Glu Met Phe Lys Lys Pro Thr Pro Ser Thr Leu Lys Ala Gly
    1640                1645                1650

Glu Leu Arg Thr His Val Ser Arg Cys Gln Val Cys Met Arg Arg
    1655                1660                1665

Thr

<210> SEQ ID NO 67
<211> LENGTH: 17
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (17)..(17)
<223> OTHER INFORMATION: phenylalanine or no amino acid

<400> SEQUENCE: 67

Xaa Ala Ile Ser Ser Pro Thr Val Ser Arg Leu Thr Asp Thr Thr Lys
1               5                   10                  15

Xaa

<210> SEQ ID NO 68
<211> LENGTH: 331
<212> TYPE: PRT
<213> ORGANISM: human

<400> SEQUENCE: 68

Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
                20                  25                  30

Ile Leu Lys Gln Ser Met Thr Leu Asn Leu Ala Asp Pro Val Gly Ser
            35                  40                  45

Leu Lys Pro His Leu Arg Ala Lys Asn Ser Asp Leu Leu Thr Ser Pro
        50                  55                  60

Asp Val Gly Leu Leu Lys Leu Ala Ser Pro Glu Leu Glu Arg Leu Ile
65              70                  75                  80

Ile Gln Ser Ser Asn Gly His Ile Thr Thr Thr Pro Thr Pro Thr Gln
                85                  90                  95
```

```
Phe Leu Cys Pro Lys Asn Val Thr Asp Glu Gln Glu Gly Phe Ala Glu
                100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
        130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 69
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (8)..(8)
<223> OTHER INFORMATION: Citrulline
<220> FEATURE:
<221> NAME/KEY: MISC_FEATURE
<222> LOCATION: (21)..(21)
<223> OTHER INFORMATION: glutamic acid or no amino acid

<400> SEQUENCE: 69

Xaa Thr Gly Gly Ala Val Asp Xaa Leu Thr Asp Thr Ser Arg Tyr Thr
1               5                   10                  15

Gly Ser His Lys Xaa
            20

<210> SEQ ID NO 70
<211> LENGTH: 21
<212> TYPE: PRT
<213> ORGANISM: artificial sequence
<220> FEATURE:
```

```
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (21)..(21)
<223> OTHER INFORMATION: glutamic acid or no amino acid

<400> SEQUENCE: 70

Xaa Thr Gly Gly Ala Val Asp Arg Leu Thr Asp Thr Ser Arg Tyr Thr
1               5                   10                  15

Gly Ser His Lys Xaa
            20

<210> SEQ ID NO 71
<211> LENGTH: 21
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: lysine or no amino acid
<220> FEATURE:
<221> NAME/KEY: MISC_FEATURE
<222> LOCATION: (21)..(21)
<223> OTHER INFORMATION: asparagine or no amino acid

<400> SEQUENCE: 71

Xaa Gly Ile Ala Gly Arg Gln Asp Ile Leu Asp Ser Gly Tyr Val
1               5                   10                  15

Ser Ala Tyr Lys Xaa
            20

<210> SEQ ID NO 72
<211> LENGTH: 195
<212> TYPE: PRT
<213> ORGANISM: human

<400> SEQUENCE: 72

Met Ser Ser Cys Ser Asn Val Cys Gly Ser Arg Gln Ala Gln Ala Ala
1               5                   10                  15

Ala Glu Gly Gly Tyr Gln Arg Tyr Gly Val Arg Ser Tyr Leu His Gln
                20                  25                  30

Phe Tyr Glu Asp Cys Thr Ala Ser Ile Trp Glu Tyr Glu Asp Asp Phe
            35                  40                  45

Gln Ile Gln Arg Ser Pro Asn Arg Trp Ser Val Phe Trp Lys Val
    50                  55                  60

Gly Leu Ile Ser Gly Thr Val Phe Val Ile Leu Gly Leu Thr Val Leu
65                  70                  75                  80

Ala Val Gly Phe Leu Val Pro Pro Lys Ile Glu Ala Phe Gly Glu Ala
                85                  90                  95

Asp Phe Val Val Val Asp Thr His Ala Val Gln Phe Asn Ser Ala Leu
            100                 105                 110

Asp Met Tyr Lys Leu Ala Gly Ala Val Leu Phe Cys Ile Gly Gly Thr
        115                 120                 125

Ser Met Ala Gly Cys Leu Leu Met Ser Val Phe Val Lys Ser Tyr Ser
    130                 135                 140

Lys Glu Glu Lys Phe Leu Gln Gln Lys Phe Lys Glu Arg Ile Ala Asp
145                 150                 155                 160
```

```
Ile Lys Ala His Thr Gln Pro Val Thr Lys Ala Pro Gly Pro Gly Glu
                165                 170                 175

Thr Lys Ile Pro Val Thr Leu Ser Arg Val Gln Asn Val Gln Pro Leu
            180                 185                 190

Leu Ala Thr
        195

<210> SEQ ID NO 73
<211> LENGTH: 371
<212> TYPE: PRT
<213> ORGANISM: human

<400> SEQUENCE: 73

Met Ala Glu Leu Gln Glu Val Gln Ile Thr Glu Glu Lys Pro Leu Leu
1               5                   10                  15

Pro Gly Gln Thr Pro Glu Ala Ala Lys Glu Ala Glu Leu Ala Ala Arg
            20                  25                  30

Ile Leu Leu Asp Gln Gly Gln Thr His Ser Val Glu Thr Pro Tyr Gly
        35                  40                  45

Ser Val Thr Phe Thr Val Tyr Gly Thr Pro Lys Pro Lys Arg Pro Ala
50                  55                  60

Ile Leu Thr Tyr His Asp Val Gly Leu Asn Tyr Lys Ser Cys Phe Gln
65                  70                  75                  80

Pro Leu Phe Gln Phe Glu Asp Met Gln Glu Ile Ile Gln Asn Phe Val
                85                  90                  95

Arg Val His Val Asp Ala Pro Gly Met Glu Glu Gly Ala Pro Val Phe
            100                 105                 110

Pro Leu Gly Tyr Gln Tyr Pro Ser Leu Asp Gln Leu Ala Asp Met Ile
        115                 120                 125

Pro Cys Val Leu Gln Tyr Leu Asn Phe Ser Thr Ile Ile Gly Val Gly
130                 135                 140

Val Gly Ala Gly Ala Tyr Ile Leu Ala Arg Tyr Ala Leu Asn His Pro
145                 150                 155                 160

Asp Thr Val Glu Gly Leu Val Leu Ile Asn Ile Asp Pro Asn Ala Lys
                165                 170                 175

Gly Trp Met Asp Trp Ala Ala His Lys Leu Thr Gly Leu Thr Ser Ser
            180                 185                 190

Ile Pro Glu Met Ile Leu Gly His Leu Phe Ser Gln Glu Glu Leu Ser
        195                 200                 205

Gly Asn Ser Glu Leu Ile Gln Lys Tyr Arg Asn Ile Ile Thr His Ala
210                 215                 220

Pro Asn Leu Asp Asn Ile Glu Leu Tyr Trp Asn Ser Tyr Asn Asn Arg
225                 230                 235                 240

Arg Asp Leu Asn Phe Glu Arg Gly Gly Asp Ile Thr Leu Arg Cys Pro
                245                 250                 255

Val Met Leu Val Val Gly Asp Gln Ala Pro His Glu Asp Ala Val Val
            260                 265                 270

Glu Cys Asn Ser Lys Leu Asp Pro Thr Gln Thr Ser Phe Leu Lys Met
        275                 280                 285

Ala Asp Ser Gly Gly Gln Pro Gln Leu Thr Gln Pro Gly Lys Leu Thr
        290                 295                 300

Glu Ala Phe Lys Tyr Phe Leu Gln Gly Met Gly Tyr Met Ala Ser Ser
305                 310                 315                 320

Cys Met Thr Arg Leu Ser Arg Ser Arg Thr Ala Ser Leu Thr Ser Ala
```

```
                    325                 330                 335
Ala Ser Val Asp Gly Asn Arg Ser Arg Ser Arg Thr Leu Ser Gln Ser
            340                 345                 350

Ser Glu Ser Gly Thr Leu Ser Ser Gly Pro Pro Gly His Thr Met Glu
        355                 360                 365

Val Ser Cys
    370

<210> SEQ ID NO 74
<211> LENGTH: 18
<212> TYPE: PRT
<213> ORGANISM: artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: arginine or no amino acid
<220> FEATURE:
<221> NAME/KEY: MISC_FEATURE
<222> LOCATION: (18)..(18)
<223> OTHER INFORMATION: serine or no amino acid

<400> SEQUENCE: 74

Xaa Thr Ala Ser Leu Thr Ser Ala Ala Ser Val Asp Gly Asn Arg Ser
1               5                   10                  15

Arg Xaa

<210> SEQ ID NO 75
<211> LENGTH: 92
<212> TYPE: PRT
<213> ORGANISM: human

<400> SEQUENCE: 75

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90

<210> SEQ ID NO 76
<211> LENGTH: 434
<212> TYPE: PRT
<213> ORGANISM: human

<400> SEQUENCE: 76

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60
```

Ala Val Asp His Ile Asn Ser Thr Ile Ala Pro Ala Leu Ile Ser Ser
65                  70                  75                  80

Gly Leu Ser Val Val Glu Gln Glu Lys Leu Asp Asn Leu Met Leu Glu
            85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
            115                 120                 125

Pro Leu Tyr Arg His Ile Ala Gln Leu Ala Gly Asn Ser Asp Leu Ile
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
            165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
            195                 200                 205

Asp Glu Gly Gly Phe Ala Pro Asn Ile Leu Glu Asn Ser Glu Ala Leu
210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
            245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
            275                 280                 285

Val Val Ser Ile Glu Asp Pro Phe Asp Gln Asp Asp Trp Ala Ala Trp
290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
            325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
            355                 360                 365

Val Ser His Arg Ser Gly Glu Thr Glu Asp Thr Phe Ile Ala Asp Leu
            370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
            405                 410                 415

Leu Gly Asp Glu Ala Arg Phe Ala Gly His Asn Phe Arg Asn Pro Ser
            420                 425                 430

Val Leu

<210> SEQ ID NO 77
<211> LENGTH: 76
<212> TYPE: PRT
<213> ORGANISM: human

<400> SEQUENCE: 77

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 78
<211> LENGTH: 758
<212> TYPE: PRT
<213> ORGANISM: human

<400> SEQUENCE: 78

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
```

```
            290                 295                 300
Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
        530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
            595                 600                 605

Gly Ser Lys Asp Asn Ile Lys His Val Pro Gly Gly Gly Ser Val Gln
        610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys Ala Lys Thr Asp
        690                 695                 700

His Gly Ala Glu Ile Val Tyr Lys Ser Pro Val Val Ser Gly Asp Thr
705                 710                 715                 720
```

Ser Pro Arg His Leu Ser Asn Val Ser Ser Thr Gly Ser Ile Asp Met
              725                 730                 735

Val Asp Ser Pro Gln Leu Ala Thr Leu Ala Asp Glu Val Ser Ala Ser
              740                 745                 750

Leu Ala Lys Gln Gly Leu
        755

<210> SEQ ID NO 79
<211> LENGTH: 543
<212> TYPE: PRT
<213> ORGANISM: human

<400> SEQUENCE: 79

Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190

Met Glu Ala Arg Lys Gly Ala Asp Glu Ala Ala Leu Ala Arg Ala Glu
        195                 200                 205

Leu Glu Lys Arg Ile Asp Ser Leu Met Asp Glu Ile Ser Phe Leu Lys
    210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
            260                 265                 270

Met Gln Asn Ala Glu Glu Trp Phe Lys Ser Arg Phe Thr Val Leu Thr
        275                 280                 285

Glu Ser Ala Ala Lys Asn Thr Asp Ala Val Arg Ala Ala Lys Asp Glu
    290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu

```
                  325                 330                 335
Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
            355                 360                 365

Leu Lys Glu Tyr Gln Asp Leu Leu Asn Val Lys Met Ala Leu Asp Ile
            370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
            405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
            435                 440                 445

Glu Glu Gln Ile Glu Val Glu Glu Thr Ile Glu Ala Ala Lys Ala Glu
            450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Ala Ala Glu Glu Glu Glu Glu
            485                 490                 495

Ala Ala Lys Glu Glu Ser Glu Glu Ala Lys Glu Glu Glu Glu Gly Gly
            500                 505                 510

Glu Gly Glu Glu Gly Glu Glu Thr Lys Glu Ala Glu Glu Glu Glu Lys
            515                 520                 525

Lys Val Glu Gly Ala Gly Glu Glu Gln Ala Ala Lys Lys Lys Asp
            530                 535                 540

<210> SEQ ID NO 80
<211> LENGTH: 1026
<212> TYPE: PRT
<213> ORGANISM: human

<400> SEQUENCE: 80

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
            35                  40                  45

Ser Trp Thr Arg Thr Ser Val Ser Val Ser Ala Ser Pro Ser Arg
        50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
            85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
            115                 120                 125

Ala Ala Ala Leu Arg Gln Gln Gln Ala Gly Arg Ser Ala Met Gly Glu
            130                 135                 140

Leu Tyr Glu Arg Glu Val Arg Glu Met Arg Gly Ala Val Leu Arg Leu
145                 150                 155                 160
```

```
Gly Ala Ala Arg Gly Gln Leu Arg Leu Glu Gln Glu His Leu Leu Glu
            165                 170                 175

Asp Ile Ala His Val Arg Gln Arg Leu Asp Asp Glu Ala Arg Gln Arg
        180                 185                 190

Glu Glu Ala Glu Ala Ala Arg Ala Leu Ala Arg Phe Ala Gln Glu
            195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Val Gly Glu
225                 230                 235                 240

Leu Leu Gly Gln Ile Gln Gly Ser Gly Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
        355                 360                 365

Ala Glu Leu Arg Asn Thr Lys Trp Glu Met Ala Ala Gln Leu Arg Glu
    370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
        435                 440                 445

Lys Ser Glu Lys Glu Thr Val Ile Val Glu Glu Gln Thr Glu Glu Thr
    450                 455                 460

Gln Val Thr Glu Glu Val Thr Glu Glu Glu Lys Glu Ala Lys Glu
465                 470                 475                 480

Glu Glu Gly Lys Glu Glu Glu Gly Gly Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
        515                 520                 525

Glu Ala Lys Ser Pro Glu Lys Glu Ala Lys Ser Pro Ala Glu Val
    530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
                565                 570                 575

Glu Val Lys Ser Pro Glu Lys Ala Lys Ser Pro Ala Lys Glu Glu Ala
```

-continued

```
                580                 585                 590
Lys Ser Pro Ala Glu Ala Lys Ser Pro Glu Lys Ala Lys Ser Pro Val
                    595                 600                 605
Lys Glu Glu Ala Lys Ser Pro Ala Glu Ala Lys Ser Pro Val Lys Glu
                    610                 615                 620
Glu Ala Lys Ser Pro Ala Glu Val Lys Ser Pro Glu Lys Ala Lys Ser
625                 630                 635                 640
Pro Thr Lys Glu Glu Ala Lys Ser Pro Glu Lys Ala Lys Ser Pro Glu
                    645                 650                 655
Lys Ala Lys Ser Pro Glu Lys Glu Ala Lys Ser Pro Glu Lys Ala
                    660                 665                 670
Lys Ser Pro Val Lys Ala Glu Ala Lys Ser Pro Glu Lys Ala Lys Ser
                    675                 680                 685
Pro Val Lys Ala Glu Ala Lys Ser Pro Glu Lys Ala Lys Ser Pro Val
                    690                 695                 700
Lys Glu Glu Ala Lys Ser Pro Glu Lys Ala Lys Ser Pro Val Lys Glu
705                 710                 715                 720
Glu Ala Lys Ser Pro Glu Lys Ala Lys Ser Pro Val Lys Glu Glu Ala
                    725                 730                 735
Lys Thr Pro Glu Lys Ala Lys Ser Pro Val Lys Glu Glu Ala Lys Ser
                    740                 745                 750
Pro Glu Lys Ala Lys Ser Pro Glu Lys Ala Lys Thr Leu Asp Val Lys
                    755                 760                 765
Ser Pro Glu Ala Lys Thr Pro Ala Lys Glu Glu Ala Arg Ser Pro Ala
                    770                 775                 780
Asp Lys Phe Pro Glu Lys Ala Lys Ser Pro Val Lys Glu Glu Val Lys
785                 790                 795                 800
Ser Pro Glu Lys Ala Lys Ser Pro Leu Lys Glu Asp Ala Lys Ala Pro
                    805                 810                 815
Glu Lys Glu Ile Pro Lys Lys Glu Glu Val Lys Ser Pro Val Lys Glu
                    820                 825                 830
Glu Glu Lys Pro Gln Glu Val Lys Val Lys Glu Pro Pro Lys Lys Ala
                    835                 840                 845
Glu Glu Glu Lys Ala Pro Ala Thr Pro Lys Thr Glu Glu Lys Lys Asp
                    850                 855                 860
Ser Lys Lys Glu Glu Ala Pro Lys Lys Glu Ala Pro Lys Pro Lys Val
865                 870                 875                 880
Glu Glu Lys Lys Glu Pro Ala Val Glu Lys Pro Lys Glu Ser Lys Val
                    885                 890                 895
Glu Ala Lys Lys Glu Glu Ala Glu Asp Lys Lys Val Pro Thr Pro
                    900                 905                 910
Glu Lys Glu Ala Pro Ala Lys Val Glu Val Lys Glu Asp Ala Lys Pro
                    915                 920                 925
Lys Glu Lys Thr Glu Val Ala Lys Lys Glu Pro Asp Asp Ala Lys Ala
                    930                 935                 940
Lys Glu Pro Ser Lys Pro Ala Glu Lys Glu Ala Ala Pro Glu Lys
945                 950                 955                 960
Lys Asp Thr Lys Glu Glu Lys Ala Lys Lys Pro Glu Glu Lys Pro Lys
                    965                 970                 975
Thr Glu Ala Lys Ala Lys Glu Asp Asp Lys Thr Leu Ser Lys Glu Pro
                    980                 985                 990
Ser Lys Pro Lys Ala Glu Lys Ala  Glu Lys Ser Ser Ser Thr Asp Gln
                    995                 1000                1005
```

-continued

```
Lys Asp Ser Lys Pro Pro Glu Lys Ala Thr Glu Asp Lys Ala Ala
    1010                1015                1020
Lys Gly Lys
    1025

<210> SEQ ID NO 81
<211> LENGTH: 434
<212> TYPE: PRT
<213> ORGANISM: human

<400> SEQUENCE: 81

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Ser Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Trp Ala Ala Trp
    290                 295                 300

Ser Lys Phe Thr Ala Asn Val Gly Ile Gln Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
```

```
                340                 345                 350
Ala Ile Gln Ala Cys Lys Leu Ala Gln Glu Asn Gly Trp Gly Val Met
            355                 360                 365
Val Ser His Arg Ser Gly Glu Thr Glu Asp Thr Phe Ile Ala Asp Leu
        370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Met Arg Ile Glu Glu Glu
                405                 410                 415
Leu Gly Asp Glu Ala Arg Phe Ala Gly His Asn Phe Arg Asn Pro Ser
            420                 425                 430
Val Leu

<210> SEQ ID NO 82
<211> LENGTH: 622
<212> TYPE: PRT
<213> ORGANISM: human

<400> SEQUENCE: 82

Met Ala His Val Arg Gly Leu Gln Leu Pro Gly Cys Leu Ala Leu Ala
1               5                   10                  15
Ala Leu Cys Ser Leu Val His Ser Gln His Val Phe Leu Ala Pro Gln
            20                  25                  30
Gln Ala Arg Ser Leu Leu Gln Arg Val Arg Arg Ala Asn Thr Phe Leu
        35                  40                  45
Glu Glu Val Arg Lys Gly Asn Leu Glu Arg Glu Cys Val Glu Glu Thr
    50                  55                  60
Cys Ser Tyr Glu Glu Ala Phe Glu Ala Leu Glu Ser Ser Thr Ala Thr
65                  70                  75                  80
Asp Val Phe Trp Ala Lys Tyr Thr Ala Cys Glu Thr Ala Arg Thr Pro
                85                  90                  95
Arg Asp Lys Leu Ala Ala Cys Leu Glu Gly Asn Cys Ala Glu Gly Leu
            100                 105                 110
Gly Thr Asn Tyr Arg Gly His Val Asn Ile Thr Arg Ser Gly Ile Glu
        115                 120                 125
Cys Gln Leu Trp Arg Ser Arg Tyr Pro His Lys Pro Glu Ile Asn Ser
    130                 135                 140
Thr Thr His Pro Gly Ala Asp Leu Gln Glu Asn Phe Cys Arg Asn Pro
145                 150                 155                 160
Asp Ser Ser Thr Thr Gly Pro Trp Cys Tyr Thr Thr Asp Pro Thr Val
                165                 170                 175
Arg Arg Gln Glu Cys Ser Ile Pro Val Cys Gly Gln Asp Gln Val Thr
            180                 185                 190
Val Ala Met Thr Pro Arg Ser Glu Gly Ser Ser Val Asn Leu Ser Pro
        195                 200                 205
Pro Leu Glu Gln Cys Val Pro Asp Arg Gly Gln Gln Tyr Gln Gly Arg
    210                 215                 220
Leu Ala Val Thr Thr His Gly Leu Pro Cys Leu Ala Trp Ala Ser Ala
225                 230                 235                 240
Gln Ala Lys Ala Leu Ser Lys His Gln Asp Phe Asn Ser Ala Val Gln
                245                 250                 255
Leu Val Glu Asn Phe Cys Arg Asn Pro Asp Gly Asp Glu Glu Gly Val
            260                 265                 270
Trp Cys Tyr Val Ala Gly Lys Pro Gly Asp Phe Gly Tyr Cys Asp Leu
```

```
            275                 280                 285
Asn Tyr Cys Glu Glu Ala Val Glu Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
            325                 330                 335

Gly Leu Arg Pro Leu Phe Glu Lys Lys Ser Leu Glu Asp Lys Thr Glu
        340                 345                 350

Arg Glu Leu Leu Glu Ser Tyr Ile Asp Gly Arg Ile Val Glu Gly Ser
                355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 83
<211> LENGTH: 885
<212> TYPE: PRT
<213> ORGANISM: human

<400> SEQUENCE: 83

Met Ala Pro Pro Ser Thr Arg Glu Pro Arg Val Leu Ser Ala Thr Ser
1               5                   10                  15

Ala Thr Lys Ser Asp Gly Glu Met Val Leu Pro Gly Phe Pro Asp Ala
            20                  25                  30
```

```
Asp Ser Phe Val Lys Phe Ala Leu Gly Ser Val Ala Val Thr Lys
         35                  40                  45

Ala Ser Gly Gly Leu Pro Gln Phe Gly Asp Glu Tyr Asp Phe Tyr Arg
 50                  55                  60

Ser Phe Pro Gly Phe Gln Ala Phe Cys Glu Thr Gln Gly Asp Arg Leu
 65                  70                  75                  80

Leu Gln Cys Met Ser Arg Val Met Gln Tyr His Gly Cys Arg Ser Asn
                 85                  90                  95

Ile Lys Asp Arg Ser Lys Val Thr Glu Leu Glu Asp Lys Phe Asp Leu
                100                 105                 110

Leu Val Asp Ala Asn Asp Val Ile Leu Glu Arg Val Gly Ile Leu Leu
                115                 120                 125

Asp Glu Ala Ser Gly Val Asn Lys Asn Gln Gln Pro Val Leu Pro Ala
        130                 135                 140

Gly Leu Gln Val Pro Lys Thr Val Val Ser Ser Trp Asn Arg Lys Ala
145                 150                 155                 160

Ala Glu Tyr Gly Lys Lys Ala Lys Ser Glu Thr Phe Arg Leu Leu His
                165                 170                 175

Ala Lys Asn Ile Ile Arg Pro Gln Leu Lys Phe Arg Glu Lys Ile Asp
                180                 185                 190

Asn Ser Asn Thr Pro Phe Leu Pro Lys Ile Phe Ile Lys Pro Asn Ala
                195                 200                 205

Gln Lys Pro Leu Pro Gln Ala Leu Ser Lys Glu Arg Arg Glu Arg Pro
        210                 215                 220

Gln Asp Arg Pro Glu Asp Leu Asp Val Pro Pro Ala Leu Ala Asp Phe
225                 230                 235                 240

Ile His Gln Gln Arg Thr Gln Gln Val Glu Gln Asp Met Phe Ala His
                245                 250                 255

Pro Tyr Gln Tyr Glu Leu Asn His Phe Thr Pro Ala Asp Ala Val Leu
                260                 265                 270

Gln Lys Pro Gln Pro Gln Leu Tyr Arg Pro Ile Glu Glu Thr Pro Cys
                275                 280                 285

His Phe Ile Ser Ser Leu Asp Glu Leu Val Glu Leu Asn Glu Lys Leu
        290                 295                 300

Leu Asn Cys Gln Glu Phe Ala Val Asp Leu Glu His Ser Tyr Arg
305                 310                 315                 320

Ser Phe Leu Gly Leu Thr Cys Leu Met Gln Ile Ser Thr Arg Thr Glu
                325                 330                 335

Asp Phe Ile Ile Asp Thr Leu Glu Leu Arg Ser Asp Met Tyr Ile Leu
                340                 345                 350

Asn Glu Ser Leu Thr Asp Pro Ala Ile Val Lys Val Phe His Gly Ala
                355                 360                 365

Asp Ser Asp Ile Glu Trp Leu Gln Lys Asp Phe Gly Leu Tyr Val Val
        370                 375                 380

Asn Met Phe Asp Thr His Gln Ala Ala Arg Leu Leu Asn Leu Gly Arg
385                 390                 395                 400

His Ser Leu Asp His Leu Leu Lys Leu Tyr Cys Asn Val Asp Ser Asn
                405                 410                 415

Lys Gln Tyr Gln Leu Ala Asp Trp Arg Ile Arg Pro Leu Pro Glu Glu
                420                 425                 430

Met Leu Ser Tyr Ala Arg Asp Asp Thr His Tyr Leu Leu Tyr Ile Tyr
                435                 440                 445

Asp Lys Met Arg Leu Glu Met Trp Glu Arg Gly Asn Gly Gln Pro Val
```

-continued

```
            450                 455                 460
Gln Leu Gln Val Val Trp Gln Arg Ser Arg Asp Ile Cys Leu Lys Lys
465                 470                 475                 480

Phe Ile Lys Pro Ile Phe Thr Asp Glu Ser Tyr Leu Glu Leu Tyr Arg
                    485                 490                 495

Lys Gln Lys Lys His Leu Asn Thr Gln Gln Leu Thr Ala Phe Gln Leu
                500                 505                 510

Leu Phe Ala Trp Arg Asp Lys Thr Ala Arg Arg Glu Asp Glu Ser Tyr
            515                 520                 525

Gly Tyr Val Leu Pro Asn His Met Met Leu Lys Ile Ala Glu Glu Leu
        530                 535                 540

Pro Lys Glu Pro Gln Gly Ile Ile Ala Cys Cys Asn Pro Val Pro Pro
545                 550                 555                 560

Leu Val Arg Gln Gln Ile Asn Glu Met His Leu Leu Ile Gln Gln Ala
                    565                 570                 575

Arg Glu Met Pro Leu Leu Lys Ser Glu Val Ala Ala Gly Val Lys Lys
                580                 585                 590

Ser Gly Pro Leu Pro Ser Ala Glu Arg Leu Glu Asn Val Leu Phe Gly
            595                 600                 605

Pro His Asp Cys Ser His Ala Pro Pro Asp Gly Tyr Pro Ile Ile Pro
        610                 615                 620

Thr Ser Gly Ser Val Pro Val Gln Lys Gln Ala Ser Leu Phe Pro Asp
625                 630                 635                 640

Glu Lys Glu Asp Asn Leu Leu Gly Thr Thr Cys Leu Ile Ala Thr Ala
                    645                 650                 655

Val Ile Thr Leu Phe Asn Glu Pro Ser Ala Glu Asp Ser Lys Lys Gly
                660                 665                 670

Pro Leu Thr Val Ala Gln Lys Lys Ala Gln Asn Ile Met Glu Ser Phe
            675                 680                 685

Glu Asn Pro Phe Arg Met Phe Leu Pro Ser Leu Gly His Arg Ala Pro
        690                 695                 700

Val Ser Gln Ala Ala Lys Phe Asp Pro Ser Thr Lys Ile Tyr Glu Ile
705                 710                 715                 720

Ser Asn Arg Trp Lys Leu Ala Gln Val Gln Val Lys Asp Ser Lys
                    725                 730                 735

Glu Ala Val Lys Lys Lys Ala Ala Glu Gln Thr Ala Ala Arg Glu Gln
                740                 745                 750

Ala Lys Glu Ala Cys Lys Ala Ala Glu Gln Ala Ile Ser Val Arg
            755                 760                 765

Gln Gln Val Val Leu Glu Asn Ala Ala Lys Lys Arg Glu Arg Ala Thr
        770                 775                 780

Ser Asp Pro Arg Thr Thr Glu Gln Lys Gln Lys Lys Arg Leu Lys
785                 790                 795                 800

Ile Ser Lys Lys Pro Lys Asp Pro Glu Pro Glu Lys Glu Phe Thr
                    805                 810                 815

Pro Tyr Asp Tyr Ser Gln Ser Asp Phe Lys Ala Phe Ala Gly Asn Ser
                820                 825                 830

Lys Ser Lys Val Ser Ser Gln Phe Asp Pro Asn Lys Gln Thr Pro Ser
            835                 840                 845

Gly Lys Lys Cys Ile Ala Ala Lys Ile Lys Gln Ser Val Gly Asn
        850                 855                 860

Lys Ser Met Ser Phe Pro Thr Gly Lys Ser Asp Arg Gly Phe Arg Tyr
865                 870                 875                 880
```

Asn Trp Pro Gln Arg
          885

<210> SEQ ID NO 84
<211> LENGTH: 2419
<212> TYPE: PRT
<213> ORGANISM: human

<400> SEQUENCE: 84

Met Glu Gln Phe Pro Lys Glu Thr Val Val Glu Ser Gly Pro Lys
1               5                   10                  15

Val Leu Glu Thr Ala Glu Glu Ile Gln Glu Arg Arg Gln Glu Val Leu
            20                  25                  30

Thr Arg Tyr Gln Ser Phe Lys Glu Arg Val Ala Glu Arg Gly Gln Lys
        35                  40                  45

Leu Glu Asp Ser Tyr His Leu Gln Val Phe Lys Arg Asp Ala Asp Asp
    50                  55                  60

Leu Gly Lys Trp Ile Met Glu Lys Val Asn Ile Leu Thr Asp Lys Ser
65                  70                  75                  80

Tyr Glu Asp Pro Thr Asn Ile Gln Gly Lys Tyr Gln Lys His Gln Ser
                85                  90                  95

Leu Glu Ala Glu Val Gln Thr Lys Ser Arg Leu Met Ser Glu Leu Glu
            100                 105                 110

Lys Thr Arg Glu Glu Arg Phe Thr Met Gly His Ser Ala His Glu Glu
        115                 120                 125

Thr Lys Ala His Ile Glu Glu Leu Arg His Leu Trp Asp Leu Leu Leu
    130                 135                 140

Glu Leu Thr Leu Glu Lys Gly Asp Gln Leu Leu Arg Ala Leu Lys Phe
145                 150                 155                 160

Gln Gln Tyr Val Gln Glu Cys Ala Asp Ile Leu Glu Trp Ile Gly Asp
                165                 170                 175

Lys Glu Ala Ile Ala Thr Ser Val Glu Leu Gly Glu Asp Trp Glu Arg
            180                 185                 190

Thr Glu Val Leu His Lys Lys Phe Glu Asp Phe Gln Val Glu Leu Val
        195                 200                 205

Ala Lys Glu Gly Arg Val Val Glu Val Asn Gln Tyr Ala Asn Glu Cys
    210                 215                 220

Ala Glu Glu Asn His Pro Asp Leu Pro Leu Ile Gln Ser Lys Gln Asn
225                 230                 235                 240

Glu Val Asn Ala Ala Trp Glu Arg Leu Arg Gly Leu Ala Leu Gln Arg
                245                 250                 255

Gln Lys Ala Leu Ser Asn Ala Ala Asn Leu Gln Arg Phe Lys Arg Asp
            260                 265                 270

Val Thr Glu Ala Ile Gln Trp Ile Lys Glu Lys Glu Pro Val Leu Thr
        275                 280                 285

Ser Glu Asp Tyr Gly Lys Asp Leu Val Ala Ser Glu Gly Leu Phe His
    290                 295                 300

Ser His Lys Gly Leu Glu Arg Asn Leu Ala Val Met Ser Asp Lys Val
305                 310                 315                 320

Lys Glu Leu Cys Ala Lys Ala Glu Lys Leu Thr Leu Ser His Pro Ser
                325                 330                 335

Asp Ala Pro Gln Ile Gln Glu Met Lys Glu Asp Leu Val Ser Ser Trp
            340                 345                 350

Glu His Ile Arg Ala Leu Ala Thr Ser Arg Tyr Glu Lys Leu Gln Ala

```
            355                 360                 365
Thr Tyr Trp Tyr His Arg Phe Ser Ser Asp Phe Asp Glu Leu Ser Gly
    370                 375                 380

Trp Met Asn Glu Lys Thr Ala Ala Ile Asn Ala Asp Glu Leu Pro Thr
385                 390                 395                 400

Asp Val Ala Gly Gly Glu Val Leu Leu Asp Arg His Gln Gln His Lys
                405                 410                 415

His Glu Ile Asp Ser Tyr Asp Asp Arg Phe Gln Ser Ala Asp Glu Thr
            420                 425                 430

Gly Gln Asp Leu Val Asn Ala Asn His Glu Ala Ser Asp Glu Val Arg
        435                 440                 445

Glu Lys Met Glu Ile Leu Asp Asn Asn Trp Thr Ala Leu Leu Glu Leu
    450                 455                 460

Trp Asp Glu Arg His Arg Gln Tyr Glu Gln Cys Leu Asp Phe His Leu
465                 470                 475                 480

Phe Tyr Arg Asp Ser Glu Gln Val Asp Ser Trp Met Ser Arg Gln Glu
                485                 490                 495

Ala Phe Leu Glu Asn Glu Asp Leu Gly Asn Ser Leu Gly Ser Ala Glu
            500                 505                 510

Ala Leu Leu Gln Lys His Glu Asp Phe Glu Glu Ala Phe Thr Ala Gln
        515                 520                 525

Glu Glu Lys Ile Ile Thr Val Asp Lys Thr Ala Thr Lys Leu Ile Gly
    530                 535                 540

Asp Asp His Tyr Asp Ser Glu Asn Ile Lys Ala Ile Arg Asp Gly Leu
545                 550                 555                 560

Leu Ala Arg Arg Asp Ala Leu Arg Glu Lys Ala Ala Thr Arg Arg Arg
                565                 570                 575

Leu Leu Lys Glu Ser Leu Leu Leu Gln Lys Leu Tyr Glu Asp Ser Asp
            580                 585                 590

Asp Leu Lys Asn Trp Ile Asn Lys Lys Lys Leu Ala Asp Asp Glu
        595                 600                 605

Asp Tyr Lys Asp Ile Gln Asn Leu Lys Ser Arg Val Gln Lys Gln Gln
    610                 615                 620

Val Phe Glu Lys Glu Leu Ala Val Asn Lys Thr Gln Leu Glu Asn Ile
625                 630                 635                 640

Gln Lys Thr Gly Gln Glu Met Ile Glu Gly Gly His Tyr Ala Ser Asp
                645                 650                 655

Asn Val Thr Thr Arg Leu Ser Glu Val Ala Ser Leu Trp Glu Glu Leu
            660                 665                 670

Leu Glu Ala Thr Lys Gln Lys Gly Thr Gln Leu His Glu Ala Asn Gln
        675                 680                 685

Gln Leu Gln Phe Glu Asn Asn Ala Glu Asp Leu Gln Arg Trp Leu Glu
    690                 695                 700

Asp Val Glu Trp Gln Val Thr Ser Glu Asp Tyr Gly Lys Gly Leu Ala
705                 710                 715                 720

Glu Val Gln Asn Arg Leu Arg Lys His Gly Leu Leu Glu Ser Ala Val
                725                 730                 735

Ala Ala Arg Gln Asp Gln Val Asp Ile Leu Thr Asp Leu Ala Ala Tyr
            740                 745                 750

Phe Glu Glu Ile Gly His Pro Asp Ser Lys Asp Ile Arg Ala Arg Gln
        755                 760                 765

Glu Ser Leu Val Cys Arg Phe Glu Ala Leu Lys Glu Pro Leu Ala Thr
    770                 775                 780
```

```
Arg Lys Lys Lys Leu Leu Asp Leu Leu His Leu Gln Leu Ile Cys Arg
785                 790                 795                 800

Asp Thr Glu Asp Glu Glu Ala Trp Ile Gln Glu Thr Glu Pro Ser Ala
            805                 810                 815

Thr Ser Thr Tyr Leu Gly Lys Asp Leu Ile Ala Ser Lys Lys Leu Leu
            820                 825                 830

Asn Arg His Arg Val Ile Leu Glu Asn Ile Ala Ser His Glu Pro Arg
            835                 840                 845

Ile Gln Glu Ile Thr Glu Arg Gly Asn Lys Met Val Glu Glu Gly His
850                 855                 860

Phe Ala Ala Glu Asp Val Ala Ser Arg Val Lys Ser Leu Asn Gln Asn
865                 870                 875                 880

Met Glu Ser Leu Arg Ala Arg Ala Ala Arg Gln Asn Asp Leu Glu
                885                 890                 895

Ala Asn Val Gln Phe Gln Gln Tyr Leu Ala Asp Leu His Glu Ala Glu
            900                 905                 910

Thr Trp Ile Arg Glu Lys Glu Pro Ile Val Asp Asn Thr Asn Tyr Gly
            915                 920                 925

Ala Asp Glu Glu Ala Ala Gly Ala Leu Leu Lys Lys His Glu Ala Phe
930                 935                 940

Leu Leu Asp Leu Asn Ser Phe Gly Asp Ser Met Lys Ala Leu Arg Asn
945                 950                 955                 960

Gln Ala Asn Ala Cys Gln Gln Gln Ala Ala Pro Val Glu Gly Val
                965                 970                 975

Ala Gly Glu Gln Arg Val Met Ala Leu Tyr Asp Phe Gln Ala Arg Ser
            980                 985                 990

Pro Arg Glu Val Thr Met Lys Lys Gly Asp Val Leu Thr Leu Leu Ser
            995                 1000                1005

Ser Ile Asn Lys Asp Trp Trp Lys Val Glu Ala Ala Asp His Gln
    1010                1015                1020

Gly Ile Val Pro Ala Val Tyr Val Arg Arg Leu Ala His Asp Glu
    1025                1030                1035

Phe Pro Met Leu Pro Gln Arg Arg Glu Glu Pro Gly Asn Ile
    1040                1045                1050

Thr Gln Arg Gln Glu Gln Ile Glu Asn Gln Tyr Arg Ser Leu Leu
    1055                1060                1065

Asp Arg Ala Glu Glu Arg Arg Arg Leu Leu Gln Arg Tyr Asn
    1070                1075                1080

Glu Phe Leu Leu Ala Tyr Glu Ala Gly Asp Met Leu Glu Trp Ile
    1085                1090                1095

Gln Glu Lys Lys Ala Glu Asn Thr Gly Val Glu Leu Asp Asp Val
    1100                1105                1110

Trp Glu Leu Gln Lys Lys Phe Asp Glu Phe Gln Lys Asp Leu Asn
    1115                1120                1125

Thr Asn Glu Pro Arg Leu Arg Asp Ile Asn Lys Val Ala Asp Asp
    1130                1135                1140

Leu Leu Phe Glu Gly Leu Leu Thr Pro Glu Gly Ala Gln Ile Arg
    1145                1150                1155

Gln Glu Leu Asn Ser Arg Trp Gly Ser Leu Gln Arg Leu Ala Asp
    1160                1165                1170

Glu Gln Arg Gln Leu Leu Gly Ser Ala His Ala Val Glu Val Phe
    1175                1180                1185
```

His Arg Glu Ala Asp Asp Thr Lys Glu Gln Ile Glu Lys Lys Cys
1190             1195                 1200

Gln Ala Leu Ser Ala Ala Asp Pro Gly Ser Asp Leu Phe Ser Val
1205             1210                 1215

Gln Ala Leu Gln Arg Arg His Glu Gly Phe Glu Arg Asp Leu Val
1220             1225                 1230

Pro Leu Gly Asp Lys Val Thr Ile Leu Gly Glu Thr Ala Glu Arg
1235             1240                 1245

Leu Ser Glu Ser His Pro Asp Ala Thr Glu Asp Leu Gln Arg Gln
1250             1255                 1260

Lys Met Glu Leu Asn Glu Ala Trp Glu Asp Leu Gln Gly Arg Thr
1265             1270                 1275

Lys Asp Arg Lys Glu Ser Leu Asn Glu Ala Gln Lys Phe Tyr Leu
1280             1285                 1290

Phe Leu Ser Lys Ala Arg Asp Leu Gln Asn Trp Ile Ser Ser Ile
1295             1300                 1305

Gly Gly Met Val Ser Ser Gln Glu Leu Ala Glu Asp Leu Thr Gly
1310             1315                 1320

Ile Glu Ile Leu Leu Glu Arg His Gln Glu His Arg Ala Asp Met
1325             1330                 1335

Glu Ala Glu Ala Pro Thr Phe Gln Ala Leu Glu Asp Phe Ser Ala
1340             1345                 1350

Glu Leu Ile Asp Ser Gly His His Ala Ser Pro Glu Ile Glu Lys
1355             1360                 1365

Lys Leu Gln Ala Val Lys Leu Glu Arg Asp Asp Leu Glu Lys Ala
1370             1375                 1380

Trp Glu Lys Arg Lys Lys Ile Leu Asp Gln Cys Leu Glu Leu Gln
1385             1390                 1395

Met Phe Gln Gly Asn Cys Asp Gln Val Glu Ser Trp Met Val Ala
1400             1405                 1410

Arg Glu Asn Ser Leu Arg Ser Asp Asp Lys Ser Ser Leu Asp Ser
1415             1420                 1425

Leu Glu Ala Leu Met Lys Lys Arg Asp Asp Leu Asp Lys Ala Ile
1430             1435                 1440

Thr Ala Gln Glu Gly Lys Ile Thr Asp Leu Glu His Phe Ala Glu
1445             1450                 1455

Ser Leu Ile Ala Asp Glu His Tyr Ala Lys Glu Glu Ile Ala Thr
1460             1465                 1470

Arg Leu Gln Arg Val Leu Asp Arg Trp Lys Ala Leu Lys Ala Gln
1475             1480                 1485

Leu Ile Asp Glu Arg Thr Lys Leu Gly Asp Tyr Ala Asn Leu Lys
1490             1495                 1500

Gln Phe Tyr Arg Asp Leu Glu Glu Leu Glu Glu Trp Ile Ser Glu
1505             1510                 1515

Met Leu Pro Thr Ala Cys Asp Glu Ser Tyr Lys Asp Ala Thr Asn
1520             1525                 1530

Ile Gln Arg Lys Tyr Leu Lys His Gln Thr Phe Ala His Glu Val
1535             1540                 1545

Asp Gly Arg Ser Glu Gln Val His Gly Val Ile Asn Leu Gly Asn
1550             1555                 1560

Ser Leu Ile Glu Cys Ser Ala Cys Asp Gly Asn Glu Glu Ala Met
1565             1570                 1575

Lys Glu Gln Leu Glu Gln Leu Lys Glu His Trp Asp His Leu Leu

-continued

```
           1580                1585                1590
Glu Arg Thr Asn Asp Lys Gly Lys Lys Leu Asn Glu Ala Ser Arg
    1595                1600                1605
Gln Gln Arg Phe Asn Thr Ser Ile Arg Asp Phe Glu Phe Trp Leu
    1610                1615                1620
Ser Glu Ala Glu Thr Leu Leu Ala Met Lys Asp Gln Ala Arg Asp
    1625                1630                1635
Leu Ala Ser Ala Gly Asn Leu Leu Lys Lys His Gln Leu Leu Glu
    1640                1645                1650
Arg Glu Met Leu Ala Arg Glu Asp Ala Leu Lys Asp Leu Asn Thr
    1655                1660                1665
Leu Ala Glu Asp Leu Leu Ser Ser Gly Thr Phe Asn Val Asp Gln
    1670                1675                1680
Ile Val Lys Lys Lys Asp Asn Val Asn Lys Arg Phe Leu Asn Val
    1685                1690                1695
Gln Glu Leu Ala Ala Ala His His Glu Lys Leu Lys Glu Ala Tyr
    1700                1705                1710
Ala Leu Phe Gln Phe Phe Gln Asp Leu Asp Asp Glu Glu Ser Trp
    1715                1720                1725
Ile Glu Glu Lys Leu Ile Arg Val Ser Ser Gln Asp Tyr Gly Arg
    1730                1735                1740
Asp Leu Gln Gly Val Gln Asn Leu Leu Lys Lys His Lys Arg Leu
    1745                1750                1755
Glu Gly Glu Leu Val Ala His Glu Pro Ala Ile Gln Asn Val Leu
    1760                1765                1770
Asp Met Ala Glu Lys Leu Lys Asp Lys Ala Ala Val Gly Gln Glu
    1775                1780                1785
Glu Ile Gln Leu Arg Leu Ala Gln Phe Val Glu His Trp Glu Lys
    1790                1795                1800
Leu Lys Glu Leu Ala Lys Ala Arg Gly Leu Lys Leu Glu Glu Ser
    1805                1810                1815
Leu Glu Tyr Leu Gln Phe Met Gln Asn Ala Glu Glu Glu Glu Ala
    1820                1825                1830
Trp Ile Asn Glu Lys Asn Ala Leu Ala Val Arg Gly Asp Cys Gly
    1835                1840                1845
Asp Thr Leu Ala Ala Thr Gln Ser Leu Leu Met Lys His Glu Ala
    1850                1855                1860
Leu Glu Asn Asp Phe Ala Val His Glu Thr Arg Val Gln Asn Val
    1865                1870                1875
Cys Ala Gln Gly Glu Asp Ile Leu Asn Lys Val Leu Gln Glu Glu
    1880                1885                1890
Ser Gln Asn Lys Glu Ile Ser Ser Lys Ile Glu Ala Leu Asn Glu
    1895                1900                1905
Lys Thr Pro Ser Leu Ala Lys Ala Ile Ala Ala Trp Lys Leu Gln
    1910                1915                1920
Leu Glu Asp Asp Tyr Ala Phe Gln Glu Phe Asn Trp Lys Ala Asp
    1925                1930                1935
Val Val Glu Ala Trp Ile Ala Asp Lys Glu Thr Ser Leu Lys Thr
    1940                1945                1950
Asn Gly Asn Gly Ala Asp Leu Gly Asp Phe Leu Thr Leu Leu Ala
    1955                1960                1965
Lys Gln Asp Thr Leu Asp Ala Ser Leu Gln Ser Phe Gln Gln Glu
    1970                1975                1980
```

```
Arg Leu Pro Glu Ile Thr Asp Leu Lys Asp Lys Leu Ile Ser Ala
    1985            1990                1995

Gln His Asn Gln Ser Lys Ala Ile Glu Glu Arg Tyr Ala Ala Leu
    2000            2005                2010

Leu Lys Arg Trp Glu Gln Leu Leu Glu Ala Ser Ala Val His Arg
    2015            2020                2025

Gln Lys Leu Leu Glu Lys Gln Leu Pro Leu Gln Lys Ala Glu Asp
    2030            2035                2040

Leu Phe Val Glu Phe Ala His Lys Ala Ser Ala Leu Asn Asn Trp
    2045            2050                2055

Cys Glu Lys Met Glu Glu Asn Leu Ser Glu Pro Val His Cys Val
    2060            2065                2070

Ser Leu Asn Glu Ile Arg Gln Leu Gln Lys Asp His Glu Asp Phe
    2075            2080                2085

Leu Ala Ser Leu Ala Arg Ala Gln Ala Asp Phe Lys Cys Leu Leu
    2090            2095                2100

Glu Leu Asp Gln Gln Ile Lys Ala Leu Gly Val Pro Ser Ser Pro
    2105            2110                2115

Tyr Thr Trp Leu Thr Val Glu Val Leu Glu Arg Thr Trp Lys His
    2120            2125                2130

Leu Ser Asp Ile Ile Glu Glu Arg Glu Gln Leu Gln Lys Glu
    2135            2140                2145

Glu Ala Arg Gln Val Lys Asn Phe Glu Met Cys Gln Glu Phe Glu
    2150            2155                2160

Gln Asn Ala Ser Thr Phe Leu Gln Trp Ile Leu Glu Thr Arg Ala
    2165            2170                2175

Tyr Phe Leu Asp Gly Ser Leu Leu Lys Glu Thr Gly Thr Leu Glu
    2180            2185                2190

Ser Gln Leu Glu Ala Asn Lys Arg Lys Gln Lys Glu Ile Gln Ala
    2195            2200                2205

Met Lys Arg Gln Leu Thr Lys Ile Val Asp Leu Gly Asp Asn Leu
    2210            2215                2220

Glu Asp Ala Leu Ile Leu Asp Ile Lys Tyr Ser Thr Ile Gly Leu
    2225            2230                2235

Ala Gln Gln Trp Asp Gln Leu Tyr Gln Leu Gly Leu Arg Met Gln
    2240            2245                2250

His Asn Leu Glu Gln Gln Ile Gln Ala Lys Asp Ile Lys Gly Val
    2255            2260                2265

Ser Glu Glu Thr Leu Lys Glu Phe Ser Thr Ile Tyr Lys His Phe
    2270            2275                2280

Asp Glu Asn Leu Thr Gly Arg Leu Thr His Lys Glu Phe Arg Ser
    2285            2290                2295

Cys Leu Arg Gly Leu Asn Tyr Tyr Leu Pro Met Val Glu Glu Asp
    2300            2305                2310

Glu His Glu Pro Lys Phe Glu Lys Phe Leu Asp Ala Val Asp Pro
    2315            2320                2325

Gly Arg Lys Gly Tyr Val Ser Leu Glu Asp Tyr Thr Ala Phe Leu
    2330            2335                2340

Ile Asp Lys Glu Ser Glu Asn Ile Lys Ser Ser Asp Glu Ile Glu
    2345            2350                2355

Asn Ala Phe Gln Ala Leu Ala Glu Gly Lys Ser Tyr Ile Thr Lys
    2360            2365                2370
```

```
Glu Asp Met Lys Gln Ala Leu Thr Pro Glu Gln Val Ser Phe Cys
    2375            2380                2385

Ala Thr His Met Gln Gln Tyr Met Asp Pro Arg Gly Arg Ser His
    2390            2395                2400

Leu Ser Gly Tyr Asp Tyr Val Gly Phe Thr Asn Ser Tyr Phe Gly
    2405            2410                2415

Asn

<210> SEQ ID NO 85
<211> LENGTH: 745
<212> TYPE: PRT
<213> ORGANISM: human

<400> SEQUENCE: 85

Met Gly Val Pro Phe Phe Ser Ser Leu Arg Cys Met Val Asp Leu Gly
1               5                   10                  15

Pro Cys Trp Ala Gly Gly Leu Thr Ala Glu Met Lys Leu Leu Leu Ala
                20                  25                  30

Leu Ala Gly Leu Leu Ala Ile Leu Ala Thr Pro Gln Pro Ser Glu Gly
            35                  40                  45

Ala Ala Pro Ala Val Leu Gly Glu Val Asp Thr Ser Leu Val Leu Ser
50                  55                  60

Ser Met Glu Glu Ala Lys Gln Leu Val Asp Lys Ala Tyr Lys Glu Arg
65                  70                  75                  80

Arg Glu Ser Ile Lys Gln Arg Leu Arg Ser Gly Ser Ala Ser Pro Met
                85                  90                  95

Glu Leu Leu Ser Tyr Phe Lys Gln Pro Val Ala Ala Thr Arg Thr Ala
            100                 105                 110

Val Arg Ala Ala Asp Tyr Leu His Val Ala Leu Asp Leu Leu Glu Arg
        115                 120                 125

Lys Leu Arg Ser Leu Trp Arg Arg Pro Phe Asn Val Thr Asp Val Leu
130                 135                 140

Thr Pro Ala Gln Leu Asn Val Leu Ser Lys Ser Ser Gly Cys Ala Tyr
145                 150                 155                 160

Gln Asp Val Gly Val Thr Cys Pro Glu Gln Asp Lys Tyr Arg Thr Ile
                165                 170                 175

Thr Gly Met Cys Asn Asn Arg Arg Ser Pro Thr Leu Gly Ala Ser Asn
            180                 185                 190

Arg Ala Phe Val Arg Trp Leu Pro Ala Glu Tyr Glu Asp Gly Phe Ser
        195                 200                 205

Leu Pro Tyr Gly Trp Thr Pro Gly Val Lys Arg Asn Gly Phe Pro Val
    210                 215                 220

Ala Leu Ala Arg Ala Val Ser Asn Glu Ile Val Arg Phe Pro Thr Asp
225                 230                 235                 240

Gln Leu Thr Pro Asp Gln Glu Arg Ser Leu Met Phe Met Gln Trp Gly
                245                 250                 255

Gln Leu Leu Asp His Asp Leu Asp Phe Thr Pro Glu Pro Ala Ala Arg
            260                 265                 270

Ala Ser Phe Val Thr Gly Val Asn Cys Glu Thr Ser Cys Val Gln Gln
        275                 280                 285

Pro Pro Cys Phe Pro Leu Lys Ile Pro Pro Asn Asp Pro Arg Ile Lys
    290                 295                 300

Asn Gln Ala Asp Cys Ile Pro Phe Phe Arg Ser Cys Pro Ala Cys Pro
305                 310                 315                 320
```

```
Gly Ser Asn Ile Thr Ile Arg Asn Gln Ile Asn Ala Leu Thr Ser Phe
                325                 330                 335

Val Asp Ala Ser Met Val Tyr Gly Ser Glu Pro Leu Ala Arg Asn
        340                 345                 350

Leu Arg Asn Met Ser Asn Gln Leu Gly Leu Leu Ala Val Asn Gln Arg
            355                 360                 365

Phe Gln Asp Asn Gly Arg Ala Leu Leu Pro Phe Asp Asn Leu His Asp
    370                 375                 380

Asp Pro Cys Leu Leu Thr Asn Arg Ser Ala Arg Ile Pro Cys Phe Leu
385                 390                 395                 400

Ala Gly Asp Thr Arg Ser Ser Glu Met Pro Glu Leu Thr Ser Met His
            405                 410                 415

Thr Leu Leu Leu Arg Glu His Asn Arg Leu Ala Thr Glu Leu Lys Ser
            420                 425                 430

Leu Asn Pro Arg Trp Asp Gly Glu Arg Leu Tyr Gln Glu Ala Arg Lys
        435                 440                 445

Ile Val Gly Ala Met Val Gln Ile Ile Thr Tyr Arg Asp Tyr Leu Pro
        450                 455                 460

Leu Val Leu Gly Pro Thr Ala Met Arg Lys Tyr Leu Pro Thr Tyr Arg
465                 470                 475                 480

Ser Tyr Asn Asp Ser Val Asp Pro Arg Ile Ala Asn Val Phe Thr Asn
            485                 490                 495

Ala Phe Arg Tyr Gly His Thr Leu Ile Gln Pro Phe Met Phe Arg Leu
        500                 505                 510

Asp Asn Arg Tyr Gln Pro Met Glu Pro Asn Pro Arg Val Pro Leu Ser
        515                 520                 525

Arg Val Phe Phe Ala Ser Trp Arg Val Val Leu Glu Gly Gly Ile Asp
        530                 535                 540

Pro Ile Leu Arg Gly Leu Met Ala Thr Pro Ala Lys Leu Asn Arg Gln
545                 550                 555                 560

Asn Gln Ile Ala Val Asp Glu Ile Arg Glu Arg Leu Phe Glu Gln Val
            565                 570                 575

Met Arg Ile Gly Leu Asp Leu Pro Ala Leu Asn Met Gln Arg Ser Arg
        580                 585                 590

Asp His Gly Leu Pro Gly Tyr Asn Ala Trp Arg Arg Phe Cys Gly Leu
        595                 600                 605

Pro Gln Pro Glu Thr Val Gly Gln Leu Gly Thr Val Leu Arg Asn Leu
    610                 615                 620

Lys Leu Ala Arg Lys Leu Met Glu Gln Tyr Gly Thr Pro Asn Asn Ile
625                 630                 635                 640

Asp Ile Trp Met Gly Gly Val Ser Glu Pro Leu Lys Arg Lys Gly Arg
            645                 650                 655

Val Gly Pro Leu Leu Ala Cys Ile Ile Gly Thr Gln Phe Arg Lys Leu
        660                 665                 670

Arg Asp Gly Asp Arg Phe Trp Trp Glu Asn Gly Val Phe Ser Met
    675                 680                 685

Gln Gln Arg Gln Ala Leu Ala Gln Ile Ser Leu Pro Arg Ile Cys
    690                 695                 700

Asp Asn Thr Gly Ile Thr Thr Val Ser Lys Asn Ile Phe Met Ser
705                 710                 715                 720

Asn Ser Tyr Pro Arg Asp Phe Val Asn Cys Ser Thr Leu Pro Ala Leu
            725                 730                 735

Asn Leu Ala Ser Trp Arg Glu Ala Ser
```

<210> SEQ ID NO 86
<211> LENGTH: 1048
<212> TYPE: PRT
<213> ORGANISM: human

<400> SEQUENCE: 86

Met Ser Leu Gln Phe Ile Gly Leu Gln Arg Arg Asp Val Val Ala Leu
1               5                   10                  15

Val Asn Phe Leu Arg His Leu Thr Gln Lys Pro Asp Val Asp Leu Glu
            20                  25                  30

Ala His Pro Lys Ile Leu Lys Lys Cys Gly Glu Lys Arg Leu His Arg
        35                  40                  45

Arg Thr Val Leu Phe Asn Glu Leu Met Leu Trp Leu Gly Tyr Tyr Arg
    50                  55                  60

Glu Leu Arg Phe His Asn Pro Asp Leu Ser Ser Val Leu Glu Glu Phe
65                  70                  75                  80

Glu Val Arg Cys Val Ala Val Ala Arg Arg Gly Tyr Thr Tyr Pro Phe
                85                  90                  95

Gly Asp Arg Gly Lys Ala Arg Asp His Leu Ala Val Leu Asp Arg Thr
            100                 105                 110

Glu Phe Asp Thr Asp Val Arg His Asp Ala Glu Ile Val Glu Arg Ala
        115                 120                 125

Leu Val Ser Ala Val Ile Leu Ala Lys Met Ser Val Arg Glu Thr Leu
    130                 135                 140

Val Thr Ala Ile Gly Gln Thr Glu Pro Ile Ala Phe Val His Leu Lys
145                 150                 155                 160

Asp Thr Glu Val Gln Arg Ile Glu Glu Asn Leu Glu Gly Val Arg Arg
                165                 170                 175

Asn Met Phe Cys Val Lys Pro Leu Asp Leu Asn Leu Asp Arg His Ala
            180                 185                 190

Asn Thr Ala Leu Val Asn Ala Val Asn Lys Leu Val Tyr Thr Gly Arg
        195                 200                 205

Leu Ile Met Asn Val Arg Arg Ser Trp Glu Leu Glu Arg Lys Cys
    210                 215                 220

Leu Ala Arg Ile Gln Glu Arg Cys Lys Leu Leu Val Lys Glu Leu Arg
225                 230                 235                 240

Met Cys Leu Ser Phe Asp Ser Asn Tyr Cys Arg Asn Ile Leu Lys His
                245                 250                 255

Ala Val Glu Asn Gly Asp Ser Ala Asp Thr Leu Leu Glu Leu Leu Ile
            260                 265                 270

Glu Asp Phe Asp Ile Tyr Val Asp Ser Phe Pro Gln Ser Ala His Thr
        275                 280                 285

Phe Leu Gly Ala Arg Ser Pro Ser Leu Glu Phe Asp Asp Ala Asn
    290                 295                 300

Leu Leu Ser Leu Gly Gly Ser Ala Phe Ser Val Pro Lys Lys
305                 310                 315                 320

His Val Pro Thr Gln Pro Leu Asp Gly Trp Ser Trp Ile Ala Ser Pro
                325                 330                 335

Trp Lys Gly His Lys Pro Phe Arg Phe Glu Ala His Gly Ser Leu Ala
            340                 345                 350

Pro Ala Ala Glu Ala His Ala Ala Arg Ser Ala Ala Val Gly Tyr Tyr
        355                 360                 365

```
Asp Glu Glu Lys Arg Arg Glu Arg Gln Lys Arg Val Asp Asp Glu
    370                 375                 380

Val Val Gln Arg Glu Lys Gln Gln Leu Lys Ala Trp Glu Glu Arg Gln
385                 390                 395                 400

Gln Asn Leu Gln Gln Arg Gln Gln Gln Pro Pro Pro Ala Arg Lys
                405                 410                 415

Pro Ser Ala Ser Arg Arg Leu Phe Gly Ser Ser Ala Asp Glu Asp
            420                 425                 430

Asp Asp Asp Asp Asp Glu Lys Asn Ile Phe Thr Pro Ile Lys Lys Pro
        435                 440                 445

Gly Thr Ser Gly Lys Gly Ala Ala Ser Gly Gly Val Ser Ser Ile
    450                 455                 460

Phe Ser Gly Leu Leu Ser Ser Gly Ser Gln Lys Pro Thr Ser Gly Pro
465                 470                 475                 480

Leu Asn Ile Pro Gln Gln Gln Arg His Ala Ala Phe Ser Leu Val
                485                 490                 495

Ser Pro Gln Val Thr Lys Ala Ser Pro Gly Arg Val Arg Arg Asp Ser
            500                 505                 510

Ala Trp Asp Val Arg Pro Leu Thr Glu Thr Arg Gly Asp Leu Phe Ser
    515                 520                 525

Gly Asp Glu Asp Ser Asp Ser Ser Asp Gly Tyr Pro Pro Asn Arg Gln
    530                 535                 540

Asp Pro Arg Phe Thr Asp Thr Leu Val Asp Ile Thr Asp Thr Glu Thr
545                 550                 555                 560

Ser Ala Lys Pro Pro Val Thr Thr Ala Tyr Lys Phe Glu Gln Pro Thr
                565                 570                 575

Leu Thr Phe Gly Ala Gly Val Asn Val Pro Ala Gly Ala Gly Ala Ala
            580                 585                 590

Ile Leu Thr Pro Thr Pro Val Asn Pro Ser Thr Ala Pro Ala Pro Ala
        595                 600                 605

Pro Thr Pro Thr Phe Ala Gly Thr Gln Thr Pro Val Asn Gly Asn Ser
    610                 615                 620

Pro Trp Ala Pro Thr Ala Pro Leu Pro Gly Asp Met Asn Pro Ala Asn
625                 630                 635                 640

Trp Pro Arg Glu Arg Ala Trp Ala Leu Lys Asn Pro His Leu Ala Tyr
                645                 650                 655

Asn Pro Phe Arg Met Pro Thr Thr Ser Thr Ala Ser Gln Asn Thr Val
            660                 665                 670

Ser Thr Thr Pro Arg Arg Pro Ser Thr Pro Arg Ala Ala Val Thr Gln
        675                 680                 685

Thr Ala Ser Arg Asp Ala Ala Asp Glu Val Trp Ala Leu Arg Asp Gln
    690                 695                 700

Thr Ala Glu Ser Pro Val Glu Asp Ser Glu Glu Asp Asp Ser
705                 710                 715                 720

Ser Asp Thr Gly Ser Val Val Ser Leu Gly His Thr Thr Pro Ser Ser
                725                 730                 735

Asp Tyr Asn Asn Asp Val Ile Ser Pro Pro Ser Gln Thr Pro Glu Gln
            740                 745                 750

Ser Thr Pro Ser Arg Ile Arg Lys Ala Lys Leu Ser Ser Pro Met Thr
        755                 760                 765

Thr Thr Ser Thr Ser Gln Lys Pro Val Leu Gly Lys Arg Val Ala Thr
    770                 775                 780

Pro His Ala Ser Ala Arg Ala Gln Thr Val Thr Ser Thr Pro Val Gln
```

```
                785                 790                 795                 800
Gly Arg Leu Glu Lys Gln Val Ser Gly Thr Pro Ser Thr Val Pro Ala
                    805                 810                 815

Thr Leu Leu Gln Pro Gln Pro Ala Ser Ser Lys Thr Thr Ser Ser Arg
                    820                 825                 830

Asn Val Thr Ser Gly Ala Gly Thr Ser Ser Ala Ser Ser Ala Arg Gln
                    835                 840                 845

Pro Ser Ala Ser Ala Ser Val Leu Ser Pro Thr Glu Asp Val Val
850                 855                 860

Ser Pro Ala Thr Ser Pro Leu Ser Met Leu Ser Ser Ala Ser Pro Ser
865                 870                 875                 880

Pro Ala Lys Ser Ala Pro Pro Ser Pro Val Lys Gly Arg Gly Ser Arg
                    885                 890                 895

Val Gly Val Pro Ser Leu Lys Pro Thr Leu Gly Gly Lys Ala Val Val
                    900                 905                 910

Gly Arg Pro Pro Ser Val Pro Val Ser Gly Ser Ala Pro Gly Arg Leu
                    915                 920                 925

Ser Gly Ser Ser Arg Ala Ala Ser Thr Thr Pro Thr Tyr Pro Ala Val
                    930                 935                 940

Thr Thr Val Tyr Pro Pro Ser Ser Thr Ala Lys Ser Ser Val Ser Asn
945                 950                 955                 960

Ala Pro Pro Val Ala Ser Pro Ser Ile Leu Lys Pro Gly Ala Ser Ala
                    965                 970                 975

Ala Leu Gln Ser Arg Arg Ser Thr Gly Thr Ala Ala Val Gly Ser Pro
                    980                 985                 990

Val Lys Ser Thr Thr Gly Met Lys Thr Val Ala Phe Asp Leu Ser Ser
                    995                 1000                1005

Pro Gln Lys Ser Gly Thr Gly Pro Gln Pro Gly Ser Ala Gly Met
                    1010                1015                1020

Gly Gly Ala Lys Thr Pro Ser Asp Ala Val Gln Asn Ile Leu Gln
                    1025                1030                1035

Lys Ile Glu Lys Ile Lys Asn Thr Glu Glu
                    1040                1045

<210> SEQ ID NO 87
<211> LENGTH: 812
<212> TYPE: PRT
<213> ORGANISM: human

<400> SEQUENCE: 87

Leu Phe Pro Leu Ala Glu Arg Pro Asp Arg Val Glu Leu Met Pro Leu
1               5                   10                  15

Pro Pro Trp Gln Pro Val Gly Glu Asn Phe Thr Leu Ser Cys Arg Val
                20                  25                  30

Pro Gly Ala Gly Pro Arg Ala Ser Leu Thr Leu Thr Leu Leu Arg Gly
            35                  40                  45

Ala Gln Glu Leu Ile Arg Arg Ser Phe Ala Gly Glu Pro Pro Arg Ala
        50                  55                  60

Arg Gly Ala Val Leu Thr Ala Thr Val Leu Ala Arg Arg Glu Asp His
65                  70                  75                  80

Gly Ala Asn Phe Ser Cys Arg Ala Glu Leu Asp Leu Arg Pro His Gly
                85                  90                  95

Leu Gly Leu Phe Glu Asn Ser Ser Ala Pro Arg Glu Leu Arg Thr Phe
                100                 105                 110
```

```
Ser Leu Ser Pro Asp Ala Pro Arg Leu Ala Ala Pro Arg Leu Leu Glu
            115                 120                 125

Val Gly Ser Glu Arg Pro Val Ser Cys Thr Leu Asp Gly Leu Phe Pro
        130                 135                 140

Ala Ser Glu Ala Arg Val Tyr Leu Ala Leu Gly Asp Gln Asn Leu Ser
145                 150                 155                 160

Pro Asp Val Thr Leu Glu Gly Asp Ala Phe Val Ala Thr Ala Thr Ala
                165                 170                 175

Thr Ala Ser Ala Glu Gln Glu Gly Ala Arg Gln Leu Ile Cys Asn Val
            180                 185                 190

Thr Leu Gly Gly Glu Asn Arg Glu Thr Arg Glu Asn Val Thr Ile Tyr
        195                 200                 205

Ser Phe Pro Ala Pro Leu Leu Thr Leu Ser Glu Pro Ser Val Ser Glu
    210                 215                 220

Gly Gln Met Val Thr Val Thr Cys Ala Ala Gly Thr Gln Ala Leu Val
225                 230                 235                 240

Thr Leu Glu Gly Val Pro Ala Ala Val Pro Gly Gln Pro Ala Gln Leu
                245                 250                 255

Gln Leu Asn Ala Thr Glu Asn Asp Asp Arg Arg Ser Phe Phe Cys Asp
            260                 265                 270

Ala Thr Leu Asp Val Asp Gly Glu Thr Leu Ile Lys Asn Arg Ser Ala
        275                 280                 285

Glu Leu Arg Val Leu Tyr Ala Pro Arg Leu Asp Asp Ser Asp Cys Pro
    290                 295                 300

Arg Ser Trp Thr Trp Pro Glu Gly Pro Glu Gln Thr Leu Arg Cys Glu
305                 310                 315                 320

Ala Arg Gly Asn Pro Glu Pro Ser Val His Cys Ala Arg Ser Asp Gly
                325                 330                 335

Gly Ala Val Leu Ala Leu Gly Leu Leu Gly Pro Val Thr Arg Ala Leu
            340                 345                 350

Ser Gly Thr Tyr Arg Cys Lys Ala Ala Asn Asp Gln Gly Glu Ala Val
        355                 360                 365

Lys Asp Val Thr Leu Thr Val Glu Tyr Ala Pro Ala Leu Asp Ser Val
370                 375                 380

Gly Cys Pro Glu Arg Ile Thr Trp Leu Glu Gly Thr Glu Ala Ser Leu
385                 390                 395                 400

Ser Cys Val Ala His Gly Val Pro Pro Asp Val Ile Cys Val Arg
            405                 410                 415

Ser Gly Glu Leu Gly Ala Val Ile Glu Gly Leu Leu Arg Val Ala Arg
        420                 425                 430

Glu His Ala Gly Thr Tyr Arg Cys Glu Ala Thr Asn Pro Arg Gly Ser
    435                 440                 445

Ala Ala Lys Asn Val Ala Val Thr Val Glu Tyr Gly Pro Arg Phe Glu
450                 455                 460

Glu Pro Ser Cys Pro Ser Asn Trp Thr Trp Val Glu Gly Ser Gly Arg
465                 470                 475                 480

Leu Phe Ser Cys Glu Val Asp Gly Lys Pro Gln Pro Ser Val Lys Cys
            485                 490                 495

Val Gly Ser Gly Gly Ala Thr Glu Gly Val Leu Leu Pro Leu Ala Pro
        500                 505                 510

Pro Asp Pro Ser Pro Arg Ala Pro Arg Ile Pro Arg Val Leu Ala Pro
    515                 520                 525

Gly Ile Tyr Val Cys Asn Ala Thr Asn Arg His Gly Ser Val Ala Lys
```

```
                    530                535               540
Thr Val Val Ser Ala Glu Ser Pro Glu Met Asp Glu Ser Thr
545                     550               555                 560

Cys Pro Ser His Gln Thr Trp Leu Glu Gly Ala Glu Ser Ala Leu
                565               570               575

Ala Cys Ala Ala Arg Gly Arg Pro Ser Pro Gly Val Arg Cys Ser Arg
                580                   585                 590

Glu Gly Ile Pro Trp Pro Glu Gln Gln Arg Val Ser Arg Glu Asp Ala
            595                 600                 605

Gly Thr Tyr His Cys Val Ala Thr Asn Ala His Gly Thr Asp Ser Arg
        610                 615                 620

Thr Val Thr Val Gly Val Glu Tyr Arg Pro Val Val Ala Glu Leu Ala
625                 630                 635                 640

Ala Ser Pro Pro Gly Gly Val Arg Pro Gly Asn Phe Thr Leu Thr
                    645               650               655

Cys Arg Ala Glu Ala Trp Pro Pro Ala Gln Ile Ser Trp Arg Ala Pro
                660               665               670

Pro Gly Ala Leu Asn Ile Gly Leu Ser Ser Asn Asn Ser Thr Leu Ser
            675               680               685

Val Ala Gly Ala Met Gly Ser His Gly Gly Glu Tyr Glu Cys Ala Ala
        690                 695               700

Thr Asn Ala His Gly Arg His Ala Arg Arg Ile Thr Val Arg Val Ala
705                 710                 715                 720

Gly Pro Trp Leu Trp Val Ala Val Gly Ala Ala Gly Gly Ala Ala
                    725               730               735

Leu Leu Ala Ala Gly Ala Gly Leu Ala Phe Tyr Val Gln Ser Thr Ala
                740                 745               750

Cys Lys Lys Gly Glu Tyr Asn Val Gln Glu Ala Glu Ser Ser Gly Glu
            755                 760               765

Ala Val Cys Leu Asn Gly Ala Gly Gly Ala Gly Gly Ala Ala Gly
                770               775               780

Ala Glu Gly Gly Pro Glu Ala Ala Gly Ala Ala Glu Ser Pro Ala
785                 790               795               800

Glu Gly Glu Val Phe Ala Ile Gln Leu Thr Ser Ala
                805                 810

<210> SEQ ID NO 88
<211> LENGTH: 342
<212> TYPE: PRT
<213> ORGANISM: human

<400> SEQUENCE: 88

Met Leu Gln Gly His Ser Ser Val Phe Gln Ala Leu Leu Gly Thr Phe
1               5                   10                  15

Phe Thr Trp Gly Met Thr Ala Ala Gly Ala Ala Leu Val Phe Val Phe
                20                  25                  30

Ser Ser Gly Gln Arg Arg Ile Leu Asp Gly Ser Leu Gly Phe Ala Ala
            35                  40                  45

Gly Val Met Leu Ala Ala Ser Tyr Trp Ser Leu Leu Ala Pro Ala Val
        50                  55                  60

Glu Met Ala Thr Ser Ser Gly Phe Gly Ala Phe Ala Phe Pro
65                  70                  75                  80

Val Ala Val Gly Phe Thr Leu Gly Ala Ala Phe Val Tyr Leu Ala Asp
                85                  90                  95
```

Leu Leu Met Pro His Leu Gly Ala Ala Glu Asp Pro Gln Thr Thr Leu
            100                 105                 110

Ala Leu Asn Phe Gly Ser Thr Leu Met Lys Lys Ser Asp Pro Glu
        115                 120                 125

Gly Pro Ala Leu Leu Phe Pro Glu Ser Glu Leu Ser Ile Arg Ile Gly
        130                 135                 140

Arg Ala Gly Leu Leu Ser Asp Lys Ser Glu Asn Gly Glu Ala Tyr Gln
145                 150                 155                 160

Arg Lys Lys Ala Ala Thr Gly Leu Pro Glu Gly Pro Ala Val Pro
                165                 170                 175

Val Pro Ser Arg Gly Asn Leu Ala Gln Pro Gly Gly Ser Ser Trp Arg
        180                 185                 190

Arg Ile Ala Leu Leu Ile Leu Ala Ile Thr Ile His Asn Val Pro Glu
        195                 200                 205

Gly Leu Ala Val Gly Val Gly Phe Gly Ala Ile Glu Lys Thr Ala Ser
        210                 215                 220

Ala Thr Phe Glu Ser Ala Arg Asn Leu Ala Ile Gly Ile Gly Ile Gln
225                 230                 235                 240

Asn Phe Pro Glu Gly Leu Ala Val Ser Leu Pro Leu Arg Gly Ala Gly
                245                 250                 255

Phe Ser Thr Trp Arg Ala Phe Trp Tyr Gly Gln Leu Ser Gly Met Val
                260                 265                 270

Glu Pro Leu Ala Gly Val Phe Gly Ala Phe Ala Val Leu Ala Glu
        275                 280                 285

Pro Ile Leu Pro Tyr Ala Leu Ala Phe Ala Ala Gly Ala Met Val Tyr
        290                 295                 300

Val Val Met Asp Asp Ile Ile Pro Glu Ala Gln Ile Ser Gly Asn Gly
305                 310                 315                 320

Lys Leu Ala Ser Trp Ala Ser Ile Leu Gly Phe Val Val Met Met Ser
                325                 330                 335

Leu Asp Val Gly Leu Gly
            340

<210> SEQ ID NO 89
<211> LENGTH: 1827
<212> TYPE: PRT
<213> ORGANISM: human

<400> SEQUENCE: 89

Met Ala Asp Glu Arg Lys Asp Glu Ala Lys Ala Pro His Trp Thr Ser
1               5                   10                  15

Ala Pro Leu Thr Glu Ala Ser Ala His Ser His Pro Pro Glu Ile Lys
            20                  25                  30

Asp Gln Gly Gly Ala Gly Glu Gly Leu Val Arg Ser Ala Asn Gly Phe
        35                  40                  45

Pro Tyr Arg Glu Asp Glu Glu Gly Ala Phe Gly Glu His Gly Ser Gln
    50                  55                  60

Gly Thr Tyr Ser Asn Thr Lys Glu Asn Gly Ile Asn Gly Glu Leu Thr
65                  70                  75                  80

Ser Ala Asp Arg Glu Thr Ala Glu Glu Val Ser Ala Arg Ile Val Gln
                85                  90                  95

Val Val Thr Ala Glu Ala Val Ala Val Leu Lys Gly Glu Gln Glu Lys
            100                 105                 110

Glu Ala Gln His Lys Asp Gln Thr Ala Ala Leu Pro Leu Ala Ala Glu
        115                 120                 125

```
Glu Thr Ala Asn Leu Pro Pro Ser Pro Pro Ser Pro Ala Ser Glu
    130                 135             140
Gln Thr Val Thr Val Glu Asp Leu Leu Thr Ala Ser Lys Met Glu
145                 150                 155                 160
Phe His Asp Gln Gln Glu Leu Thr Pro Ser Thr Ala Glu Pro Ser Asp
                165                 170                 175
Gln Lys Glu Lys Glu Ser Glu Lys Gln Ser Lys Pro Gly Glu Asp Leu
            180                 185                 190
Lys His Ala Ala Leu Val Ser Gln Pro Glu Thr Thr Lys Thr Tyr Pro
        195                 200                 205
Asp Lys Lys Asp Met Gln Gly Thr Glu Glu Lys Ala Pro Leu Ala
    210                 215                 220
Leu Phe Gly His Thr Leu Val Ala Ser Leu Glu Asp Met Lys Gln Lys
225                 230                 235                 240
Thr Glu Pro Ser Leu Val Val Pro Gly Ile Asp Leu Pro Lys Glu Pro
                245                 250                 255
Pro Thr Pro Lys Glu Gln Lys Asp Trp Phe Ile Glu Met Pro Thr Glu
            260                 265                 270
Ala Lys Lys Asp Glu Trp Gly Leu Val Ala Pro Ile Ser Pro Gly Pro
        275                 280                 285
Leu Thr Pro Met Arg Glu Lys Asp Val Phe Asp Ile Pro Lys Trp
290                 295                 300
Glu Gly Lys Gln Phe Asp Ser Pro Met Pro Ser Pro Phe Gln Gly Gly
305                 310                 315                 320
Ser Phe Thr Leu Pro Leu Asp Val Met Lys Asn Glu Ile Val Thr Glu
                325                 330                 335
Thr Ser Pro Phe Ala Pro Ala Phe Leu Gln Pro Asp Asp Lys Lys Ser
            340                 345                 350
Leu Gln Gln Thr Ser Gly Pro Ala Thr Ala Lys Asp Ser Phe Lys Ile
        355                 360                 365
Glu Glu Pro His Glu Ala Lys Pro Asp Lys Met Ala Glu Ala Pro Pro
    370                 375                 380
Ser Glu Ala Met Thr Leu Pro Lys Asp Ala His Ile Pro Val Val Glu
385                 390                 395                 400
Glu His Val Met Gly Lys Val Leu Glu Glu Lys Glu Ala Ile Asn
                405                 410                 415
Gln Glu Thr Val Gln Gln Arg Asp Thr Phe Thr Pro Ser Gly Gln Glu
            420                 425                 430
Pro Ile Leu Thr Glu Lys Glu Thr Glu Leu Lys Leu Glu Glu Lys Thr
        435                 440                 445
Thr Ile Ser Asp Lys Glu Ala Val Pro Lys Glu Ser Lys Pro Pro Lys
    450                 455                 460
Pro Ala Asp Glu Glu Ile Gly Ile Ile Gln Thr Ser Thr Glu His Thr
465                 470                 475                 480
Phe Ser Glu Gln Lys Asp Gln Glu Pro Thr Thr Asp Met Leu Lys Gln
                485                 490                 495
Asp Ser Phe Pro Val Ser Leu Glu Gln Ala Val Thr Asp Ser Ala Met
            500                 505                 510
Thr Ser Lys Thr Leu Glu Lys Ala Met Thr Glu Pro Ser Ala Leu Ile
        515                 520                 525
Glu Lys Ser Ser Ile Gln Glu Leu Phe Glu Met Arg Val Asp Asp Lys
    530                 535                 540
```

-continued

Asp Lys Ile Glu Gly Val Gly Ala Ala Thr Ser Ala Glu Leu Asp Met
545                 550                 555                 560

Pro Phe Tyr Glu Asp Lys Ser Gly Met Ser Lys Tyr Phe Glu Thr Ser
            565                 570                 575

Ala Leu Lys Glu Glu Ala Thr Lys Ser Ile Glu Pro Gly Ser Asp Tyr
        580                 585                 590

Tyr Glu Leu Ser Asp Thr Arg Glu Ser Val His Glu Ser Ile Asp Thr
    595                 600                 605

Met Ser Pro Met His Lys Asn Gly Asp Lys Glu Phe Gln Thr Gly Lys
610                 615                 620

Glu Ser Gln Pro Ser Pro Ala Gln Glu Ala Gly Tyr Ser Thr Leu
625                 630                 635                 640

Ala Gln Ser Tyr Pro Ser Asp Leu Pro Glu Glu Pro Ser Ser Pro Gln
            645                 650                 655

Glu Arg Met Phe Thr Ile Asp Pro Lys Val Tyr Gly Glu Lys Arg Asp
        660                 665                 670

Leu His Ser Lys Asn Lys Asp Leu Thr Leu Ser Arg Ser Leu Gly
    675                 680                 685

Leu Gly Gly Arg Ser Ala Ile Glu Gln Arg Ser Met Ser Ile Asn Leu
690                 695                 700

Pro Met Ser Cys Leu Asp Ser Ile Ala Leu Gly Phe Asn Phe Gly Arg
705                 710                 715                 720

Gly His Asp Leu Ser Pro Leu Ala Ser Asp Ile Leu Thr Asn Thr Ser
            725                 730                 735

Gly Ser Met Asp Glu Gly Asp Asp Tyr Leu Pro Ala Thr Thr Pro Ala
        740                 745                 750

Leu Glu Lys Ala Pro Cys Phe Pro Val Glu Ser Lys Glu Glu Glu Gln
    755                 760                 765

Ile Glu Lys Val Lys Ala Thr Gly Glu Glu Ser Thr Gln Ala Glu Ile
770                 775                 780

Ser Cys Glu Ser Pro Phe Leu Ala Lys Asp Phe Tyr Lys Asn Gly Thr
785                 790                 795                 800

Val Met Ala Pro Asp Leu Pro Glu Met Leu Asp Leu Ala Gly Thr Arg
            805                 810                 815

Ser Arg Leu Ala Ser Val Ser Ala Asp Ala Glu Val Ala Arg Arg Lys
        820                 825                 830

Ser Val Pro Ser Glu Thr Val Val Glu Asp Ser Arg Thr Gly Leu Pro
    835                 840                 845

Pro Val Thr Asp Glu Asn His Val Ile Val Lys Thr Asp Ser Gln Leu
850                 855                 860

Glu Asp Leu Gly Tyr Cys Val Phe Asn Lys Tyr Thr Val Pro Leu Pro
865                 870                 875                 880

Ser Pro Val Gln Asp Ser Glu Asn Leu Ser Gly Ser Gly Thr Phe
            885                 890                 895

Tyr Glu Gly Thr Asp Asp Lys Val Arg Arg Asp Leu Ala Thr Asp Leu
        900                 905                 910

Ser Leu Ile Glu Val Lys Leu Ala Ala Ala Gly Arg Val Lys Asp Glu
    915                 920                 925

Phe Ser Val Asp Lys Glu Ala Ser Ala His Ile Ser Gly Asp Lys Ser
930                 935                 940

Gly Leu Ser Lys Glu Phe Asp Gln Glu Lys Lys Ala Asn Asp Arg Leu
945                 950                 955                 960

Asp Thr Val Leu Glu Lys Ser Glu Glu His Ala Asp Ser Lys Glu His

```
                965                 970                 975
Ala Lys Lys Thr Glu Glu Ala Gly Asp Glu Ile Glu Thr Phe Gly Leu
                    980                 985                 990
Gly Val Thr Tyr Glu Gln Ala Leu Ala Lys Asp Leu Ser Ile Pro Thr
            995                1000                1005
Asp Ala Ser Ser Glu Lys Ala Glu Lys Gly Leu Ser Ser Val Pro
    1010                1015                1020
Glu Ile Ala Glu Val Glu Pro Ser Lys Lys Val Glu Gln Gly Leu
    1025                1030                1035
Asp Phe Ala Val Gln Gly Gln Leu Asp Val Lys Ile Ser Asp Phe
    1040                1045                1050
Gly Gln Met Ala Ser Gly Leu Asn Ile Asp Asp Arg Arg Ala Thr
    1055                1060                1065
Glu Leu Lys Leu Glu Ala Thr Gln Asp Met Thr Pro Ser Ser Lys
    1070                1075                1080
Ala Pro Gln Glu Ala Asp Ala Phe Met Gly Val Glu Ser Gly His
    1085                1090                1095
Met Lys Glu Gly Thr Lys Val Ser Glu Thr Glu Val Lys Glu Lys
    1100                1105                1110
Val Ala Lys Pro Asp Leu Val His Gln Glu Ala Val Asp Lys Glu
    1115                1120                1125
Glu Ser Tyr Glu Ser Ser Gly Glu His Glu Ser Leu Thr Met Glu
    1130                1135                1140
Ser Leu Lys Ala Asp Glu Gly Lys Lys Glu Thr Ser Pro Glu Ser
    1145                1150                1155
Ser Leu Ile Gln Asp Glu Ile Ala Val Lys Leu Ser Val Glu Ile
    1160                1165                1170
Pro Cys Pro Pro Ala Val Ser Glu Ala Asp Leu Ala Thr Asp Glu
    1175                1180                1185
Arg Ala Asp Val Gln Met Glu Phe Ile Gln Gly Pro Lys Glu Glu
    1190                1195                1200
Ser Lys Glu Thr Pro Asp Ile Ser Ile Thr Pro Ser Asp Val Ala
    1205                1210                1215
Glu Pro Leu His Glu Thr Ile Val Ser Glu Pro Ala Glu Ile Gln
    1220                1225                1230
Ser Glu Glu Glu Ile Glu Ala Gln Gly Glu Tyr Asp Lys Leu
    1235                1240                1245
Leu Phe Arg Ser Asp Thr Leu Gln Ile Thr Asp Leu Gly Val Ser
    1250                1255                1260
Gly Ala Arg Glu Glu Phe Val Glu Thr Cys Pro Ser Glu His Lys
    1265                1270                1275
Gly Val Ile Glu Ser Val Val Thr Ile Glu Asp Phe Ile Thr
    1280                1285                1290
Val Val Gln Thr Thr Thr Asp Glu Gly Glu Ser Gly Ser His Ser
    1295                1300                1305
Val Arg Phe Ala Ala Leu Glu Gln Pro Glu Val Glu Arg Arg Pro
    1310                1315                1320
Ser Pro His Asp Glu Glu Phe Glu Val Glu Glu Ala Ala Glu
    1325                1330                1335
Ala Gln Ala Glu Pro Lys Asp Gly Ser Pro Glu Ala Pro Ala Ser
    1340                1345                1350
Pro Glu Arg Glu Glu Val Ala Leu Ser Glu Tyr Lys Thr Glu Thr
    1355                1360                1365
```

```
Tyr Asp Asp Tyr Lys Asp Glu Thr Thr Ile Asp Asp Ser Ile Met
    1370            1375            1380

Asp Ala Asp Ser Leu Trp Val Asp Thr Gln Asp Asp Asp Arg Ser
    1385            1390            1395

Ile Met Thr Glu Gln Leu Glu Thr Ile Pro Lys Glu Glu Lys Ala
    1400            1405            1410

Glu Lys Glu Ala Arg Arg Ser Ser Leu Glu Lys His Arg Lys Glu
    1415            1420            1425

Lys Pro Phe Lys Thr Gly Arg Gly Arg Ile Ser Thr Pro Glu Arg
    1430            1435            1440

Lys Val Ala Lys Lys Glu Pro Ser Thr Val Ser Arg Asp Glu Val
    1445            1450            1455

Arg Arg Lys Lys Ala Val Tyr Lys Lys Ala Glu Leu Ala Lys Lys
    1460            1465            1470

Thr Glu Val Gln Ala His Ser Pro Ser Arg Lys Phe Ile Leu Lys
    1475            1480            1485

Pro Ala Ile Lys Tyr Thr Arg Pro Thr His Leu Ser Cys Val Lys
    1490            1495            1500

Arg Lys Thr Thr Ala Ala Gly Gly Glu Ser Ala Leu Ala Pro Ser
    1505            1510            1515

Val Phe Lys Gln Ala Lys Asp Lys Val Ser Asp Gly Val Thr Lys
    1520            1525            1530

Ser Pro Glu Lys Arg Ser Ser Leu Pro Arg Pro Ser Ser Ile Leu
    1535            1540            1545

Pro Pro Arg Arg Gly Val Ser Gly Asp Arg Asp Glu Asn Ser Phe
    1550            1555            1560

Ser Leu Asn Ser Ser Ile Ser Ser Ser Ala Arg Arg Thr Thr Arg
    1565            1570            1575

Ser Glu Pro Ile Arg Arg Ala Gly Lys Ser Gly Thr Ser Thr Pro
    1580            1585            1590

Thr Thr Pro Gly Ser Thr Ala Ile Thr Pro Gly Thr Pro Pro Ser
    1595            1600            1605

Tyr Ser Ser Arg Thr Pro Gly Thr Pro Gly Thr Pro Ser Tyr Pro
    1610            1615            1620

Arg Thr Pro His Thr Pro Gly Thr Pro Lys Ser Ala Ile Leu Val
    1625            1630            1635

Pro Ser Glu Lys Lys Val Ala Ile Ile Arg Thr Pro Pro Lys Ser
    1640            1645            1650

Pro Ala Thr Pro Lys Gln Leu Arg Leu Ile Asn Gln Pro Leu Pro
    1655            1660            1665

Asp Leu Lys Asn Val Lys Ser Lys Ile Gly Ser Thr Asp Asn Ile
    1670            1675            1680

Lys Tyr Gln Pro Lys Gly Gly Gln Val Gln Ile Val Thr Lys Lys
    1685            1690            1695

Ile Asp Leu Ser His Val Thr Ser Lys Cys Gly Ser Leu Lys Asn
    1700            1705            1710

Ile Arg His Arg Pro Gly Gly Gly Arg Val Lys Ile Glu Ser Val
    1715            1720            1725

Lys Leu Asp Phe Lys Glu Lys Ala Gln Ala Lys Val Gly Ser Leu
    1730            1735            1740

Asp Asn Ala His His Val Pro Gly Gly Gly Asn Val Lys Ile Asp
    1745            1750            1755
```

```
Ser Gln Lys Leu Asn Phe Arg Glu His Ala Lys Ala Arg Val Asp
    1760                1765                1770

His Gly Ala Glu Ile Ile Thr Gln Ser Pro Gly Arg Ser Ser Val
    1775                1780                1785

Ala Ser Pro Arg Arg Leu Ser Asn Val Ser Ser Ser Gly Ser Ile
    1790                1795                1800

Asn Leu Leu Glu Ser Pro Gln Leu Ala Thr Leu Ala Glu Asp Val
    1805                1810                1815

Thr Ala Ala Leu Ala Lys Gln Gly Leu
    1820                1825

<210> SEQ ID NO 90
<211> LENGTH: 758
<212> TYPE: PRT
<213> ORGANISM: human

<400> SEQUENCE: 90

Met Ala Glu Pro Arg Gln Glu Phe Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
                35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
                180                 185                 190

Leu Gly Asp Leu His Gln Glu Gly Pro Pro Leu Lys Gly Ala Gly Gly
            195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
                260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
    290                 295                 300
```

```
Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
                340                 345                 350

Glu Pro Ser Glu Lys Gln Pro Ala Ala Ala Pro Arg Gly Lys Pro Val
                355                 360                 365

Ser Arg Val Pro Gln Leu Lys Ala Arg Met Val Ser Lys Ser Lys Asp
            370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
                420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
                500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
            530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
            595                 600                 605

Gly Ser Lys Asp Asn Ile Lys His Val Pro Gly Gly Gly Ser Val Gln
            610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys Ala Lys Thr Asp
            690                 695                 700

His Gly Ala Glu Ile Val Tyr Lys Ser Pro Val Val Ser Gly Asp Thr
705                 710                 715                 720
```

Ser Pro Arg His Leu Ser Asn Val Ser Ser Thr Gly Ser Ile Asp Met
                    725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 91
<211> LENGTH: 422
<212> TYPE: PRT
<213> ORGANISM: human

<400> SEQUENCE: 91

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Leu Gly Thr Leu Ile Phe
        35                  40                  45

Cys Ala Val Leu Gly Asn Ala Cys Val Val Ala Ala Ile Ala Leu Glu
    50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140

Val Asn Lys Arg Thr Pro Arg Arg Ala Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

```
Leu Ala Arg Glu Arg Lys Thr Val Lys Thr Leu Gly Ile Ile Met Gly
                340                 345                 350

Thr Phe Ile Leu Cys Trp Leu Pro Phe Phe Ile Val Ala Leu Val Leu
                355                 360                 365

Pro Phe Cys Glu Ser Ser Cys His Met Pro Thr Leu Leu Gly Ala Ile
                370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415

Cys Lys Phe Cys Arg Gln
                420

<210> SEQ ID NO 92
<211> LENGTH: 1894
<212> TYPE: PRT
<213> ORGANISM: human

<400> SEQUENCE: 92

Met Lys Ala Met Pro Trp Asn Trp Thr Cys Leu Leu Ser His Leu Leu
1               5                   10                  15

Met Val Gly Met Gly Ser Ser Thr Leu Thr Arg Gln Pro Ala Pro
                20                  25                  30

Leu Ser Gln Lys Gln Arg Ser Phe Val Thr Phe Arg Gly Glu Pro Ala
                35                  40                  45

Glu Gly Phe Asn His Leu Val Val Asp Glu Arg Thr Gly His Ile Tyr
50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
                100                 105                 110

Asn Val Asn Lys Met Leu Leu Ile Asp Tyr Lys Glu Asn Arg Leu Ile
                115                 120                 125

Ala Cys Gly Ser Leu Tyr Gln Gly Ile Cys Lys Leu Leu Arg Leu Glu
                130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
                180                 185                 190

Pro Glu Tyr Phe Pro Thr Ile Ser Ser Arg Lys Leu Thr Lys Asn Ser
                195                 200                 205

Glu Ala Asp Gly Met Phe Ala Tyr Val Phe His Asp Glu Phe Val Ala
                210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Gly Ser Thr Thr Lys
                260                 265                 270

Glu Gln Val Tyr Thr Ser Lys Leu Val Arg Leu Cys Lys Glu Asp Thr
```

```
              275                 280                 285
Ala Phe Asn Ser Tyr Val Glu Val Pro Ile Gly Cys Glu Arg Ser Gly
290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Asp Leu Leu Phe
                325                 330                 335

Thr Val Phe Ser Lys Gly Gln Lys Arg Lys Met Lys Ser Leu Asp Glu
                340                 345                 350

Ser Ala Leu Cys Ile Phe Ile Leu Lys Gln Ile Asn Asp Arg Ile Lys
                355                 360                 365

Glu Arg Leu Gln Ser Cys Tyr Arg Gly Glu Gly Thr Leu Asp Leu Ala
                370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
                420                 425                 430

Thr Ser Val Ile Ala Tyr Val Tyr Lys Asn His Ser Leu Ala Phe Val
                435                 440                 445

Gly Thr Lys Ser Gly Lys Leu Lys Lys Ile Arg Val Asp Gly Pro Arg
                450                 455                 460

Gly Asn Ala Leu Gln Tyr Glu Thr Val Gln Val Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
                500                 505                 510

Tyr Gln Ser Cys Gly Glu Cys Leu Gly Ser Gly Asp Pro His Cys Gly
                515                 520                 525

Trp Cys Val Leu His Asn Thr Cys Thr Arg Lys Glu Arg Cys Glu Arg
                530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575

Leu Val Leu Glu Thr Tyr Asn Val Pro Glu Leu Ser Ala Gly Val Asn
                580                 585                 590

Cys Thr Phe Glu Asp Leu Ser Glu Met Asp Gly Leu Val Val Gly Asn
                595                 600                 605

Gln Ile Gln Cys Tyr Ser Pro Ala Ala Lys Glu Val Pro Arg Ile Ile
                610                 615                 620

Thr Glu Asn Gly Asp His His Val Val Gln Leu Gln Leu Lys Ser Lys
625                 630                 635                 640

Glu Thr Gly Met Thr Phe Ala Ser Thr Ser Phe Val Phe Tyr Asn Cys
                645                 650                 655

Ser Val His Asn Ser Cys Leu Ser Cys Val Glu Ser Pro Tyr Arg Cys
                660                 665                 670

His Trp Cys Lys Tyr Arg His Val Cys Thr His Asp Pro Lys Thr Cys
                675                 680                 685

Ser Phe Gln Glu Gly Arg Val Lys Leu Pro Glu Asp Cys Pro Gln Leu
690                 695                 700
```

```
Leu Arg Val Asp Lys Ile Leu Val Pro Val Glu Val Ile Lys Pro Ile
705                 710                 715                 720

Thr Leu Lys Ala Lys Asn Leu Pro Gln Pro Gln Ser Gly Gln Arg Gly
                725                 730                 735

Tyr Glu Cys Ile Leu Asn Ile Gln Gly Ser Glu Gln Arg Val Pro Ala
            740                 745                 750

Leu Arg Phe Asn Ser Ser Val Gln Cys Gln Asn Thr Ser Tyr Ser
            755                 760                 765

Tyr Glu Gly Met Glu Ile Asn Asn Leu Pro Val Glu Leu Thr Val Val
770                 775                 780

Trp Asn Gly His Phe Asn Ile Asp Asn Pro Ala Gln Asn Lys Val His
785                 790                 795                 800

Leu Tyr Lys Cys Gly Ala Met Arg Glu Ser Cys Gly Leu Cys Leu Lys
                805                 810                 815

Ala Asp Pro Asp Phe Ala Cys Gly Trp Cys Gln Gly Pro Gly Gln Cys
            820                 825                 830

Thr Leu Arg Gln His Cys Pro Ala Gln Glu Ser Gln Trp Leu Glu Leu
            835                 840                 845

Ser Gly Ala Lys Ser Lys Cys Thr Asn Pro Arg Ile Thr Glu Ile Ile
850                 855                 860

Pro Val Thr Gly Pro Arg Glu Gly Gly Thr Lys Val Thr Ile Arg Gly
865                 870                 875                 880

Glu Asn Leu Gly Leu Glu Phe Arg Asp Ile Ala Ser His Val Lys Val
            885                 890                 895

Ala Gly Val Glu Cys Ser Pro Leu Val Asp Gly Tyr Ile Pro Ala Glu
            900                 905                 910

Gln Ile Val Cys Glu Met Gly Glu Ala Lys Pro Ser Gln His Ala Gly
            915                 920                 925

Phe Val Glu Ile Cys Val Ala Val Cys Arg Pro Glu Phe Met Ala Arg
            930                 935                 940

Ser Ser Gln Leu Tyr Tyr Phe Met Thr Leu Thr Leu Ser Asp Leu Lys
945                 950                 955                 960

Pro Ser Arg Gly Pro Met Ser Gly Gly Thr Gln Val Thr Ile Thr Gly
                965                 970                 975

Thr Asn Leu Asn Ala Gly Ser Asn Val Val Val Met Phe Gly Lys Gln
            980                 985                 990

Pro Cys Leu Phe His Arg Arg Ser Pro Ser Tyr Ile Val Cys Asn Thr
            995                 1000                1005

Thr Ser Ser Asp Glu Val Leu Glu Met Lys Val Ser Val Gln Val
    1010                1015                1020

Asp Arg Ala Lys Ile His Gln Asp Leu Val Phe Gln Tyr Val Glu
    1025                1030                1035

Asp Pro Thr Ile Val Arg Ile Glu Pro Glu Trp Ser Ile Val Ser
    1040                1045                1050

Gly Asn Thr Pro Ile Ala Val Trp Gly Thr His Leu Asp Leu Ile
    1055                1060                1065

Gln Asn Pro Gln Ile Arg Ala Lys His Gly Gly Lys Glu His Ile
    1070                1075                1080

Asn Ile Cys Glu Val Leu Asn Ala Thr Glu Met Thr Cys Gln Ala
    1085                1090                1095

Pro Ala Leu Ala Leu Gly Pro Asp His Gln Ser Asp Leu Thr Glu
    1100                1105                1110
```

```
Arg Pro Glu Glu Phe Gly Phe Ile Leu Asp Asn Val Gln Ser Leu
1115                 1120                1125

Leu Ile Leu Asn Lys Thr Asn Phe Thr Tyr Tyr Pro Asn Pro Val
1130                 1135                1140

Phe Glu Ala Phe Gly Pro Ser Gly Ile Leu Glu Leu Lys Pro Gly
1145                 1150                1155

Thr Pro Ile Ile Leu Lys Gly Lys Asn Leu Ile Pro Pro Val Ala
1160                 1165                1170

Gly Gly Asn Val Lys Leu Asn Tyr Thr Val Leu Val Gly Glu Lys
1175                 1180                1185

Pro Cys Thr Val Thr Val Ser Asp Val Gln Leu Leu Cys Glu Ser
1190                 1195                1200

Pro Asn Leu Ile Gly Arg His Lys Val Met Ala Arg Val Gly Gly
1205                 1210                1215

Met Glu Tyr Ser Pro Gly Met Val Tyr Ile Ala Pro Asp Ser Pro
1220                 1225                1230

Leu Ser Leu Pro Ala Ile Val Ser Ile Ala Val Ala Gly Gly Leu
1235                 1240                1245

Leu Ile Ile Phe Ile Val Ala Val Leu Ile Ala Tyr Lys Arg Lys
1250                 1255                1260

Ser Arg Glu Ser Asp Leu Thr Leu Lys Arg Leu Gln Met Gln Met
1265                 1270                1275

Asp Asn Leu Glu Ser Arg Val Ala Leu Glu Cys Lys Glu Ala Phe
1280                 1285                1290

Ala Glu Leu Gln Thr Asp Ile His Glu Leu Thr Ser Asp Leu Asp
1295                 1300                1305

Gly Ala Gly Ile Pro Phe Leu Asp Tyr Arg Thr Tyr Thr Met Arg
1310                 1315                1320

Val Leu Phe Pro Gly Ile Glu Asp His Pro Val Leu Arg Asp Leu
1325                 1330                1335

Glu Val Pro Gly Tyr Arg Gln Glu Arg Val Glu Lys Gly Leu Lys
1340                 1345                1350

Leu Phe Ala Gln Leu Ile Asn Asn Lys Val Phe Leu Leu Ser Phe
1355                 1360                1365

Ile Arg Thr Leu Glu Ser Gln Arg Ser Phe Ser Met Arg Asp Arg
1370                 1375                1380

Gly Asn Val Ala Ser Leu Ile Met Thr Val Leu Gln Ser Lys Leu
1385                 1390                1395

Glu Tyr Ala Thr Asp Val Leu Lys Gln Leu Leu Ala Asp Leu Ile
1400                 1405                1410

Asp Lys Asn Leu Glu Ser Lys Asn His Pro Lys Leu Leu Leu Arg
1415                 1420                1425

Arg Thr Glu Ser Val Ala Glu Lys Met Leu Thr Asn Trp Phe Thr
1430                 1435                1440

Phe Leu Leu Tyr Lys Phe Leu Lys Glu Cys Ala Gly Glu Pro Leu
1445                 1450                1455

Phe Ser Leu Phe Cys Ala Ile Lys Gln Gln Met Glu Lys Gly Pro
1460                 1465                1470

Ile Asp Ala Ile Thr Gly Glu Ala Arg Tyr Ser Leu Ser Glu Asp
1475                 1480                1485

Lys Leu Ile Arg Gln Gln Ile Asp Tyr Lys Thr Leu Val Leu Ser
1490                 1495                1500

Cys Val Ser Pro Asp Asn Ala Asn Ser Pro Glu Val Pro Val Lys
```

```
              1505                1510                1515

Ile Leu Asn Cys Asp Thr Ile Thr Gln Val Lys Glu Lys Ile Leu
          1520                1525                1530

Asp Ala Ile Phe Lys Asn Val Pro Cys Ser His Arg Pro Lys Ala
          1535                1540                1545

Ala Asp Met Asp Leu Glu Trp Arg Gln Gly Ser Gly Ala Arg Met
          1550                1555                1560

Ile Leu Gln Asp Glu Asp Ile Thr Thr Lys Ile Glu Asn Asp Trp
          1565                1570                1575

Lys Arg Leu Asn Thr Leu Ala His Tyr Gln Val Pro Asp Gly Ser
          1580                1585                1590

Val Val Ala Leu Val Ser Lys Gln Val Thr Ala Tyr Asn Ala Val
          1595                1600                1605

Asn Asn Ser Thr Val Ser Arg Thr Ser Ala Ser Lys Tyr Glu Asn
          1610                1615                1620

Met Ile Arg Tyr Thr Gly Ser Pro Asp Ser Leu Arg Ser Arg Thr
          1625                1630                1635

Pro Met Ile Thr Pro Asp Leu Glu Ser Gly Val Lys Met Trp His
          1640                1645                1650

Leu Val Lys Asn His Glu His Gly Asp Gln Lys Glu Gly Asp Arg
          1655                1660                1665

Gly Ser Lys Met Val Ser Glu Ile Tyr Leu Thr Arg Leu Leu Ala
          1670                1675                1680

Thr Lys Gly Thr Leu Gln Lys Phe Val Asp Asp Leu Phe Glu Thr
          1685                1690                1695

Ile Phe Ser Thr Ala His Arg Gly Ser Ala Leu Pro Leu Ala Ile
          1700                1705                1710

Lys Tyr Met Phe Asp Phe Leu Asp Glu Gln Ala Asp Lys His Gly
          1715                1720                1725

Ile His Asp Pro His Val Arg His Thr Trp Lys Ser Asn Cys Leu
          1730                1735                1740

Pro Leu Arg Phe Trp Val Asn Met Ile Lys Asn Pro Gln Phe Val
          1745                1750                1755

Phe Asp Ile His Lys Asn Ser Ile Thr Asp Ala Cys Leu Ser Val
          1760                1765                1770

Val Ala Gln Thr Phe Met Asp Ser Cys Ser Thr Ser Glu His Arg
          1775                1780                1785

Leu Gly Lys Asp Ser Pro Ser Asn Lys Leu Leu Tyr Ala Lys Asp
          1790                1795                1800

Ile Pro Ser Tyr Lys Asn Trp Val Glu Arg Tyr Tyr Ser Asp Ile
          1805                1810                1815

Gly Lys Met Pro Ala Ile Ser Asp Gln Asp Met Asn Ala Tyr Leu
          1820                1825                1830

Ala Glu Gln Ser Arg Met His Met Asn Glu Phe Asn Thr Met Ser
          1835                1840                1845

Ala Leu Ser Glu Ile Phe Ser Tyr Val Gly Lys Tyr Ser Glu Glu
          1850                1855                1860

Ile Leu Gly Pro Leu Asp His Asp Asp Gln Cys Gly Lys Gln Lys
          1865                1870                1875

Leu Ala Tyr Lys Leu Glu Gln Val Ile Thr Leu Met Ser Leu Asp
          1880                1885                1890

Ser
```

```
<210> SEQ ID NO 93
<211> LENGTH: 184
<212> TYPE: PRT
<213> ORGANISM: human

<400> SEQUENCE: 93

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Tyr Ile
            20                  25                  30

Leu Asp Gly Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Ser Thr Lys Val Leu Ile Gln Phe Leu Gln Lys
        115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

<210> SEQ ID NO 94
<211> LENGTH: 306
<212> TYPE: PRT
<213> ORGANISM: human

<400> SEQUENCE: 94

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140
```

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
                290                 295                 300

Cys Ser
305

<210> SEQ ID NO 95
<211> LENGTH: 114
<212> TYPE: PRT
<213> ORGANISM: human

<400> SEQUENCE: 95

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
                20                  25                  30

His Pro Ser Cys Lys Val Thr Ala Met Lys Cys Phe Leu Leu Glu Leu
                35                  40                  45

Gln Val Ser Leu Glu Ser Gly Asp Ala Ser Ile His Asp Thr Val Glu
            50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 96
<211> LENGTH: 137
<212> TYPE: PRT
<213> ORGANISM: human

<400> SEQUENCE: 96

Met Ile Val Lys Ala Gly Ile Thr Ile Pro Arg Asn Pro Gly Cys Pro
1               5                   10                  15

Asn Ser Glu Asp Lys Asn Phe Pro Arg Thr Val Met Val Asn Leu Asn
                20                  25                  30

Ile His Asn Arg Asn Thr Asn Thr Asn Pro Lys Arg Ser Ser Asp Tyr
```

```
                35                  40                  45
Tyr Asn Arg Ser Thr Ser Pro Trp Asn Leu His Arg Asn Glu Asp Pro
 50                  55                  60
Glu Arg Tyr Pro Ser Val Ile Trp Glu Ala Lys Cys Arg His Leu Gly
 65                  70                  75                  80
Cys Ile Asn Ala Asp Gly Asn Val Asp Tyr His Met Asn Ser Val Pro
                 85                  90                  95
Ile Gln Gln Glu Ile Leu Val Leu Arg Arg Glu Pro Pro His Cys Pro
                100                 105                 110
Asn Ser Phe Arg Leu Glu Lys Ile Leu Val Ser Val Gly Cys Thr Cys
                115                 120                 125
Val Thr Pro Ile Val His His Val Ala
                130                 135

<210> SEQ ID NO 97
<211> LENGTH: 153
<212> TYPE: PRT
<213> ORGANISM: human

<400> SEQUENCE: 97

Met Arg Pro Ser Gly Arg Lys Ser Ser Lys Met Gln Ala Phe Arg Ile
  1               5                  10                  15
Trp Asp Val Asn Gln Lys Thr Phe Tyr Leu Arg Asn Asn Gln Leu Val
                 20                  25                  30
Ala Gly Tyr Leu Gln Gly Pro Asn Val Asn Leu Glu Glu Lys Ile Asp
                 35                  40                  45
Val Val Pro Ile Glu Pro His Ala Leu Phe Leu Gly Ile His Gly Gly
 50                  55                  60
Lys Met Cys Leu Ser Cys Val Lys Ser Gly Asp Glu Thr Arg Leu Gln
 65                  70                  75                  80
Leu Glu Ala Val Asn Ile Thr Asp Leu Ser Glu Asn Arg Lys Gln Asp
                 85                  90                  95
Lys Arg Phe Ala Phe Ile Arg Ser Asp Ser Gly Pro Thr Thr Ser Phe
                100                 105                 110
Glu Ser Ala Ala Cys Pro Gly Trp Phe Leu Cys Thr Ala Met Glu Ala
                115                 120                 125
Asp Gln Pro Val Ser Leu Thr Asn Met Pro Asp Glu Gly Val Met Val
                130                 135                 140
Thr Lys Phe Tyr Phe Gln Glu Asp Glu
145                 150

<210> SEQ ID NO 98
<211> LENGTH: 162
<212> TYPE: PRT
<213> ORGANISM: human

<400> SEQUENCE: 98

Met Asp Ser Val Cys Pro Gln Gly Lys Tyr Ile His Pro Gln Asn Asn
  1               5                  10                  15
Ser Ile Cys Cys Thr Lys Cys His Lys Gly Thr Tyr Leu Tyr Asn Asp
                 20                  25                  30
Cys Pro Gly Pro Gly Gln Asp Thr Asp Cys Arg Glu Cys Glu Ser Gly
                 35                  40                  45
Ser Phe Thr Ala Ser Glu Asn His Leu Arg His Cys Leu Ser Cys Ser
 50                  55                  60
Lys Cys Arg Lys Glu Met Gly Gln Val Glu Ile Ser Ser Cys Thr Val
```

```
                65                  70                  75                  80
Asp Arg Asp Thr Val Cys Gly Cys Arg Lys Asn Gln Tyr Arg His Tyr
                    85                  90                  95

Trp Ser Glu Asn Leu Phe Gln Cys Phe Asn Cys Ser Leu Cys Leu Asn
                100                 105                 110

Gly Thr Val His Leu Ser Cys Gln Glu Lys Gln Asn Thr Val Cys Thr
                115                 120                 125

Cys His Ala Gly Phe Phe Leu Arg Glu Asn Glu Cys Val Ser Cys Ser
                130                 135                 140

Asn Cys Lys Lys Ser Leu Glu Cys Thr Lys Leu Cys Leu Pro Gln Ile
145                 150                 155                 160

Glu Asn

<210> SEQ ID NO 99
<211> LENGTH: 165
<212> TYPE: PRT
<213> ORGANISM: human

<400> SEQUENCE: 99

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
                35                  40                  45

Pro Ser Cys Val Pro Leu Met Arg Cys Gly Gly Cys Cys Asn Asp Glu
50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn Pro Cys Gly Pro Cys Ser Glu Arg Arg Lys His Leu Phe
                115                 120                 125

Val Gln Asp Pro Gln Thr Cys Lys Cys Ser Cys Lys Asn Thr Asp Ser
                130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 100
<211> LENGTH: 673
<212> TYPE: PRT
<213> ORGANISM: human

<400> SEQUENCE: 100

Phe Lys Ile Glu Thr Thr Pro Glu Ser Arg Tyr Leu Ala Gln Ile Gly
1               5                   10                  15

Asp Ser Val Ser Leu Thr Cys Ser Thr Thr Gly Cys Glu Ser Pro Phe
                20                  25                  30

Phe Ser Trp Arg Thr Gln Ile Asp Ser Pro Leu Asn Gly Lys Val Thr
                35                  40                  45

Asn Glu Gly Thr Thr Ser Thr Leu Thr Met Asn Pro Val Ser Phe Gly
50                  55                  60
```

```
Asn Glu His Ser Tyr Leu Cys Thr Ala Thr Cys Glu Ser Arg Lys Leu
65                  70                  75                  80

Glu Lys Gly Ile Gln Val Glu Ile Tyr Ser Phe Pro Lys Asp Pro Glu
                85                  90                  95

Ile His Leu Ser Gly Pro Leu Glu Ala Gly Lys Pro Ile Thr Val Lys
            100                 105                 110

Cys Ser Val Ala Asp Val Tyr Pro Phe Asp Arg Leu Glu Ile Asp Leu
            115                 120                 125

Leu Lys Gly Asp His Leu Met Lys Ser Gln Glu Phe Leu Glu Asp Ala
            130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
            180                 185                 190

Leu Gln Val Tyr Ile Ser Pro Lys Asn Thr Val Ile Ser Val Asn Pro
            195                 200                 205

Ser Thr Lys Leu Gln Glu Gly Gly Ser Val Thr Met Thr Cys Ser Ser
210                 215                 220

Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
            275                 280                 285

Phe Thr Val Glu Ile Ser Pro Gly Pro Arg Ile Ala Ala Gln Ile Gly
            290                 295                 300

Asp Ser Val Met Leu Thr Cys Ser Val Met Gly Cys Glu Ser Pro Ser
305                 310                 315                 320

Phe Ser Trp Arg Thr Gln Ile Asp Ser Pro Leu Ser Gly Lys Val Arg
                325                 330                 335

Ser Glu Gly Thr Asn Ser Thr Leu Thr Leu Ser Pro Val Ser Phe Glu
            340                 345                 350

Asn Glu His Ser Tyr Leu Cys Thr Val Thr Cys Gly His Lys Lys Leu
            355                 360                 365

Glu Lys Gly Ile Gln Val Glu Leu Tyr Ser Phe Pro Arg Asp Pro Glu
            370                 375                 380

Ile Glu Met Ser Gly Gly Leu Val Asn Gly Ser Ser Val Thr Val Ser
385                 390                 395                 400

Cys Lys Val Pro Ser Val Tyr Pro Leu Asp Arg Leu Glu Ile Glu Leu
                405                 410                 415

Leu Lys Gly Glu Thr Ile Leu Glu Asn Ile Glu Phe Leu Glu Asp Thr
            420                 425                 430

Asp Met Lys Ser Leu Glu Asn Lys Ser Leu Glu Met Thr Phe Ile Pro
            435                 440                 445

Thr Ile Glu Asp Thr Gly Lys Ala Leu Val Cys Gln Ala Lys Leu His
            450                 455                 460

Ile Asp Asp Met Glu Phe Glu Pro Lys Gln Arg Gln Ser Thr Gln Thr
465                 470                 475                 480
```

-continued

Leu Tyr Val Asn Val Ala Pro Arg Asp Thr Thr Val Leu Val Ser Pro
            485                 490                 495

Ser Ser Ile Leu Glu Glu Gly Ser Ser Val Asn Met Thr Cys Leu Ser
        500                 505                 510

Gln Gly Phe Pro Ala Pro Lys Ile Leu Trp Ser Arg Gln Leu Pro Asn
            515                 520                 525

Gly Glu Leu Gln Pro Leu Ser Glu Asn Ala Thr Leu Thr Leu Ile Ser
        530                 535                 540

Thr Lys Met Glu Asp Ser Gly Val Tyr Leu Cys Glu Gly Ile Asn Gln
545                 550                 555                 560

Ala Gly Arg Ser Arg Lys Glu Val Glu Leu Ile Ile Gln Val Thr Pro
                565                 570                 575

Lys Asp Ile Lys Leu Thr Ala Phe Pro Ser Glu Ser Val Lys Glu Gly
            580                 585                 590

Asp Thr Val Ile Ile Ser Cys Thr Cys Gly Asn Val Pro Glu Thr Trp
        595                 600                 605

Ile Ile Leu Lys Lys Lys Ala Glu Thr Gly Asp Thr Val Leu Lys Ser
            610                 615                 620

Ile Asp Gly Ala Tyr Thr Ile Arg Lys Ala Gln Leu Lys Asp Ala Gly
625                 630                 635                 640

Val Tyr Glu Cys Glu Ser Lys Asn Lys Val Gly Ser Gln Leu Arg Ser
                645                 650                 655

Leu Thr Leu Asp Val Gln Gly Arg Glu Asn Asn Lys Asp Tyr Phe Ser
            660                 665                 670

Pro

<210> SEQ ID NO 101
<211> LENGTH: 466
<212> TYPE: PRT
<213> ORGANISM: human

<400> SEQUENCE: 101

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

```
Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
            195                 200                 205

Pro Gln Gly Arg Ile Val Gly Lys Val Cys Pro Lys Gly Glu Cys
        210                 215                 220

Pro Trp Gln Val Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
        290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
        370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
        450                 455                 460

Phe Pro
465

<210> SEQ ID NO 102
<211> LENGTH: 1487
<212> TYPE: PRT
<213> ORGANISM: human

<400> SEQUENCE: 102

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80
```

```
Pro Phe Gly Glu Cys Cys Pro Ile Cys Pro Thr Asp Leu Ala Thr Ala
                85                  90                  95
Ser Gly Gln Pro Gly Pro Lys Gly Gln Lys Gly Glu Pro Gly Asp Ile
            100                 105                 110
Lys Asp Ile Val Gly Pro Lys Gly Pro Pro Gly Pro Gln Gly Pro Ala
        115                 120                 125
Gly Glu Gln Gly Pro Arg Gly Asp Arg Gly Asp Lys Gly Glu Lys Gly
    130                 135                 140
Ala Pro Gly Pro Arg Gly Arg Asp Gly Glu Pro Gly Thr Pro Gly Asn
145                 150                 155                 160
Pro Gly Pro Pro Gly Pro Pro Gly Pro Pro Gly Pro Pro Gly Leu Gly
                165                 170                 175
Gly Asn Phe Ala Ala Gln Met Ala Gly Gly Phe Asp Glu Lys Ala Gly
            180                 185                 190
Gly Ala Gln Leu Gly Val Met Gln Gly Pro Met Gly Pro Met Gly Pro
        195                 200                 205
Arg Gly Pro Pro Gly Pro Ala Gly Ala Pro Gly Pro Gln Gly Phe Gln
    210                 215                 220
Gly Asn Pro Gly Glu Pro Gly Glu Pro Gly Val Ser Gly Pro Met Gly
225                 230                 235                 240
Pro Arg Gly Pro Pro Gly Pro Pro Gly Lys Pro Gly Asp Asp Gly Glu
                245                 250                 255
Ala Gly Lys Pro Gly Lys Ala Gly Glu Arg Gly Pro Pro Gly Pro Gln
            260                 265                 270
Gly Ala Arg Gly Phe Pro Gly Thr Pro Gly Leu Pro Gly Val Lys Gly
        275                 280                 285
His Arg Gly Tyr Pro Gly Leu Asp Gly Ala Lys Gly Glu Ala Gly Ala
    290                 295                 300
Pro Gly Val Lys Gly Glu Ser Gly Ser Pro Gly Glu Asn Gly Ser Pro
305                 310                 315                 320
Gly Pro Met Gly Pro Arg Gly Leu Pro Gly Glu Arg Gly Arg Thr Gly
                325                 330                 335
Pro Ala Gly Ala Ala Gly Ala Arg Gly Asn Asp Gly Gln Pro Gly Pro
            340                 345                 350
Ala Gly Pro Pro Gly Pro Val Gly Pro Ala Gly Gly Pro Gly Phe Pro
        355                 360                 365
Gly Ala Pro Gly Ala Lys Gly Glu Ala Gly Pro Thr Gly Ala Arg Gly
    370                 375                 380
Pro Glu Gly Ala Gln Gly Pro Arg Gly Glu Pro Gly Thr Pro Gly Ser
385                 390                 395                 400
Pro Gly Pro Ala Gly Ala Ser Gly Asn Pro Gly Thr Asp Gly Ile Pro
                405                 410                 415
Gly Ala Lys Gly Ser Ala Gly Ala Pro Gly Ile Ala Gly Ala Pro Gly
            420                 425                 430
Phe Pro Gly Pro Arg Gly Pro Pro Gly Pro Gln Gly Ala Thr Gly Pro
        435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
```

```
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
        515                 520                 525
Ala Pro Gly Glu Arg Gly Pro Ser Gly Leu Ala Gly Pro Lys Gly Ala
    530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                565                 570                 575
Pro Ser Gly Ala Pro Gly Glu Asp Gly Arg Pro Gly Pro Pro Gly Pro
            580                 585                 590
Gln Gly Ala Arg Gly Gln Pro Gly Val Met Gly Phe Pro Gly Pro Lys
        595                 600                 605
Gly Ala Asn Gly Glu Pro Gly Lys Ala Gly Glu Lys Gly Leu Pro Gly
    610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
                645                 650                 655
Gly Ala Pro Gly Pro Ser Gly Phe Gln Gly Leu Pro Gly Pro Pro Gly
            660                 665                 670
Pro Pro Gly Glu Gly Gly Lys Pro Gly Asp Gln Gly Val Pro Gly Glu
        675                 680                 685
Ala Gly Ala Pro Gly Leu Val Gly Pro Arg Gly Glu Arg Gly Phe Pro
    690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
                725                 730                 735
Ala Gly Pro Pro Gly Ala Gln Gly Pro Pro Gly Leu Gln Gly Met Pro
            740                 745                 750
Gly Glu Arg Gly Ala Ala Gly Ile Ala Gly Pro Lys Gly Asp Arg Gly
        755                 760                 765
Asp Val Gly Glu Lys Gly Pro Glu Ala Pro Gly Lys Asp Gly Gly
    770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                805                 810                 815
Ala Arg Gly Ala Pro Gly Glu Arg Gly Glu Thr Gly Pro Pro Gly Pro
            820                 825                 830
Ala Gly Phe Ala Gly Pro Pro Gly Ala Asp Gly Gln Pro Gly Ala Lys
        835                 840                 845
Gly Glu Gln Gly Glu Ala Gly Gln Lys Gly Asp Ala Gly Ala Pro Gly
    850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
                885                 890                 895
Gly Phe Pro Gly Ala Ala Gly Arg Val Gly Pro Pro Gly Ser Asn Gly
            900                 905                 910
Asn Pro Gly Pro Pro Gly Pro Pro Gly Pro Ser Gly Lys Asp Gly Pro
```

|     |     | 915 |     |     | 920 |     |     | 925 |     |     |     |
| --- | --- | --- | --- | --- | --- | --- | --- | --- | --- | --- | --- |

Lys Gly Ala Arg Gly Asp Ser Gly Pro Pro Gly Arg Ala Gly Glu Pro
930                     935                     940

Gly Leu Gln Gly Pro Ala Gly Pro Pro Gly Glu Lys Gly Glu Pro Gly
945                     950                     955                     960

Asp Asp Gly Pro Ser Gly Ala Glu Gly Pro Pro Gly Pro Gln Gly Leu
                965                     970                     975

Ala Gly Gln Arg Gly Ile Val Gly Leu Pro Gly Gln Arg Gly Glu Arg
            980                     985                     990

Gly Phe Pro Gly Leu Pro Gly Pro Ser Gly Glu Pro Gly Lys Gln Gly
            995                     1000                    1005

Ala Pro Gly Ala Ser Gly Asp Arg Gly Pro Pro Gly Pro Val Gly
    1010                    1015                    1020

Pro Pro Gly Leu Thr Gly Pro Ala Gly Glu Pro Gly Arg Glu Gly
    1025                    1030                    1035

Ser Pro Gly Ala Asp Gly Pro Pro Gly Arg Asp Gly Ala Ala Gly
    1040                    1045                    1050

Val Lys Gly Asp Arg Gly Glu Thr Gly Ala Val Gly Ala Pro Gly
    1055                    1060                    1065

Ala Pro Gly Pro Pro Gly Ser Pro Gly Pro Ala Gly Pro Thr Gly
    1070                    1075                    1080

Lys Gln Gly Asp Arg Gly Glu Ala Gly Ala Gln Gly Pro Met Gly
    1085                    1090                    1095

Pro Ser Gly Pro Ala Gly Ala Arg Gly Ile Gln Gly Pro Gln Gly
    1100                    1105                    1110

Pro Arg Gly Asp Lys Gly Glu Ala Gly Glu Pro Gly Glu Arg Gly
    1115                    1120                    1125

Leu Lys Gly His Arg Gly Phe Thr Gly Leu Gln Gly Leu Pro Gly
    1130                    1135                    1140

Pro Pro Gly Pro Ser Gly Asp Gln Gly Ala Ser Gly Pro Ala Gly
    1145                    1150                    1155

Pro Ser Gly Pro Arg Gly Pro Pro Gly Pro Val Gly Pro Ser Gly
    1160                    1165                    1170

Lys Asp Gly Ala Asn Gly Ile Pro Gly Pro Ile Gly Pro Pro Gly
    1175                    1180                    1185

Pro Arg Gly Arg Ser Gly Glu Thr Gly Pro Ala Gly Pro Pro Gly
    1190                    1195                    1200

Asn Pro Gly Pro Pro Gly Pro Gly Pro Pro Gly Pro Gly Ile
    1205                    1210                    1215

Asp Met Ser Ala Phe Ala Gly Leu Gly Pro Arg Glu Lys Gly Pro
    1220                    1225                    1230

Asp Pro Leu Gln Tyr Met Arg Ala Asp Gln Ala Ala Gly Gly Leu
    1235                    1240                    1245

Arg Gln His Asp Ala Glu Val Asp Ala Thr Leu Lys Ser Leu Asn
    1250                    1255                    1260

Asn Gln Ile Glu Ser Ile Arg Ser Pro Glu Gly Ser Arg Lys Asn
    1265                    1270                    1275

Pro Ala Arg Thr Cys Arg Asp Leu Lys Leu Cys His Pro Glu Trp
    1280                    1285                    1290

Lys Ser Gly Asp Tyr Trp Ile Asp Pro Asn Gln Gly Cys Thr Leu
    1295                    1300                    1305

Asp Ala Met Lys Val Phe Cys Asn Met Glu Thr Gly Glu Thr Cys
    1310                    1315                    1320

```
Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485

<210> SEQ ID NO 103
<211> LENGTH: 119
<212> TYPE: PRT
<213> ORGANISM: human

<400> SEQUENCE: 103

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 104
<211> LENGTH: 53
<212> TYPE: PRT
<213> ORGANISM: human

<400> SEQUENCE: 104

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30
```

His Ser Asp Phe Cys Leu Gly Cys Ala Ala Ala Pro Pro Ala Pro Phe
        35                  40                  45

Arg Leu Leu Trp Pro
        50

<210> SEQ ID NO 105
<211> LENGTH: 174
<212> TYPE: PRT
<213> ORGANISM: human

<400> SEQUENCE: 105

Met Ala Pro Glu Pro Gly Ser Thr Cys Arg Leu Arg Glu Tyr Tyr Asp
1               5                   10                  15

Gln Thr Ala Gln Met Cys Cys Ser Lys Cys Ser Pro Gly Gln His Ala
            20                  25                  30

Lys Val Phe Cys Thr Lys Thr Ser Asp Thr Val Cys Asp Ser Cys Glu
        35                  40                  45

Asp Ser Thr Tyr Thr Gln Leu Trp Asn Trp Val Pro Glu Cys Leu Ser
    50                  55                  60

Cys Gly Ser Arg Cys Ser Ser Asp Gln Val Glu Thr Gln Ala Cys Thr
65                  70                  75                  80

Arg Glu Gln Asn Arg Ile Cys Thr Cys Arg Pro Gly Trp Tyr Cys Ala
                85                  90                  95

Leu Ser Lys Gln Glu Gly Cys Arg Leu Cys Ala Pro Leu Arg Lys Cys
            100                 105                 110

Arg Pro Gly Phe Gly Val Ala Arg Pro Gly Thr Glu Thr Ser Asp Val
        115                 120                 125

Val Cys Lys Pro Cys Ala Pro Gly Thr Phe Ser Asn Thr Thr Ser Ser
    130                 135                 140

Thr Asp Ile Cys Arg Pro His Gln Ile Cys Asn Val Val Ala Ile Pro
145                 150                 155                 160

Gly Asn Ala Ser Met Asp Ala Val Cys Thr Ser Thr Ser Pro
                165                 170

<210> SEQ ID NO 106
<211> LENGTH: 102
<212> TYPE: PRT
<213> ORGANISM: human

<400> SEQUENCE: 106

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

His Glu Ile Asn Thr Ile Tyr Leu Gly Gly Pro Phe Ser Pro Asn Val
65                  70                  75                  80

Leu Asn Trp Arg Ala Leu Lys Tyr Glu Val Gln Gly Glu Val Phe Thr
                85                  90                  95

Lys Pro Gln Leu Trp Pro
            100

<210> SEQ ID NO 107

```
<211> LENGTH: 76
<212> TYPE: PRT
<213> ORGANISM: human

<400> SEQUENCE: 107

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly
65                  70                  75

<210> SEQ ID NO 108
<211> LENGTH: 152
<212> TYPE: PRT
<213> ORGANISM: human

<400> SEQUENCE: 108

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
    50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
    130                 135                 140

Phe Phe Gly Ala Leu Lys Leu Leu
145                 150

<210> SEQ ID NO 109
<211> LENGTH: 31
<212> TYPE: PRT
<213> ORGANISM: human

<400> SEQUENCE: 109

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 110
<211> LENGTH: 733
<212> TYPE: PRT
<213> ORGANISM: human
```

<400> SEQUENCE: 110

Met Pro Glu Glu Thr Gln Ala Gln Asp Gln Pro Met Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
50                      55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
            115                 120                 125

Ser Met Ile Gly Gln Phe Gly Val Gly Phe Tyr Ser Ala Tyr Leu Val
130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
            165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
            195                 200                 205

Lys His Ser Gln Phe Ile Gly Tyr Pro Ile Thr Leu Phe Val Glu Lys
210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Asp Asp Lys Pro
            245                 250                 255

Glu Ile Glu Asp Val Gly Ser Asp Glu Glu Glu Glu Lys Lys Asp
            260                 265                 270

Gly Asp Lys Lys Lys Lys Lys Ile Lys Glu Lys Tyr Ile Asp Gln
            275                 280                 285

Glu Glu Leu Asn Lys Thr Lys Pro Ile Trp Thr Arg Asn Pro Asp Asp
290                 295                 300

Ile Thr Asn Glu Glu Tyr Gly Glu Phe Tyr Lys Ser Leu Thr Asn Asp
305                 310                 315                 320

Trp Glu Asp His Leu Ala Val Lys His Phe Ser Val Glu Gly Gln Leu
            325                 330                 335

Glu Phe Arg Ala Leu Leu Phe Val Pro Arg Arg Ala Pro Phe Asp Leu
            340                 345                 350

Phe Glu Asn Arg Lys Lys Lys Asn Asn Ile Lys Leu Tyr Val Arg Arg
            355                 360                 365

Val Phe Ile Met Asp Asn Cys Glu Glu Leu Ile Pro Glu Tyr Leu Asn
            370                 375                 380

Phe Ile Arg Gly Val Val Asp Ser Glu Asp Leu Pro Leu Asn Ile Ser
385                 390                 395                 400

Arg Glu Met Leu Gln Gln Ser Lys Ile Leu Lys Val Ile Arg Lys Asn
            405                 410                 415

-continued

Leu Val Lys Lys Cys Leu Glu Leu Phe Thr Glu Leu Ala Glu Asp Lys
            420                 425                 430

Glu Asn Tyr Lys Lys Phe Tyr Glu Gln Phe Ser Lys Asn Ile Lys Leu
            435                 440                 445

Gly Ile His Glu Asp Ser Gln Asn Arg Lys Lys Leu Ser Glu Leu Leu
450                 455                 460

Arg Tyr Tyr Thr Ser Ala Ser Gly Asp Glu Met Val Ser Leu Lys Asp
465                 470                 475                 480

Tyr Cys Thr Arg Met Lys Glu Asn Gln Lys His Ile Tyr Tyr Ile Thr
                485                 490                 495

Gly Glu Thr Lys Asp Gln Val Ala Asn Ser Ala Phe Val Glu Arg Leu
            500                 505                 510

Arg Lys His Gly Leu Glu Val Ile Tyr Met Ile Glu Pro Ile Asp Glu
            515                 520                 525

Tyr Cys Val Gln Gln Leu Lys Glu Phe Glu Gly Lys Thr Leu Val Ser
            530                 535                 540

Val Thr Lys Glu Gly Leu Glu Leu Pro Glu Asp Glu Glu Glu Lys Lys
545                 550                 555                 560

Lys Gln Glu Glu Lys Lys Thr Lys Phe Glu Asn Leu Cys Lys Ile Met
                565                 570                 575

Lys Asp Ile Leu Glu Lys Lys Val Glu Lys Val Val Val Ser Asn Arg
            580                 585                 590

Leu Val Thr Ser Pro Cys Cys Ile Val Thr Ser Thr Tyr Gly Trp Thr
            595                 600                 605

Ala Asn Met Glu Arg Ile Met Lys Ala Gln Ala Leu Arg Asp Asn Ser
610                 615                 620

Thr Met Gly Tyr Met Ala Ala Lys Lys His Leu Glu Ile Asn Pro Asp
625                 630                 635                 640

His Ser Ile Ile Glu Thr Leu Arg Gln Lys Ala Glu Ala Asp Lys Asn
                645                 650                 655

Asp Lys Ser Val Lys Asp Leu Val Ile Leu Leu Tyr Glu Thr Ala Leu
            660                 665                 670

Leu Ser Ser Gly Phe Ser Leu Glu Asp Pro Gln Thr His Ala Asn Arg
            675                 680                 685

Ile Tyr Arg Met Ile Lys Leu Gly Leu Gly Ile Asp Glu Asp Asp Pro
690                 695                 700

Thr Ala Asp Asp Ser Ser Ala Ala Val Thr Glu Glu Met Pro Pro Leu
705                 710                 715                 720

Glu Gly Asp Asp Asp Thr Ser Arg Met Glu Glu Val Asp
                725                 730

```
<210> SEQ ID NO 111
<211> LENGTH: 53
<212> TYPE: PRT
<213> ORGANISM: human

<400> SEQUENCE: 111
```

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
            35                  40                  45

Trp Trp Glu Leu Arg

<210> SEQ ID NO 112
<211> LENGTH: 1744
<212> TYPE: PRT
<213> ORGANISM: human

<400> SEQUENCE: 112

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

```
Leu Asp Leu Ser Lys Thr Lys Arg His Leu Val Pro Gly Ala Pro Phe
370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
                435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Met Ile Leu Ser Arg
                500                 505                 510

Gly Gln Ile Val Phe Met Asn Arg Glu Pro Lys Arg Thr Leu Thr Ser
                515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
            610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
                660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
```

```
            785                 790                 795                 800
Asp Ser Leu Thr Thr Trp Glu Ile His Gly Leu Ser Leu Ser Lys Thr
                    805                 810                 815

Lys Gly Leu Cys Val Ala Thr Pro Val Gln Leu Arg Val Phe Arg Glu
                    820                 825                 830

Phe His Leu His Leu Arg Leu Pro Met Ser Val Arg Phe Glu Gln
                    835                 840                 845

Leu Glu Leu Arg Pro Val Leu Tyr Asn Tyr Leu Asp Lys Asn Leu Thr
                    850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                    885                 890                 895

Val Ala Phe Ser Val Val Pro Thr Ala Ala Ala Val Ser Leu Lys
                    900                 905                 910

Val Val Ala Arg Gly Ser Phe Glu Phe Pro Val Gly Asp Ala Val Ser
                    915                 920                 925

Lys Val Leu Gln Ile Glu Lys Glu Gly Ala Ile His Arg Glu Glu Leu
                    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                    965                 970                 975

Tyr Val Arg Val Thr Ala Ser Asp Pro Leu Asp Thr Leu Gly Ser Glu
                    980                 985                 990

Gly Ala Leu Ser Pro Gly Gly Val Ala Ser Leu Leu Arg Leu Pro Arg
                    995                 1000                1005

Gly Cys Gly Glu Gln Thr Met Ile Tyr Leu Ala Pro Thr Leu Ala
        1010                1015                1020

Ala Ser Arg Tyr Leu Asp Lys Thr Glu Gln Trp Ser Thr Leu Pro
        1025                1030                1035

Pro Glu Thr Lys Asp His Ala Val Asp Leu Ile Gln Lys Gly Tyr
        1040                1045                1050

Met Arg Ile Gln Gln Phe Arg Lys Ala Asp Gly Ser Tyr Ala Ala
        1055                1060                1065

Trp Leu Ser Arg Asp Ser Ser Thr Trp Leu Thr Ala Phe Val Leu
        1070                1075                1080

Lys Val Leu Ser Leu Ala Gln Glu Gln Val Gly Gly Ser Pro Glu
        1085                1090                1095

Lys Leu Gln Glu Thr Ser Asn Trp Leu Leu Ser Gln Gln Gln Ala
        1100                1105                1110

Asp Gly Ser Phe Gln Asp Pro Cys Pro Val Leu Asp Arg Ser Met
        1115                1120                1125

Gln Gly Gly Leu Val Gly Asn Asp Glu Thr Val Ala Leu Thr Ala
        1130                1135                1140

Phe Val Thr Ile Ala Leu His His Gly Leu Ala Val Phe Gln Asp
        1145                1150                1155

Glu Gly Ala Glu Pro Leu Lys Gln Arg Val Glu Ala Ser Ile Ser
        1160                1165                1170

Lys Ala Asn Ser Phe Leu Gly Glu Lys Ala Ser Ala Gly Leu Leu
        1175                1180                1185

Gly Ala His Ala Ala Ala Ile Thr Ala Tyr Ala Leu Thr Leu Thr
        1190                1195                1200
```

-continued

```
Lys Ala Pro Val Asp Leu Leu Gly Val Ala His Asn Asn Leu Met
1205                1210                1215

Ala Met Ala Gln Glu Thr Gly Asp Asn Leu Tyr Trp Gly Ser Val
1220                1225                1230

Thr Gly Ser Gln Ser Asn Ala Val Ser Pro Thr Pro Ala Pro Arg
1235                1240                1245

Asn Pro Ser Asp Pro Met Pro Gln Ala Pro Ala Leu Trp Ile Glu
1250                1255                1260

Thr Thr Ala Tyr Ala Leu Leu His Leu Leu His Glu Gly Lys
1265                1270                1275

Ala Glu Met Ala Asp Gln Ala Ser Ala Trp Leu Thr Arg Gln Gly
1280                1285                1290

Ser Phe Gln Gly Gly Phe Arg Ser Thr Gln Asp Thr Val Ile Ala
1295                1300                1305

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Asp Tyr Glu Tyr Asp Glu Leu Pro Ala Lys
1415                1420                1425

Asp Asp Pro Asp Ala Pro Leu Gln Pro Val Thr Pro Leu Gln Leu
1430                1435                1440

Phe Glu Gly Arg Arg Asn Arg Arg Arg Glu Ala Pro Lys Val
1445                1450                1455

Val Glu Glu Gln Glu Ser Arg Val His Tyr Thr Val Cys Ile Trp
1460                1465                1470

Arg Asn Gly Lys Val Gly Leu Ser Gly Met Ala Ile Ala Asp Val
1475                1480                1485

Thr Leu Leu Ser Gly Phe His Ala Leu Arg Ala Asp Leu Glu Lys
1490                1495                1500

Leu Thr Ser Leu Ser Asp Arg Tyr Val Ser His Phe Glu Thr Glu
1505                1510                1515

Gly Pro His Val Leu Leu Tyr Phe Asp Ser Val Pro Thr Ser Arg
1520                1525                1530

Glu Cys Val Gly Phe Glu Ala Val Gln Glu Val Pro Val Gly Leu
1535                1540                1545

Val Gln Pro Ala Ser Ala Thr Leu Tyr Asp Tyr Tyr Asn Pro Glu
1550                1555                1560

Arg Arg Cys Ser Val Phe Tyr Gly Ala Pro Ser Lys Ser Arg Leu
1565                1570                1575

Leu Ala Thr Leu Cys Ser Ala Glu Val Cys Gln Cys Ala Glu Gly
1580                1585                1590
```

```
Lys Cys Pro Arg Gln Arg Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val
```

```
<210> SEQ ID NO 113
<211> LENGTH: 1663
<212> TYPE: PRT
<213> ORGANISM: human

<400> SEQUENCE: 113
```

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
                100                 105                 110

Gly Thr Gln Val Val Glu Lys Val Val Leu Val Ser Leu Gln Ser Gly
            115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
                180                 185                 190

Trp Asp Ile Pro Glu Leu Val Asn Met Gly Gln Trp Lys Ile Arg Ala
                195                 200                 205
```

```
Tyr Tyr Glu Asn Ser Pro Gln Gln Val Phe Ser Thr Glu Phe Glu Val
    210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
                260                 265                 270
Phe Gly Ile Gln Asp Gly Glu Gln Arg Ile Ser Leu Pro Glu Ser Leu
            275                 280                 285
Lys Arg Ile Pro Ile Glu Asp Gly Ser Gly Glu Val Val Leu Ser Arg
290                 295                 300
Lys Val Leu Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
            340                 345                 350
Tyr Gln Ile His Phe Thr Lys Thr Pro Lys Tyr Phe Lys Pro Gly Met
        355                 360                 365
Pro Phe Asp Leu Met Val Phe Val Thr Asn Pro Asp Gly Ser Pro Ala
370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
    450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
            515                 520                 525
Phe Arg Leu Val Ala Tyr Tyr Thr Leu Ile Gly Ala Ser Gly Gln Arg
530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
                595                 600                 605
Asn Lys Leu Thr Gln Ser Lys Ile Trp Asp Val Glu Lys Ala Asp
        610                 615                 620
Ile Gly Cys Thr Pro Gly Ser Gly Lys Asp Tyr Ala Gly Val Phe Ser
```

```
                625                 630                 635                 640
Asp Ala Gly Leu Thr Phe Thr Ser Ser Ser Gly Gln Gln Thr Ala Gln
                        645                 650                 655

Arg Ala Glu Leu Gln Cys Pro Gln Pro Ala Arg Arg Arg Ser
                660                 665                 670

Val Gln Leu Thr Glu Lys Arg Met Asp Lys Val Gly Lys Tyr Pro Lys
                675                 680                 685

Glu Leu Arg Lys Cys Cys Glu Asp Gly Met Arg Glu Asn Pro Met Arg
            690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                    725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
            755                 760                 765

Glu Ser Trp Leu Trp Asn Val Glu Asp Leu Lys Glu Pro Pro Lys Asn
        770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                    805                 810                 815

Val Ala Asp Pro Phe Glu Val Thr Val Met Gln Asp Phe Phe Ile Asp
                820                 825                 830

Leu Arg Leu Pro Tyr Ser Val Arg Asn Glu Gln Val Glu Ile Arg
            835                 840                 845

Ala Val Leu Tyr Asn Tyr Arg Gln Asn Gln Glu Leu Lys Val Arg Val
        850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                    885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                    965                 970                 975

Glu Thr Arg Ile Leu Leu Gln Gly Thr Pro Val Ala Gln Met Thr Glu
                980                 985                 990

Asp Ala Val Asp Ala Glu Arg Leu Lys His Leu Ile Val Thr Pro Ser
            995                 1000                1005

Gly Cys Gly Glu Gln Asn Met Ile Gly Met Thr Pro Thr Val Ile
        1010                1015                1020

Ala Val His Tyr Leu Asp Glu Thr Glu Gln Trp Glu Lys Phe Gly
        1025                1030                1035

Leu Glu Lys Arg Gln Gly Ala Leu Glu Leu Ile Lys Lys Gly Tyr
        1040                1045                1050
```

```
Thr Gln Gln Leu Ala Phe Arg Gln Pro Ser Ser Ala Phe Ala Ala
    1055            1060            1065

Phe Val Lys Arg Ala Pro Ser Thr Trp Leu Thr Ala Tyr Val Val
    1070            1075            1080

Lys Val Phe Ser Leu Ala Val Asn Leu Ile Ala Ile Asp Ser Gln
    1085            1090            1095

Val Leu Cys Gly Ala Val Lys Trp Leu Ile Leu Glu Lys Gln Lys
    1100            1105            1110

Pro Asp Gly Val Phe Gln Glu Asp Ala Pro Val Ile His Gln Glu
    1115            1120            1125

Met Ile Gly Gly Leu Arg Asn Asn Asn Glu Lys Asp Met Ala Leu
    1130            1135            1140

Thr Ala Phe Val Leu Ile Ser Leu Gln Glu Ala Lys Asp Ile Cys
    1145            1150            1155

Glu Glu Gln Val Asn Ser Leu Pro Gly Ser Ile Thr Lys Ala Gly
    1160            1165            1170

Asp Phe Leu Glu Ala Asn Tyr Met Asn Leu Gln Arg Ser Tyr Thr
    1175            1180            1185

Val Ala Ile Ala Gly Tyr Ala Leu Ala Gln Met Gly Arg Leu Lys
    1190            1195            1200

Gly Pro Leu Leu Asn Lys Phe Leu Thr Thr Ala Lys Asp Lys Asn
    1205            1210            1215

Arg Trp Glu Asp Pro Gly Lys Gln Leu Tyr Asn Val Glu Ala Thr
    1220            1225            1230

Ser Tyr Ala Leu Leu Ala Leu Leu Gln Leu Lys Asp Phe Asp Phe
    1235            1240            1245

Val Pro Pro Val Val Arg Trp Leu Asn Glu Gln Arg Tyr Tyr Gly
    1250            1255            1260

Gly Gly Tyr Gly Ser Thr Gln Ala Thr Phe Met Val Phe Gln Ala
    1265            1270            1275

Leu Ala Gln Tyr Gln Lys Asp Ala Pro Asp His Gln Glu Leu Asn
    1280            1285            1290

Leu Asp Val Ser Leu Gln Leu Pro Ser Arg Ser Ser Lys Ile Thr
    1295            1300            1305

His Arg Ile His Trp Glu Ser Ala Ser Leu Leu Arg Ser Glu Glu
    1310            1315            1320

Thr Lys Glu Asn Glu Gly Phe Thr Val Thr Ala Glu Gly Lys Gly
    1325            1330            1335

Gln Gly Thr Leu Ser Val Val Thr Met Tyr His Ala Lys Ala Lys
    1340            1345            1350

Asp Gln Leu Thr Cys Asn Lys Phe Asp Leu Lys Val Thr Ile Lys
    1355            1360            1365

Pro Ala Pro Glu Thr Glu Lys Arg Pro Gln Asp Ala Lys Asn Thr
    1370            1375            1380

Met Ile Leu Glu Ile Cys Thr Arg Tyr Arg Gly Asp Gln Asp Ala
    1385            1390            1395

Thr Met Ser Ile Leu Asp Ile Ser Met Met Thr Gly Phe Ala Pro
    1400            1405            1410

Asp Thr Asp Asp Leu Lys Gln Leu Ala Asn Gly Val Asp Arg Tyr
    1415            1420            1425

Ile Ser Lys Tyr Glu Leu Asp Lys Ala Phe Ser Asp Arg Asn Thr
    1430            1435            1440
```

-continued

Leu Ile Ile Tyr Leu Asp Lys Val Ser His Ser Glu Asp Asp Cys
1445                1450                1455

Leu Ala Phe Lys Val His Gln Tyr Phe Asn Val Glu Leu Ile Gln
1460                1465                1470

Pro Gly Ala Val Lys Val Tyr Ala Tyr Tyr Asn Leu Glu Glu Ser
1475                1480                1485

Cys Thr Arg Phe Tyr His Pro Glu Lys Glu Asp Gly Lys Leu Asn
1490                1495                1500

Lys Leu Cys Arg Asp Glu Leu Cys Arg Cys Ala Glu Glu Asn Cys
1505                1510                1515

Phe Ile Gln Lys Ser Asp Asp Lys Val Thr Leu Glu Glu Arg Leu
1520                1525                1530

Asp Lys Ala Cys Glu Pro Gly Val Asp Tyr Val Tyr Lys Thr Arg
1535                1540                1545

Leu Val Lys Val Gln Leu Ser Asn Asp Phe Asp Glu Tyr Ile Met
1550                1555                1560

Ala Ile Glu Gln Thr Ile Lys Ser Gly Ser Asp Glu Val Gln Val
1565                1570                1575

Gly Gln Gln Arg Thr Phe Ile Ser Pro Ile Lys Cys Arg Glu Ala
1580                1585                1590

Leu Lys Leu Glu Glu Lys Lys His Tyr Leu Met Trp Gly Leu Ser
1595                1600                1605

Ser Asp Phe Trp Gly Glu Lys Pro Asn Leu Ser Tyr Ile Ile Gly
1610                1615                1620

Lys Asp Thr Trp Val Glu His Trp Pro Glu Glu Asp Glu Cys Gln
1625                1630                1635

Asp Glu Glu Asn Gln Lys Gln Cys Gln Asp Leu Gly Ala Phe Thr
1640                1645                1650

Glu Ser Met Val Val Phe Gly Cys Pro Asn
1655                1660

<210> SEQ ID NO 114
<211> LENGTH: 245
<212> TYPE: PRT
<213> ORGANISM: human

<400> SEQUENCE: 114

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
                20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

```
Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
                195                 200                 205

Leu Gln Gln Gly Asp Gln Val Trp Val Glu Lys Asp Pro Lys Lys Gly
210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 115
<211> LENGTH: 866
<212> TYPE: PRT
<213> ORGANISM: human

<400> SEQUENCE: 115

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
            115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
            195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
```

```
            260                 265                 270
Gly Ser Thr Ser Tyr Gly Thr Gly Ser Glu Thr Glu Ser Pro Arg Asn
            275                 280                 285

Pro Ser Ser Ala Gly Ser Trp Asn Ser Gly Ser Ser Gly Pro Gly Ser
            290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                    325                 330                 335

Gly Ser Ser Gly Thr Gly Ser Thr Gly Asn Gln Asn Pro Gly Ser Pro
                    340                 345                 350

Arg Pro Gly Ser Thr Gly Thr Trp Asn Pro Gly Ser Ser Glu Arg Gly
                    355                 360                 365

Ser Ala Gly His Trp Thr Ser Glu Ser Ser Val Ser Gly Ser Thr Gly
                    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                    405                 410                 415

Ser Gly Asn Val Ser Pro Gly Thr Arg Arg Glu Tyr His Thr Glu Lys
                    420                 425                 430

Leu Val Thr Ser Lys Gly Asp Lys Glu Leu Arg Thr Gly Lys Glu Lys
                    435                 440                 445

Val Thr Ser Gly Ser Thr Thr Thr Thr Arg Arg Ser Cys Ser Lys Thr
                    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                    485                 490                 495

Leu Gly Thr Leu Ser Gly Ile Gly Thr Leu Asp Gly Phe Arg His Arg
                    500                 505                 510

His Pro Asp Glu Ala Ala Phe Phe Asp Thr Ala Ser Thr Gly Lys Thr
                    515                 520                 525

Phe Pro Gly Phe Phe Ser Pro Met Leu Gly Glu Phe Val Ser Glu Thr
                    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                    565                 570                 575

Ser Ser Tyr Ser Lys Gln Phe Thr Ser Ser Thr Ser Tyr Asn Arg Gly
                    580                 585                 590

Asp Ser Thr Phe Glu Ser Lys Ser Tyr Lys Met Ala Asp Glu Ala Gly
                    595                 600                 605

Ser Glu Ala Asp His Glu Gly Thr His Ser Thr Lys Arg Gly His Ala
                    610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                    645                 650                 655

Lys Ile Phe Ser Val Tyr Cys Asp Gln Glu Thr Ser Leu Gly Gly Trp
                    660                 665                 670

Leu Leu Ile Gln Gln Arg Met Asp Gly Ser Leu Asn Phe Asn Arg Thr
                    675                 680                 685
```

```
Trp Gln Asp Tyr Lys Arg Gly Phe Gly Ser Leu Asn Asp Glu Gly Glu
        690                 695                 700

Gly Glu Phe Trp Leu Gly Asn Asp Tyr Leu His Leu Leu Thr Gln Arg
705                     710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
                740                 745                 750

Leu Gln Val Ser Ser Tyr Glu Gly Thr Ala Gly Asp Ala Leu Ile Glu
        755                 760                 765

Gly Ser Val Glu Glu Gly Ala Glu Tyr Thr Ser His Asn Asn Met Gln
770                     775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
                820                 825                 830

Ser Pro Tyr Glu Ile Glu Asn Gly Val Val Trp Val Ser Phe Arg Gly
        835                 840                 845

Ala Asp Tyr Ser Leu Arg Ala Val Arg Met Lys Ile Arg Pro Leu Val
        850                 855                 860

Thr Gln
865
```